US012703761B2

(12) United States Patent
Bandyopadhyay et al.

(10) Patent No.: US 12,703,761 B2
(45) Date of Patent: Aug. 11, 2026

(54) ANTI-HER2 ANTIBODIES AND METHODS OF USE THEREOF

(71) Applicant: Denali Therapeutics Inc., South San Francisco, CA (US)

(72) Inventors: Abira Bandyopadhyay, Pleasanton, CA (US); Allisa Jayne Clemens, San Jose, CA (US); Do Jin Kim, Albany, NY (US); Michelle E. Pizzo, Pacifica, CA (US); Lu Shan, Belmont, CA (US); Richard Théolis, Jr., Santa Cruz, CA (US); Raymond Ka Hang Tong, South San Francisco, CA (US)

(73) Assignee: Denali Therapeutics Inc., South San Francisco, CA (US)

( * ) Notice: Subject to any disclaimer, the term of this patent is extended or adjusted under 35 U.S.C. 154(b) by 0 days.

(21) Appl. No.: 19/352,786

(22) Filed: Oct. 8, 2025

(65) Prior Publication Data

US 2026/0109781 A1 Apr. 23, 2026

Related U.S. Application Data

(63) Continuation of application No. 18/685,587, filed as application No. PCT/US2022/075438 on Aug. 25, 2022.

(60) Provisional application No. 63/237,104, filed on Aug. 25, 2021.

(51) Int. Cl.
*C07K 16/32* (2006.01)
*A61K 35/00* (2006.01)
*A61K 39/00* (2006.01)
*A61K 45/06* (2006.01)

(52) U.S. Cl.
CPC .............. *C07K 16/32* (2013.01); *A61K 35/00* (2013.01); *A61K 45/06* (2013.01); *A61K 2039/505* (2013.01); *C07K 2317/31* (2013.01); *C07K 2317/526* (2013.01); *C07K 2317/565* (2013.01); *C07K 2317/71* (2013.01); *C07K 2317/72* (2013.01); *C07K 2317/732* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,154,924 | A | 10/1992 | Friden |
| 5,254,342 | A | 10/1993 | Shen et al. |
| 5,527,527 | A | 6/1996 | Friden |
| 5,821,333 | A | 10/1998 | Carter et al. |
| 5,821,337 | A | 10/1998 | Carter et al. |
| 5,821,377 | A | 10/1998 | Buyscb et al. |
| 5,981,217 | A | 11/1999 | Subramanium et al. |
| 6,054,297 | A | 4/2000 | Carter et al. |
| 6,333,348 | B1 | 12/2001 | Vogel et al. |
| 6,399,063 | B1 | 6/2002 | Hudziak et al. |
| 6,407,213 | B1 | 6/2002 | Carter et al. |
| 6,476,198 | B1 | 11/2002 | Kang |
| 6,485,943 | B2 | 11/2002 | Stevens et al. |
| 6,627,196 | B1 | 9/2003 | Baughman et al. |
| 6,632,979 | B2 | 10/2003 | Erickson et al. |
| 6,639,055 | B1 | 10/2003 | Carter et al. |
| 6,639,142 | B2 | 10/2003 | Takahashi |
| 6,719,971 | B1 | 4/2004 | Carter et al. |
| 6,737,056 | B1 | 5/2004 | Presta |
| 6,743,893 | B2 | 6/2004 | Engler et al. |
| 6,800,738 | B1 | 10/2004 | Carter et al. |
| 6,949,245 | B1 | 9/2005 | Sliwkowski |
| 7,241,449 | B1 | 7/2007 | Myers et al. |
| 7,371,376 | B1 | 5/2008 | Fendly |
| 7,371,379 | B2 | 5/2008 | Baughman et al. |
| 7,371,826 | B2 | 5/2008 | Presta |
| 7,435,797 | B2 | 10/2008 | Lowman et al. |
| 7,449,184 | B2 | 11/2008 | Allison et al. |
| 7,485,302 | B2 | 2/2009 | Adams et al. |
| 7,485,704 | B2 | 2/2009 | Fahmer et al. |
| 7,498,030 | B2 | 3/2009 | Adams et al. |
| 7,501,122 | B2 | 3/2009 | Adams et al. |

(Continued)

FOREIGN PATENT DOCUMENTS

| | | | |
|---|---|---|---|
| CN | 1326881 | C | 7/2007 |
| CN | 101098891 | A1 | 1/2008 |

(Continued)

OTHER PUBLICATIONS

Abstract 2955: Herceptarg, a novel heterodimeric biparatopic common light chain IgG1 antibody based on trastuzumab and pertuzumab, exerts potent anti-tumoral activity, Experimental and Molecular Therapeutics, (Jul. 2016).

(Continued)

*Primary Examiner* — Zachariah Lucas
*Assistant Examiner* — Sarah A Alsomairy
(74) *Attorney, Agent, or Firm* — Alston & Bird LLP

(57) ABSTRACT

In one aspect, antibodies that bind to subdomain II of human HER2 are provided. In another aspect, antibodies comprising a light chain polypeptide that pairs with both a heavy chain polypeptide for binding to subdomain II of human HER2 and a heavy chain polypeptide for binding to subdomain IV of human HER2 are provided. In a further aspect, antibodies that bind to both subdomain II and subdomain IV of human HER2 comprising a common light chain polypeptide are provided. Methods of treating a cancer or treating brain metastasis of a cancer using these antibodies are also provided.

21 Claims, 9 Drawing Sheets

Specification includes a Sequence Listing.

(56) References Cited

U.S. PATENT DOCUMENTS

| | | | |
|---|---|---|---|
| 7,537,931 | B2 | 5/2009 | Adams et al. |
| 7,560,111 | B2 | 7/2009 | Kao et al. |
| 7,618,631 | B2 | 11/2009 | Sliwkowski |
| 7,670,600 | B2 | 3/2010 | Dall'Acqua et al. |
| 7,682,609 | B2 | 3/2010 | Andya et al. |
| 7,741,446 | B2 | 6/2010 | Pardridge et al. |
| 7,744,879 | B2 | 6/2010 | Shusta et al. |
| 7,846,441 | B1 | 12/2010 | Hellmann |
| 7,850,966 | B2 | 12/2010 | Lowman et al. |
| 7,862,817 | B2 | 1/2011 | Adams et al. |
| 7,879,325 | B2 | 2/2011 | Kao et al. |
| 7,892,549 | B2 | 2/2011 | Paton et al. |
| 7,951,917 | B1 | 5/2011 | Arathoon et al. |
| 7,993,834 | B2 | 8/2011 | Mass |
| 8,053,567 | B2 | 11/2011 | Pardridge et al. |
| 8,075,890 | B2 | 12/2011 | Carter et al. |
| 8,076,066 | B2 | 12/2011 | Mass |
| 8,084,254 | B2 | 12/2011 | Couraud et al. |
| 8,088,376 | B2 | 1/2012 | Chamberlain et al. |
| 8,227,577 | B2 | 7/2012 | Klein et al. |
| 8,241,630 | B2 | 8/2012 | Kao et al. |
| 8,242,247 | B2 | 8/2012 | Klien et al. |
| 8,293,495 | B2 | 10/2012 | Shusta et al. |
| 8,313,924 | B2 | 11/2012 | Jensen et al. |
| 8,333,964 | B2 | 12/2012 | Agus |
| 8,372,395 | B2 | 2/2013 | Yu et al. |
| 8,372,396 | B2 | 2/2013 | Andya et al. |
| 8,394,925 | B2 | 3/2013 | Chamberlain et al. |
| 8,404,234 | B2 | 3/2013 | Allison et al. |
| 8,417,465 | B2 | 4/2013 | Prabhakarpandian et al. |
| 8,425,908 | B2 | 4/2013 | Hellmann |
| 8,440,402 | B2 | 5/2013 | Mass |
| 8,475,792 | B2 | 7/2013 | Dall'Acqua et al. |
| 8,497,246 | B2 | 7/2013 | Pardridge et al. |
| 8,591,897 | B2 | 11/2013 | Bryant |
| 8,609,065 | B2 | 12/2013 | Kuik-Romejin et al. |
| 8,642,745 | B2 | 2/2014 | Arathoon et al. |
| 8,648,176 | B2 | 2/2014 | Davis Orcutt et al. |
| 8,652,474 | B2 | 2/2014 | Harris et al. |
| 8,691,232 | B2 | 4/2014 | Derynck et al. |
| 8,703,132 | B2 | 4/2014 | Imhof-Jung et al. |
| 8,722,859 | B2 | 5/2014 | Miller et al. |
| 8,753,610 | B2 | 6/2014 | Pardridge et al. |
| 8,759,297 | B2 | 6/2014 | Pardridge et al. |
| 8,771,988 | B2 | 7/2014 | Goepfert |
| 8,796,424 | B2 | 8/2014 | Croasdale et al. |
| 8,859,738 | B2 | 10/2014 | Himmler et al. |
| 8,900,865 | B2 | 12/2014 | Harlow et al. |
| 8,921,279 | B2 | 12/2014 | Himmler et al. |
| 8,969,526 | B2 | 3/2015 | Baehner et al. |
| 9,005,973 | B2 | 4/2015 | Cost et al. |
| 9,017,671 | B2 | 4/2015 | Andya et al. |
| 9,133,274 | B2 | 9/2015 | Himmler et al. |
| 9,150,856 | B2 | 10/2015 | Jefferies et al. |
| 9,156,889 | B2 | 10/2015 | Nomoto et al. |
| 9,181,346 | B2 | 11/2015 | Harris et al. |
| 9,249,218 | B2 | 2/2016 | Basey et al. |
| 9,345,661 | B2 | 5/2016 | Adler et al. |
| 9,364,542 | B2 | 6/2016 | Chang |
| 9,364,567 | B2 | 6/2016 | Vitalis et al. |
| 9,415,050 | B2 | 8/2016 | Chen et al. |
| 9,428,548 | B2 | 8/2016 | Brown et al. |
| 9,513,280 | B2 | 12/2016 | Kim et al. |
| 9,527,927 | B2 | 12/2016 | Chowdhury et al. |
| 9,611,323 | B2 | 4/2017 | Dennis et al. |
| 9,631,031 | B2 | 4/2017 | Kadouche et al. |
| 9,670,269 | B2 | 6/2017 | Igawa et al. |
| 9,708,406 | B2 | 7/2017 | Zhang et al. |
| 9,803,023 | B2 | 10/2017 | Chamberlain et al. |
| 9,856,311 | B2 | 1/2018 | Ruker et al. |
| 9,890,209 | B2 | 2/2018 | Kaluza et al. |
| 9,914,785 | B2 | 3/2018 | Corper et al. |
| 9,968,676 | B2 | 5/2018 | Adler et al. |
| 9,993,530 | B2 | 6/2018 | Vitalis et al. |
| 9,993,564 | B2 | 6/2018 | Freskgard et al. |
| 9,994,641 | B2 | 6/2018 | Sonoda et al. |
| 10,143,187 | B2 | 12/2018 | Dennis et al. |
| 10,144,783 | B2 | 12/2018 | Pardridge et al. |
| 10,160,811 | B2 | 12/2018 | Baughman et al. |
| 10,190,170 | B2 | 1/2019 | Chang et al. |
| 10,233,252 | B2 | 3/2019 | Shusta et al. |
| 10,251,952 | B2 | 4/2019 | Bader et al. |
| 10,323,089 | B2 | 6/2019 | Dengl et al. |
| 10,364,292 | B2 | 7/2019 | Rueger et al. |
| 10,385,118 | B2 | 8/2019 | Himmler et al. |
| 10,457,717 | B2 | 10/2019 | Chen et al. |
| 10,487,155 | B2 | 11/2019 | Moore et al. |
| 10,508,151 | B2 | 12/2019 | Zhang et al. |
| 10,584,178 | B2 | 3/2020 | Croasdale-Wood et al. |
| 10,759,864 | B2 | 9/2020 | Sonoda et al. |
| 10,766,960 | B2 | 9/2020 | Igawa et al. |
| 10,774,119 | B2 | 9/2020 | Hinner et al. |
| 10,808,036 | B2 | 10/2020 | Zhang et al. |
| 10,808,043 | B2 | 10/2020 | Xu et al. |
| 10,870,837 | B2 | 12/2020 | Henry et al. |
| 11,008,403 | B2 | 5/2021 | Liu et al. |
| 11,098,105 | B2 | 8/2021 | Escobar-Cabrera |
| 11,111,308 | B2 | 9/2021 | Sonoda et al. |
| 11,124,567 | B2 | 9/2021 | Dennis et al. |
| 11,142,563 | B2 | 10/2021 | Igawa et al. |
| 11,155,631 | B2 | 10/2021 | Pardridge et al. |
| 11,370,832 | B2 | 6/2022 | Chen et al. |
| 11,396,557 | B2 | 7/2022 | Xu et al. |
| 11,643,446 | B2 | 5/2023 | Cherf et al. |
| 11,732,023 | B2 | 8/2023 | Chen et al. |
| 11,795,232 | B2 | 10/2023 | Chen et al. |
| 11,866,742 | B2 | 1/2024 | Henry et al. |
| 11,884,944 | B2 | 1/2024 | Giese et al. |
| 11,912,778 | B2 | 2/2024 | Chen et al. |
| 12,162,948 | B2 | 12/2024 | Chen et al. |
| 2002/0001587 | A1 | 1/2002 | Erickson et al. |
| 2003/0074141 | A1 | 4/2003 | Russell |
| 2005/0106658 | A1 | 5/2005 | DeFrees et al. |
| 2005/0170394 | A1 | 8/2005 | Zerangue |
| 2006/0193776 | A1 | 8/2006 | Goldsmith et al. |
| 2006/0275305 | A1 | 12/2006 | Bryant |
| 2009/0226466 | A1 | 9/2009 | Fong et al. |
| 2010/0009863 | A1 | 1/2010 | Himmler et al. |
| 2010/0048877 | A1 | 2/2010 | Ruker et al. |
| 2010/0093979 | A1 | 4/2010 | Lazar |
| 2010/0273200 | A1 | 10/2010 | Niwa et al. |
| 2011/0110928 | A1 | 5/2011 | Chamberlain et al. |
| 2012/0195900 | A1 | 8/2012 | Ghayur et al. |
| 2012/0276125 | A1 | 11/2012 | Ast et al. |
| 2012/0282176 | A1 | 11/2012 | Bohrmann et al. |
| 2013/0318641 | A1 | 11/2013 | Bradley et al. |
| 2013/0318643 | A1 | 11/2013 | Bradley et al. |
| 2014/0066599 | A2 | 3/2014 | Blein et al. |
| 2014/0079689 | A1 | 3/2014 | Elliott et al. |
| 2014/0142370 | A1 | 5/2014 | Wong et al. |
| 2014/0199294 | A1 | 7/2014 | Mimoto et al. |
| 2014/0212423 | A1 | 7/2014 | Hanzatian et al. |
| 2014/0295547 | A1 | 10/2014 | Kuo et al. |
| 2014/0302028 | A1 | 10/2014 | Zha |
| 2014/0348754 | A1 | 11/2014 | Wiley et al. |
| 2014/0356381 | A1 | 12/2014 | Moore et al. |
| 2014/0377269 | A1 | 12/2014 | Mabry et al. |
| 2015/0044140 | A1 | 2/2015 | Giralt Lledo et al. |
| 2015/0093399 | A1 | 4/2015 | Jefferies |
| 2015/0094451 | A1 | 4/2015 | Fischer et al. |
| 2015/0110791 | A1 | 4/2015 | Zhang et al. |
| 2015/0166636 | A1 | 6/2015 | Igawa et al. |
| 2015/0196663 | A1 | 7/2015 | Shusta et al. |
| 2015/0210763 | A1 | 7/2015 | Kuramochi et al. |
| 2015/0299331 | A1 | 10/2015 | Washburn et al. |
| 2015/0307594 | A1 | 10/2015 | Corper et al. |
| 2015/0307628 | A1 | 10/2015 | Kim et al. |
| 2015/0315296 | A1 | 11/2015 | Schaefer et al. |
| 2015/0322149 | A1 | 11/2015 | Bohrmann et al. |
| 2015/0329636 | A1 | 11/2015 | Dennis et al. |
| 2015/0344570 | A1 | 12/2015 | Igawa et al. |
| 2015/0353639 | A1 | 12/2015 | Watts et al. |
| 2016/0002343 | A1 | 1/2016 | Hanzatian et al. |
| 2016/0008485 | A1 | 1/2016 | Marquette et al. |

(56) References Cited

U.S. PATENT DOCUMENTS

2016/0039947 A1 2/2016 Demarest et al.
2016/0040125 A1 2/2016 Da Silva Ferreira et al.
2016/0102135 A1 4/2016 Esobar-Cabrera
2016/0122434 A1 5/2016 Olive et al.
2016/0137712 A1 5/2016 Lu et al.
2016/0168213 A1 6/2016 Xiong et al.
2016/0168247 A1 6/2016 Van Der Brink et al.
2016/0168253 A1 6/2016 Bohrmann et al.
2016/0208008 A1 7/2016 Alper
2016/0271269 A1 9/2016 Moghimi et al.
2016/0289335 A1 10/2016 Weisser et al.
2016/0324984 A1 11/2016 Brinkmann et al.
2016/0347821 A1 12/2016 Vitalis et al.
2016/0355599 A1 12/2016 Sagert et al.
2017/0029527 A1 2/2017 Paton et al.
2017/0174777 A1 6/2017 Barbour et al.
2017/0218085 A1 8/2017 Geierstanger et al.
2017/0226189 A1 8/2017 Peters et al.
2017/0291955 A1* 10/2017 Li .......................... C07K 16/30
2017/0348416 A1 12/2017 Hasler et al.
2018/0000962 A1 1/2018 Eigenbrot, Jr. et al.
2018/0051307 A1 2/2018 Igawa et al.
2018/0171012 A1 6/2018 Sonoda et al.
2018/0179291 A1 6/2018 Sonoda et al.
2018/0221488 A1 8/2018 Andya et al.
2018/0222992 A1 8/2018 Duerr et al.
2018/0222993 A1 8/2018 Duerr et al.
2018/0235195 A1 8/2018 Dennis et al.
2018/0237496 A1 8/2018 Chen et al.
2018/0250397 A1 9/2018 Benyunes et al.
2018/0251557 A1 9/2018 Chui et al.
2018/0291110 A1 10/2018 Klein et al.
2018/0344869 A1 12/2018 Fischer et al.
2018/0355034 A1 12/2018 Mondon et al.
2019/0022244 A1 1/2019 Jefferies et al.
2019/0030160 A1 1/2019 Watts et al.
2019/0274291 A1 9/2019 Dennis et al.
2020/0095310 A1 3/2020 Regula et al.
2020/0140568 A1 5/2020 Xiao et al.
2020/0216422 A1 7/2020 Chen et al.
2020/0223935 A1 7/2020 Chen et al.
2020/0262890 A1 8/2020 Chen et al.
2020/0277373 A1 9/2020 Chen et al.
2020/0277584 A1 9/2020 Astarita et al.
2020/0289627 A1 9/2020 Dennis et al.
2020/0291131 A1 9/2020 Croasdale-Wood et al.
2020/0317749 A1 10/2020 Dennis et al.
2020/0369746 A1 11/2020 Chen et al.
2020/0384061 A1 12/2020 Sonoda et al.
2021/0070881 A1 3/2021 Dennis et al.
2021/0087288 A1 3/2021 Zhang et al.
2021/0130485 A1 5/2021 Dennis et al.
2021/0188925 A1 6/2021 Cherf et al.
2021/0198640 A1 7/2021 Astarita et al.
2021/0214438 A1 7/2021 Dennis et al.
2021/0238296 A1 8/2021 De Jong et al.
2021/0269543 A1 9/2021 Sonoda et al.
2021/0277150 A1 9/2021 Von Kreudenstein et al.
2021/0284702 A1 9/2021 Di Paolo et al.
2021/0395388 A1 12/2021 Escobar-Cabrera et al.
2021/0395389 A1 12/2021 Fischer et al.
2021/0396772 A1 12/2021 Astarita et al.
2022/0017634 A1 1/2022 Kannan et al.
2022/0025065 A1 1/2022 Arguello et al.
2022/0089726 A1 3/2022 Brennan et al.
2022/0115824 A1 4/2022 Aridah et al.
2022/0119533 A1 4/2022 Cheung et al.
2022/0177576 A1 6/2022 Dennis et al.
2022/0184186 A1 6/2022 Anderson et al.
2022/0213155 A1 7/2022 Cherf et al.
2022/0220172 A1 7/2022 Cherf et al.
2023/0062800 A1 3/2023 Giese et al.
2023/0082623 A1 3/2023 Papapetrpoulos et al.
2023/0092681 A1 3/2023 Arguello et al.
2023/0192887 A1 6/2023 Kannan et al.
2023/0235072 A1 7/2023 Chen et al.
2023/0265137 A1 8/2023 Cherf et al.
2023/0381286 A1 11/2023 Dennis et al.
2023/0406898 A1 12/2023 Di Paolo et al.
2024/0018253 A1 1/2024 Chen et al.
2024/0024432 A1 1/2024 Chen et al.
2024/0141058 A1 5/2024 Chen et al.
2024/0150736 A1 5/2024 Giese et al.
2024/0271326 A1 8/2024 Chen et al.
2024/0271327 A1 8/2024 Chen et al.
2024/0299575 A1 9/2024 Barker et al.
2025/0136713 A1 5/2025 Bandyopadhyay et al.

FOREIGN PATENT DOCUMENTS

CN 1029611745 B 2/2015
CN 106554419 4/2017
CN 104418952 B 8/2017
CN 111196856 5/2020
EP 0327378 B1 12/1996
EP 2546268 A1 1/2013
EP 2568051 A1 3/2013
EP 2842969 A1 3/2015
EP 3004174 A1 4/2016
EP 2 009 101 B1 10/2017
EP 3 083 696 B1 2/2018
EP 3 313 890 A1 5/2018
EP 3 327 038 B1 5/2018
EP 2766040 B1 5/2019
EP 3 243 840 B1 7/2020
JP 2018-522549 A 8/2018
TW 202003038 A 1/2020
WO WO 1989/006692 7/1989
WO WO 1991/04753 4/1991
WO WO 1991/005038 A1 4/1991
WO WO 1994/004679 3/1994
WO WO 1994/028121 A1 12/1994
WO WO 95/009917 4/1995
WO WO 98/54031 A1 12/1998
WO WO 1999/000150 A2 1/1999
WO WO 2001/016181 A2 3/2001
WO WO 2001/059459 A2 8/2001
WO WO 2001/064849 A1 9/2001
WO WO 2002/021141 A2 3/2002
WO WO 2002/060919 A2 8/2002
WO WO 2003/003007 A2 1/2003
WO WO 2003/087131 10/2003
WO WO 2004/020404 A2 3/2004
WO WO 2004/020405 A2 3/2004
WO WO 2004/063351 A2 7/2004
WO WO 2004/094647 A2 11/2004
WO WO 2005/077981 A2 8/2005
WO WO 2006/033700 A2 3/2006
WO WO 2006/072620 A1 7/2006
WO WO 2007/146968 A2 12/2007
WO WO 2008/012629 A2 1/2008
WO WO 2008/024188 A2 2/2008
WO WO 2008/131242 A1 10/2008
WO WO 2008/143954 A2 11/2008
WO WO 2009/018386 A1 2/2009
WO WO 2009/080253 A1 7/2009
WO WO 2009/099961 A2 8/2009
WO WO 2010/014622 A2 2/2010
WO WO 2010/106180 A2 9/2010
WO WO 2010/112193 A1 10/2010
WO WO 2010/115589 A1 10/2010
WO WO 2010/121766 A1 10/2010
WO WO 2010/145792 A1 12/2010
WO WO 2011/003557 A1 12/2010
WO WO 2011/028952 A1 3/2011
WO WO 2011/069074 A2 6/2011
WO WO 2011/117330 A1 9/2011
WO WO 2011/122011 A2 10/2011
WO WO 2011/131746 A2 10/2011
WO WO 2012/025525 A1 3/2012
WO WO 2012/025530 A1 3/2012
WO WO 2012/032080 A1 3/2012
WO WO 2012/058768 A1 5/2012
WO WO 2012/075037 A1 6/2012

(56) References Cited

FOREIGN PATENT DOCUMENTS

| | | | |
|---|---|---|---|
| WO | WO 2012/091718 | A1 | 7/2012 |
| WO | WO 2012/106587 | A1 | 8/2012 |
| WO | WO 2012/125850 | A1 | 9/2012 |
| WO | WO 2012/135345 | A1 | 10/2012 |
| WO | WO 2012/143379 | A1 | 10/2012 |
| WO | WO 2012/143523 | A1 | 10/2012 |
| WO | WO 2013/026831 | A1 | 2/2013 |
| WO | WO 2013/070655 | A1 | 5/2013 |
| WO | WO 2013/091637 | A1 | 6/2013 |
| WO | WO 2013/096221 | A1 | 6/2013 |
| WO | WO 2013/138400 | A1 | 9/2013 |
| WO | WO 2013/138643 | A1 | 9/2013 |
| WO | WO 2013/166604 | A1 | 11/2013 |
| WO | WO 2013/177062 | A2 | 11/2013 |
| WO | WO 2013/184514 | A1 | 12/2013 |
| WO | WO 2014/033074 | A1 | 3/2014 |
| WO | WO 2014/074695 | A1 | 5/2014 |
| WO | WO 2014/081955 | A1 | 5/2014 |
| WO | WO 2014/138449 | A1 | 9/2014 |
| WO | WO 2014/144357 | A1 | 9/2014 |
| WO | WO 2014/144600 | A2 | 9/2014 |
| WO | WO 2014/177459 | A2 | 11/2014 |
| WO | WO 2014/189973 | A2 | 11/2014 |
| WO | WO 2014/190441 | A9 | 12/2014 |
| WO | WO 2015/014884 | A1 | 2/2015 |
| WO | WO 2015/014979 | A1 | 2/2015 |
| WO | WO 2015/073743 | A2 | 5/2015 |
| WO | WO 2015/075011 | A1 | 5/2015 |
| WO | WO 2015/077891 | A1 | 6/2015 |
| WO | WO 2015/091738 | A1 | 6/2015 |
| WO | WO 2015/101586 | A1 | 7/2015 |
| WO | WO 2015/138907 | A2 | 9/2015 |
| WO | WO 2015/157592 | A1 | 10/2015 |
| WO | WO 2015/164723 | A1 | 10/2015 |
| WO | WO 2015/173756 | A2 | 11/2015 |
| WO | WO 2015/181805 | A1 | 12/2015 |
| WO | WO 2015/188135 | A1 | 12/2015 |
| WO | WO 2016/038123 | A1 | 3/2016 |
| WO | WO 2016/077840 | A2 | 5/2016 |
| WO | WO 2016/079081 | A1 | 5/2016 |
| WO | WO 2016/081640 | A1 | 5/2016 |
| WO | WO 2016/081643 | A1 | 5/2016 |
| WO | WO 2016/082044 | A1 | 6/2016 |
| WO | WO 2016/087416 | A1 | 6/2016 |
| WO | WO 2016/090486 | A1 | 6/2016 |
| WO | WO 2016/106158 | A1 | 6/2016 |
| WO | WO 2016/110267 | A1 | 7/2016 |
| WO | WO 2016/130516 | A1 | 8/2016 |
| WO | WO 2016/179707 | A1 | 11/2016 |
| WO | WO 2016/207091 | A1 | 12/2016 |
| WO | WO 2016/207240 | A1 | 12/2016 |
| WO | WO 2016/208695 | A1 | 12/2016 |
| WO | WO 2017/007796 | A1 | 1/2017 |
| WO | WO 2017/035119 | A1 | 3/2017 |
| WO | WO 2017/049004 | A1 | 3/2017 |
| WO | WO 2017/059551 | A1 | 4/2017 |
| WO | WO 2017/087280 | A1 | 5/2017 |
| WO | WO 2017/096361 | A1 | 6/2017 |
| WO | WO 2017/100709 | A1 | 6/2017 |
| WO | WO 2017/106462 | A1 | 6/2017 |
| WO | WO 2017/117179 | A1 | 7/2017 |
| WO | WO 2017/134197 | A1 | 8/2017 |
| WO | WO 2017/188570 | A1 | 11/2017 |
| WO | WO 2017/193032 | A9 | 11/2017 |
| WO | WO 2017/205436 | A1 | 11/2017 |
| WO | WO 2018/011353 | A1 | 1/2018 |
| WO | WO 2018/014864 | A1 | 1/2018 |
| WO | WO 2018/018047 | A1 | 1/2018 |
| WO | WO 2018/031424 | A1 | 2/2018 |
| WO | WO 2018/045110 | A1 | 3/2018 |
| WO | WO 2018/117613 | A1 | 6/2018 |
| WO | WO 2018/136412 | A2 | 7/2018 |
| WO | WO 2018/152285 | | 8/2018 |
| WO | WO 2018/152359 | A1 | 8/2018 |
| WO | WO 2018/154580 | A1 | 8/2018 |
| WO | WO 2018/160654 | A2 | 9/2018 |
| WO | WO 2018/175383 | A1 | 9/2018 |
| WO | WO 2018/177966 | A1 | 10/2018 |
| WO | WO 2018/191188 | A1 | 10/2018 |
| WO | WO 2018/200505 | A1 | 11/2018 |
| WO | WO 2018/201016 | A1 | 11/2018 |
| WO | WO 2018/237338 | A1 | 12/2018 |
| WO | WO 2019/032955 | A1 | 2/2019 |
| WO | WO 2019/033046 | A1 | 2/2019 |
| WO | WO 2019/055841 | A1 | 3/2019 |
| WO | WO 2019/070577 | A1 | 4/2019 |
| WO | WO 2019/089395 | A1 | 5/2019 |
| WO | WO 2019/094576 | A1 | 5/2019 |
| WO | WO 2019/094608 | A1 | 5/2019 |
| WO | WO 2019/140050 | A1 | 7/2019 |
| WO | WO 2019/157308 | A1 | 8/2019 |
| WO | WO 2019/190293 | A1 | 10/2019 |
| WO | WO 2019/190359 | A1 | 10/2019 |
| WO | WO 2019/207021 | A1 | 10/2019 |
| WO | WO 2019/224153 | A1 | 11/2019 |
| WO | WO 2019/232525 | A1 | 12/2019 |
| WO | WO 2019/246071 | A1 | 12/2019 |
| WO | WO 2020/041604 | A1 | 2/2020 |
| WO | WO 2020/056327 | A1 | 3/2020 |
| WO | WO 2020/088365 | A1 | 5/2020 |
| WO | WO 2020/088403 | A1 | 5/2020 |
| WO | WO 2020/103629 | A1 | 5/2020 |
| WO | WO 2020/112889 | A2 | 6/2020 |
| WO | WO 2020/156555 | A1 | 8/2020 |
| WO | WO 2020/206320 | A1 | 10/2020 |
| WO | WO 2020/221198 | A1 | 11/2020 |
| WO | WO 2020/221791 | A1 | 11/2020 |
| WO | WO 2020/242503 | A1 | 12/2020 |
| WO | WO 2021/020846 | A1 | 2/2021 |
| WO | WO 2021/023267 | A1 | 2/2021 |
| WO | WO 2021/080428 | A1 | 4/2021 |
| WO | WO 2021/089588 | A1 | 5/2021 |
| WO | WO 2021/091953 | A1 | 5/2021 |
| WO | WO 2021/110107 | A1 | 6/2021 |
| WO | WO 2021/158986 | A1 | 8/2021 |
| WO | WO 2021/168194 | A1 | 8/2021 |
| WO | WO 2021/174113 | A1 | 9/2021 |
| WO | WO 2021/190636 | A1 | 9/2021 |
| WO | WO 2021/190637 | A1 | 9/2021 |
| WO | WO 2021/219046 | A1 | 11/2021 |
| WO | WO 2021/219127 | A1 | 11/2021 |
| WO | WO 2021/232057 | A1 | 11/2021 |
| WO | WO 2021/244328 | A1 | 12/2021 |
| WO | WO 2021/259890 | A1 | 12/2021 |
| WO | WO 2022/013189 | A1 | 1/2022 |
| WO | WO 2022/017401 | A1 | 1/2022 |
| WO | WO 2022/019259 | A1 | 1/2022 |
| WO | WO 2022/029496 | A1 | 2/2022 |
| WO | WO 2022/081765 | A1 | 4/2022 |
| WO | WO 2015/191934 | A2 | 10/2025 |
| WO | WO 2016/202343 | A1 | 10/2025 |
| WO | WO 2022/020588 | A1 | 2/2026 |

OTHER PUBLICATIONS

Dillon et al., "Efficient production of bispecific IgG of different isotypes and species of origin in single mammalian cells," MABS, 9(2):213-230, (2017).

Kelley et al., "Thermodynamic Analysis of an Antibody Functional Epitope," Biochemistry, 32:6828-6835, (1993).

Merchant et al., "An efficient route to human bispecific IgG," Nature Biotechnology, 16:677-681, (Jul. 1998).

Wu et al., "Building blocks for bispecific and trispecific antibodies," Methods, 154:3-9, (2019).

EP Application No. 22862264.3, extended European Search report mailed Oct. 20, 2025.

JP Application No. 2022-549653, Decision of Rejection mailed Oct. 9, 2025.

Abraham et al., "Structural basis for receptor recognition by New World hemorrhagic fever arenaviruses," Nat. Struct. Mol. Biol., pp. 1-8, (2010).

(56) References Cited

OTHER PUBLICATIONS

Al Qaraghuli et al., "Antibody-protein binding and conformational changes: identifying allosteric signaling pathways to engineer a better effector response," Sci. Rep., 10:13696, (2020).
Almagro et al., "Progress and Challenges in the Design and Clinical Development of Antibodies for Cancer Therapy," Frontiers in Immunology, 8:1751, (2018).
Alvarez et al., "Intermolecular disulfide bonds are not required for the expression of the dimeric state and functional activity of the transferrin receptor," The EMBO Journal, 8(8):231-2240, (1989).
Atwal et al., "A Therapeutic Antibody Targeting BACE1 Inhibits Amyloid-13 Production in Vivo," Sci Transl. Med., 3(84):1-12, (May 25, 2011).
Baird et al. "Circular permutation and receptor insertion within green fluorescent proteins", Proc. Natl. Acad. Sci. USA, 96:11241-11246, (Sep. 1999).
Banks, "Mouse Models of Neurological Disorders: A View From the Blood-brain Barrier," Biochim Biophys Acta, 1802(10):881-888, (2010).
Bhattacharya et al., "Impact of Genetic Variation on Three Dimensional Structure and Function of Proteins," Plos One, 12(3):e0171355, (Mar. 15, 2017).
Biocom AG, Denali bags F-Star Gamma. European Biotechnology, European Biotechnology, 2 pgs., May 31, 2018, [retrieved online from https://european-biotechnology.com/up-to-date/latest-news/news/denali-gabs-f-star-gamma.html].
Bork et al., "Go hunting in sequence databases but watch out for the traps," Trends in Genetics, 12(10):425-427, (1996).
Bork et al., "Powers and Pitfalls in Sequence Analysis: The 70% Hurdle," Genome Research, 10:398-400, (2000).
Brenner, S., "Errors in genome annotation," Trends in Genetics, 15(4):132-33, (1999).
Brinkmann et al., "The making of bispecific antibodies," MABS, 9(2):182-212, (2017).
Buchegger et al., "Functional analysis of human/chicken transferrin receptor chimeras indicates that the carboxy-terminal region is important for ligand binding," Eur. J. Biochem., 235:9-17, (1996).
Castoldi et al., "Molecular characterization of novel trispecific ErbB-cMet-IGF1R antibodies and their antigen-binding properties," Protein Engineering Design and Selection, 25(10):551-559, (2012).
Chen et al., "Protein-protein interactions: General trends in the relationship between binding affinity and interfacial buried surface area," The Protein Society, p. 510-515, (Feb. 7, 2013).
Cheng et al., "Structure of the Human Transferrin Receptor-Transferrin Complex," Cell Press, 116:565-576, (Feb. 20, 2004).
Clarke et al., "Single Domain Shark Antibody Targeting the Transferrin Receptor 1 Delivers a TrkB Agonist Antibody Across the Blood Brain Barrier to Provide Full Neuroprotection in a Mouse Model of Parkinson's Disease," [Available online at https://www.biorxiv.org/content/10.1101/2020.03.12.987313v3.full.pdf], 25 pgs., (Jun. 5, 2021).
Database Geneseq [Online], "immunostimulatory fusion protein production related protein, SEQ ID 6," retrieved from EBI accession No. GSP:AYM52804, Database accession No. AYM52804, 2 pgs., (Feb. 3, 2011).
Database NCBI, "ChainA, Ig gamma-1 chain C region," GenPept, PDB: 4X4M_a, 3 pgs., [online], (Apr. 8, 2015).
Davies et al., "Structural Determinants of Unique Properties of Human IgG4-Fc," Journal of Molecular Biology, 426(3):630-644, (2014).
Denali Therapeutics Inc., "F-star Announces Collaborative Agreement with Denali Therapeutics for the Development of a Multispecific Antibody Platform to Deliver Therapeutics Across the Blood-Brain Barrier", F-Star, 3 pages.
Denali Therapeutics Inc., Form S-1 Registration Statement, as filed with the U.S. Securities and Exchange Commission on Nov. 13, 2017, [retrieved online at <https://www.sec.gov/Archives/edgar/data/1714899/000119312517340997/d445892ds1.htm>], 291 pgs., (Mar. 20, 2018).
Dimasi et al., "The design and characterization of oligospecific antibodies for simultaneous targeting of multiple disease mediator," Journal of Molecular Biology, 393(3):672-692, (Oct. 30, 2009).
Doerks et al., "Protein annotation: detective work for function prediction," Trends in Genetics, 14(6):248-250, (1998).
Dominguez et al., "Beyond editing: repurposing CRISPR-Cas9 for precision genome regulation and interrogation," Nature Rev. Molec Cell. Biol., 17:5-15, (2016).
Du et al., "Engineering Bifunctional Antibodies with Constant Region Fusion Architectures," Journal of the American Chemical Society, 139(51):18607-18615, (2017).
Eckenroth et al., "How the binding of human transferrin primes the transferrin receptor potentiating iron release at endosomal pH," Proceedings of the National Academy of Sciences, 108(32):13089-13094 (2011).
Edwards et al., "The Remarkable Flexibility of the Human Antibody Repertoire; Isolation of Over One Thousand Different Antibodies to a Single Protein, BLyS," Journal of Molecular Biology, 334(1)103-118, (2003).
Escobar-Cabrera et al., "Asymmetric Fe Engineering for Bispecific Antibodies with Reduced Effector Function," Antibodies, pp. 1-16, (2017).
Fendly et al., "Characterization of Murine Monoclonal Antibodies Reactive to Either the Human Epidermal Growth Factor Receptor or HER2/neu Gene Product," Cancer Research, 50:1550-1558, (Mar. 1990).
Fenton et al., "Rheostat Positions: A New Classification of Protein Positions Relevant to Pharmacogenomics," Medicinal Chemistry Research 29, 1133-1146, (2020).
Gadkar et al., "Mathematical PKPD and safety model of bispecific TfR/BACE1 antibodies for the optimization of antibody uptake in brain," European Journal of Pharmaceutics and Biopharmaceutics, 101:53-61, (2016).
Genentech Inc., "Denali Therapeutics at Morgan Stanley Healthcare Conference—Final," ProQuest document ID 2112664917, 8 pgs., [retrieved online on Dec. 21, 2023 from https://www.proquest.com/wire-feeds/denali-therapeuticsinc-at-morganstanley/docview/2112664917/se-2?accountid=14753], (2018).
Gershoni et al., "Epitope Mapping. The First Step in Developing Epitope-Based Vaccines," Biodrugs, 21(3):145-156, (2007).
Golay et al., "Design and Validation of a Novel Generic Platform for the Production of Tetravalent IgG1-like Bispecific Antibodies," Journal of Immunology, 196:3199-3211, (2016).
Goldman Sachs, "Denali Therapeutics Inc. at Goldman Sachs Global Healthcare Conference—Final," ProQuest document ID 2059116901, 9 pgs., [Retrieved online on Dec. 21, 2023 from https://www.proquest.com/wirefeeds/denali-therapeutics-inc-at-goldman-sachsglobal/docview/2059116901/se-2?accountid=14753], (2018).
Gu et al., "Rationale and development of multispecific antibody drugs," Expert rev. Clin. Pharmacol., 3(4):491-508, (2010).
Guo et al., "Protein Tolerance to Random Amino Acid Change," PNAS, 101(25):9205-9210, (Jun. 22, 2004).
Ha et al., "Immunoglobulin Fe Heterodimer Platform Technology: From Design to Applications in Therapeutic Antibodies and Proteins," Frontiers in Immunology, 7:1-16, DOI: 10.3389/fimmu.2016.00394, (2016).
Hanzatian et al., "Brake update of multivalent and multi-specific DVD-Ig proteins after systemic administration," mAbs, 10(5):765-777, (2018).
Haqqani et al. "Intracellular sorting and Transcytosis of the rat transferrin receptor antibody OX26 across the blood-brain barrier in vitro is dependent on its binding affinity," Journal of Neurochemistry, 146:735-752, (2018).
Helguera et al., "An Antibody Recognizing the Apical Domain of Human Transferrin Receptor 1 Efficiently Inhibits the Entry of All New World Hemorrhagic Fever Arenaviruses," Journal of Virology, 86(7):4024-4028, (2012).
Hultqvist et al., "Bivalent Brain Shuttle Increases Antibody Uptake by Monovalent Binding to the Transferrin Receptor," Theragnostic, 7(2):308-318. DOI: 10.7150/thno.17155, (2017).
Idrus, "Denali acquires F-star's blood-brain barrier bispecific antibody tech in deal worth up to $471M," ProQuest document ID

(56) References Cited

OTHER PUBLICATIONS 2046913483, 3 pgs., [retrieved online on Dec. 21, 2023 from https://www.proquest.com/tradejournals/denali-acquires-f-stars-blood-brainbarrier/docview/2046913483/se-2?accountid=14753], (2018).
Ji et al., "Efficient creation of an APOE knockout rabbit," Transgenic Res., 24:227-235, (2015).
Kang et al., "Engineering multivalent antibodies to target heregulin-induced HER3 signaling in breast cancer cells," mAbs, 6(2):340-353, (2014).
Kariolis et al., "Brain delivery of therapeutic proteins using an Fe fragment blood-brain barrier transport vehicle in mice and monkeys," Science Translational Medicine, Downloaded from http://stm.sciencemag.org/, pp. 1-13, (May 27, 2020).
Kim et al., "Catabolism of the Murine IgG1 Molecule: Evidence that Both CH2—CH3 Domain Interfaces are Required for Persistence of IgG1 in the Circulation of Mice," Scand. J. Immunol., 40:457-465, (1994).
Lawrence et al., "Crystal Structure of the Ectodomain of Human Transferrin Receptor," Science, 286:779-782, (1999).
Lee et al., "Receptor mediated uptake of peptides that bind the human transferrin receptor," Eur. J. Biochem., 268:2004-2012, (2001).
Leoh et al., "Insights into the Effector Functions of Human IGG3 in the Context of an Antibody Targeting Transferrin Receptor 1," Molecular Immunology, 67(2):407-415, (Oct. 2015).
Li et al., "Bispecific Antibody to ErbB2 Overcomes Trastuzumab Resistance through Comprehensive Blockade of ErbB2 Heterodimerization," Cancer Research, 73(21)6471-6483, (Nov. 2013).
Li et al., "Production of Genetically Engineered Golden Syrian Hamsters by Pronuclear Injection of the CRISPR/Cas9 Complex," J. Vis. Exp., 9(131):1-8, (2018).
Liu et al., "Fe Engineering for developing therapeutic bispecific antibodies and novel scaffolds," Frontiers in Immunology, 8(38):1-15, (Jan. 26, 2017).
Liu et al., "Pharmacokinetics of IgG1 monoclonal antibodies produced in humanized Pichia pastoris with specific glycofoams: a comparative study with CHO produced materials," Biologicals, 39(4):205-210, (2011).
Lloyd et al., "Modelling the human immune response: performance of a 10" human antibody repertoire against a broad panel of therapeutically relevant antigens," Protein Engineering, Design and Selection, 22(3):159-168, (2009).
Lobner et al., "Engineered IgGI-Fc—one fragment to bind them all," Immunological Reviews, 270(1):113-131, (2016).
Ma et al., "Generation of eGFP and Cre knockin rats by CRISPR/Cas9," FEBS Journal, 281:3779-3790, (2016).
Maccallum et al., "Antibody-antigen interactions: contact analysis and binding site topography," J. Mol. Biol, 262:732-745, (1996).
Mager et al., "Targeting blood-brain-barrier transcytosis e perspectives for drug delivery", Elsevier, 120:4-7, (2017).
Marri et al., "Human Biochemistry," Moscow "Mir", v. 1, 3 pgs., (1993).
Mcgraw et al., "Functional Expression of the Human Transferrin Receptor cDNA in Chinese Hamster Ovary Cells Deficient in Endogenous Transferrin Receptor," J. Cell Biology, 105:207-214, (1987).
Metz et al., "Bispecific antibody derivatives with restricted binding functionalities that are activated by proteolytic processing," Protein Engineering, Design and Selection, 25(10):571-580, (2012).
Milstone et al., "Stratum-Specific Expression of Human Transferrin Receptor Increases Iron in Mouse Epidermas," J. Invest. Dermatol, 126:648-652, (2006).
Mizutani et al., "Transferrin Receptor 1 Facilitates Poliovirus Permeation of Mouse Brain Capillary Endothelial Cells," Journal of Biological Chemistry, 291(6):2829-2836, (2016).
Moody et al., "Receptor Crosslinking: A General Method to Trigger Internalization and Lysosomal Targeting of Therapeutic Receptor: Ligand Complexes," Molecular Therapy, 23(12):1888-1898, (Dec. 2015).
Moura et al., "Identification of the Transferrin Receptor as a Novel Immunoglobulin (Ig)a1 Receptor and Its Enhanced Expression on Mesangial Cells in Iga Nephropathy," The Journal of Experimental Medicine, 194(4):417-425, (Aug. 20, 2021).
Murray et al., Human Biochemistry, 1:34, Mir Publishers, Moscow, (1993).
Naito et al., "Expression of exogenous DNA in the gonads of chimeric chicken embryos produced by transfer of primordial germ cells transfected in vitro and subsequent fate of the introduced DNA," J. Reprod. Fert., 113:137-143, (1998).
Ni et al., "Mechanistic Insights into How the Single Point Mutation Change the Autoantibody Repertoire," The Protein Journal, 43:683-696, (2024).
Niewoehner et al., "Increased Brain Penetration and Potency of a Therapeutic Antibody Using a Monovalent Molecular Shuttle," Neuron, 81:49-60, DOI: 10.1016/J.Neuron.2013.10.061, (2014).
Nounou et al., "Anti-cancer antibody trastuzumab-melanotransferrin conjugate (BT2111) for the treatment of metastatic HER2+ breast cancer tumors in the brain: An in-vivo study," Pharm Res., 33(12):2930-2942, (Dec. 2016).
Orcutt et al., "A modular IgG-scFv bispecific antibody topology," Protein Engineering, Design & Selection, 23(4):221-228, (2010).
Palermo et al., "Residues in the Apical Domain of the Feline and Canine Transferrin Receptors Control Host-Specific Binding and Cell Infection of Canine and Feline Parvoviruses," Journal of Virology, 77(16,):8915-8923, (2003).
Pardridge et al., "Blood-brain barrier drug delivery of IgG fusion proteins with a transferrin receptor monoclonal antibody," Expert Opinion on Drug Deliv., 12(2):207-222, (2015).
Park et al., "The Highly Evolvable Antibody Fe Domain," Trends in Biotechnology, 34(11):895-908, (2016).
Raina, A. et al., "Testis mediated gene transfer: In vitro transfection in goat testis by electroporation," Gene, 554: 96-100, (2015).
Ramirez-Solis et al., "Gene Targeting in Embryonic Stem Cells," Methods in Enzymology, 225:855-878, (1993).
Saxena et al., "Advances in Therapeutic Fe Engineering—Modulation of IgG-Associated Effector Functions and Serum Half-life," Frontiers in Immunology, 7(580):1-11, (Dec. 12, 2016).
Schroeder et al., "Structure and function of immunoglobulins," Journal of Allergy and Clinical Immunology, 125(2, Suppl. 2):S41-52, (2010).
Sela-Culang et al., "The structural basis of antibody-antigen recognition," Frontiers in Immunology, 4:302, (2013).
Shin et al., "Transferrin-antibody fusion proteins are effective in brain targeting," PNAS, 92:2820-2824, (Mar. 1995).
Skolnick et al., "From genes to protein structure and function: novel applications of computational approaches in the genomic era," Trends Biotechnol., 18(1):34-39, (2000).
Smith et al., "The challenges of genome sequence annotation or 'The devil is in the details'," Nat Biotechnol., 15:1222-1223, (1997).
Sohet et al, "Genetic mouse models to study blood-brain barrier development and function," Fluids and Barriers of the CNS, 10(3):1-18, (2013).
Syrovaya et al., "Amino Acids Through the Eyes of Chemists, Pharmacists, Biologists," Shchedra sadiba plus, 1:1-228, (Machine Translation Provided), (2014).
Tokuriki et al., "Stability effects of mutations and protein evolvability," Curr Opin Struct Biol, 19(5):596-604, (2009).
Ullman et al., "Brain delivery and activity of a lysosomal enzyme using a blood-brain barrier transport vehicle in mice," Science Translational Medicine, [Downloaded from http://stm.sciencemag.org/], pp. 1-13, (May 27, 2020).
UniProtKB—P23088 (HVCM_HETFR), Ig Heavy Chain C Region, Membrane-Bound Form, 6 pgs., (1991).
Vajdos et al., "Comprehensive functional maps of the antigen-binding site of an anti-ErB2 antibody obtained with shotgun scanning mutagenesis," J. Mol. Biol., 320(2):415-428, (2002).
Weber et al., "Brain Shuttle Antibody for Alzheimer's Disease with Attenuated Peripheral Effector Function due to an Inverted Binding Mode," Cell Reports, 22:149-162, DOI: 10.1016/j.celrep.2017.12.019, (2018).

(56) References Cited

OTHER PUBLICATIONS

Weidle et al., "The Blood-Brain Barrier Challenge for the Treatment of Brain Cancer, Secondary Brain Metastases, and Neurological Diseases", Cancer Genomics & Proteomics, 12(4):167-177, (Jul. 2015).
Wen et al. "Soluble Form of Canine Transferrin Receptor Inhibits Canine Parvovirus Infection In Vitro and In Vivo," BioMed Research Intl., 2013:pp. 1-8, (2013).
Wilkinson et al., "Fc-engineered antibodies with immune effector functions completely abolished," PLOS One, 16(12):e0260954, (2021).
Winkler et al., "Changing the Antigen Binding Specificity by Single Point Mutations of an Anti-p24 (HIV-1) Antibody," Journal of Immunology, 165(8):4505-4514, (2000).
Winnard. et al., "Development of novel chimeric transmembrane proteins for multimodality imaging of cancer cells," Cancer Biol. & Ther., 6(12):1889-1899, (2007).
Wozniak-Knopp et al., "An antibody with Fab-constant domains exchanged for a pair of CH3 domains," PloS One, 13(4), e0195442:1-19, (2018).
Wozniak-Knopp et al., "Introducing antigen-binding sites in structural loops of immunoglobulin constant domains: Fe fragments with engineered HER2/neu-binding sites and antibody properties," Protein Engineering, Design and Selection, 23(4):289-297, (2010).
Wozniak-Knopp et al., "Stabilisation of the Fe Fragment of Human IgG1 by Engineered Intradomain Disulfide Bonds," Plos One, 7(1):1-11, (Jul. 2012).
Wyatt et al., "Method of establishing breast cancer brain metastases affects brain uptake and efficacy of targeted, therapeutic nanoparticles," Bioengineering & Translation Medicine, 4:30-37, (2019).
Yang et al., "Bispecific Antibodies as a Development Platform for New Concepts and Treatment Strategies," International Journal of Molecular Sciences, 18:1-21, DOI: 10.3390/ijms18010048, (2016).
Ying et al., "Engineered antibody domains with significantly increased transcytosis and half-life in macaques mediated by FcRn," Mabs, 7(5):922-930, DOI: 10.1080/19420862.2015.1067353, (2015).
Ying et al., "Engineered Fe based antibody domains and fragments as novel scaffolds," Elsevier, Biochimica et Biophysica Acta (BBA)—Proteins and Proteomics, 1844:1977-1982, DOI: 10.1016/J.BBAPAP.2014.04.018, (2014).
Yu et al., "Boosting Brain Uptake of a Therapeutic Antibody by Reducing Its Affinity for a Transcytosis Target," Science Translational Medicine, 3(84):1-9, (May 25, 2011).
Yu et al., "Development and clinical application bof anti-HER2 monoclonal and bispecific antibodies for cancer treatment," Experimental Hematology & Oncology, 6:31, (2017).
Yu et al., "Therapeutic bispecific antibodies cross the blood-brain barrier in nonhuman primates," Science Translational Medicine, 6(261):1-10, (2014).
Zhang et al., "Reflections on quality control standards for therapeutic monoclonal antibody based products," China Licensed Pharmacist, 10(1)25-36, (Jan. 2013), English abstract.
Zhao et al., "Therapeutic TVs for Crossing Barriers in the Brain," Cell, 182(2):267-269, (2020).
Zuchero et al., "Discovery of Novel Blood-Brain Barrier Targets to Enhance Brain Uptake of Therapeutic Antibodies," Neuron, 89(1):70-82, (Jan. 6, 2016).
EA Application No. 202292358, Office Action mailed Mar. 28, 2025.
EA Application No. 202490537, Office Action mailed Dec. 11, 2024.
EP Application No. 18843180.3, EESR mailed Jun. 4, 2021.
EP Application No. 22867902.3, partial supplementary EP Search Report mailed Sep. 5, 2025.
EP Application No. 19849330.6, Partial ESR mailed Apr. 7, 2022.
JP Application No. 2022-549653, Office Action mailed Mar. 6, 2025.
TW Application No. 110105842, Office Action and Search Report mailed May 22, 2025.
U.S. Appl. No. 17/819,182, Published Application mailed (2023).
U.S. Appl. No. 18/685,583, Published Application mailed (2024).
U.S. Appl. No. 18/685,587, Published Application mailed (2024).
WIPO Application No. PCT/US2018/018371, PCT International Search Report and Written Opinion of the International Searching Authority mailed Apr. 17, 2018.
WIPO Application No. PCT/US2018/046199, PCT International Search Report and Written Opinion of the International Searching Authority mailed Oct. 25, 2018.
WIPO Application No. PCT/US2018/046337, PCT International Search Report and Written Opinion of the International Searching Authority mailed Nov. 15, 2018.
WIPO Application No. PCT/US2019/012990, PCT International Search Report and Written Opinion of the International Searching Authority mailed May 2, 2019.
WIPO Application No. PCT/US2019/046705, PCT International Search Report and Written Opinion of the International Searching Authority mailed Aug. 5, 2019.
WIPO Application No. PCT/US2019/047728, PCT International Search Report and Written Opinion of the International Searching Authority mailed Nov. 15, 2019.
WIPO Application No. PCT/US22/75438, PCT International Search Report and Written Opinion of the International Searching Authority mailed Apr. 10, 2023.

* cited by examiner

| | Bispecific Antibody #1 (control) | Bispecific Antibody #2 | Bispecific Antibody #3 | Bispecific Antibody #4 | Bispecific Antibody #5 |
|---|---|---|---|---|---|
| Max %growth inhibition | 77.4 | 56.4 | 57.9 | 71.3 | 67.8 |
| IC50(nM) | 0.19 | 0.13 | 0.037 | 0.13 | 0.13 |

ANTI-HER2 ANTIBODIES AND METHODS OF USE THEREOF

CROSS-REFERENCE TO RELATED APPLICATIONS

This application is a continuation of U.S. application Ser. No. 18/685,587, filed Feb. 22, 2024, which is a National Stage Application, filed under 35 U.S.C. § 371, of International Application No. PCT/US2022/075438, filed Aug. 25, 2022 which claims the benefit of U.S. Provisional Patent Application No. 63/237,104, filed on Aug. 25, 2021, each of which is incorporated herein by reference in its entirety for all purposes.

SEQUENCE LISTING

The Sequence Listing written in file DNL-010-06-WO_SeqList is 168,854 bytes in size, was created Jan. 5, 2026, and is hereby incorporated by reference.

BACKGROUND

Treatment of brain metastases of cancers such as breast cancer currently poses a daunting clinical challenge. Among breast cancer patients, the incidence of brain metastases is as high as 50%. Clinical data indicate that there is a proclivity for HER2-positive breast cancers to metastasize to the brain. Notably, anti-HER2 therapies have proven useful for the control of extracranial tumors but not intracranial lesions. The failure of these therapies to control metastatic lesions such as brain metastases of HER2-positive breast cancer is mostly attributed to an inability of the therapeutic agents to cross the blood brain barrier (BBB) and access the brain parenchyma.

SUMMARY

In one aspect, the disclosure provides an isolated antibody comprising one or more (e.g., one, two, or all three) complementarity determining regions (CDRs) selected from the group consisting of:

(a) a heavy chain CDR1 comprising the amino acid sequence of SEQ ID NO:89;
(b) a heavy chain CDR2 comprising the amino acid sequence of SEQ ID NO:90; and
(c) a heavy chain CDR3 comprising the amino acid sequence of SEQ ID NO:91, wherein at least one of:
$X_1$ in SEQ ID NO: 89 is not T;
$X_2$ in SEQ ID NO: 89 is not F;
$X_3$ in SEQ ID NO: 89 is not T;
$X_1$ in SEQ ID NO: 90 is not N;
$X_2$ in SEQ ID NO: 90 is not N;
$X_3$ in SEQ ID NO: 90 is not S;
$X_4$ in SEQ ID NO: 90 is not G;
$X_5$ in SEQ ID NO: 90 is not G;
$X_6$ in SEQ ID NO: 90 is not Q;
$X_1$ in SEQ ID NO: 91 is not L;
$X_2$ in SEQ ID NO: 91 is not G;
$X_3$ in SEQ ID NO: 91 is not P; and
$X_4$ in SEQ ID NO: 91 is not S.

In some embodiments, the heavy chain CDR1 comprises the amino acid sequence of SEQ ID NO:89, wherein $X_1$ is N, K, M, or H. In some embodiments, the heavy chain CDR2 comprises the amino acid sequence of SEQ ID NO:90, wherein $X_5$ is Q. In some embodiments, the heavy chain CDR2 comprises the amino acid sequence of SEQ ID NO:90, wherein $X_6$ is R, H, or T. In some embodiments, the heavy chain CDR3 comprises the amino acid sequence of SEQ ID NO:91, wherein $X_4$ is W, F, D, L, or Y. In some embodiments, the heavy chain CDR3 comprises the amino acid sequence of SEQ ID NO:91, wherein $X_4$ is L.

In some embodiments, the antibody comprises one or more (e.g., one, two, or all three) CDRs selected from the group consisting of:

(a) a heavy chain CDR1 comprising the amino acid sequence of SEQ ID NO:89;
(b) a heavy chain CDR2 comprising the amino acid sequence of SEQ ID NO:90, wherein $X_5$ is Q; and
(c) a heavy chain CDR3 comprising the amino acid sequence of SEQ ID NO:91, wherein $X_4$ is L.

In some embodiments, the antibody comprises one or more (e.g., one, two, or all three) CDRs selected from the group consisting of:

(a) a heavy chain CDR1 having at least 90% (e.g., 91%, 92%, 93%, 94%, 95%, 96%, 97%, 98%, 99%, or 100%) sequence identity to an amino acid sequence selected from the group consisting of SEQ ID NOS:4 and 49-52 or having up to two amino acid substitutions relative to an amino acid sequence selected from the group consisting of SEQ ID NOS:4 and 49-52;
(b) a heavy chain CDR2 having at least 90% (e.g., 91%, 92%, 93%, 94%, 95%, 96%, 97%, 98%, 99%, or 100%) sequence identity to an amino acid sequence selected from the group consisting of SEQ ID NOS:5-6 and 53-55 or having up to two amino acid substitutions relative to an amino acid sequence selected from the group consisting of SEQ ID NOS:5-6 and 53-55; and
(c) a heavy chain CDR3 having at least 90% (e.g., 91%, 92%, 93%, 94%, 95%, 96%, 97%, 98%, 99%, or 100%) sequence identity to an amino acid sequence selected from the group consisting of SEQ ID NOS:7-8 and 56-59 or having up to two amino acid substitutions relative to an amino acid sequence selected from the group consisting of SEQ ID NOS:7-8 and 56-59.

In some embodiments, the antibody comprises one or more (e.g., one, two, or all three) CDRs selected from the group consisting of:

(a) a heavy chain CDR1 having at least 90% (e.g., 91%, 92%, 93%, 94%, 95%, 96%, 97%, 98%, 99%, or 100%) sequence identity to the amino acid sequence of SEQ ID NO:4 or having up to two amino acid substitutions relative to the amino acid sequence of SEQ ID NO:4;
(b) a heavy chain CDR2 having at least 90% (e.g., 91%, 92%, 93%, 94%, 95%, 96%, 97%, 98%, 99%, or 100%) sequence identity to the amino acid sequence of SEQ ID NO:5 or SEQ ID NO:6 or having up to two amino acid substitutions relative to the amino acid sequence of SEQ ID NO:5 or SEQ ID NO:6; and
(c) a heavy chain CDR3 having at least 90% (e.g., 91%, 92%, 93%, 94%, 95%, 96%, 97%, 98%, 99%, or 100%) sequence identity to the amino acid sequence of SEQ ID NO:7 or SEQ ID NO:8 or having up to two amino acid substitutions relative to the amino acid sequence of SEQ ID NO:7 or SEQ ID NO:8.

In some embodiments, the antibody comprises one or more (e.g., one, two, or all three) CDRs selected from the group consisting of:

(a) a heavy chain CDR1 comprising the amino acid sequence of SEQ ID NO:4;
(b) a heavy chain CDR2 comprising the amino acid sequence of SEQ ID NO:5 or SEQ ID NO:6; and
(c) a heavy chain CDR3 comprising the amino acid sequence of SEQ ID NO:7 or SEQ ID NO:8.

In some embodiments, the antibody comprises one or more (e.g., one, two, or all three) CDRs selected from the group consisting of:

(a) a heavy chain CDR1 comprising the amino acid sequence of SEQ ID NO:4;
(b) a heavy chain CDR2 comprising the amino acid sequence of SEQ ID NO:6; and (c) a heavy chain CDR3 comprising the amino acid sequence of SEQ ID NO:7.

In some embodiments, the antibody comprises one or more (e.g., one, two, or all three) CDRs selected from the group consisting of:

(a) a heavy chain CDR1 comprising the amino acid sequence of SEQ ID NO:4;
(b) a heavy chain CDR2 comprising the amino acid sequence of SEQ ID NO:5; and
(c) a heavy chain CDR3 comprising the amino acid sequence of SEQ ID NO:8.

In some embodiments, the antibody comprises one or more (e.g., one, two, or all three) CDRs selected from the group consisting of:

(a) a heavy chain CDR1 comprising the amino acid sequence of SEQ ID NO:4;
(b) a heavy chain CDR2 comprising the amino acid sequence of SEQ ID NO:6; and
(c) a heavy chain CDR3 comprising the amino acid sequence of SEQ ID NO:8.

In some embodiments, the antibody comprises a heavy chain variable region comprising an amino acid sequence having at least 90% (e.g., 91%, 92%, 93%, 94%, 95%, 96%, 97%, 98%, 99%, or 100%) sequence identity to any one of SEQ ID NOS:1-3. In some embodiments, the antibody comprises a heavy chain variable region comprising the amino acid sequence of any one of SEQ ID NOS:1-3.

In a related aspect, the disclosure provides an isolated antibody heavy chain comprising one or more (e.g., one, two, or all three) of the CDRs described above. In some embodiments, the antibody heavy chain comprises a heavy chain variable region comprising an amino acid sequence having at least 90% (e.g., 91%, 92%, 93%, 94%, 95%, 96%, 97%, 98%, 99%, or 100%) sequence identity to any one of SEQ ID NOS:1-3. In some embodiments, the antibody heavy chain comprises a heavy chain variable region comprising the amino acid sequence of any one of SEQ ID NOS:1-3.

In another aspect, the disclosure provides an isolated antibody comprising:

(a) a light chain CDR3 comprising the amino acid sequence of SEQ ID NO:13 or 14.

In some embodiments, the antibody further comprises one or more (e.g., one or both) CDRs selected from the group consisting of:

(b) a light chain CDR1 having at least 90% (e.g., 91%, 92%, 93%, 94%, 95%, 96%, 97%, 98%, 99%, or 100%) sequence identity to the amino acid sequence of SEQ ID NO:11 or having up to two amino acid substitutions relative to the amino acid sequence of SEQ ID NO:11; and
(c) alight chain CDR2 having up to two amino acid substitutions relative to the amino acid sequence of SEQ ID NO:12.

In some embodiments, the antibody further comprises one or more (e.g., one or both) CDRs selected from the group consisting of:

(b) a light chain CDR1 comprising the amino acid sequence of SEQ ID NO:11; and
(c) a light chain CDR2 comprising the amino acid sequence of SEQ ID NO:12.

In some embodiments, the light chain CDR3 comprises the amino acid sequence of SEQ ID NO: 13. In some embodiments, the light chain CDR3 comprises the amino acid sequence of SEQ ID NO:14.

In some embodiments, the antibody comprises a light chain variable region comprising an amino acid sequence having at least 90% (e.g., 91%, 92%, 93%, 94%, 95%, 96%, 97%, 98%, 99%, or 100%) sequence identity to any one of SEQ ID NOS:9-10. In some embodiments, the antibody comprises a light chain variable region comprising the amino acid sequence of any one of SEQ ID NOS:9-10.

In a related aspect, the disclosure provides an isolated antibody light chain comprising one or more (e.g., one, two, or all three) of the CDRs described above. In some embodiments, the antibody light chain comprises a light chain variable region comprising an amino acid sequence having at least 90% (e.g., 91%, 92%, 93%, 94%, 95%, 96%, 97%, 98%, 99%, or 100%) sequence identity to any one of SEQ ID NOS:9-10. In some embodiments, the antibody light chain comprises a light chain variable region comprising the amino acid sequence of any one of SEQ ID NOS:9-10.

In yet another aspect, the disclosure provides an isolated antibody comprising an antigen binding site comprising:

(a) a heavy chain CDR1 having at least 90% (e.g., 91%, 92%, 93%, 94%, 95%, 96%, 97%, 98%, 99%, or 100%) sequence identity to an amino acid sequence selected from the group consisting of SEQ ID NOS:4 and 49-52 or having up to two amino acid substitutions relative to an amino acid sequence selected from the group consisting of SEQ ID NOS:4 and 49-52;
(b) a heavy chain CDR2 having at least 90% (e.g., 91%, 92%, 93%, 94%, 95%, 96%, 97%, 98%, 99%, or 100%) sequence identity to an amino acid sequence selected from the group consisting of SEQ ID NOS:5-6 and 53-55 or having up to two amino acid substitutions relative to an amino acid sequence selected from the group consisting of SEQ ID NOS:5-6 and 53-55; and
(c) a heavy chain CDR3 having at least 90% (e.g., 91%, 92%, 93%, 94%, 95%, 96%, 97%, 98%, 99%, or 100%) sequence identity to an amino acid sequence selected from the group consisting of SEQ ID NOS:7-8 and 56-59 or having up to two amino acid substitutions relative to an amino acid sequence selected from the group consisting of SEQ ID NOS:7-8 and 56-59;
(d) a light chain CDR1 having at least 90% (e.g., 91%, 92%, 93%, 94%, 95%, 96%, 97%, 98%, 99%, or 100%) sequence identity to the amino acid sequence of SEQ ID NO:11 or having up to two amino acid substitutions relative to the amino acid sequence of SEQ ID NO:11;
(e) alight chain CDR2 having up to two amino acid substitutions relative to the amino acid sequence of SEQ ID NO:12; and
(f) a light chain CDR3 comprising the amino acid sequence of SEQ ID NO:13 or 14.

In some embodiments, the antigen binding site comprises:

(a) a heavy chain CDR1 having at least 90% (e.g., 91%, 92%, 93%, 94%, 95%, 96%, 97%, 98%, 99%, or 100%) sequence identity to the amino acid sequence of SEQ ID NO:4 or having up to two amino acid substitutions relative to the amino acid sequence of SEQ ID NO:4;
(b) a heavy chain CDR2 having at least 90% (e.g., 91%, 92%, 93%, 94%, 95%, 96%, 97%, 98%, 99%, or 100%) sequence identity to the amino acid sequence of SEQ ID NO:5 or SEQ ID NO:6 or having up to two amino acid substitutions relative to the amino acid sequence of SEQ ID NO:5 or SEQ ID NO:6;

(c) a heavy chain CDR3 having at least 90% (e.g., 91%, 92%, 93%, 94%, 95%, 96%, 97%, 98%, 99%, or 100%) sequence identity to the amino acid sequence of SEQ ID NO:7 or SEQ ID NO:8 or having up to two amino acid substitutions relative to the amino acid sequence of SEQ ID NO:7 or SEQ ID NO:8;

(d) a light chain CDR1 having at least 90% (e.g., 91%, 92%, 93%, 94%, 95%, 96%, 97%, 98%, 99%, or 100%) sequence identity to the amino acid sequence of SEQ ID NO:11 or having up to two amino acid substitutions relative to the amino acid sequence of SEQ ID NO:11;

(e) alight chain CDR2 having up to two amino acid substitutions relative to the amino acid sequence of SEQ ID NO:12; and (f) a light chain CDR3 comprising the amino acid sequence of SEQ ID NO:13 or 14.

In some embodiments, the antigen binding site comprises a heavy chain variable region comprising an amino acid sequence having at least 90% (e.g., 91%, 92%, 93%, 94%, 95%, 96%, 97%, 98%, 99%, or 100%) sequence identity to any one of SEQ ID NOS:1-3 and a light chain variable region comprising an amino acid sequence having at least 90% (e.g., 91%, 92%, 93%, 94%, 95%, 96%, 97%, 98%, 99%, or 100%) sequence identity to any one of SEQ ID NOS:9-10. In some embodiments, the antigen binding site comprises a heavy chain variable region comprising the amino acid sequence of any one of SEQ ID NOS: 1-3 and a light chain variable region comprising the amino acid sequence of any one of SEQ ID NOS:9-10.

In some embodiments, the antibody further comprises a second antigen binding site comprising one or more CDRs selected from the group consisting of:

(a) a heavy chain CDR1 comprising the amino acid sequence of SEQ ID NO: 16 or having up to two amino acid substitutions relative to the amino acid sequence of SEQ ID NO:16;

(b) a heavy chain CDR2 having at least 90% (e.g., 91%, 92%, 93%, 94%, 95%, 96%, 97%, 98%, 99%, or 100%) sequence identity to the amino acid sequence of SEQ ID NO:17 or having up to two amino acid substitutions relative to the amino acid sequence of SEQ ID NO:17; and (c) a heavy chain CDR3 having at least 90% (e.g., 91%, 92%, 93%, 94%, 95%, 96%, 97%, 98%, 99%, or 100%) sequence identity to the amino acid sequence of SEQ ID NO:18 or having up to two amino acid substitutions relative to the amino acid sequence of SEQ ID NO:18.

In some embodiments, the second antigen binding site comprises a heavy chain variable region comprising an amino acid sequence having at least 90% (e.g., 91%, 92%, 93%, 94%, 95%, 96%, 97%, 98%, 99%, or 100%) sequence identity to SEQ ID NO:15. In some embodiments, the second antigen binding site comprises a heavy chain variable region comprising the sequence of SEQ ID NO:15.

In some embodiments, the second antigen binding site further comprises one or more CDRs selected from the group consisting of:

(a) a light chain CDR1 having at least 90% (e.g., 91%, 92%, 93%, 94%, 95%, 96%, 97%, 98%, 99%, or 100%) sequence identity to the amino acid sequence of SEQ ID NO:11 or having up to two amino acid substitutions relative to the amino acid sequence of SEQ ID NO:11;

(b) alight chain CDR2 having up to two amino acid substitutions relative to the amino acid sequence of SEQ ID NO:12; and (c) alight chain CDR3 having up to two amino acid substitutions relative to the amino acid sequence of SEQ ID NO:13 or 14.

In some embodiments, the second antigen binding site comprises a light chain variable region comprising an amino acid sequence having at least 90% (e.g., 91%, 92%, 93%, 94%, 95%, 96%, 97%, 98%, 99%, or 100%) sequence identity to any one of SEQ ID NOS:9-10. In some embodiments, the second antigen binding site comprises a light chain variable region comprising the sequence of any one of SEQ ID NOS:9-10.

In some embodiments, the first and second antigen binding sites comprise the same light chain CDR1, CDR2, and CDR3 sequences. In some embodiments, the antibody comprises heavy and light chain CDRs selected from the combinations listed in Table 1.

In a related aspect, the disclosure provides an isolated antibody comprising heavy and light chains selected from the combinations listed in Table 2.

In a further aspect, the disclosure provides an isolated antibody comprising:

(a) a first antigen binding site for human epidermal growth factor receptor 2 (HER2) subdomain IV;

(b) a second antigen binding site for human HER2 subdomain II; and (c) a modified Fc polypeptide dimer comprising a first Fc polypeptide that contains modifications that create a TfR-binding site, wherein a light chain polypeptide sequence in the first antigen binding site is identical to a light chain polypeptide sequence in the second antigen binding site.

In a related aspect, the disclosure provides an isolated antibody comprising:

(a) a first antigen binding site for human HER2 subdomain II;

(b) a second antigen binding site for human HER2 subdomain IV; and (c) a modified Fc polypeptide dimer comprising a first Fc polypeptide that contains modifications that create a TfR-binding site, wherein a light chain polypeptide sequence in the first antigen binding site is identical to a light chain polypeptide sequence in the second antigen binding site.

In some embodiments, the first Fc polypeptide comprises a modified CH3 domain comprising the TfR-binding site. In some embodiments, the modified CH3 domain is derived from a human IgG1, IgG2, IgG3, or IgG4 CH3 domain.

In some embodiments, the modified CH3 domain comprises one, two, three, four, five, six, seven, eight, nine, ten, or eleven substitutions in a set of amino acid positions comprising 380, 384, 386, 387, 388, 389, 390, 413, 415, 416, and 421, according to EU numbering. In some embodiments, the modified CH3 domain comprises Glu, Leu, Ser, Val, Trp, Tyr, or Gln at position 380; Leu, Tyr, Phe, Trp, Met, Pro, or Val at position 384; Leu, Thr, His, Pro, Asn, Val, or Phe at position 386; Val, Pro, Ile, or an acidic amino acid at position 387; Trp at position 388; an aliphatic amino acid, Gly, Ser, Thr, or Asn at position 389; Gly, His, Gln, Leu, Lys, Val, Phe, Ser, Ala, Asp, Glu, Asn, Arg, or Thr at position 390; an acidic amino acid, Ala, Ser, Leu, Thr, Pro, Ile, or His at position 413; Glu, Ser, Asp, Gly, Thr, Pro, Gln, or Arg at position 415; Thr, Arg, Asn, or an acidic amino acid at position 416; and/or an aromatic amino acid, His, or Lys at position 421, according to EU numbering.

In some embodiments, the first Fc polypeptide that contains modifications that create the TfR-binding site binds to the apical domain of TfR.

In some embodiments, the first Fc polypeptide and the second Fc polypeptide each comprises modifications that promote heterodimerization. In some embodiments, the first Fc polypeptide comprises a T366W substitution and the second Fc polypeptide comprises T366S, L368A, and Y407V substitutions, according to EU numbering. In other embodiments, the first Fc polypeptide comprises T366S, L368A, and Y407V substitutions and the second Fc polypeptide comprises a T366W substitution, according to EU numbering.

In some embodiments, the first Fc polypeptide and/or the second Fc polypeptide independently comprises modifications that reduce TfR-mediated effector function. In some embodiments, the modifications that reduce effector function are L234A and L235A substitutions, according to EU numbering. In certain embodiments, the first Fc polypeptide specifically binds to TfR and comprises L234A and L235A substitutions. In certain embodiments, the first Fc polypeptide further comprises a P329G or a P329S substitution, according to EU numbering. In certain embodiments, the second Fc polypeptide comprises Leu at positions 234 and 235 and a proline at position 329, according to EU numbering. In other embodiments, the second Fc polypeptide specifically binds to TfR and comprises L234A and L235A substitutions. In certain embodiments, the second Fc polypeptide further comprises a P329G or a P329S substitution, according to EU numbering. In certain embodiments, the first Fc polypeptide comprises Leu at positions 234 and 235 and a proline at position 329, according to EU numbering.

In some embodiments, a hinge region or a portion thereof is linked to the N-terminus of the first Fc polypeptide and/or the second Fc polypeptide.

In some embodiments, the first Fc polypeptide and/or the second Fc polypeptide independently comprises a sequence having at least 90% (e.g., 91%, 92%, 93%, 94%, 95%, 96%, 97%, 98%, 99%, or 100%) identity to a sequence selected from the group consisting of SEQ ID NOS: 71-86 and 98-100. In some embodiments, the first Fc polypeptide or the second Fc polypeptide comprises a sequence having at least 90% (e.g., 91%, 92%, 93%, 94%, 95%, 96%, 97%, 98%, 99%, or 100%) identity to a sequence selected from the group consisting of SEQ ID NOS:71-73, 85, and 99-100. In other embodiments, the first Fc polypeptide or the second Fc polypeptide comprises a sequence having at least 90% (e.g., 91%, 92%, 93%, 94%, 95%, 96%, 97%, 98%, 99%, or 100%) identity to a sequence selected from the group consisting of SEQ ID NOS: 74-84, 86 and 98.

In some embodiments of this antibody, the first antigen binding site comprises the amino acid sequence of SEQ ID NO:15; the second antigen binding site comprises an amino acid sequence selected from the group consisting of SEQ ID NOS:1-3 and 60-70; the first Fc polypeptide that contains modifications that create the TfR-binding site comprises an amino acid sequence selected from the group consisting of SEQ ID NOS:74-84, 86, and 98; and the light chain polypeptide sequence comprises the amino acid sequence of SEQ ID NO:9 or SEQ ID NO:10. In some embodiments, the antibody further comprises a second Fc polypeptide comprising an amino acid sequence selected from the group consisting of SEQ ID NOS:71-73, 85, and 99-100.

In other embodiments of this antibody, the first antigen binding site comprises an amino acid sequence selected from the group consisting of SEQ ID NOS:1-3 and 60-70; the second antigen binding site comprises the amino acid sequence of SEQ ID NO:15; the first Fc polypeptide that contains modifications that create the TfR-binding site comprises an amino acid sequence selected from the group consisting of SEQ ID NOS:74-84, 86, and 98; and the light chain polypeptide sequence comprises the amino acid sequence of SEQ ID NO:9 or SEQ ID NO:10. In some embodiments, the antibody further comprises a second Fc polypeptide comprising an amino acid sequence selected from the group consisting of SEQ ID NOS:71-73, 85, and 99-100.

In some embodiments, the first Fc polypeptide and/or the second Fc polypeptide independently comprises a S239D and/or a I332E substitution, according to EU numbering. In some embodiments, the first Fc polypeptide and/or the second Fc polypeptide independently comprising the S239D and/or the I332E substitution is capable of enhancing HER2-mediated effector function.

In some embodiments of this antibody:

(a) the first Fc polypeptide comprises a S239D substitution and the second Fc polypeptide comprises a S239D substitution, according to EU numbering;

(b) the first Fc polypeptide comprises a I332E substitution and the second Fc polypeptide comprises a S239D substitution, according to EU numbering;

(c) the first Fc polypeptide comprises a S239D and a I332E substitution and the second Fc polypeptide comprises a S239D substitution, according to EU numbering;

(d) the second Fc polypeptide comprises a S239D substitution, according to EU numbering;

(e) the first Fc polypeptide comprises a S239D substitution and the second Fc polypeptide comprises a I332E substitution, according to EU numbering;

(f) the first Fc polypeptide comprises a I332E substitution and the second Fc polypeptide comprises a I332E substitution, according to EU numbering;

(g) the first Fc polypeptide comprises a S239D and a I332E substitution and the second Fc polypeptide comprises a I332E substitution, according to EU numbering;

(h) the second Fc polypeptide comprises a I332E substitution, according to EU numbering;

(i) the first Fc polypeptide comprises a S239D substitution and the second Fc polypeptide comprises a S239D and a I332E substitution, according to EU numbering;

(j) the first Fc polypeptide comprises a I332E substitution and the second Fc polypeptide comprises a S239D and a I332E substitution, according to EU numbering;

(k) the first Fc polypeptide comprises a S239D and a I332E substitution and the second Fc polypeptide comprises a S239D and a I332E substitution, according to EU numbering;

(l) the second Fc polypeptide comprises a S239D and a I332E substitution, according to EU numbering;

(m) the first Fc polypeptide comprises a S239D substitution, according to EU numbering;

(n) the first Fc polypeptide comprises a I332E substitution, according to EU numbering; or (o) the first Fc polypeptide comprises a S239D and a I332E substitution, according to EU numbering.

In certain embodiments of this antibody:

(a) the first Fc polypeptide comprises a I332E substitution and the second Fc polypeptide comprises a S239D substitution, according to EU numbering;

(b) the first Fc polypeptide comprises a S239D and a I332E substitution and the second Fc polypeptide comprises a S239D substitution, according to EU numbering;

(c) the first Fc polypeptide comprises a S239D substitution and the second Fc polypeptide comprises a I332E substitution, according to EU numbering;

(d) the second Fc polypeptide comprises a I332E substitution, according to EU numbering;

(e) the first Fc polypeptide comprises a S239D substitution and the second Fc polypeptide comprises a S239D and a I332E substitution, according to EU numbering; or (f) the first Fc polypeptide comprises a I332E substitution, according to EU numbering.

In particular embodiments of this antibody:

(a) the first Fc polypeptide comprises a I332E substitution and a serine at position 239, and the second Fc polypeptide comprises a S239D substitution and a isoleucine at position 332, according to EU numbering;

(b) the first Fc polypeptide comprises a S239D and a I332E substitution, and the second Fc polypeptide comprises a S239D substitution and a isoleucine at position 332, according to EU numbering;

(c) the first Fc polypeptide comprises a S239D substitution and a isoleucine at position 332, and the second Fc polypeptide comprises a I332E substitution and a serine at position 239, according to EU numbering;

(d) the first Fc polypeptide comprises a serine at position 239 and a isoleucine at 332, and the second Fc polypeptide comprises a I332E substitution and a serine at position 239, according to EU numbering;

(e) the first Fc polypeptide comprises a S239D substitution and a isoleucine at position 332, and the second Fc polypeptide comprises a S239D and a I332E substitution, according to EU numbering; or (f) the first Fc polypeptide comprises a I332E substitution and a serine at position 239, according to EU numbering, and the second Fc polypeptide comprises a serine at position 239 and a isoleucine at 332.

In some embodiments, the antibody comprises two heavy chains and two light chains. In certain embodiments, the antibody comprises heavy and light chains selected from the combinations listed in Table 2. In certain embodiments, the first heavy chain comprises a $V_H$ and a Fc sequence selected from the combinations in Table 3 and the second heavy chain comprises a $V_H$ and a Fc sequence selected from the combinations in Table 4. In certain embodiments, the first heavy chain comprises a $V_H$ and a Fc sequence selected from the combinations in Table 5 and the second heavy chain comprises a $V_H$ and a Fc sequence selected from the combinations in Table 6.

In another aspect, the disclosure provides a pharmaceutical composition comprising any of the antibodies described herein and a pharmaceutically acceptable carrier.

In another aspect, the disclosure provides an isolated polynucleotide comprising a nucleotide sequence encoding an antibody described herein.

In another aspect, the disclosure provides a vector comprising the polynucleotide of the previous aspect.

In another aspect, the disclosure provides a host cell comprising the polynucleotide or the vector.

In another aspect, the disclosure provides a method for treating a cancer or treating brain metastasis of a cancer in a subject, the method comprising administering to the subject a therapeutically effective amount of an antibody described herein or a pharmaceutical composition thereof.

In some embodiments, the antibody is adminstered in combination with a chemotherapy or radiation therapy. In some embodiments, the cancer is a metastatic cancer. In some embodiments, the cancer is a breast cancer. In some embodiments, the cancer is a HER2-positive cancer.

BRIEF DESCRIPTION OF THE DRAWINGS

FIG. 3A: BT-474; FIG. 3B: OE19.

FIG. 4A: BT-474; FIG. 4B: OE19.

FIG. 5A: BT-474; FIG. 5B: OE19.

DETAILED DESCRIPTION

I. Introduction

Figure 1:
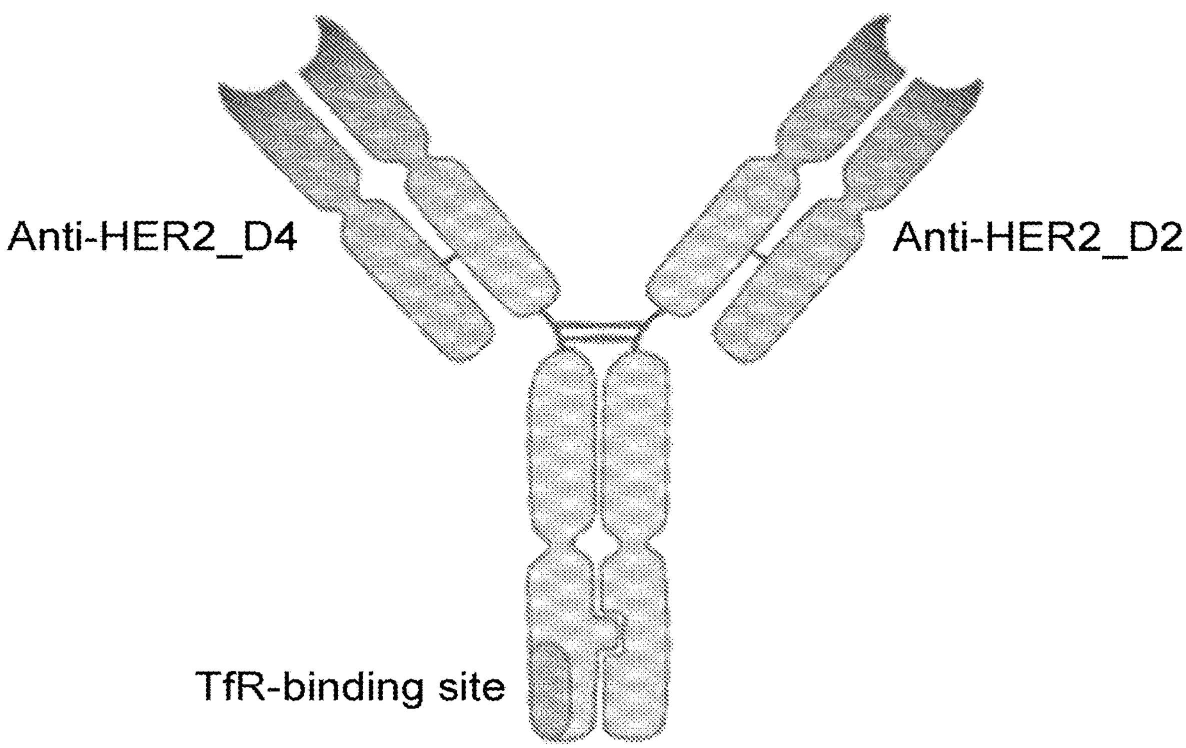
FIG. 1 is a schematic drawing showing an exemplary bispecific antibody having a first antigen binding site for human HER2 subdomain IV ("Anti-HER2_D4") and a second antigen binding site for human HER2 subdomain II ("Anti-HER2_D2"), in which the first and second antigen binding sites include the identical light chain polypeptide, and an Fc polypeptide dimer comprising a first Fc polypeptide having a TfR-binding site and a knob mutation and a second Fc polypeptide having a hole mutation.

Described herein are anti-HER2 bispecific antibodies that utilize a common light chain approach, i.e., two antigen binding domains that are paired with an identical light chain but still retain separate specificities. The use of a common light chain prevents light chain mispairing and as a result makes it easier to manufacture these bispecific antibodies. In some embodiments, the bispecific antibodies comprise a first antigen binding site for human HER2 subdomain IV and a second antigen binding site for human HER2 subdomain II, wherein the light chain polypeptide sequence in the first antigen binding site is identical to the light chain polypeptide sequence in the second antigen binding site. In another embodiment, the bispecific antibodies comprise a first antigen binding site for human HER2 subdomain II and a second antigen binding site for human HER2 subdomain IV, wherein the light chain polypeptide sequence in the first antigen binding site is identical to the light chain polypeptide sequence in the second antigen binding site.

Furthermore, previous therapies have failed to control brain metastases of HER2-positive breast cancer mostly because of the inability of the therapeutic agents to cross the blood brain barrier (BBB) and access the brain parenchyma. Thus, there is a need for new therapeutic agents that can cross the BBB and target HER2 in the brain parenchyma. We previously described the use of transferrin receptor (TfR)- binding as a method to enable BBB delivery across the brain endothelium, as the expression of TfR is highly expressed in brain endothelial cells and can enable BBB delivery via receptor-mediated transcytosis. Interestingly, TfR is highly expressed in various cancers, including HER2-positive breast cancers. The mechanism by which cancer cells acquire increased TfR expression likely relates to tumor cell proliferation and increased metabolic demand such as iron uptake. In fact, public microarray datasets demonstrated a correlation of TfR expression to breast cancer prognosis (Miller et al., Cancer Res. 71:6728, 2011). There have also been some reports on the use of TfR as a pharmacological target for various types of cancers.

In some embodiments, the anti-HER2 bispecific antibody comprises one or more modified Fc polypeptides that specifically bind to a BBB receptor, e.g., TfR (i.e., TfR-binding Fc polypeptides). In some embodiments, the anti-HER2 bispecific antibody is capable of being transported across the BBB. In some embodiments, the anti-HER2 bispecific antibodies binding to both HER2 and TfR as described herein can provide additional anti-tumor benefits upon binding to HER2-positive tumor cells which also express high levels of TfR, compared to other therapeutic agents that bind to HER2 alone. Specifically, since these antibodies can bind both the TfR and HER2 at the same time, this could enhance their potency and/or efficacy.

II. Definitions

As used herein, the singular forms "a," "an," and "the" include plural referents unless the content clearly dictates otherwise. Thus, for example, reference to "an antibody" optionally includes a combination of two or more such molecules, and the like.

As used herein, the terms "about" and "approximately," when used to modify an amount specified in a numeric value or range indicate that the numeric value as well as reasonable deviations from the value known to the skilled person in the art, for example ±20%, ±10%, or ±5%, are within the intended meaning of the recited value.

The terms "human epidermal growth factor receptor 2," "HER2," "HER2/neu," and "ERBB2" (also known as CD340, receptor tyrosine-protein kinase erbB-2, proto-oncogene and Neu,) refer to a tyrosine receptor kinase protein encoded by the ERBB2 gene in humans that is a member of the human epidermal growth factor receptor (HER/EGFR/ERBB) family.

Amplification or overexpression of HER2 plays a significant role in the development and progression of certain aggressive types of cancer, including breast cancer. Non-limiting examples of human HER2 nucleotide sequences are set forth in GenBank reference numbers NP 001005862, NP_001289936, NP_001289937, NP_001289938, and NP_004448. Non-limiting examples of human HER2 peptide sequences are set forth in GenBank reference numbers NP_001005862, NP_001276865, NP_001276866, NP_001276867, and NP_004439.

The extracellular domain of HER2, which contains approximately 600 amino acids, includes four subdomains (subdomains I, II, III, and IV). Subdomains I and III form a ligand binding site. The cysteine-rich subdomains II and IV are involved in receptor homodimerization and heterodimerization. Anti-HER2 antibodies can bind to specific subdomains (e.g., subdomain II and/or subdomain IV).

As used herein, the term "anti-HER2_D2" or "anti-HER2_D4" refers to an antibody that binds to subdomain II or IV, respectively, of human HER2.

As used herein, the term "antibody" refers to a protein with an immunoglobulin fold that specifically binds to an antigen via its variable regions. The term encompasses intact polyclonal antibodies, intact monoclonal antibodies, single chain antibodies, multispecific antibodies such as bispecific antibodies, monospecific antibodies, monovalent antibodies, chimeric antibodies, humanized antibodies, and human antibodies. The term "antibody," as used herein, also includes antibody fragments that retain antigen-binding specificity, including but not limited to Fab, $F(ab')_2$, Fv, scFv, and bivalent scFv. Antibodies can contain light chains that are classified as either kappa or lambda. Antibodies can contain heavy chains that are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light chain" ($V_L$) and "variable heavy chain" ($V_H$) refer to these light and heavy chains, respectively.

The term "variable region" or "variable domain" refers to a domain in an antibody heavy chain or light chain that is derived from a germline Variable (V) gene, Diversity (D) gene, or Joining (J) gene (and not derived from a Constant (Cμ and Cδ) gene segment), and that gives an antibody its specificity for binding to an antigen. Typically, an antibody variable region comprises four conserved "framework" regions interspersed with three hypervariable "complementarity determining regions."

The term "complementarity determining region" or "CDR" refers to the three hypervariable regions in each chain that interrupt the four framework regions established by the light and heavy chain variable regions. The CDRs are primarily responsible for antibody binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 or CDR-H3 is located in the variable region of the heavy chain of the antibody in which it is found, whereas a $V_L$ CDR1 or CDR-L1 is the CDR1 from the variable region of the light chain of the antibody in which it is found.

The "framework regions" or "FRs" of different light or heavy chains are relatively conserved within a species. The framework region of an antibody, that is the combined framework regions of the constituent light and heavy chains, serves to position and align the CDRs in three-dimensional space. Framework sequences can be obtained from public DNA databases or published references that include germline antibody gene sequences. For example, germline DNA sequences for human heavy and light chain variable region genes can be found in the "VBASE2" germline variable gene sequence database for human and mouse sequences.

The amino acid sequences of the CDRs and framework regions can be determined using various well known definitions in the art, e.g., Kabat, Chothia, international ImMunoGeneTics database (IMGT), AbM, and observed antigen contacts ("Contact"). In some embodiments, CDRs are determined according to the Contact definition. See, MacCallum et al., *J. Mol. Biol.* 262:732-745, 1996. In some embodiments, CDRs are determined by a combination of Kabat, Chothia, and/or Contact CDR definitions.

The term "epitope" refers to the area or region of an antigen to which a molecule, e.g., the CDRs of an antibody, specifically binds and can include a few amino acids or portions of a few amino acids, e.g., 5 or 6, or more, e.g., 20 or more amino acids, or portions of those amino acids. In some cases, the epitope includes non-protein components, e.g., from a carbohydrate, nucleic acid, or lipid. In some cases, the epitope is a three-dimensional moiety. Thus, for example, where the target is a protein, the epitope can be comprised of consecutive amino acids (e.g., a linear epitope), or amino acids from different parts of the protein that are brought into proximity by protein folding (e.g., a discontinuous or conformational epitope).

As used herein, the phrase "recognizes an epitope," as used with reference to an antibody, means that the antibody CDRs interact with or specifically bind to the antigen at that epitope or a portion of the antigen containing that epitope.

A "humanized antibody" is a chimeric immunoglobulin derived from a non-human source (e.g., murine) that contains minimal sequences derived from the non-human immunoglobulin outside the CDRs. In general, a humanized antibody will comprise at least one (e.g., two) variable domain(s), in which the CDR regions substantially correspond to those of the non-human immunoglobulin and the framework regions substantially correspond to those of a human immunoglobulin sequence. In some instances, certain framework region residues of a human immunoglobulin can be replaced with the corresponding residues from a non-human species to, e.g., improve specificity, affinity, and/or serum half-life. The humanized antibody can also comprise at least a portion of an immunoglobulin constant region (Fc), typically that of a human immunoglobulin sequence. Methods of antibody humanization are known in the art.

A "human antibody" or a "fully human antibody" is an antibody having human heavy chain and light chain sequences, typically derived from human germline genes. In some embodiments, the antibody is produced by a human cell, by a non-human animal that utilizes human antibody repertoires (e.g., transgenic mice that are genetically engineered to express human antibody sequences), or by phage display platforms.

The term "specifically binds" refers to a molecule, e.g., an antibody as described herein, that binds to an epitope or target with greater affinity, greater avidity, and/or greater duration to that epitope or target in a sample than it binds to another epitope or non-target compound (e.g., a structurally different antigen). In some embodiments, a molecule that specifically binds to an epitope or target is a molecule that binds to the epitope or target with at least 5-fold greater affinity than other epitopes or non-target compounds, e.g., at least 6-fold, 7-fold, 8-fold, 9-fold, 10-fold, 25-fold, 50-fold, 100-fold, 1000-fold, 10,000-fold, or greater affinity. The term "specific binding," "specifically binds to," or "is specific for" a particular epitope or target, as used herein, can be exhibited, for example, by a molecule having an equilibrium dissociation constant $K_D$ for the epitope or target to which it binds of, e.g., $10^{-4}$ M or smaller, e.g., $10^{-5}$ M, $10^{-6}$ M, $10^{-7}$ M, $10^{-8}$ M, $10^{-9}$ M, $10^{-10}$ M, $10^{-11}$ M, or $10^{-12}$ M. It will be recognized by one of skill that a molecule that specifically binds to a target from one species may also specifically bind to orthologs of that target.

The term "binding affinity" is used herein to refer to the strength of a non-covalent interaction between two molecules, e.g., between an antibody as described herein and an antigen. Thus, for example, the term may refer to 1:1 interactions between an antibody and an antigen, unless otherwise indicated or clear from context. Binding affinity may be quantified by measuring an equilibrium dissociation constant ($K_D$), which refers to the dissociation rate constant ($k_d$, time$^{-1}$) divided by the association rate constant ($k_a$, time$^{-1}$ M$^{-1}$). $K_D$ can be determined by measurement of the kinetics of complex formation and dissociation, e.g., using Surface Plasmon Resonance (SPR) methods, e.g., a Biacore™ system; kinetic exclusion assays such as KinExA®; and BioLayer interferometry (e.g., using the ForteBio® Octet platform). As used herein, "binding affinity" includes not only formal binding affinities, such as those reflecting 1:1 interactions between an antibody and an antigen, but also apparent affinities for which $K_D$'s are calculated that may reflect avid binding.

A "transferrin receptor" or "TfR," as used herein, refers to transferrin receptor protein 1. The human transferrin receptor 1 polypeptide sequence is set forth in SEQ ID NO:150. Transferrin receptor protein 1 sequences from other species are also known (e.g., chimpanzee, accession number XP_003310238.1; rhesus monkey, NP_001244232.1; dog, NP_001003111.1; cattle, NP_001193506.1; mouse, NP_035768.1; rat, NP_073203.1; and chicken, NP_990587.1). The term "transferrin receptor" also encompasses allelic variants of exemplary reference sequences, e.g., human sequences, that are encoded by a gene at a transferrin receptor protein 1 chromosomal locus. Full-length transferrin receptor protein includes a short N-terminal intracellular region, a transmembrane region, and a large extracellular domain. The extracellular domain is characterized by three domains: a protease-like domain, a helical domain, and an apical domain.

As used herein, the term "Fc polypeptide" refers to the C-terminal region of a naturally occurring immunoglobulin heavy chain polypeptide that is characterized by an Ig fold as a structural domain. An Fc polypeptide contains constant region sequences including at least the CH2 domain and/or the CH3 domain and may contain at least part of the hinge region, but does not contain a variable region.

A "modified Fc polypeptide" refers to an Fc polypeptide that has at least one mutation, e.g., a substitution, deletion or insertion, as compared to a wild-type immunoglobulin heavy chain Fc polypeptide sequence, but retains the overall Ig fold or structure of the native Fc polypeptide.

As used herein, "FcRn" refers to the neonatal Fc receptor. Binding of Fc polypeptides to FcRn reduces clearance and increases serum half-life of the Fc polypeptide. The human FcRn protein is a heterodimer that is composed of a protein of about 50 kDa in size that is similar to a major histocompatibility (MHC) class I protein and a 02-microglobulin of about 15 kDa in size.

As used herein, an "FcRn binding site" refers to the region of an Fc polypeptide that binds to FcRn. In human IgG, the FcRn binding site, as numbered using the EU index, includes L251, M252, I253, S254, R255, T256, M428, H433, N434, H435, and Y436. These positions correspond to positions 21 to 26, 198, and 203 to 206 of SEQ ID NO:95.

As used herein, a "native FcRn binding site" refers to a region of an Fc polypeptide that binds to FcRn and that has the same amino acid sequence as the region of a naturally occurring Fc polypeptide that binds to FcRn.

As used herein, the terms "CH3 domain" and "CH2 domain" refer to immunoglobulin constant region domain polypeptides. For purposes of this application, a CH3 domain polypeptide refers to the segment of amino acids from about position 341 to about position 447 as numbered according to the EU numbering scheme, and a CH2 domain polypeptide refers to the segment of amino acids from about position 231 to about position 340 as numbered according to the EU numbering scheme and does not include hinge region sequences. CH2 and CH3 domain polypeptides may also be numbered by the IMGT (ImMunoGeneTics) numbering scheme in which the CH2 domain numbering is 1-110 and the CH3 domain numbering is 1-107, according to the IMGT Scientific chart numbering (IMGT website). CH2 and CH3 domains are part of the Fc region of an immunoglobulin. An Fc region refers to the segment of amino acids from about position 231 to about position 447 as numbered according to the EU numbering scheme, but as used herein, can include at least a part of a hinge region of an antibody. An illustrative hinge region sequence is the human IgG1 hinge sequence EPKSCDKTHTCPPCP (SEQ ID NO:96).

The terms "wild-type," "native," and "naturally occurring," as used with reference to a CH3 or CH2 domain, refer to a domain that has a sequence that occurs in nature.

As used herein, the term "mutant," as used with reference to a mutant polypeptide or mutant polynucleotide is used interchangeably with "variant." A variant with respect to a given wild-type CH3 or CH2 domain reference sequence can include naturally occurring allelic variants. A "non-naturally" occurring CH3 or CH2 domain refers to a variant or mutant domain that is not present in a cell in nature and that is produced by genetic modification, e.g., using genetic engineering technology or mutagenesis techniques, of a native CH3 domain or CH2 domain polynucleotide or polypeptide. A "variant" includes any domain comprising at least one amino acid mutation with respect to wild-type. Mutations may include substitutions, insertions, and deletions.

The term "isolated," as used with reference to a nucleic acid or protein, denotes that the nucleic acid or protein is essentially free of other cellular components with which it is associated in the natural state. It is preferably in a homogeneous state. Purity and homogeneity are typically determined using analytical chemistry techniques such as electrophoresis (e.g., polyacrylamide gel electrophoresis) or chromatography (e.g., high performance liquid chromatography). In some embodiments, an isolated nucleic acid or protein is at least 85% pure, at least 90% pure, at least 95% pure, or at least 99% pure.

The term "amino acid" refers to naturally occurring and synthetic amino acids, as well as amino acid analogs and amino acid mimetics that function in a manner similar to the naturally occurring amino acids. Naturally occurring are those encoded by the genetic code, as well as those amino acids that are later modified, e.g., hydroxyproline, γ-carboxyglutamate and O-phosphoserine. Naturally occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of a naturally occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof. "Amino acid analogs" refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission.

The terms "polypeptide" and "peptide" are used interchangeably herein to refer to a polymer of amino acid residues in a single chain. The terms apply to amino acid polymers in which one or more amino acid residue is an artificial chemical mimetic of a corresponding naturally occurring amino acid, as well as to naturally occurring amino acid polymers and non-naturally occurring amino acid polymers. Amino acid polymers may comprise entirely L-amino acids, entirely D-amino acids, or a mixture of L and D amino acids.

The term "protein" as used herein refers to either a polypeptide or a dimer (i.e., two) or multimer (i.e., three or more) of single chain polypeptides. The single chain polypeptides of a protein may be joined by a covalent bond, e.g., a disulfide bond, or non-covalent interactions.

The terms "polynucleotide" and "nucleic acid" interchangeably refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. Examples of polynucleotides contemplated herein include single- and double-stranded DNA, single- and double-stranded RNA, and hybrid molecules having mixtures of single- and double-stranded DNA and RNA.

The terms "conservative substitution" and "conservative mutation" refer to an alteration that results in the substitution of an amino acid with another amino acid that can be categorized as having a similar feature. Examples of categories of conservative amino acid groups defined in this manner can include: a "charged/polar group" including Glu (Glutamic acid or E), Asp (Aspartic acid or D), Asn (Asparagine or N), Gln (Glutamine or Q), Lys (Lysine or K), Arg (Arginine or R), and His (Histidine or H); an "aromatic group" including Phe (Phenylalanine or F), Tyr (Tyrosine or Y), Trp (Tryptophan or W), and (Histidine or H); and an "aliphatic group" including Gly (Glycine or G), Ala (Alanine or A), Val (Valine or V), Leu (Leucine or L), Ile (Isoleucine or I), Met (Methionine or M), Ser (Serine or S), Thr (Threonine or T), and Cys (Cysteine or C). Within each group, subgroups can also be identified. For example, the group of charged or polar amino acids can be sub-divided into sub-groups including: a "positively-charged sub-group" comprising Lys, Arg and His; a "negatively-charged sub-group" comprising Glu and Asp; and a "polar sub-group" comprising Asn and Gln. In another example, the aromatic or cyclic group can be sub-divided into sub-groups including: a "nitrogen ring sub-group" comprising Pro, His and Trp; and a "phenyl sub-group" comprising Phe and Tyr. In another further example, the aliphatic group can be sub-divided into sub-groups, e.g., an "aliphatic non-polar sub-group" comprising Val, Leu, Gly, and Ala; and an "aliphatic slightly-polar sub-group" comprising Met, Ser, Thr, and Cys. Examples of categories of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —$NH_2$ can be maintained. In some embodiments, hydrophobic amino acids are substituted for naturally occurring hydrophobic amino acid, e.g., in the active site, to preserve hydrophobicity.

The terms "identical" or percent "identity," in the context of two or more polypeptide sequences, refer to two or more sequences or subsequences that are the same or have a specified percentage of amino acid residues, e.g., at least 60%, at least 65%, at least 70%, at least 75%, at least 80%, at least 85%, at least 90%, or at least 95% or greater, that are identical over a specified region when compared and aligned for maximum correspondence over a comparison window or designated region as measured using a sequence comparison algorithm or by manual alignment and visual inspection.

For sequence comparison of polypeptides, typically one amino acid sequence acts as a reference sequence, to which a candidate sequence is compared. Alignment can be performed using various methods available to one of skill in the art, e.g., visual alignment or using publicly available software using known algorithms to achieve maximal alignment. Such programs include the BLAST programs, ALIGN, ALIGN-2 (Genentech, South San Francisco, Calif.) or Megalign (DNASTAR). The parameters employed for an alignment to achieve maximal alignment can be determined by one of skill in the art. For sequence comparison of polypeptide sequences for purposes of this application, the BLASTP algorithm standard protein BLAST for aligning two proteins sequence with the default parameters is used.

The terms "corresponding to," "determined with reference to," or "numbered with reference to" when used in the context of the identification of a given amino acid residue in a polypeptide sequence, refers to the position of the residue of a specified reference sequence when the given amino acid sequence is maximally aligned and compared to the reference sequence. Thus, for example, an amino acid residue in a modified Fc polypeptide "corresponds to" an amino acid in SEQ ID NO:95, when the residue aligns with the amino acid in SEQ ID NO:95 when optimally aligned to SEQ ID NO:95. The polypeptide that is aligned to the reference sequence need not be the same length as the reference sequence.

The terms "subject," "individual," and "patient," as used interchangeably herein, refer to a mammal, including but not limited to humans, non-human primates, rodents (e.g., rats, mice, and guinea pigs), rabbits, cows, pigs, horses, and other mammalian species. In one embodiment, the patient is a human.

The terms "treatment," "treating," and the like are used herein to generally mean obtaining a desired pharmacologic and/or physiologic effect. "Treating" or "treatment" may refer to any indicia of success in the treatment or amelioration of a cancer (e.g., a HER2-positive and/or metastatic cancer), including any objective or subjective parameter such as abatement, remission, improvement in patient survival, increase in survival time or rate, diminishing of symptoms or making the disease more tolerable to the patient, slowing in the rate of degeneration or decline, or improving a patient's physical or mental well-being. The treatment or amelioration of symptoms can be based on objective or subjective parameters. The effect of treatment can be compared to an individual or pool of individuals not receiving the treatment, or to the same patient prior to treatment or at a different time during treatment.

The term "pharmaceutically acceptable excipient" refers to a non-active pharmaceutical ingredient that is biologically or pharmacologically compatible for use in humans or animals, such as, but not limited to a buffer, carrier, or preservative.

As used herein, a "therapeutic amount" or "therapeutically effective amount" of a molecule (e.g., an antibody as described herein) is an amount of the molecule that treats, alleviates, abates, or reduces the severity of symptoms of a disease in a subject.

The term "administer" refers to a method of delivering molecules or compositions to the desired site of biological action. These methods include, but are not limited to, topical delivery, parenteral delivery, intravenous delivery, intradermal delivery, intramuscular delivery, intrathecal delivery, colonic delivery, rectal delivery, or intraperitoneal delivery. In one embodiment, an antibody as described herein is administered intravenously.

III. Anti-HER2 Antibodies

In one aspect, antibodies that bind to both subdomain II and subdomain IV of human HER2 comprising a common light chain polypeptide are provided. In some embodiments, one or both of the Fc polypeptides of the antibodies is a modified Fc polypeptide (e.g., modified to promote TfR binding and/or to enhance heterodimerization of the Fc polypeptides). A schematic drawing of such a bispecific antibody is shown in FIG. 1.

In some embodiments, an anti-HER2 antibody comprises:
- (a) a first antigen binding site for human HER2 subdomain IV;
- (b) a second antigen binding site for human HER2 subdomain II; and
- (c) a modified Fc polypeptide dimer comprising a first Fc polypeptide that contains modifications that create a TfR-binding site, wherein a light chain polypeptide sequence in the first antigen binding site is identical to a light chain polypeptide sequence in the second antigen binding site.

In other embodiments, an anti-HER2 antibody comprises:
- (a) a first antigen binding site for human HER2 subdomain II;
- (b) a second antigen binding site for human HER2 subdomain IV; and
- (c) a modified Fc polypeptide dimer comprising a first Fc polypeptide that contains modifications that create a TfR-binding site, wherein a light chain polypeptide sequence in the first antigen binding site is identical to a light chain polypeptide sequence in the second antigen binding site.

In some embodiments, the first Fc polypeptide comprises a modified CH3 domain comprising the TfR-binding site. In certain embodiments, the modified CH3 domain comprises substitutions in a set of amino acid positions as described herein that create the TfR-binding site.

In some embodiments, the first Fc polypeptide and the second Fc polypeptide each comprises modifications that promote heterodimerization. For example, the first Fc polypeptide can comprise a T366W substitution and the second Fc polypeptide can comprise T366S, L368A, and Y407V substitutions, according to EU numbering. In another example, the first Fc polypeptide can comprise T366S, L368A, and Y407V substitutions and the second Fc polypeptide can comprise a T366W substitution, according to EU numbering. Further, the first Fc polypeptide and/or the second Fc polypeptide independently can comprise modifications that reduce TfR-mediated effector function, i.e., reduce effector function upon TfR binding.

For example, the modifications that reduce TfR-mediated effector function are (i) L234A and L235A substitutions or (ii) L234A and L235A substitutions and a P329G or a P329S substitution, according to EU numbering.

In some embodiments, the first Fc polypeptide and/or the second Fc polypeptide independently comprises a S239D and/or a I332E substitution, according to EU numbering. In certain embodiments, the first Fc polypeptide or the second Fc polypeptide comprises a S239D and/or a I332E substitution, according to EU numbering. In certain other embodiments, the first Fc polypeptide comprises a S239D and/or a I332E substitution and the second Fc polypeptide comprises a S239D and/or a I332E substitution, according to EU numbering. In particular embodiments, the first Fc polypeptide and/or the second Fc polypeptide independently comprising the S239D and/or the I332E substitution is capable of enhancing HER2-mediated effector function, i.e., enhancing effector function upon HER2 binding.

In some embodiments, the first Fc polypeptide comprises a S239D substitution and the second Fc polypeptide comprises a S239D substitution, according to EU numbering. In some embodiments, the first Fc polypeptide comprises a I332E substitution and the second Fc polypeptide comprises a S239D substitution, according to EU numbering. In some embodiments, the first Fc polypeptide comprises a S239D and a I332E substitution and the second Fc polypeptide comprises a S239D substitution, according to EU numbering. In some embodiments, the second Fc polypeptide comprises a S239D substitution, according to EU numbering. In some embodiments, the first Fc polypeptide comprises a S239D substitution and the second Fc polypeptide comprises a I332E substitution, according to EU numbering. In some embodiments, the first Fc polypeptide comprises a I332E substitution and the second Fc polypeptide comprises a I332E substitution, according to EU numbering. In some embodiments, the first Fc polypeptide comprises a S239D and a I332E substitution and the second Fc polypeptide comprises a I332E substitution, according to EU numbering. In some embodiments, the second Fc polypeptide comprises a I332E substitution, according to EU numbering. In some embodiments, the first Fc polypeptide comprises a S239D substitution and the second Fc polypeptide comprises a S239D and a I332E substitution, according to EU numbering. In some embodiments, the first Fc polypeptide comprises a I332E substitution and the second Fc polypeptide comprises a S239D and a I332E substitution, according to EU numbering. In some embodiments, the first Fc polypeptide comprises a S239D and a I332E substitution and the second Fc polypeptide comprises a S239D and a I332E substitution, according to EU numbering. In some embodiments, the second Fc polypeptide comprises a S239D and a I332E substitution, according to EU numbering. In some embodiments, the first Fc polypeptide comprises a S239D substitution, according to EU numbering. In some embodiments, the first Fc polypeptide comprises a I332E substitution, according to EU numbering. In some embodiments, the first Fc polypeptide comprises a S239D and a I332E substitution, according to EU numbering.

In certain embodiments, the first Fc polypeptide comprises a I332E substitution and the second Fc polypeptide comprises a S239D substitution, according to EU numbering. In particular embodiments, the first Fc polypeptide comprises a I332E substitution and a serine at position 239, and the second Fc polypeptide comprises a S239D substitution and a isoleucine at position 332, according to EU numbering.

In certain embodiments, the first Fc polypeptide comprises a S239D and a I332E substitution and the second Fc polypeptide comprises a S239D substitution, according to EU numbering. In particular embodiments, the first Fc polypeptide comprises a S239D and a I332E substitution, and the second Fc polypeptide comprises a S239D substitution and a isoleucine at position 332, according to EU numbering.

In certain embodiments, the first Fc polypeptide comprises a S239D substitution and the second Fc polypeptide comprises a I332E substitution, according to EU numbering. In particular embodiments, the first Fc polypeptide comprises a S239D substitution and a isoleucine at position 332, and the second Fc polypeptide comprises a I332E substitution and a serine at position 239, according to EU numbering.

In certain embodiments, the second Fc polypeptide comprises a I332E substitution, according to EU numbering. In particular embodiments, the first Fc polypeptide comprises a serine at position 239 and a isoleucine at 332, and the second Fc polypeptide comprises a I332E substitution and a serine at position 239, according to EU numbering.

In certain embodiments, the first Fc polypeptide comprises a S239D substitution and the second Fc polypeptide comprises a S239D and a I332E substitution, according to EU numbering. In particular embodiments, the first Fc polypeptide comprises a S239D substitution and a isoleucine at position 332, and the second Fc polypeptide comprises a S239D and a I332E substitution, according to EU numbering.

In certain embodiments, the first Fc polypeptide comprises a I332E substitution, according to EU numbering. In particular embodiments, the first Fc polypeptide comprises a I332E substitution and a serine at position 239, according to EU numbering, and the second Fc polypeptide comprises a serine at position 239 and a isoleucine at 332.

In some embodiments, the first Fc polypeptide comprises the TfR-binding site, a T366W substitution, L234A and L235A substitutions (optionally including a P329G or a P329S substitution), and optionally a S239D and/or a I332E substitution, according to EU numbering, and the second Fc polypeptide comprises T366S, L368A, and Y407V substitutions and optionally a S239D and/or a I332E substitution, according to EU numbering. For example, the first Fc polypeptide can comprise a sequence having at least 90% (e.g., 91%, 92%, 93%, 94%, 95%, 96%, 97%, 98%, 99%, or 100%) identity to the sequence of any one of SEQ ID NOS:74-84, 86 and 98, and the second Fc polypeptide can comprise a sequence having at least 90% (e.g., 91%, 92%, 93%, 94%, 95%, 96%, 97%, 98%, 99%, or 100%) identity to the sequence of any one of SEQ ID NOS:71-73, 85, and 99-100.

In certain embodiments, the first Fc polypeptide comprises the TfR-binding site and contains L234A and L235A substitutions (optionally including a P329G or a P329S substitution) and the second Fc polypeptide does not include the L234A or L325A substitutions (or the P329G or P329S substitution if present in the first Fc polypeptide), according to EU numbering. In certain other embodiments, the first Fc polypeptide comprises the TfR-binding site and does not include the L234A or L325A substitutions (or the P329G or P329S substitution if present in the second Fc polypeptide) and the second Fc polypeptide contains L234A and L235A substitutions (optionally including a P329G or a P329S substitution), according to EU numbering.

In some embodiments, one or both of the Fc polypeptides can have its C-terminal lysine removed (e.g., the Lys residue at position 447 of the Fc polypeptide, according to EU numbering). In some embodiments, removal of the C-terminal lysines in the Fc polypeptides can improve the stability of the antibody.

In some embodiments, the antigen binding site for human HER2 subdomain II in the anti-HER2 antibody comprises one or more (e.g., one, two, or all three) CDRs selected from the group consisting of:

(a) a heavy chain CDR1 comprising the amino acid sequence of SEQ ID NO:89;

(b) a heavy chain CDR2 comprising the amino acid sequence of SEQ ID NO:90; and (c) a heavy chain CDR3 comprising the amino acid sequence of SEQ ID NO:91.

In certain embodiments, at least one of: $X_1$ in SEQ ID NO: 89 is not T; $X_2$ in SEQ ID NO: 89 is not F; $X_3$ in SEQ ID NO: 89 is not T; $X_1$ in SEQ ID NO: 90 is not N; $X_2$ in SEQ ID NO: 90 is not N; $X_3$ in SEQ ID NO: 90 is not S; $X_4$ in SEQ ID NO: 90 is not G; $X_5$ in SEQ ID NO: 90 is not G; $X_6$ in SEQ ID NO: 90 is not Q; $X_1$ in SEQ ID NO: 91 is not L; $X_2$ in SEQ ID NO: 91 is not G; $X_3$ in SEQ ID NO: 91 is not P; and $X_4$ in SEQ ID NO: 91 is not S.

In some embodiments, the heavy chain CDR1 comprises the amino acid sequence of SEQ ID NO:89, wherein $X_1$ is N, K, M, or H. In some embodiments, the heavy chain CDR2 comprises the amino acid sequence of SEQ ID NO:90, wherein $X_5$ is Q. In some embodiments, the heavy chain CDR2 comprises the amino acid sequence of SEQ ID NO:90, wherein $X_6$ is R, H, or T. In some embodiments, the heavy chain CDR3 comprises the amino acid sequence of SEQ ID NO:91, wherein $X_4$ is W, F, D, L, or Y. In some embodiments, the heavy chain CDR3 comprises the amino acid sequence of SEQ ID NO:91, wherein $X_4$ is L.

In some embodiments, the antigen binding site for human HER2 subdomain II in the anti-HER2 antibody comprises one or more (e.g., one, two, or all three) CDRs selected from the group consisting of (a) a heavy chain CDR1 comprising the amino acid sequence of SEQ ID NO:89;

(b) a heavy chain CDR2 comprising the amino acid sequence of SEQ ID NO:90, wherein $X_5$ is Q; and (c) a heavy chain CDR3 comprising the amino acid sequence of SEQ ID NO:91, wherein $X_4$ is L.

In some embodiments, the antigen binding site for human HER2 subdomain II in the anti-HER2 antibody comprises one or more (e.g., one, two, or all three) CDRs selected from the group consisting of:

(a) a heavy chain CDR1 having at least 90% (e.g., 91%, 92%, 93%, 94%, 95%, 96%, 97%, 98%, 99%, or 100%) sequence identity to an amino acid sequence selected from the group consisting of SEQ ID NOS:4 and 49-52 or having up to two amino acid substitutions relative to an amino acid sequence selected from the group consisting of SEQ ID NOS:4 and 49-52;

(b) a heavy chain CDR2 having at least 90% (e.g., 91%, 92%, 93%, 94%, 95%, 96%, 97%, 98%, 99%, or 100%) sequence identity to an amino acid sequence selected from the group consisting of SEQ ID NOS:5-6 and 53-55 or having up to two amino acid substitutions relative to an amino acid sequence selected from the group consisting of SEQ ID NOS:5-6 and 53-55; and (c) a heavy chain CDR3 having at least 90% (e.g., 91%, 92%, 93%, 94%, 95%, 96%, 97%, 98%, 99%, or 100%) sequence identity to an amino acid sequence selected from the group consisting of SEQ ID NOS:7-8 and 56-59 or having up to two amino acid substitutions relative to an amino acid sequence selected from the group consisting of SEQ ID NOS:7-8 and 56-59.

In some embodiments, the antigen binding site for human HER2 subdomain II in the anti-HER2 antibody comprises one or more (e.g., one, two, or all three) CDRs selected from the group consisting of:

(a) a heavy chain CDR1 having at least 90% (e.g., 91%, 92%, 93%, 94%, 95%, 96%, 97%, 98%, 99%, or 100%) sequence identity to the amino acid sequence of SEQ ID NO:4 or having up to two amino acid substitutions relative to the amino acid sequence of SEQ ID NO:4;

(b) a heavy chain CDR2 having at least 90% (e.g., 91%, 92%, 93%, 94%, 95%, 96%, 97%, 98%, 99%, or 100%) sequence identity to the amino acid sequence of SEQ ID NO:5 or SEQ ID NO:6 or having up to two amino acid substitutions relative to the amino acid sequence of SEQ ID NO:5 or SEQ ID NO:6; and (c) a heavy chain CDR3 having at least 90% (e.g., 91%, 92%, 93%, 94%, 95%, 96%, 97%, 98%, 99%, or 100%) sequence identity to the amino acid sequence of SEQ ID NO:7 or SEQ ID NO:8 or having up to two amino acid substitutions relative to the amino acid sequence of SEQ ID NO:7 or SEQ ID NO:8.

In some embodiments, the antigen binding site for human HER2 subdomain II in the anti-HER2 antibody comprises one or more (e.g., one, two, or all three) CDRs selected from the group consisting of:

(a) a heavy chain CDR1 comprising the amino acid sequence of SEQ ID NO:4;

(b) a heavy chain CDR2 comprising the amino acid sequence of SEQ ID NO:5 or SEQ ID NO:6; and (c) a heavy chain CDR3 comprising the amino acid sequence of SEQ ID NO:7 or SEQ ID NO:8.

In some embodiments, the antigen binding site for human HER2 subdomain II in the anti-HER2 antibody comprises one or more (e.g., one, two, or all three) CDRs selected from the group consisting of:

(a) a heavy chain CDR1 comprising the amino acid sequence of SEQ ID NO:4;

(b) a heavy chain CDR2 comprising the amino acid sequence of SEQ ID NO:6; and (c) a heavy chain CDR3 comprising the amino acid sequence of SEQ ID NO:7.

In some embodiments, the antigen binding site for human HER2 subdomain II in the anti-HER2 antibody comprises one or more (e.g., one, two, or all three) CDRs selected from the group consisting of:

(a) a heavy chain CDR1 comprising the amino acid sequence of SEQ ID NO:4;

(b) a heavy chain CDR2 comprising the amino acid sequence of SEQ ID NO:5; and (c) a heavy chain CDR3 comprising the amino acid sequence of SEQ ID NO:8.

In some embodiments, the antigen binding site for human HER2 subdomain II in the anti-HER2 antibody comprises one or more (e.g., one, two, or all three) CDRs selected from the group consisting of:

(a) a heavy chain CDR1 comprising the amino acid sequence of SEQ ID NO:4;

(b) a heavy chain CDR2 comprising the amino acid sequence of SEQ ID NO:6; and (c) a heavy chain CDR3 comprising the amino acid sequence of SEQ ID NO:8.

In some embodiments, the antigen binding site for human HER2 subdomain II in the anti-HER2 antibody comprises a heavy chain variable region comprising an amino acid sequence having at least 90% (e.g., 91%, 92%, 93%, 94%, 95%, 96%, 97%, 98%, 99%, or 100%) sequence identity to any one of SEQ ID NOS:1-3 and 60-70. In some embodiments, the antigen binding site for human HER2 subdomain II in the anti-HER2 antibody comprises a heavy chain variable region comprising the amino acid sequence of any one of SEQ ID NOS:1-3 and 60-70.

In some embodiments, the antigen binding site for human HER2 subdomain IV in the anti-HER2 antibody comprises one or more (e.g., one, two, or all three) CDRs selected from the group consisting of:

(a) a heavy chain CDR1 comprising the amino acid sequence of SEQ ID NO: 16 or having up to two amino acid substitutions relative to the amino acid sequence of SEQ ID NO:16;

(b) a heavy chain CDR2 having at least 90% (e.g., 91%, 92%, 93%, 94%, 95%, 96%, 97%, 98%, 99%, or 100%) sequence identity to the amino acid sequence of SEQ ID NO:17 or having up to two amino acid substitutions relative to the amino acid sequence of SEQ ID NO:17; and (c) a heavy chain CDR3 having at least 90% (e.g., 91%, 92%, 93%, 94%, 95%, 96%, 97%, 98%, 99%, or 100%) sequence identity to the amino acid sequence of SEQ ID NO:18 or having up to two amino acid substitutions relative to the amino acid sequence of SEQ ID NO:18.

In some embodiments, the antigen binding site for human HER2 subdomain IV in the anti-HER2 antibody comprises one or more (e.g., one, two, or all three) CDRs selected from the group consisting of:

(a) a heavy chain CDR1 comprising the amino acid sequence of SEQ ID NO:16;

(b) a heavy chain CDR2 comprising the amino acid sequence of SEQ ID NO: 17; and (c) a heavy chain CDR3 comprising the amino acid sequence of SEQ ID NO:18.

In some embodiments, the antigen binding site for human HER2 subdomain IV in the anti-HER2 antibody comprises a heavy chain variable region comprising an amino acid sequence having at least 90% (e.g., 91%, 92%, 93%, 94%, 95%, 96%, 97%, 98%, 99%, or 100%) sequence identity to SEQ ID NO:15. In some embodiments, the antigen binding site for human HER2 subdomain IV in the anti-HER2 antibody comprises a heavy chain variable region comprising the sequence of SEQ ID NO:15.

In some embodiments, the light chain polypeptide sequence in the first and second antigen binding sites, i.e., one for HER2 subdomain II and the other for HER2 subdomain IV, in the anti-HER2 antibody comprises one or more (e.g., one, two, or all three) CDRs selected from the group consisting of:

(a) a light chain CDR1 having at least 90% (e.g., 91%, 92%, 93%, 94%, 95%, 96%, 97%, 98%, 99%, or 100%) sequence identity to the amino acid sequence of SEQ ID NO:11 or having up to two amino acid substitutions relative to the amino acid sequence of SEQ ID NO:11;

(b) alight chain CDR2 having up to two amino acid substitutions relative to the amino acid sequence of SEQ ID NO:12; and (c) alight chain CDR3 having up to two amino acid substitutions relative to the amino acid sequence of SEQ ID NO:13 or 14.

In some embodiments, the light chain polypeptide sequence comprises one or more (e.g., one, two, or all three) CDRs selected from the group consisting of:

(a) a light chain CDR1 comprising the amino acid sequence of SEQ ID NO:11;

(b) a light chain CDR2 comprising the amino acid sequence of SEQ ID NO:12; and (c) a light chain CDR3 comprising the amino acid sequence of SEQ ID NO:13 or 14.

In some embodiments, the light chain polypeptide sequence comprises one or more (e.g., one, two, or all three) CDRs selected from the group consisting of:

(a) a light chain CDR1 comprising the amino acid sequence of SEQ ID NO:11;

(b) a light chain CDR2 comprising the amino acid sequence of SEQ ID NO:12; and (c) a light chain CDR3 comprising the amino acid sequence of SEQ ID NO:13.

In some embodiments, the light chain polypeptide sequence comprises one or more (e.g., one, two, or all three) CDRs selected from the group consisting of:

(a) a light chain CDR1 comprising the amino acid sequence of SEQ ID NO:11;

(b) a light chain CDR2 comprising the amino acid sequence of SEQ ID NO:12; and (c) a light chain CDR3 comprising the amino acid sequence of SEQ ID NO:14.

In certain embodiments, the light chain polypeptide sequence comprises a light chain CDR3 comprising the amino acid sequence of SEQ ID NO: 13 or 14 and optionally further comprises one or more (e.g., one or both) CDRs selected from the group consisting of: a light chain CDR1 having at least 90% (e.g., 91%, 92%, 93%, 94%, 95%, 96%, 97%, 98%, 99%, or 100%) sequence identity to the amino acid sequence of SEQ ID NO:11 or having up to two amino acid substitutions relative to the amino acid sequence of SEQ ID NO: 11; and a light chain CDR2 having up to two amino acid substitutions relative to the amino acid sequence of SEQ ID NO:12. In particular embodiments, the light chain polypeptide sequence comprises the amino acid sequence of SEQ ID NO: 13 or 14 and optionally further comprises one or more (e.g., one or both) CDRs selected from the group consisting of: a light chain CDR1 comprising the amino acid sequence of SEQ ID NO: 11; and a light chain CDR2 comprising the amino acid sequence of SEQ ID NO:12.

In some embodiments, the light chain polypeptide sequence comprises a light chain variable region comprising an amino acid sequence having at least 90% (e.g., 91%, 92%, 93%, 94%, 95%, 96%, 97%, 98%, 99%, or 100%) sequence identity to any one of SEQ ID NOS:9-10. In some embodiments, the light chain polypeptide sequence comprises a light chain variable region comprising the amino acid sequence of any one of SEQ ID NOS:9-10.

In some embodiments, the anti-HER2 antibody comprises heavy and light chain CDRs selected from the combinations listed in Table 1, i.e., any one of Combo #A-AC.

In particular embodiments of this antibody:

(a) the first heavy chain comprises a heavy chain CDR1 comprising the amino acid sequence of SEQ ID NO:16, a heavy chain CDR2 comprising the amino acid sequence of SEQ ID NO:17, and a heavy chain CDR3 comprising the amino acid sequence of SEQ ID NO:18;

(b) the second heavy chain comprises a heavy chain CDR1 comprising the amino acid sequence of any one of SEQ ID NOS:4 and 49-52, a heavy chain CDR2 comprising the amino acid sequence of any one of SEQ ID NOS: 5-6 and 53-55, and a heavy chain CDR3 comprising the amino acid sequence of any one of SEQ ID NOS:7-8 and 56-59; and (c) the light chain comprises a light chain CDR1 comprising the amino acid sequence of SEQ ID NO:11, a light chain CDR2 comprising the amino acid sequence of SEQ ID NO:12, and a light chain CDR3 comprising the amino acid sequence of any one of SEQ ID NOS: 13-14.

In certain embodiments of the anti-HER2 antibody, the first antigen binding site comprises an amino acid sequence selected from the group consisting of SEQ ID NO:15; the second antigen binding site comprises the amino acid sequence of SEQ ID NOS:1-3 and 60-70; the first Fc polypeptide comprises an amino acid sequence selected from the group consisting of SEQ ID NOS:74-84, 86, and 98; and the light chain polypeptide sequence comprises an amino acid sequence selected from the group consisting of SEQ ID NOS:9-10 and 19. In some embodiments, the antibody further comprises a second Fc polypeptide comprising an amino acid sequence selected from the group consisting of SEQ ID NOS:71-73, 85, and 99-100.

In certain other embodiments of the anti-HER2 antibody, the first antigen binding site comprises an amino acid sequence selected from the group consisting of SEQ ID NOS:1-3 and 60-70; the second antigen binding site comprises the amino acid sequence of SEQ ID NO:15; the first Fc polypeptide comprises an amino acid sequence selected from the group consisting of SEQ ID NOS:74-84, 86, and 98; and the light chain polypeptide sequence comprises an amino acid sequence selected from the group consisting of SEQ ID NOS:9-10 and 19. In some embodiments, the antibody further comprises a second Fc polypeptide comprising an amino acid sequence selected from the group consisting of SEQ ID NOS:71-73, 85, and 99-100.

In some embodiments, the anti-HER2 antibody comprises a first heavy chain for binding to human HER2 subdomain II or IV, a second heavy chain for binding to the other HER2 subdomain, and two identical light chains.

In certain embodiments, the anti-HER2 antibody comprises heavy and light chains each having at least 90% (e.g., 91%, 92%, 93%, 94%, 95%, 96%, 97%, 98%, 99%, or 100%) sequence identity to the amino acid sequences selected from the combinations listed in Table 2, i.e., any one of Combo #A-AT.

In particular embodiments of this antibody:

(a) the first heavy chain comprises SEQ ID NO:37, the second heavy chain comprises SEQ ID NO:25, and the light chain comprises SEQ ID NO:9;

(b) the first heavy chain comprises SEQ ID NO:31, the second heavy chain comprises SEQ ID NO:30, and the light chain comprises SEQ ID NO:9;

(c) the first heavy chain comprises SEQ ID NO:31, the second heavy chain comprises SEQ ID NO:29, and the light chain comprises SEQ ID NO:9;

(d) the first heavy chain comprises SEQ ID NO:38, the second heavy chain comprises SEQ ID NO:30, and the light chain comprises SEQ ID NO:9;

(e) the first heavy chain comprises SEQ ID NO:32, the second heavy chain comprises SEQ ID NO:30, and the light chain comprises SEQ ID NO:9;

(f) the first heavy chain comprises SEQ ID NO:32, the second heavy chain comprises SEQ ID NO:29, and the light chain comprises SEQ ID NO:9;

(g) the first heavy chain comprises SEQ ID NO:39, the second heavy chain comprises SEQ ID NO:30, and the light chain comprises SEQ ID NO:9;

(h) the first heavy chain comprises SEQ ID NO:37, the second heavy chain comprises SEQ ID NO:26, and the light chain comprises SEQ ID NO:9;

(i) the first heavy chain comprises SEQ ID NO:31, the second heavy chain comprises SEQ ID NO:34, and the light chain comprises SEQ ID NO:9;

(j) the first heavy chain comprises SEQ ID NO:31, the second heavy chain comprises SEQ ID NO:33, and the light chain comprises SEQ ID NO:9;

(k) the first heavy chain comprises SEQ ID NO:38, the second heavy chain comprises SEQ ID NO:34, and the light chain comprises SEQ ID NO:9;

(l) the first heavy chain comprises SEQ ID NO:32, the second heavy chain comprises SEQ ID NO:34, and the light chain comprises SEQ ID NO:9;

(m) the first heavy chain comprises SEQ ID NO:32, the second heavy chain comprises SEQ ID NO:33, and the light chain comprises SEQ ID NO:9;

(n) the first heavy chain comprises SEQ ID NO:39, the second heavy chain comprises SEQ ID NO:34, and the light chain comprises SEQ ID NO:9;

(o) the first heavy chain comprises SEQ ID NO:37, the second heavy chain comprises SEQ ID NO:27, and the light chain comprises SEQ ID NO:9;

(p) the first heavy chain comprises SEQ ID NO:31, the second heavy chain comprises SEQ ID NO:36, and the light chain comprises SEQ ID NO:9;

(q) the first heavy chain comprises SEQ ID NO:31, the second heavy chain comprises SEQ ID NO:35, and the light chain comprises SEQ ID NO:9;

(r) the first heavy chain comprises SEQ ID NO:38, the second heavy chain comprises SEQ ID NO:36, and the light chain comprises SEQ ID NO:9;

(s) the first heavy chain comprises SEQ ID NO:32, the second heavy chain comprises SEQ ID NO:36, and the light chain comprises SEQ ID NO:9;

(t) the first heavy chain comprises SEQ ID NO:32, the second heavy chain comprises SEQ ID NO:35, and the light chain comprises SEQ ID NO:9;

(u) the first heavy chain comprises SEQ ID NO:39, the second heavy chain comprises SEQ ID NO:46, and the light chain comprises SEQ ID NO:9;

(v) the first heavy chain comprises SEQ ID NO:37, the second heavy chain comprises SEQ ID NO:25, and the light chain comprises SEQ ID NO:10;

(w) the first heavy chain comprises SEQ ID NO:31, the second heavy chain comprises SEQ ID NO:30, and the light chain comprises SEQ ID NO:10;

(x) the first heavy chain comprises SEQ ID NO:31, the second heavy chain comprises SEQ ID NO:29, and the light chain comprises SEQ ID NO:10;

(y) the first heavy chain comprises SEQ ID NO:38, the second heavy chain comprises SEQ ID NO:30, and the light chain comprises SEQ ID NO:10;

(z) the first heavy chain comprises SEQ ID NO:32, the second heavy chain comprises SEQ ID NO:30, and the light chain comprises SEQ ID NO:10;

(aa) the first heavy chain comprises SEQ ID NO:32, the second heavy chain comprises SEQ ID NO:29, and the light chain comprises SEQ ID NO:10;

(ab) the first heavy chain comprises SEQ ID NO:39, the second heavy chain comprises SEQ ID NO:30, and the light chain comprises SEQ ID NO:10;

(ac) the first heavy chain comprises SEQ ID NO:37, the second heavy chain comprises SEQ ID NO:26, and the light chain comprises SEQ ID NO:10;

(ad) the first heavy chain comprises SEQ ID NO:31, the second heavy chain comprises SEQ ID NO:34, and the light chain comprises SEQ ID NO:10;

(ae) the first heavy chain comprises SEQ ID NO:31, the second heavy chain comprises SEQ ID NO:33, and the light chain comprises SEQ ID NO:10;

(af) the first heavy chain comprises SEQ ID NO:38, the second heavy chain comprises SEQ ID NO:34, and the light chain comprises SEQ ID NO:10;

(ag) the first heavy chain comprises SEQ ID NO:32, the second heavy chain comprises SEQ ID NO:34, and the light chain comprises SEQ ID NO:10;

(ah) the first heavy chain comprises SEQ ID NO:32, the second heavy chain comprises SEQ ID NO:33, and the light chain comprises SEQ ID NO:10;

(ai) the first heavy chain comprises SEQ ID NO:39, the second heavy chain comprises SEQ ID NO:34, and the light chain comprises SEQ ID NO:10;

(aj) the first heavy chain comprises SEQ ID NO:37, the second heavy chain comprises SEQ ID NO:27, and the light chain comprises SEQ ID NO:10;

(ak) the first heavy chain comprises SEQ ID NO:31, the second heavy chain comprises SEQ ID NO:36, and the light chain comprises SEQ ID NO:10;

(al) the first heavy chain comprises SEQ ID NO:31, the second heavy chain comprises SEQ ID NO:35, and the light chain comprises SEQ ID NO:10;

(am) the first heavy chain comprises SEQ ID NO:38, the second heavy chain comprises SEQ ID NO:36, and the light chain comprises SEQ ID NO:10;

(an) the first heavy chain comprises SEQ ID NO:32, the second heavy chain comprises SEQ ID NO:36, and the light chain comprises SEQ ID NO:10;

(ao) the first heavy chain comprises SEQ ID NO:32, the second heavy chain comprises SEQ ID NO:35, and the light chain comprises SEQ ID NO:10;

(ap) the first heavy chain comprises SEQ ID NO:39, the second heavy chain comprises SEQ ID NO:46, and the light chain comprises SEQ ID NO:10;

(aq) the first heavy chain comprises SEQ ID NO:20, the second heavy chain comprises SEQ ID NO:24, and the light chain comprises SEQ ID NO:19;

(ar) the first heavy chain comprises SEQ ID NO:21, the second heavy chain comprises SEQ ID NO:24, and the light chain comprises SEQ ID NO:19;

(as) the first heavy chain comprises SEQ ID NO:22, the second heavy chain comprises SEQ ID NO:24, and the light chain comprises SEQ ID NO:19; or (at) the first heavy chain comprises SEQ ID NO:23, the second heavy chain comprises SEQ ID NO:24, and the light chain comprises SEQ ID NO:19.

In certain embodiments, the anti-HER2 antibody comprises a first heavy chain comprising a $V_H$ and a Fc sequence each having at least 90% (e.g., 91%, 92%, 93%, 94%, 95%, 96%, 97%, 98%, 99%, or 100%) sequence identity to the amino acid sequences selected from the combinations in Table 3, i.e., any one of Combo #A-L, and a second heavy chain comprising a $V_H$ and a Fc sequence each having at least 90% (e.g., 91%, 92%, 93%, 94%, 95%, 96%, 97%, 98%, 99%, or 100%) sequence identity to the amino acid sequences selected from the combinations in Table 4, i.e., any one of Combo #A-L. In any of these heavy chain combinations, the light chain polypeptide sequence has at least 90% (e.g., 91%, 92%, 93%, 94%, 95%, 96%, 97%, 98%, 99%, or 100%) sequence identity to an amino acid sequence selected from the group consisting of SEQ ID NOS:9-10 and 19.

In particular embodiments of this antibody:

(a) the first heavy chain comprises SEQ ID NOS:1 and 71 and the second heavy chain comprises SEQ ID NOS:15 and 86;

(b) the first heavy chain comprises SEQ ID NOS:1 and 71 and the second heavy chain comprises SEQ ID NOS:15 and 74;

(c) the first heavy chain comprises SEQ ID NOS:1 and 71 and the second heavy chain comprises SEQ ID NOS:15 and 75;

(d) the first heavy chain comprises SEQ ID NOS:1 and 71 and the second heavy chain comprises SEQ ID NOS:15 and 76;

(e) the first heavy chain comprises SEQ ID NOS:1 and 71 and the second heavy chain comprises SEQ ID NOS:15 and 77;

(f) the first heavy chain comprises SEQ ID NOS:1 and 71 and the second heavy chain comprises SEQ ID NOS:15 and 78;

(g) the first heavy chain comprises SEQ ID NOS:1 and 71 and the second heavy chain comprises SEQ ID NOS:15 and 79;

(h) the first heavy chain comprises SEQ ID NOS:1 and 71 and the second heavy chain comprises SEQ ID NOS:15 and 80;

(i) the first heavy chain comprises SEQ ID NOS:1 and 71 and the second heavy chain comprises SEQ ID NOS:15 and 81;

(j) the first heavy chain comprises SEQ ID NOS:1 and 71 and the second heavy chain comprises SEQ ID NOS:15 and 82;

(k) the first heavy chain comprises SEQ ID NOS:1 and 71 and the second heavy chain comprises SEQ ID NOS:15 and 83; or (l) the first heavy chain comprises SEQ ID NOS:1 and 71 and the second heavy chain comprises SEQ ID NOS:15 and 84.

In particular embodiments of this antibody:

(a) the first heavy chain comprises SEQ ID NOS:2 and 71 and the second heavy chain comprises SEQ ID NOS:15 and 86;

(b) the first heavy chain comprises SEQ ID NOS:2 and 71 and the second heavy chain comprises SEQ ID NOS:15 and 74;

(c) the first heavy chain comprises SEQ ID NOS:2 and 71 and the second heavy chain comprises SEQ ID NOS:15 and 75;

(d) the first heavy chain comprises SEQ ID NOS:2 and 71 and the second heavy chain comprises SEQ ID NOS:15 and 76;

(e) the first heavy chain comprises SEQ ID NOS:2 and 71 and the second heavy chain comprises SEQ ID NOS:15 and 77;

(f) the first heavy chain comprises SEQ ID NOS:2 and 71 and the second heavy chain comprises SEQ ID NOS:15 and 78;

(g) the first heavy chain comprises SEQ ID NOS:2 and 71 and the second heavy chain comprises SEQ ID NOS:15 and 79;

(h) the first heavy chain comprises SEQ ID NOS:2 and 71 and the second heavy chain comprises SEQ ID NOS:15 and 80;

(i) the first heavy chain comprises SEQ ID NOS:2 and 71 and the second heavy chain comprises SEQ ID NOS:15 and 81;

(j) the first heavy chain comprises SEQ ID NOS:2 and 71 and the second heavy chain comprises SEQ ID NOS:15 and 82;

(k) the first heavy chain comprises SEQ ID NOS:2 and 71 and the second heavy chain comprises SEQ ID NOS:15 and 83; or (l) the first heavy chain comprises SEQ ID NOS:2 and 71 and the second heavy chain comprises SEQ ID NOS:15 and 84.

In particular embodiments of this antibody:

(a) the first heavy chain comprises SEQ ID NOS:3 and 71 and the second heavy chain comprises SEQ ID NOS:15 and 86;

(b) the first heavy chain comprises SEQ ID NOS:3 and 71 and the second heavy chain comprises SEQ ID NOS:15 and 74;

(c) the first heavy chain comprises SEQ ID NOS:3 and 71 and the second heavy chain comprises SEQ ID NOS:15 and 75;

(d) the first heavy chain comprises SEQ ID NOS:3 and 71 and the second heavy chain comprises SEQ ID NOS:15 and 76;

(e) the first heavy chain comprises SEQ ID NOS:3 and 71 and the second heavy chain comprises SEQ ID NOS:15 and 77;

(f) the first heavy chain comprises SEQ ID NOS:3 and 71 and the second heavy chain comprises SEQ ID NOS:15 and 78;

(g) the first heavy chain comprises SEQ ID NOS:3 and 71 and the second heavy chain comprises SEQ ID NOS:15 and 79;

(h) the first heavy chain comprises SEQ ID NOS:3 and 71 and the second heavy chain comprises SEQ ID NOS:15 and 80;

(i) the first heavy chain comprises SEQ ID NOS:3 and 71 and the second heavy chain comprises SEQ ID NOS:15 and 81;

(j) the first heavy chain comprises SEQ ID NOS:3 and 71 and the second heavy chain comprises SEQ ID NOS:15 and 82;

(k) the first heavy chain comprises SEQ ID NOS:3 and 71 and the second heavy chain comprises SEQ ID NOS:15 and 83; or (l) the first heavy chain comprises SEQ ID NOS:3 and 71 and the second heavy chain comprises SEQ ID NOS:15 and 84.

In particular embodiments of this antibody:

(a) the first heavy chain comprises SEQ ID NOS:1 and 72 and the second heavy chain comprises SEQ ID NOS:15 and 86;

(b) the first heavy chain comprises SEQ ID NOS:1 and 72 and the second heavy chain comprises SEQ ID NOS:15 and 74;

(c) the first heavy chain comprises SEQ ID NOS:1 and 72 and the second heavy chain comprises SEQ ID NOS:15 and 75;

(d) the first heavy chain comprises SEQ ID NOS:1 and 72 and the second heavy chain comprises SEQ ID NOS:15 and 76;

(e) the first heavy chain comprises SEQ ID NOS:1 and 72 and the second heavy chain comprises SEQ ID NOS:15 and 77;

(f) the first heavy chain comprises SEQ ID NOS:1 and 72 and the second heavy chain comprises SEQ ID NOS:15 and 78;

(g) the first heavy chain comprises SEQ ID NOS:1 and 72 and the second heavy chain comprises SEQ ID NOS:15 and 79;

(h) the first heavy chain comprises SEQ ID NOS:1 and 72 and the second heavy chain comprises SEQ ID NOS:15 and 80;

(i) the first heavy chain comprises SEQ ID NOS:1 and 72 and the second heavy chain comprises SEQ ID NOS:15 and 81;

(j) the first heavy chain comprises SEQ ID NOS:1 and 72 and the second heavy chain comprises SEQ ID NOS:15 and 82;

(k) the first heavy chain comprises SEQ ID NOS:1 and 72 and the second heavy chain comprises SEQ ID NOS:15 and 83; or (l) the first heavy chain comprises SEQ ID NOS:1 and 72 and the second heavy chain comprises SEQ ID NOS:15 and 84.

In particular embodiments of this antibody:

(a) the first heavy chain comprises SEQ ID NOS:2 and 72 and the second heavy chain comprises SEQ ID NOS:15 and 86;

(b) the first heavy chain comprises SEQ ID NOS:2 and 72 and the second heavy chain comprises SEQ ID NOS:15 and 74;

(c) the first heavy chain comprises SEQ ID NOS:2 and 72 and the second heavy chain comprises SEQ ID NOS:15 and 75;

(d) the first heavy chain comprises SEQ ID NOS:2 and 72 and the second heavy chain comprises SEQ ID NOS:15 and 76;

(e) the first heavy chain comprises SEQ ID NOS:2 and 72 and the second heavy chain comprises SEQ ID NOS:15 and 77;

(f) the first heavy chain comprises SEQ ID NOS:2 and 72 and the second heavy chain comprises SEQ ID NOS:15 and 78;

(g) the first heavy chain comprises SEQ ID NOS:2 and 72 and the second heavy chain comprises SEQ ID NOS:15 and 79;

(h) the first heavy chain comprises SEQ ID NOS:2 and 72 and the second heavy chain comprises SEQ ID NOS:15 and 80;

(i) the first heavy chain comprises SEQ ID NOS:2 and 72 and the second heavy chain comprises SEQ ID NOS:15 and 81;

(j) the first heavy chain comprises SEQ ID NOS:2 and 72 and the second heavy chain comprises SEQ ID NOS:15 and 82;

(k) the first heavy chain comprises SEQ ID NOS:2 and 72 and the second heavy chain comprises SEQ ID NOS:15 and 83; or (l) the first heavy chain comprises SEQ ID NOS:2 and 72 and the second heavy chain comprises SEQ ID NOS:15 and 84.

In particular embodiments of this antibody:

(a) the first heavy chain comprises SEQ ID NOS:3 and 72 and the second heavy chain comprises SEQ ID NOS:15 and 86;

(b) the first heavy chain comprises SEQ ID NOS:3 and 72 and the second heavy chain comprises SEQ ID NOS:15 and 74;

(c) the first heavy chain comprises SEQ ID NOS:3 and 72 and the second heavy chain comprises SEQ ID NOS:15 and 75;

(d) the first heavy chain comprises SEQ ID NOS:3 and 72 and the second heavy chain comprises SEQ ID NOS:15 and 76;
(e) the first heavy chain comprises SEQ ID NOS:3 and 72 and the second heavy chain comprises SEQ ID NOS:15 and 77;
(f) the first heavy chain comprises SEQ ID NOS:3 and 72 and the second heavy chain comprises SEQ ID NOS:15 and 78;
(g) the first heavy chain comprises SEQ ID NOS:3 and 72 and the second heavy chain comprises SEQ ID NOS:15 and 79;
(h) the first heavy chain comprises SEQ ID NOS:3 and 72 and the second heavy chain comprises SEQ ID NOS:15 and 80;
(i) the first heavy chain comprises SEQ ID NOS:3 and 72 and the second heavy chain comprises SEQ ID NOS:15 and 81;
(j) the first heavy chain comprises SEQ ID NOS:3 and 72 and the second heavy chain comprises SEQ ID NOS:15 and 82;
(k) the first heavy chain comprises SEQ ID NOS:3 and 72 and the second heavy chain comprises SEQ ID NOS:15 and 83; or
(l) the first heavy chain comprises SEQ ID NOS:3 and 72 and the second heavy chain comprises SEQ ID NOS:15 and 84.

In particular embodiments of this antibody:
(a) the first heavy chain comprises SEQ ID NOS:1 and 73 and the second heavy chain comprises SEQ ID NOS:15 and 86;
(b) the first heavy chain comprises SEQ ID NOS:1 and 73 and the second heavy chain comprises SEQ ID NOS:15 and 74;
(c) the first heavy chain comprises SEQ ID NOS:1 and 73 and the second heavy chain comprises SEQ ID NOS:15 and 75;
(d) the first heavy chain comprises SEQ ID NOS:1 and 73 and the second heavy chain comprises SEQ ID NOS:15 and 76;
(e) the first heavy chain comprises SEQ ID NOS:1 and 73 and the second heavy chain comprises SEQ ID NOS:15 and 77;
(f) the first heavy chain comprises SEQ ID NOS:1 and 73 and the second heavy chain comprises SEQ ID NOS:15 and 78;
(g) the first heavy chain comprises SEQ ID NOS:1 and 73 and the second heavy chain comprises SEQ ID NOS:15 and 79;
(h) the first heavy chain comprises SEQ ID NOS:1 and 73 and the second heavy chain comprises SEQ ID NOS:15 and 80;
(i) the first heavy chain comprises SEQ ID NOS:1 and 73 and the second heavy chain comprises SEQ ID NOS:15 and 81;
(j) the first heavy chain comprises SEQ ID NOS:1 and 73 and the second heavy chain comprises SEQ ID NOS:15 and 82;
(k) the first heavy chain comprises SEQ ID NOS:1 and 73 and the second heavy chain comprises SEQ ID NOS:15 and 83; or
(l) the first heavy chain comprises SEQ ID NOS:1 and 73 and the second heavy chain comprises SEQ ID NOS:15 and 84.

In particular embodiments of this antibody:
(a) the first heavy chain comprises SEQ ID NOS:2 and 73 and the second heavy chain comprises SEQ ID NOS:15 and 86;
(b) the first heavy chain comprises SEQ ID NOS:2 and 73 and the second heavy chain comprises SEQ ID NOS:15 and 74;
(c) the first heavy chain comprises SEQ ID NOS:2 and 73 and the second heavy chain comprises SEQ ID NOS:15 and 75;
(d) the first heavy chain comprises SEQ ID NOS:2 and 73 and the second heavy chain comprises SEQ ID NOS:15 and 76;
(e) the first heavy chain comprises SEQ ID NOS:2 and 73 and the second heavy chain comprises SEQ ID NOS:15 and 77;
(f) the first heavy chain comprises SEQ ID NOS:2 and 73 and the second heavy chain comprises SEQ ID NOS:15 and 78;
(g) the first heavy chain comprises SEQ ID NOS:2 and 73 and the second heavy chain comprises SEQ ID NOS:15 and 79;
(h) the first heavy chain comprises SEQ ID NOS:2 and 73 and the second heavy chain comprises SEQ ID NOS:15 and 80;
(i) the first heavy chain comprises SEQ ID NOS:2 and 73 and the second heavy chain comprises SEQ ID NOS:15 and 81;
(j) the first heavy chain comprises SEQ ID NOS:2 and 73 and the second heavy chain comprises SEQ ID NOS:15 and 82;
(k) the first heavy chain comprises SEQ ID NOS:2 and 73 and the second heavy chain comprises SEQ ID NOS:15 and 83; or
(l) the first heavy chain comprises SEQ ID NOS:2 and 73 and the second heavy chain comprises SEQ ID NOS:15 and 84.

In particular embodiments of this antibody:
(a) the first heavy chain comprises SEQ ID NOS:3 and 73 and the second heavy chain comprises SEQ ID NOS:15 and 86;
(b) the first heavy chain comprises SEQ ID NOS:3 and 73 and the second heavy chain comprises SEQ ID NOS:15 and 74;
(c) the first heavy chain comprises SEQ ID NOS:3 and 73 and the second heavy chain comprises SEQ ID NOS:15 and 75;
(d) the first heavy chain comprises SEQ ID NOS:3 and 73 and the second heavy chain comprises SEQ ID NOS:15 and 76;
(e) the first heavy chain comprises SEQ ID NOS:3 and 73 and the second heavy chain comprises SEQ ID NOS:15 and 77;
(f) the first heavy chain comprises SEQ ID NOS:3 and 73 and the second heavy chain comprises SEQ ID NOS:15 and 78;
(g) the first heavy chain comprises SEQ ID NOS:3 and 73 and the second heavy chain comprises SEQ ID NOS:15 and 79;
(h) the first heavy chain comprises SEQ ID NOS:3 and 73 and the second heavy chain comprises SEQ ID NOS:15 and 80;
(i) the first heavy chain comprises SEQ ID NOS:3 and 73 and the second heavy chain comprises SEQ ID NOS:15 and 81;
(j) the first heavy chain comprises SEQ ID NOS:3 and 73 and the second heavy chain comprises SEQ ID NOS:15 and 82;

(k) the first heavy chain comprises SEQ ID NOS:3 and 73 and the second heavy chain comprises SEQ ID NOS:15 and 83; or (l) the first heavy chain comprises SEQ ID NOS:3 and 73 and the second heavy chain comprises SEQ ID NOS:15 and 84.

In particular embodiments of this antibody:

(a) the first heavy chain comprises SEQ ID NOS:1 and 85 and the second heavy chain comprises SEQ ID NOS:15 and 86;

(b) the first heavy chain comprises SEQ ID NOS:1 and 85 and the second heavy chain comprises SEQ ID NOS:15 and 74;

(c) the first heavy chain comprises SEQ ID NOS:1 and 85 and the second heavy chain comprises SEQ ID NOS:15 and 75;

(d) the first heavy chain comprises SEQ ID NOS:1 and 85 and the second heavy chain comprises SEQ ID NOS:15 and 76;

(e) the first heavy chain comprises SEQ ID NOS:1 and 85 and the second heavy chain comprises SEQ ID NOS:15 and 77;

(f) the first heavy chain comprises SEQ ID NOS:1 and 85 and the second heavy chain comprises SEQ ID NOS:15 and 78;

(g) the first heavy chain comprises SEQ ID NOS:1 and 85 and the second heavy chain comprises SEQ ID NOS:15 and 79;

(h) the first heavy chain comprises SEQ ID NOS:1 and 85 and the second heavy chain comprises SEQ ID NOS:15 and 80;

(i) the first heavy chain comprises SEQ ID NOS:1 and 85 and the second heavy chain comprises SEQ ID NOS:15 and 81;

(j) the first heavy chain comprises SEQ ID NOS:1 and 85 and the second heavy chain comprises SEQ ID NOS:15 and 82;

(k) the first heavy chain comprises SEQ ID NOS:1 and 85 and the second heavy chain comprises SEQ ID NOS:15 and 83; or (l) the first heavy chain comprises SEQ ID NOS:1 and 85 and the second heavy chain comprises SEQ ID NOS:15 and 84.

In particular embodiments of this antibody:

(a) the first heavy chain comprises SEQ ID NOS:2 and 85 and the second heavy chain comprises SEQ ID NOS:15 and 86;

(b) the first heavy chain comprises SEQ ID NOS:2 and 85 and the second heavy chain comprises SEQ ID NOS:15 and 74;

(c) the first heavy chain comprises SEQ ID NOS:2 and 85 and the second heavy chain comprises SEQ ID NOS:15 and 75;

(d) the first heavy chain comprises SEQ ID NOS:2 and 85 and the second heavy chain comprises SEQ ID NOS:15 and 76;

(e) the first heavy chain comprises SEQ ID NOS:2 and 85 and the second heavy chain comprises SEQ ID NOS:15 and 77;

(f) the first heavy chain comprises SEQ ID NOS:2 and 85 and the second heavy chain comprises SEQ ID NOS:15 and 78;

(g) the first heavy chain comprises SEQ ID NOS:2 and 85 and the second heavy chain comprises SEQ ID NOS:15 and 79;

(h) the first heavy chain comprises SEQ ID NOS:2 and 85 and the second heavy chain comprises SEQ ID NOS:15 and 80;

(i) the first heavy chain comprises SEQ ID NOS:2 and 85 and the second heavy chain comprises SEQ ID NOS:15 and 81;

(j) the first heavy chain comprises SEQ ID NOS:2 and 85 and the second heavy chain comprises SEQ ID NOS:15 and 82;

(k) the first heavy chain comprises SEQ ID NOS:2 and 85 and the second heavy chain comprises SEQ ID NOS:15 and 83; or (l) the first heavy chain comprises SEQ ID NOS:2 and 85 and the second heavy chain comprises SEQ ID NOS:15 and 84.

In particular embodiments of this antibody:

(a) the first heavy chain comprises SEQ ID NOS:3 and 85 and the second heavy chain comprises SEQ ID NOS:15 and 86;

(b) the first heavy chain comprises SEQ ID NOS:3 and 85 and the second heavy chain comprises SEQ ID NOS:15 and 74;

(c) the first heavy chain comprises SEQ ID NOS:3 and 85 and the second heavy chain comprises SEQ ID NOS:15 and 75;

(d) the first heavy chain comprises SEQ ID NOS:3 and 85 and the second heavy chain comprises SEQ ID NOS:15 and 76;

(e) the first heavy chain comprises SEQ ID NOS:3 and 85 and the second heavy chain comprises SEQ ID NOS:15 and 77;

(f) the first heavy chain comprises SEQ ID NOS:3 and 85 and the second heavy chain comprises SEQ ID NOS:15 and 78;

(g) the first heavy chain comprises SEQ ID NOS:3 and 85 and the second heavy chain comprises SEQ ID NOS:15 and 79;

(h) the first heavy chain comprises SEQ ID NOS:3 and 85 and the second heavy chain comprises SEQ ID NOS:15 and 80;

(i) the first heavy chain comprises SEQ ID NOS:3 and 85 and the second heavy chain comprises SEQ ID NOS:15 and 81;

(j) the first heavy chain comprises SEQ ID NOS:3 and 85 and the second heavy chain comprises SEQ ID NOS:15 and 82;

(k) the first heavy chain comprises SEQ ID NOS:3 and 85 and the second heavy chain comprises SEQ ID NOS:15 and 83; or (l) the first heavy chain comprises SEQ ID NOS:3 and 85 and the second heavy chain comprises SEQ ID NOS:15 and 84.

In certain other embodiments, the anti-HER2 antibody comprises a first heavy chain comprising a $V_H$ and a Fc sequence each having at least 90% (e.g., 91%, 92%, 93%, 94%, 95%, 96%, 97%, 98%, 99%, or 100%) sequence identity to the amino acid sequences selected from the combinations in Table 5, i.e., any one of Combo #A-AJ, and a second heavy chain comprising a $V_H$ and a Fc sequence each having at least 90% (e.g., 91%, 92%, 93%, 94%, 95%, 96%, 97%, 98%, 99%, or 100%) sequence identity to the amino acid sequences selected from the combinations in Table 6, i.e., any one of Combo #A-D. In any of these heavy chain combinations, the light chain polypeptide sequence has at least 90% (e.g., 91%, 92%, 93%, 94%, 95%, 96%, 97%, 98%, 99%, or 100%) sequence identity to an amino acid sequence selected from the group consisting of SEQ ID NOS:9-10 and 19.

IV. Fc Polypeptides and Modifications Thereof

In some aspects, any of the antibodies described herein comprises an Fc polypeptide dimer in which either one or both Fc polypeptides in the dimer contain amino acid modifications relative to a wild-type Fc polypeptide. In some embodiments, the amino acid modifications in an Fc polypeptide (e.g., a modified Fc polypeptide) can result in binding of the Fc polypeptide dimer to a BBB receptor (e.g., a TfR), promote heterodimerization of the two Fc polypeptides in the dimer, modulate effector function, extend serum half-life, influence glycosylation, and/or reduce immunogenicity in humans. In some embodiments, the Fc polypeptides present in the antibody independently have an amino acid sequence identity of at least about 85%, 90%, 95%, 96%, 97%, 98%, or 99% to a corresponding wild-type Fc polypeptide (e.g., a human IgG1, IgG2, IgG3, or IgG4 Fc polypeptide). Examples and descriptions of modified Fc polypeptides (e.g., TfR-binding Fc polypeptides) can be found, e.g., in International Patent Publication No. WO 2018/152326, which is incorporated herein by reference in its entirety.

Fc Polypeptide Modifications for BBB Receptor Binding

Provided herein are anti-HER2 antibodies that are capable of being transported across the BBB. Such a protein comprises a modified Fc polypeptide that binds to a BBB receptor. BBB receptors are expressed on BBB endothelia, as well as other cell and tissue types. In some embodiments, the BBB receptor is a TfR. A modified Fc polypeptide that binds to TfR is also referred to as having a TfR-binding site.

Amino acid residues designated in various Fc modifications, including those introduced in a modified Fc polypeptide that binds to a BBB receptor, e.g., TfR, are numbered herein using EU index numbering. Any Fc polypeptide, e.g., an IgG1, IgG2, IgG3, or IgG4 Fc polypeptide, may have modifications, e.g., amino acid substitutions, in one or more positions as described herein. In some embodiments, the domain that is modified for BBB (e.g., TfR) receptor-binding activity is a human Ig CH3 domain, such as an IgG1 CH3 domain. The CH3 domain can be of any IgG subtype, i.e., from IgG1, IgG2, IgG3, or IgG4. In the context of IgG1 antibodies, a CH3 domain refers to the segment of amino acids from about position 341 to about position 447 as numbered according to the EU numbering scheme.

In some embodiments, a modified Fc polypeptide that specifically binds to TfR binds to the apical domain of TfR and may bind to TfR without blocking or otherwise inhibiting binding of transferrin to TfR. In some embodiments, binding of transferrin to TfR is not substantially inhibited. In some embodiments, binding of transferrin to TfR is inhibited by less than about 50% (e.g., less than about 45%, 40%, 35%, 30%, 25%, 20%, 15%, 10%, or 5%).

In some embodiments, a BBB (e.g., TfR) receptor-binding Fc polypeptide present in an antibody described herein comprises one or more at least one, two, or three substitutions; and in some embodiments, at least four, five, six, seven, eight, nine, or ten substitutions at amino acid positions comprising 266, 267, 268, 269, 270, 271, 295, 297, 298, and 299, according to the EU numbering scheme. In some embodiments, a BBB (e.g., TfR) receptor-binding Fc polypeptide present in an antibody described herein comprises at least one, two, or three substitutions; and in some embodiments, at least four, five, six, seven, eight, or nine substitutions at amino acid positions comprising 274, 276, 283, 285, 286, 287, 288, 289, and 290, according to the EU numbering scheme. In some embodiments, a BBB (e.g., TfR) receptor-binding Fc polypeptide present in an antibody described herein comprises at least one, two, or three substitutions; and in some embodiments, at least four, five, six, seven, eight, nine, or ten substitutions at amino acid positions comprising 268, 269, 270, 271, 272, 292, 293, 294, 296, and 300, according to the EU numbering scheme. In some embodiments, a BBB (e.g., TfR) receptor-binding Fc polypeptide present in an antibody described herein comprises at least one, two, or three substitutions; and in some embodiments, at least four, five, six, seven, eight, or nine substitutions at amino acid positions comprising 272, 274, 276, 322, 324, 326, 329, 330, and 331, according to the EU numbering scheme. In some embodiments, a BBB (e.g., TfR) receptor-binding Fc polypeptide present in an antibody described herein comprises at least one, two, or three substitutions; and in some embodiments, at least four, five, six, or seven substitutions at amino acid positions comprising 345, 346, 347, 349, 437, 438, 439, and 440, according to the EU numbering scheme.

In some embodiments, a BBB (e.g., TfR) receptor-binding Fc polypeptide present in an antibody described herein comprises at least one, two, or three substitutions; and in some embodiments, at least four, five, six, seven, eight, or nine substitutions at amino acid positions 384, 386, 387, 388, 389, 390, 413, 416, and 421, according to the EU numbering scheme.

In some embodiments, a BBB (e.g., TfR) receptor-binding Fc polypeptide comprises at least one position having a substitution, relative to SEQ ID NO:95, as follows: Leu, Tyr, Met, or Val at position 384; Leu, Thr, His, or Pro at position 386; Val, Pro, or an acidic amino acid at position 387; an aromatic amino acid, e.g., Trp or Gly (e.g., Trp) at position 388; Val, Ser, or Ala at position 389; an acidic amino acid, Ala, Ser, Leu, Thr, or Pro at position 413; Thr or an acidic amino acid at position 416; or Trp, Tyr, His, or Phe at position 421. In some embodiments, a BBB (e.g., TfR) receptor-binding Fc polypeptide may comprise a conservative substitution, e.g., an amino acid in the same charge grouping, hydrophobicity grouping, side chain ring structure grouping (e.g., aromatic amino acids), or size grouping, and/or polar or non-polar grouping, of a specified amino acid at one or more of the positions in the set. Thus, for example, Ile may be present at position 384, 386, and/or position 413. In some embodiments, the acidic amino acid at position one, two, or each of positions 387, 413, and 416 is Glu. In other embodiments, the acidic amino acid at one, two or each of positions 387, 413, and 416 is Asp. In some embodiments, two, three, four five, six, seven, or all eight of positions 384, 386, 387, 388, 389, 413, 416, and 421 have an amino acid substitution as specified in this paragraph.

In some embodiments, a Fc polypeptide having modifications in amino acid positions 384, 386, 387, 388, 389, 390, 413, 416, and/or 421 comprises a native Asn at position 390. In some embodiments, the Fc polypeptide comprises Gly, His, Gln, Leu, Lys, Val, Phe, Ser, Ala, or Asp at position 390. In some embodiments, the Fc polypeptide further comprises one, two, three, or four substitutions at positions comprising 380, 391, 392, and 415. In some embodiments, Trp, Tyr, Leu, or Gln may be present at position 380. In some embodiments, Ser, Thr, Gln, or Phe may be present at position 391. In some embodiments, Gln, Phe, or His may be present at position 392. In some embodiments, Glu may be present at position 415.

In certain embodiments, the Fc polypeptide comprises two, three, four, five, six, seven, eight, nine, or ten positions selected from the following: Trp, Leu, or Glu at position 380; Tyr or Phe at position 384; Thr at position 386; Glu at position 387; Trp at position 388; Ser, Ala, Val, or Asn at position 389; Ser or Asn at position 390; Thr or Ser at position 413; Glu or Ser at position 415; Glu at position 416; and/or Phe at position 421. In some embodiments, the Fc polypeptide comprises all eleven positions as follows: Trp, Leu, or Glu at position 380; Tyr or Phe at position 384; Thr at position 386; Glu at position 387; Trp at position 388; Ser, Ala, Val, or Asn at position 389; Ser or Asn at position 390; Thr or Ser at position 413; Glu or Ser at position 415; Glu at position 416; and/or Phe at position 421.

In certain embodiments, the BBB (e.g., TfR) receptor-binding Fc polypeptide comprises Leu or Met at position 384; Leu, His, or Pro at position 386; Val at position 387; Trp at position 388; Val or Ala at position 389; Pro at position 413; Thr at position 416; and/or Trp at position 421. In some embodiments, the Fc polypeptide further comprises Ser, Thr, Gln, or Phe at position 391. In some embodiments, the Fc polypeptide further comprises Trp, Tyr, Leu, or Gln at position 380 and/or Gln, Phe, or His at position 392. In some embodiments, Trp is present at position 380 and/or Gln is present at position 392. In some embodiments, a BBB (e.g., TfR) receptor-binding Fc polypeptide does not have a Trp at position 380.

In other embodiments, a BBB (e.g., TfR) receptor-binding Fc polypeptide comprises Tyr at position 384; Thr at position 386; Glu or Val and position 387; Trp at position 388; Ser at position 389; Ser or Thr at position 413; Glu at position 416; and/or Phe at position 421. In some embodiments, the BBB (e.g., TfR) receptor-binding Fc polypeptide comprises a native Asn at position 390. In certain embodiments, the Fc polypeptide further comprises Trp, Tyr, Leu, or Gln at position 380; and/or Glu at position 415. In some embodiments, the Fc polypeptide further comprises Trp at position 380 and/or Glu at position 415.

In some embodiments, the BBB (e.g., TfR) receptor-binding Fc polypeptide comprises one or more of the following substitutions: Trp at position 380; Thr at position 386; Trp at position 388; Val at position 389; Ser or Thr at position 413; Glu at position 415; and/or Phe at position 421.

In additional embodiments, the BBB (e.g., TfR) receptor-binding Fc polypeptide further comprises one, two, or three positions selected from the following: position 414 is Lys, Arg, Gly, or Pro; position 424 is Ser, Thr, Glu, or Lys; and position 426 is Ser, Trp, or Gly.

In some embodiments, the BBB (e.g., TfR) receptor-binding Fc polypeptide has the sequence of SEQ ID NO:97. In some embodiments of the antibodies described herein, one of the two Fc polypeptides in the Fc polypeptide dimer can be a BBB (e.g., TfR) receptor-binding Fc polypeptide having the sequence of SEQ ID NO:97, while the other Fc polypeptide in the Fc polypeptide dimer can have the sequence of a wild-type Fc polypeptide (e.g., SEQ ID NO:95). In other embodiments of the antibodies described herein, both Fc polypeptides in the Fc polypeptide dimer can be a BBB (e.g., TfR) receptor-binding Fc polypeptide having the sequence of SEQ ID NO:97.

In some embodiments of the antibodies described herein, the first Fc polypeptide and/or the second Fc polypeptide independently comprises Tyr at position 384, Thr at position 386, Glu at position 387, Trp at position 388, Ser at position 389, Ser at position 413, Glu at position 415, Glu at position 416, and Phe at position 421, according to EU numbering, and a sequence having at least 90% (e.g., 91%, 92%, 93%, 94%, 95%, 96%, 97%, 98%, 99%, or 100%) identity to a sequence selected from SEQ ID NOS:74-84, 86, and 97-101.

In some embodiments of the antibodies described herein, one of the two Fc polypeptides in the Fc polypeptide dimer can be a BBB (e.g., TfR) receptor-binding Fc polypeptide comprising Tyr at position 384, Thr at position 386, Glu at position 387, Trp at position 388, Ser at position 389, Ser at position 413, Glu at position 415, Glu at position 416, and Phe at position 421, according to EU numbering, and a sequence having at least 90% identity to the sequence of SEQ ID NO:97, while the other Fc polypeptide in the Fc polypeptide dimer can have the sequence of a wild-type Fc polypeptide (e.g., SEQ ID NO:95).

In some embodiments of the antibodies described herein, the first Fc polypeptide and/or the second Fc polypeptide independently comprises Tyr at position 384, Thr at position 386, Glu at position 387, Trp at position 388, Ala at position 389, Thr at position 413, Glu at position 415, Glu at position 416, and Phe at position 421, according to EU numbering, and a sequence having at least 90% (e.g., 91%, 92%, 93%, 94%, 95%, 96%, 97%, 98%, 99%, or 100%) identity to a sequence selected from SEQ ID NOS:101-105.

In some embodiments of the antibodies described herein, one of the two Fc polypeptides in the Fc polypeptide dimer can be a BBB (e.g., TfR) receptor-binding Fc polypeptide comprising Tyr at position 384, Thr at position 386, Glu at position 387, Trp at position 388, Ala at position 389, Thr at position 413, Glu at position 415, Glu at position 416, and Phe at position 421, according to EU numbering, and a sequence having at least 90% identity to the sequence of SEQ ID NO:101, while the other Fc polypeptide in the Fc polypeptide dimer can have the sequence of a wild-type Fc polypeptide (e.g., SEQ ID NO:95).

In some embodiments, the BBB (e.g., TfR) receptor-binding Fc polypeptide has the sequence of SEQ ID NO:101. In some embodiments of the antibodies described herein, one of the two Fc polypeptides in the Fc polypeptide dimer can be a BBB (e.g., TfR) receptor-binding Fc polypeptide having the sequence of SEQ ID NO:101, while the other Fc polypeptide in the Fc polypeptide dimer can have the sequence of a wild-type Fc polypeptide (e.g., SEQ ID NO:95). In other embodiments of the antibodies described herein, both Fc polypeptides in the Fc polypeptide dimer can be a BBB (e.g., TfR) receptor-binding Fc polypeptide having the sequence of SEQ ID NO:101.

In some embodiments, the BBB (e.g., TfR) receptor-binding Fc polypeptide comprises the following substitutions listed in Table A below (according to EU numbering):

TABLE A

| | 378 | 379 | 380 | 381 | 382 | 383 | 384 | 385 | 386 | 387 | 388 | 389 | 390 | 391 |
|---|---|---|---|---|---|---|---|---|---|---|---|---|---|---|
| Wild-type | A | V | E | W | E | S | N | G | Q | P | E | N | N | Y |
| CH3C.35.20.1 | . | . | . | . | . | . | F | . | T | E | W | S | S | . |
| CH3C.35.20.2 | . | . | . | . | . | . | Y | . | T | E | W | A | S | . |
| CH3C.35.20.3 | . | . | . | . | . | . | Y | . | T | E | W | V | S | . |
| CH3C.35.20.4 | . | . | . | . | . | . | Y | . | T | E | W | S | S | . |

TABLE A-continued

| | | | | | | | | | | | | | | |
|---|---|---|---|---|---|---|---|---|---|---|---|---|---|---|
| CH3C.35.20.5 | . | . | . | . | . | . | F | . | T | E | W | A | S | . |
| CH3C.35.20.6 | . | . | . | . | . | . | F | . | T | E | W | V | S | . |
| CH3C.35.2.a.1 | . | . | W | . | . | . | F | . | T | E | W | S | S | . |
| CH3C.35.2.a.2 | . | . | W | . | . | . | Y | . | T | E | W | A | S | . |
| CH3C.35.2.a.3 | . | . | W | . | . | . | Y | . | T | E | W | V | S | . |
| CH3C.35.2.a.4 | . | . | W | . | . | . | Y | . | T | E | W | S | S | . |
| CH3C.35.2.a.5 | . | . | W | . | . | . | F | . | T | E | W | A | S | . |
| CH3C.35.2.a.6 | . | . | W | . | . | . | F | . | T | E | W | V | S | . |
| CH3C.35.23.1 | . | . | . | . | . | . | F | . | T | E | W | S | . | . |
| CH3C.35.23.2 | . | . | . | . | . | . | Y | . | T | E | W | A | . | . |
| CH3C.35.23.3 | . | . | . | . | . | . | Y | . | T | E | W | V | . | . |
| CH3C.35.23.4 | . | . | . | . | . | . | Y | . | T | E | W | S | . | . |
| CH3C.35.23.5 | . | . | . | . | . | . | F | . | T | E | W | A | . | . |
| CH3C.35.23.6 | . | . | . | . | . | . | F | . | T | E | W | V | . | . |
| CH3C.35.24.1 | . | . | W | . | . | . | F | . | T | E | W | S | . | . |
| CH3C.35.24.2 | . | . | W | . | . | . | Y | . | T | E | W | A | . | . |
| CH3C.35.24.3 | . | . | W | . | . | . | Y | . | T | E | W | V | . | . |
| CH3C.35.24.4 | . | . | W | . | . | . | Y | . | T | E | W | S | . | . |
| CH3C.35.24.5 | . | . | W | . | . | . | F | . | T | E | W | A | . | . |
| CH3C.35.24.6 | . | . | W | . | . | . | F | . | T | E | W | V | . | . |
| CH3C.35.21.17.1 | . | . | L | . | . | . | F | . | T | E | W | S | S | . |
| CH3C.35.21.17.2 | . | . | L | . | . | . | Y | . | T | E | W | A | S | . |
| CH3C.35.21.17.3 | . | . | L | . | . | . | Y | . | T | E | W | V | S | . |
| CH3C.35.21.17.4 | . | . | L | . | . | . | Y | . | T | E | W | S | S | . |
| CH3C.35.21.17.5 | . | . | L | . | . | . | F | . | T | E | W | A | S | . |
| CH3C.35.21.17.6 | . | . | L | . | . | . | F | . | T | E | W | V | S | . |
| CH3C.35.20 | . | . | . | . | . | . | Y | . | T | E | W | S | S | . |
| CH3C.35.21 | . | . | W | . | . | . | Y | . | T | E | W | S | S | . |
| CH3C.35.22 | . | . | W | . | . | . | Y | . | T | E | W | S | . | . |
| CH3C.35.23 | . | . | . | . | . | . | Y | . | T | E | W | S | . | . |
| CH3C.35.24 | . | . | W | . | . | . | Y | . | T | E | W | S | . | . |
| CH3C.35.21.17 | . | . | L | . | . | . | Y | . | T | E | W | S | S | . |
| CH3C.35.N390 | . | . | . | . | . | . | Y | . | T | E | W | S | . | . |
| CH3C.35.20.1.1 | | | | | | | F | | T | E | W | S | S | |
| CH3C.35.23.2.1 | | | | | | | Y | | T | E | W | A | | |
| CH3C.35.23.1.1 | | | | | | | F | | T | E | W | S | | |
| CH3C.35.S413 | | | | | | | Y | | T | E | W | S | S | |
| CH3C.35.23.3.1 | | | | | | | Y | | T | E | W | V | | |
| CH3C.35.N390.1 | | | | | | | Y | | T | E | W | S | | |
| CH3C.35.23.6.1 | | | | | | | F | | T | E | W | V | | |

| | 392 | 411 | 412 | 413 | 414 | 415 | 416 | 417 | 418 | 419 | 420 | 421 | 422 | 423 |
|---|---|---|---|---|---|---|---|---|---|---|---|---|---|---|
| Wild-type | K | T | V | D | K | S | R | W | Q | Q | G | N | V | F |
| CH3C.35.20.1 | . | . | . | T | . | E | E | . | . | . | . | F | . | . |
| CH3C.35.20.2 | . | . | . | T | . | E | E | . | . | . | . | F | . | . |
| CH3C.35.20.3 | . | . | . | T | . | E | E | . | . | . | . | F | . | . |
| CH3C.35.20.4 | . | . | . | S | . | E | E | . | . | . | . | F | . | . |
| CH3C.35.20.5 | . | . | . | T | . | E | E | . | . | . | . | F | . | . |
| CH3C.35.20.6 | . | . | . | T | . | E | E | . | . | . | . | F | . | . |
| CH3C.35.2.a.1 | . | . | . | T | . | E | E | . | . | . | . | F | . | . |
| CH3C.35.2.a.2 | . | . | . | T | . | E | E | . | . | . | . | F | . | . |
| CH3C.35.2.a.3 | . | . | . | T | . | E | E | . | . | . | . | F | . | . |
| CH3C.35.2.a.4 | . | . | . | S | . | E | E | . | . | . | . | F | . | . |
| CH3C.35.2.a.5 | . | . | . | T | . | E | E | . | . | . | . | F | . | . |
| CH3C.35.2.a.6 | . | . | . | T | . | E | E | . | . | . | . | F | . | . |
| CH3C.35.23.1 | . | . | . | T | . | E | E | . | . | . | . | F | . | . |
| CH3C.35.23.2 | . | . | . | T | . | E | E | . | . | . | . | F | . | . |
| CH3C.35.23.3 | . | . | . | T | . | E | E | . | . | . | . | F | . | . |
| CH3C.35.23.4 | . | . | . | S | . | E | E | . | . | . | . | F | . | . |
| CH3C.35.23.5 | . | . | . | T | . | E | E | . | . | . | . | F | . | . |
| CH3C.35.23.6 | . | . | . | T | . | E | E | . | . | . | . | F | . | . |
| CH3C.35.24.1 | . | . | . | T | . | E | E | . | . | . | . | F | . | . |
| CH3C.35.24.2 | . | . | . | T | . | E | E | . | . | . | . | F | . | . |
| CH3C.35.24.3 | . | . | . | T | . | E | E | . | . | . | . | F | . | . |
| CH3C.35.24.4 | . | . | . | S | . | E | E | . | . | . | . | F | . | . |
| CH3C.35.24.5 | . | . | . | T | . | E | E | . | . | . | . | F | . | . |
| CH3C.35.24.6 | . | . | . | T | . | E | E | . | . | . | . | F | . | . |
| CH3C.35.21.17.1 | . | . | . | T | . | E | E | . | . | . | . | F | . | . |
| CH3C.35.21.17.2 | . | . | . | T | . | E | E | . | . | . | . | F | . | . |
| CH3C.35.21.17.3 | . | . | . | T | . | E | E | . | . | . | . | F | . | . |
| CH3C.35.21.17.4 | . | . | . | S | . | E | E | . | . | . | . | F | . | . |
| CH3C.35.21.17.5 | . | . | . | T | . | E | E | . | . | . | . | F | . | . |
| CH3C.35.21.17.6 | . | . | . | T | . | E | E | . | . | . | . | F | . | . |
| CH3C.35.20 | . | . | . | T | . | E | E | . | . | . | . | F | . | . |
| CH3C.35.21 | . | . | . | T | . | E | E | . | . | . | . | F | . | . |
| CH3C.35.22 | . | . | . | T | . | . | E | . | . | . | . | F | . | . |
| CH3C.35.23 | . | . | . | T | . | E | E | . | . | . | . | F | . | . |
| CH3C.35.24 | . | . | . | T | . | E | E | . | . | . | . | F | . | . |
| CH3C.35.21.17 | . | . | . | T | . | E | E | . | . | . | . | F | . | . |

TABLE A-continued

| | | | | | | | | | | | | | | |
|---|---|---|---|---|---|---|---|---|---|---|---|---|---|---|
| CH3C.35.N390 | . | . | . | T | . | . | E | . | . | . | . | F | . | . |
| CH3C.35.20.1.1 | | | | S | | E | E | | | | | F | | |
| CH3C.35.23.2.1 | | | | S | | | E | | | | | F | | |
| CH3C.35.23.1.1 | | | | S | | E | E | | | | | F | | |
| CH3C.35.S413 | | | | S | | | E | | | | | F | | |
| CH3C.35.23.3.1 | | | | S | | E | E | | | | | F | | |
| CH3C.35.N390.1 | | | | S | | | E | | | | | F | | |
| CH3C.35.23.6.1 | | | | S | | E | E | | | | | F | | |

Fc Polypeptide Modifications for Heterodimerization

In some embodiments, the Fc polypeptides present in any antibody described herein include knob and hole mutations to promote heterodimer formation and hinder homodimer formation. Generally, the modifications introduce a protuberance ("knob") at the interface of a first polypeptide and a corresponding cavity ("hole") in the interface of a second polypeptide, such that the protuberance can be positioned in the cavity so as to promote heterodimer formation and thus hinder homodimer formation. Protuberances are constructed by replacing small amino acid side chains from the interface of the first polypeptide with larger side chains (e.g., tyrosine or tryptophan). Compensatory cavities of identical or similar size to the protuberances are created in the interface of the second polypeptide by replacing large amino acid side chains with smaller ones (e.g., alanine or threonine). In some embodiments, such additional mutations are at a position in the Fc polypeptide that does not have a negative effect on binding of the polypeptide to a BBB receptor, e.g., TfR.

In one illustrative embodiment of a knob and hole approach for dimerization, position 366 (numbered according to the EU numbering scheme) of one of the Fc polypeptides present in the antibody comprises a tryptophan in place of a native threonine. The other Fc polypeptide in the dimer has a valine at position 407 (numbered according to the EU numbering scheme) in place of the native tyrosine. The other Fc polypeptide may further comprise a substitution in which the native threonine at position 366 (numbered according to the EU numbering scheme) is substituted with a serine and a native leucine at position 368 (numbered according to the EU numbering scheme) is substituted with an alanine. Thus, one of the Fc polypeptides of an antibody described herein has the T366W knob mutation and the other Fc polypeptide has the Y407V mutation, which is typically accompanied by the T366S and L368A hole mutations.

In some embodiments, one or both Fc polypeptides present in an antibody described herein may also be engineered to contain other modifications for heterodimerization, e.g., electrostatic engineering of contact residues within a CH3-CH3 interface that are naturally charged or hydrophobic patch modifications.

For example, in some embodiments, an antibody described herein can contain an Fc polypeptide dimer that has one Fc polypeptide having the T366W knob mutation and at least 90% (e.g., 91%, 92%, 93%, 94%, 95%, 96%, 97%, 98%, or 99%) identity to the sequence of SEQ ID NO:107 and the other Fc polypeptide having the T366S, L368A, and Y407V hole mutations and at least 90% identity to the sequence of SEQ ID NO:85. In certain embodiments, one or both Fc polypeptides in the Fc polypeptide dimer can be a TfR-binding Fc polypeptide. In particular embodiments, an antibody described herein can contain an Fc polypeptide dimer that has (i) a first Fc polypeptide having the sequence of SEQ ID NO:85, and (ii) a second Fc polypeptide having the sequence of SEQ ID NO:98. In particular embodiments, an antibody described herein can contain an Fc polypeptide dimer that has (i) a first Fc polypeptide having the sequence of SEQ ID NO:85, and (ii) a second Fc polypeptide having the sequence of SEQ ID NO:102.

Fc Polypeptide Modifications for Modulating Effector Function

In some embodiments, one or both Fc polypeptides present in any antibody described herein may comprise modifications that reduce TfR-mediated effector function upon TfR binding, i.e., having a reduced ability to induce certain biological functions upon binding to an Fc receptor expressed on an effector cell that mediates the effector function. Examples of antibody effector functions include, but are not limited to, C1q binding and complement dependent cytotoxicity (CDC), Fc receptor binding, antibody-dependent cell-mediated cytotoxicity (ADCC), antibody-dependent cell-mediated phagocytosis (ADCP), down-regulation of cell surface receptors (e.g., B cell receptor), and B-cell activation. Effector functions may vary with the antibody class. For example, native human IgG1 and IgG3 antibodies can elicit ADCC and CDC activities upon binding to an appropriate Fc receptor present on an immune system cell; and native human IgG1, IgG2, IgG3, and IgG4 can elicit ADCP functions upon binding to the appropriate Fc receptor present on an immune cell.

In some embodiments, one or both Fc polypeptides present in an antibody described herein may comprise modifications that reduce or eliminate TfR-mediated effector function. Illustrative Fc polypeptide mutations that reduce TfR-mediated effector function include, but are not limited to, substitutions in a CH2 domain, e.g., at positions 234 and 235, according to the EU numbering scheme. For example, in some embodiments, one or both Fc polypeptides can comprise alanine residues at positions 234 and 235. Thus, one or both Fc polypeptides may have L234A and L235A (also referred to as "LALA" herein) substitutions.

Additional Fc polypeptide mutations that modulate an effector function include, but are not limited to, the following: position 329 may have a mutation in which proline is substituted with a glycine, alanine, serine, or arginine or an amino acid residue large enough to destroy the Fc/Fcγ receptor interface that is formed between proline 329 of the Fc and tryptophan residues Trp 87 and Trp 110 of FcγRIII. Additional illustrative substitutions include S228P, E233P, L235E, N297A, N297D, and P331S, according to the EU numbering scheme. Multiple substitutions may also be present, e.g., L234A and L235A of a human IgG1 Fc region; L234A, L235A, and P329G of a human IgG1 Fc region; S228P and L235E of a human IgG4 Fc region; L234A and G237A of a human IgG1 Fc region; L234A, L235A, and G237A of a human IgG1 Fc region; V234A and G237A of a human IgG2 Fc region; L235A, G237A, and E318A of a human IgG4 Fc region; and S228P and L236E of a human IgG4 Fc region, according to the EU numbering scheme. In some embodiments, one or both Fc polypeptides may have one or more amino acid substitutions that modulate ADCC, e.g., substitutions at positions 298, 333, and/or 334, according to the EU numbering scheme. In some embodiments, one or both Fc polypeptides may have L234A, L235A, and P329G or P329S substitutions, according to the EU numbering scheme.

In some embodiments, one or both Fc polypeptides present in an antibody described herein may comprise modifications that are capable of enhancing HER2-mediated effector function upon HER2 binding, i.e., enhancing the ability to induce certain biological functions upon binding to an Fc receptor expressed on an effector cell that mediates the effector function. Examples of antibody effector functions are described above. Illustrative Fc polypeptide mutations that are capable of enhancing HER2-mediated effector function include, but are not limited to, substitutions in a CH2 domain, e.g., at positions 239 and/or 332, according to the EU numbering scheme. For example, in some embodiments, one or both Fc polypeptides can comprise aspartic acid at position 239 and/or glutamic acid at position 332. Thus, one or both Fc polypeptides may have a S239D and/or a I332E substitution, according to EU numbering.

"cis-LALA" Configuration

In some embodiments of any antibody described herein, only one of the two Fc polypeptides (but not both Fc polypeptides) of the two Fc polypeptides in the antibody is modified to reduce TfR-mediated effector function upon TfR binding. The other Fc polypeptide does not contain a TfR-binding site or any modifications that reduce effector function. The Fc polypeptide dimer in the antibody that has only one of the two Fc polypeptides containing both the TfR-binding site and modifications that reduce FcγR binding (e.g., LALA substitutions) when bound to TfR, while the other Fc polypeptide does not contain a TfR-binding site or any modifications that reduce FcγR binding, is referred to as having the cis-LALA configuration.

For example, in some embodiments, an antibody described herein can contain an Fc polypeptide dimer having the cis-LALA configuration that has (i) a first Fc polypeptide having the sequence of SEQ ID NO:86, which has both a TfR-binding site and LALA substitutions, as well as a knob modification, and (ii) a second Fc polypeptide having at least 90% identity to the sequence of SEQ ID NO:85, which only has a hole modification. In some embodiments, an antibody described herein can contain an Fc polypeptide dimer having the cis-LALA configuration that has (i) a first Fc polypeptide having the sequence of SEQ ID NO:103, which has both a TfR-binding site and LALA substitutions, as well as a knob modification, and (ii) a second Fc polypeptide having at least 90% identity to the sequence of SEQ ID NO:85, which only has a hole modification.

In particular embodiments, an antibody described herein can contain an Fc polypeptide dimer having the cis-LALA configuration that has (i) a first Fc polypeptide comprising Ala at position 234, Ala at position 235, Trp at position 366, Tyr at position 384, Thr at position 386, Glu at position 387, Trp at position 388, Ser at position 389, Ser at position 413, Glu at position 415, Glu at position 416, and Phe at position 421, according to EU numbering, and a sequence having at least 90% identity to the sequence of SEQ ID NO:86, and (ii) a second Fc polypeptide comprising Ser at position 366, Ala at position 368, and Val at position 407, according to EU numbering, and a sequence having at least 90% identity to the sequence of SEQ ID NO:85.

In particular embodiments, an antibody described herein can contain an Fc polypeptide dimer having the cis-LALA configuration that has (i) a first Fc polypeptide comprises Ser at position 366, Ala at position 368, and Val at position 407, according to EU numbering, and a sequence having at least 90% identity to the sequence of SEQ ID NO:85, and (ii) a second Fc polypeptide comprises Ala at position 234, Ala at position 235, Trp at position 366, Tyr at position 384, Thr at position 386, Glu at position 387, Trp at position 388, Ser at position 389, Ser at position 413, Glu at position 415, Glu at position 416, and Phe at position 421, according to EU numbering, and a sequence having at least 90% identity to the sequence of SEQ ID NO:86.

In particular embodiments, an antibody described herein can contain an Fc polypeptide dimer having the cis-LALA configuration that has (i) a first Fc polypeptide comprising Ala at position 234, Ala at position 235, Trp at position 366, Tyr at position 384, Thr at position 386, Glu at position 387, Trp at position 388, Ala at position 389, Thr at position 413, Glu at position 415, Glu at position 416, and Phe at position 421, according to EU numbering, and a sequence having at least 90% identity to the sequence of SEQ ID NO: 103, and (ii) a second Fc polypeptide comprising Ser at position 366, Ala at position 368, and Val at position 407, according to EU numbering, and a sequence having at least 90% identity to the sequence of SEQ ID NO:85.

In particular embodiments, an antibody described herein can contain an Fc polypeptide dimer having the cis-LALA configuration that has (i) a first Fc polypeptide comprising Ser at position 366, Ala at position 368, and Val at position 407, according to EU numbering, and a sequence having at least 90% identity to the sequence of SEQ ID NO:85, and (ii) a second Fc polypeptide comprising Ala at position 234, Ala at position 235, Trp at position 366, Tyr at position 384, Thr at position 386, Glu at position 387, Trp at position 388, Ala at position 389, Thr at position 413, Glu at position 415, Glu at position 416, and Phe at position 421, according to EU numbering, and a sequence having at least 90% identity to the sequence of SEQ ID NO:103.

Fc Polypeptide Modifications for Extending Serum Half-Life

In some embodiments, modifications to enhance serum half-life may be introduced into any antibody described herein. For example, in some embodiments, one or both Fc polypeptides present in an antibody described herein may comprise a tyrosine at position 252, a threonine at position 254, and a glutamic acid at position 256, as numbered according to the EU numbering scheme. Thus, one or both Fc polypeptides may have M252Y, S254T, and T256E substitutions. Alternatively, one or both Fc polypeptides may have M428L and N434S substitutions, as numbered according to the EU numbering scheme. Alternatively, one or both Fc polypeptides may have an N434S or N434A substitution.

Fc Polypeptide with C-Terminal Lysine Residue Removed

In some embodiments of the antibodies described herein, one or both of the Fc polypeptides can have its C-terminal lysine removed (e.g., the Lys residue at position 447 of the Fc polypeptide, according to EU numbering). The C-terminal lysine residue is highly conserved in immunoglobulins across many species and may be fully or partially removed by the cellular machinery during protein production. In some embodiments, removal of the C-terminal lysines in the Fc polypeptides can improve the stability of the antibodies.

V. Preparation of Antibodies

For preparing an antibody described herein, many techniques known in the art can be used. In some embodiments, the genes encoding the heavy and light chains of an antibody of interest can be cloned from a cell, e.g., from a hybridoma. Gene libraries encoding heavy and light chains of monoclonal antibodies can also be made from hybridoma or plasma cells. Alternatively, phage or yeast display technology can be used to identify antibodies and Fab fragments that specifically bind to selected antigens.

Antibodies can be produced using any number of expression systems, including prokaryotic and eukaryotic expression systems. In some embodiments, the expression system is a mammalian cell expression system, such as a hybridoma, or a CHO cell expression system. Many such systems are widely available from commercial suppliers. In some embodiments, the polynucleotides encoding the polypeptides that comprise the antibody may be expressed using a single vector, e.g., in a di-cistronic expression unit, or under the control of different promoters. In other embodiments, the polynucleotides encoding the polypeptides that comprise the antibody may be expressed using separate vectors.

In some aspects, the disclosure provides isolated nucleic acids comprising a nucleic acid sequence encoding any of the polypeptides comprising the antibodies as described herein, vectors comprising such nucleic acids, and host cells into which the nucleic acids are introduced that are used to replicate the nucleic acids and/or to express the antibodies.

In some embodiments, a polynucleotide (e.g., an isolated polynucleotide) comprises a nucleotide sequence encoding a polypeptide that comprises the antibody as disclosed herein (e.g., as described in Section III above). In some embodiments, the polynucleotide comprises a nucleotide sequence encoding one or more amino acid sequences (e.g., heavy chain, light chain, and/or Fc polypeptide sequences) disclosed in the Informal Sequence Listing below. In some embodiments, the polynucleotide comprises a nucleotide sequence encoding an amino acid sequence having at least 85% sequence identity (e.g., at least 85%, at least 90%, at least 91%, at least 92%, at least 93%, at least 94%, at least 95%, at least 96%, at least 97%, at least 98%, or at least 99% sequence identity) to a sequence disclosed in the Informal Sequence Listing below. In some embodiments, a polynucleotide as described herein is operably linked to a heterologous nucleic acid, e.g., a heterologous promoter.

Suitable vectors containing polynucleotides encoding antibodies of the present disclosure, or fragments thereof, include cloning vectors and expression vectors. While the cloning vector selected may vary according to the host cell intended to be used, useful cloning vectors generally have the ability to self-replicate, may possess a single target for a particular restriction endonuclease, and/or may carry genes for a marker that can be used in selecting clones containing the vector. Examples include plasmids and bacterial viruses, e.g., pUC18, pUC19, Bluescript (e.g., pBS SK+) and its derivatives, mpl8, mpl9, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a nucleic acid of the present disclosure. The expression vector may replicate in the host cells either as episomes or as an integral part of the chromosomal DNA. Suitable expression vectors include but are not limited to plasmids, viral vectors, including adenoviruses, adeno-associated viruses, retroviruses, and any other vector.

Suitable host cells for cloning or expressing a polynucleotide or vector as described herein include prokaryotic or eukaryotic cells. In some embodiments, the host cell is prokaryotic. In some embodiments, the host cell is eukaryotic, e.g., Chinese Hamster Ovary (CHO) cells or lymphoid cells. In some embodiments, the host cell is a human cell, e.g., a Human Embryonic Kidney (HEK) cell.

In another aspect, methods of making an antibody as described herein are provided. In some embodiments, the method includes culturing a host cell as described herein (e.g., a host cell expressing a polynucleotide or vector as described herein) under conditions suitable for expression of the antibody. In some embodiments, the antibody is subsequently recovered from the host cell (or host cell culture medium). In some embodiments, the antibody is purified, e.g., by chromatography.

VI. Therapeutic Methods

In some aspects, provided herein are methods for treating a cancer (e.g., a HER2-positive cancer) or treating brain metastasis of a cancer (e.g., a HER2-positive cancer) in a subject by administering to the subject a therapeutically effective amount of an antibody described herein or a pharmaceutical composition thereof. Also provided herein are methods of transcytosis of an antibody variable region that is capable of binding HER2 (e.g., human HER2), or an antigen-binding fragment thereof, across an endothelium. In some embodiments, the methods comprise contacting the endothelium with a composition comprising an antibody described herein. In some embodiments, the endothelium is the blood brain barrier (BBB).

Non-limiting examples of HER2-positive cancers that can be treated according to the methods provided herein include HER2-positive breast, ovarian, bladder, salivary gland, endometrial, pancreatic, and non-small-cell lung cancer (NSCLC), as well as HER2-positive gastric adenocarcinoma and/or a HER2-positive gastroesophageal junction adnocarcinoma. In some embodiments, the HER2-positive cancer is a HER2-positive breast cancer. In some embodiments, the HER2-positive cancer is a HER2-positive gastric adenocarcinoma and/or a HER2-positive gastroesophageal junction adnocarcinoma. In some embodiments, the HER2-positive cancer is a metastatic cancer.

In still other aspects, provided herein are methods for treating metastasis of a cancer (e.g., a HER2-positive cancer). In some embodiments, the methods comprise administering to the subject a therapeutically effective amount of an antibody described herein. In some embodiments, the metastasis is a brain metastasis of a HER2-positive cancer described above. In some embodiments, the metastasis is a brain metastasis of a HER2-positive breast cancer. In some embodiments, the metastasis is a brain metastasis of a HER2-positive gastric adenocarcinoma and/or a HER2-positive gastroesophageal junction adnocarcinoma.

In some embodiments, the therapeutic benefit can comprise a decrease in or slowing of tumor growth, a decrease in tumor size (e.g., volume), a decrease in tumor cell viability, a decrease in the number of metastatic lesions, amelioration in one or more signs or symptoms of a cancer (e.g., HER2-positive cancer), and/or an increase in patient survival. In some embodiments, tumor cell survival, tumor growth, tumor size, and/or the number of metastatic lesions is decreased by at least about 10%, 20%, 30%, 40%, 50%, 60%, 70%, 80%, 90%, or more.

In some embodiments, the antibody antagonizes HER2 activity. In some embodiments, HER2 activity is inhibited (e.g., by at least about 10%, 20%, 30%, 40%, 50%, 60%, 70%, 80%, 90%, or more).

The route of administration of an an antibody described herein can be oral, intraperitoneal, transdermal, subcutaneous, intravenous, intramuscular, intrathecal, inhalational, topical, intralesional, rectal, intrabronchial, nasal, transmucosal, intestinal, ocular or otic delivery, or any other methods known in the art. In some embodiments, the antibody is administered orally, intravenously, or intraperitoneally.

VII. Pharmaceutical Compositions and Kits

In other aspects, pharmaceutical compositions and kits comprising an antibody in accordance with the disclosure are provided.

Pharmaceutical Compositions

Guidance for preparing formulations for use in the disclosure can be found in any number of handbooks for pharmaceutical preparation and formulation that are known to those of skill in the art.

In some embodiments, a pharmaceutical composition comprises an antibody as described herein and further comprises one or more pharmaceutically acceptable carriers and/or excipients. A pharmaceutically acceptable carrier includes any solvents, dispersion media, or coatings that are physiologically compatible and that do not interfere with or otherwise inhibit the activity of the active agent.

In some embodiments, the antibody can be formulated for parenteral administration by injection. Typically, a pharmaceutical composition for use in in vivo administration is sterile, e.g., heat sterilization, steam sterilization, sterile filtration, or irradiation.

Dosages and desired drug concentration of pharmaceutical compositions described herein may vary depending on the particular use envisioned.

Kits

In some embodiments, a kit for use in treating a cancer (e.g., a HER2-positive cancer) comprising an antibody described herein is provided. In some embodiments, the kit further comprises one or more additional therapeutic agents. For example, in some embodiments, the kit comprises an antibody as described herein and further comprises one or more additional therapeutic agents for use in the treatment of cancer. In some embodiments, the kit further comprises instructional materials containing directions (i.e., protocols) for the practice of the methods described herein (e.g., instructions for using the kit for administering an antibody). While the instructional materials typically comprise written or printed materials, they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD-ROM), and the like. Such media may include addresses to internet sites that provide such instructional materials.

VIII. Examples

The present invention will be described in greater detail by way of specific examples. The following examples are offered for illustrative purposes only, and are not intended to limit the invention in any manner.

Example 1. Generation of Anti-HER2 Bispecific Antibodies

Expression and Purification of Recombinant Bispecific Antibody Variants

Expression plasmids consisting of (i) a heavy chain polypeptide comprising a TfR-binding site and a knob (T366W) mutation, (ii) a heavy chain polypeptide comprising hole (T366S/L368A/Y407V) mutations, and (iii) light chains according to the combinations in Table 2 are co-transfected in Expi293 or ExpiCHO cells. Recombinant bispecific antibody variants are subsequently purified from conditioned media by loading supernatant over a protein A column (GE Mab Select SuRe). The column is washed with 10 column volumes of PBS, pH 7.4. The proteins are eluted with 50 mM sodium citrate, pH 3.0 containing 150 mM NaCl, and immediately neutralized with 200 mM arginine, 137 mM succinic acid, pH 5.0. The proteins are further purified by size-exclusion chromatography (GE Superdex200) using 200 mM arginine, 137 mM succinic acid, pH 5.0 as running buffer. The purified proteins are confirmed by intact mass LC/MS, and purity of >95% is confirmed by SDS-PAGE and analytical HPLC-SEC.

The heavy chain polypeptides may be further processed during cell culture production, such that the C-terminal lysine residue is removed. Thus, the bispecific antibodies listed in Table 2 may refer to protein molecules comprising heavy chains that are unprocessed (i.e., comprise the C-terminal lysine residue); protein molecules comprising one or more heavy chains that are processed (i.e., the C-terminal lysine residue is absent); or a mixture of protein molecules having processed and/or unprocessed heavy chains.

Example 2. Biacore Assessment of Anti-HER2 Antibodies

HER2 extracellular domain (ECD) binding affinities of engineered anti-HER2 antibodies were measured by SPR using a Biacore 8K instrument. Antibodies were captured on Biacore™ Series S CM5 sensor chips immobilized with mouse anti-human Fab (human Fab capture kit from GE Healthcare) followed by injections of serial 3-fold dilutions of recombinant HER2 ECD at a flow rate of 30 μL/min. Each sample was analyzed using a 3-minute association followed by a 10-minute dissociation. After each injection, the sensor chip was regenerated using a 50 mM glycine pH2.0 regeneration buffer. A 1:1 Languir model of simultaneous fitting of $k_{on}$ and $k_{off}$ was used for kinetics analysis.

The consensus sequence for Anti-HER2_D4 light chain control (SEQ ID NO: 87) and Anti-HER2_D2 light chain control (SEQ ID NO: 94) was analyzed. Structural analysis suggested that a Y residue at position 91 was involved in the structural organization of CDR loops for efficient HER2 D4 binding while an H residue at the same position was less involved in HER2 D2 binding. After screening of single amino acid substitutions at position 91, Y and F residues at this position were selected for further testing.

Affinity matured anti-HER2 light chain sequences (SEQ ID NOS:9 and 10) were paired with anti-HER2_D2 heavy chain control (SEQ ID NO:92) and anti-HER2_D4 heavy chain control (SEQ ID NO:93) for HER2 binding $K_D$ measurement. Results are shown in Table 7.

TABLE 7

| LC | HC | HER2 binding $K_D$ (nM) |
|---|---|---|
| Anti-HER2_D4 light chain control (SEQ ID NO: 87) | Anti-HER2_D2 heavy chain | 41 |
| SEQ ID NO: 10 | control | 14 |

TABLE 7-continued

| LC | HC | HER2 binding $K_D$ (nM) |
|---|---|---|
| SEQ ID NO: 9 | (SEQ ID NO: 92) | 13 |
| Anti-HER2_D2 light chain control (SEQ ID NO: 94) | | 2.9 |
| Anti-HER2_D4 light chain control (SEQ ID NO: 87) | Anti-HER2_D4 heavy chain | 3 |
| SEQ ID NO: 10 | control | 1.7 |
| SEQ ID NO: 9 | (SEQ ID NO: 93) | 1.5 |
| Anti-HER2_D2 light chain control (SEQ ID NO: 94) | | No binding |

SEQ ID NO:9 and 10 light chains showed HER2 binding when paired with both Anti-HER2_D2 and D4 heavy chain controls. SEQ ID NO:9 and 10 light chains showed lower HER2 binding affinity (13 $K_D$ and 14 $K_D$ respectively) compared to Anti-HER2_D2 light chain control (2.9 $K_D$) when paired with Anti-HER2_D2 heavy chain control. In contrast, SEQ ID NO:9 and 10 light chains showed higher HER2 binding affinity (1.5 $K_D$ and 1.7 $K_D$ respectively) compared to Anti-HER2_D4 light chain control (3 $K_D$) when paired with Anti-HER2_D4 heavy chain control.

Thirteen amino acid positions in CDR H1, H2, or H3 of Anti-HER2_D2 heavy chain control (SEQ ID NO: 92) were selected based on structural analysis. The selected residues were randomized to find single amino acid substitution variants with improved HER2 ECD domain II binding. Antibodies with these single point mutations were paired with Anti-HER2_D4 light chain control (SEQ ID NO: 87) and expressed in Expi293 cells and antibodies in cell culture supernatants were screened for recombinant HER2 ECD binding using SPR. Variants with improved HER2 ECD domain II were selected and expressed with SEQ ID NO: 10 light chain in Expi293 cells and purified for additional SPR binding evaluation.

Affinity matured anti-HER2_D2 heavy chain sequences comprising the $V_H$ region of SEQ ID NOS:1-2 and 60-70 were paired with anti-HER2_D4 light chain control (SEQ ID NO:87) for HER2 binding $K_D$ measurement. Results are shown in Table 8.

TABLE 8

| LC | HC | HER2 binding $K_D$ (nM) |
|---|---|---|
| Anti-HER2_D4 light chain control (SEQ ID NO: 87) | Anti-HER2_D2 heavy chain control (SEQ ID NO: 92) | 42 |
| | SEQ ID NO: 60 | 28 |
| | SEQ ID NO: 61 | 17.5 |
| | SEQ ID NO: 62 | 18.3 |
| | SEQ ID NO: 63 | 22.1 |
| | SEQ ID NO: 1 | 28 |
| | SEQ ID NO: 64 | 21 |
| | SEQ ID NO: 65 | 35 |
| | SEQ ID NO: 66 | 32.3 |
| | SEQ ID NO: 67 | 6.1 |
| | SEQ ID NO: 68 | 9.8 |
| | SEQ ID NO: 69 | 10.2 |
| | SEQ ID NO: 2 | 28 |
| | SEQ ID NO: 70 | 30 |

Affinity matured anti-HER2_D2 heavy chain sequences comprising the $V_H$ region of SEQ ID NOS:1-2 and 60-70 paired with anti-HER2_D4 light chain control (SEQ ID NO:87) showed HER2 binding and all showed HER2 binding improvement compared to Anti-HER2_D2 heavy chain control.

Affinity matured anti-HER2 light chain sequence (SEQ ID NO: 10) was paired with affinity matured anti-HER2_D2 heavy chain sequences comprising the $V_H$ region of SEQ ID NOS:1-3 for HER2 binding $K_D$ measurement. Results are shown in Table 9.

TABLE 9

| LC | HC | HER2 binding $K_D$ (nM) |
|---|---|---|
| SEQ ID NO: 10 | SEQ ID NO: 1 | 4.2 |
| | SEQ ID NO: 2 | 6.2 |
| | SEQ ID NO: 3 | 2.1 |

SEQ ID NO: 10 light chain paired with affinity matured anti-HER2_D2 heavy chain sequences comprising the $V_H$ region of SEQ ID NOS:1-3 showed improved HER2 binding affinity (4.2, 6.2, 2.1 $K_D$ respectively). As discussed above and shown in Table 7, Anti-HER2_D2 light chain control light chain paired with Anti-HER2_D2 heavy chain control had a HER2 binding affinity of 2.9 $K_D$. Therefore, SEQ ID NO: 10 light chain paired with affinity matured anti-HER2_D2 heavy chain sequences comprising the $V_H$ region of SEQ ID NOS: 3 binds HER2 with a higher affinity than the control.

Example 3. In Vitro ADCC/ADCP of Anti-HER2 Bispecific Antibodies

A human ADCC Reporter Bioassay, V variant kit (Promega G7018) was used to assess activation of human FcγRIIIa, while a human FcgRIIa ADCP Reporter Bioassay kit (Promega G9995) was used to measure activation of the human FcγRIIa reporter of the bispecific antibodies according to the combinations in Table 10. The kit contains all of the components described below. Several cell lines with varying expression levels of HER2 and TfR were tested. The cells SKBR3 (ATCC HTB-30), ZR-75-30 (ATCC CRL-1504), BT-474 (ATCC HTB-20), OE-19 (Sigma 96071721), CHO-KI+HumanTfR (ChemPartner CRO agreement) were cultured in RPMI (Liffe Technologies 61870-036) supplemented with 10% FBS (Hyclone Bovine serum SH30080.03) and 1% Penicillin-Streptomycin (Life Technologies 15140-122) to exponential phase, washed twice with PBS and resuspended at $1.0\times10^6$ cells/mL in RPMI supplemented with 10% FBS and 1% Penicillin/Streptomycin. White 96-well high binding Nunc plates (ThermoFisher) were coated with 25 μL of media containing 50,000 cells/well.

Antibody titrations were prepared in RPMI with 4% low IgG serum and 25 μl per well was added to the plates to opsonize cells, then covered and incubated for 30 minutes at 37° C., 5% $CO_2$. During antibody opsonization, 3.5 mL of medium was pre-warmed to 37° C. and the FcγR reporter cells were quickly defrosted in 37° C. water bath, without inverting, then added to pre-warmed medium in a 15 mL conical tube with gentle mixing. After 30-minute opsonization, FcγR reporter cell line was added to each plate at 25 μl per well and incubated for 6 hours (hFcγRIIIa and hFcγRIIa activation for SKBR3, ZR-75-30, BT-474) or 16 hours (hFcγRIIIa and hFcγRIIa for CHO-KI+huTfR) at 37° C., 5% $CO_2$. After incubation, plates were allowed to acclimate to room temperature and 75 μL per well of Bio-Glo luciferase substrate suspension (Promega) was added and luminescence measured on a Perkin Elmer Envision reader. Results are shown in Table 11.

TABLE 10

| | | Hole chain | | | | | | | |
|---|---|---|---|---|---|---|---|---|---|
| | | hole | hole.E | hole.D | hole.DE | hole.PG | hole.PG.D | hole.PG.E | hole.PG.DE |
| Knob | cis-LALA.CH3C.35.23.4.knob | Fc1 | Fc2 | Fc3 | Fc4 | Fc5 | Fc6 | Fc7 | Fc8 |
| chain | cis-LALA.D.CH3C.35.23.4.knob | Fc17 | Fc18 | Fc19 | Fc20 | Fc21 | Fc22 | Fc23 | Fc24 |
| | cis-LALA.E.CH3C.35.23.4.knob | Fc25 | Fc26 | Fc27 | Fc28 | Fc29 | Fc30 | Fc31 | Fc32 |
| | cis-LALA.DE.CH3C.35.23.4.knob | Fc33 | Fc34 | Fc35 | Fc36 | Fc37 | Fc38 | Fc39 | Fc40 |
| | cis-LALAPG.CH3C.35.23.4.knob | Fc41 | Fc42 | Fc43 | Fc44 | Fc45 | Fc46 | Fc47 | Fc48 |
| | cis-LALAPG.D.CH3C.35.23.4.knob | Fc49 | Fc50 | Fc51 | Fc52 | Fc53 | Fc54 | Fc55 | Fc56 |
| | cis-LALAPG.E.CH3C.35.23.4.knob | Fc57 | Fc58 | Fc59 | Fc60 | Fc61 | Fc62 | Fc63 | Fc64 |
| | cis-LALAPG.DE.CH3C.35.23.4.knob | Fc65 | Fc66 | Fc67 | Fc68 | Fc69 | Fc70 | Fc71 | Fc72 |

TABLE 11

| | Assay done | | | | | | |
|---|---|---|---|---|---|---|---|
| | TfR-mediated ADCC | HER2-mediated ADCC | | | ADCP | | |
| Cell line used | CHO-hTfR | BT-474 | OE19 | ZR-75-30 | OE19 | ZR-75-30 | SKBR3 |
| Anti-HER2_D4 (control) | 3.0E+04 | 4.3E+05 | 1.4E+06 | 4.8E+05 | 1.1E+05 | 3.6E+04 | 3.5E+04 |
| Fc1 | 2.8E+04 | 1.5E+04 | 4.9E+05 | 3.5E+04 | 9.2E+05 | 1.6E+05 | 3.1E+05 |
| Fc41 | 2.5E+04 | 3.9E+04 | 2.1E+05 | 2.8E+04 | 2.2E+05 | 8.9E+04 | 5.9E+04 |
| Fc5 | 2.7E+04 | 3.3E+04 | 2.2E+05 | 3.0E+04 | | 4.1E+04 | 3.8E+04 |
| Fc45 | 2.6E+04 | 2.3E+04 | 7.1E+04 | 2.4E+04 | 1.5E+05 | 3.6E+04 | 3.3E+04 |
| Fc42 | 2.7E+04 | 1.5E+05 | 6.5E+05 | 7.7E+04 | 2.6E+05 | 1.0E+05 | 5.7E+04 |
| Fc52 | 2.5E+04 | 4.6E+05 | 1.2E+06 | 2.1E+05 | 2.3E+05 | 8.5E+04 | 5.8E+04 |
| Fc44 | 2.6E+04 | 2.0E+05 | 7.3E+05 | 9.3E+04 | 1.6E+05 | 4.1E+04 | 3.9E+04 |
| Fc50 | 2.9E+04 | 3.2E+05 | 2.6E+06 | 1.9E+05 | 1.6E+06 | 3.4E+05 | 2.5E+05 |
| Fc68 | 2.9E+04 | 3.6E+05 | 1.8E+06 | 2.2E+05 | | | |
| Fc7 | 2.7E+04 | 3.1E+04 | 3.0E+05 | 5.0E+04 | | | |
| Fc24 | 1.4E+05 | 2.8E+05 | 1.6E+06 | 1.6E+05 | | | |
| Fc8 | 2.7E+04 | 8.9E+04 | 8.2E+05 | 1.6E+05 | | | |
| Fc40 | 2.5E+05 | 3.4E+05 | 2.0E+06 | 2.3E+05 | | | |
| Fc23 | 7.2E+04 | 1.3E+05 | 1.1E+06 | 7.1E+04 | | | |
| Fc25 | 4.8E+04 | | | 2.2E+05 | | | |
| Fc2 | 2.3E+04 | | | 2.2E+05 | | 1.6E+05 | 3.0E+05 |
| Fc26 | 4.7E+04 | | | 3.4E+05 | | | |

The aim was to develop Fe variants that did not increase TfR-mediated ADCC compared to the control and/or Fc1 and which also had a comparable level of HER2-mediated ADCC as the control and/or improved level of HER2-mediated ADCC levels compared to Fc1. As shown above in Table 11, Fc1, Fc41, Fc5, Fc45, Fc42, Fc52, Fc44, Fc50, Fc68, Fc7, Fc8, Fc2, Fc34, and Fc4 all had a comparable levels of TfR-mediated ADCC in TfR-overexpressing CHO cells as the control. Fc50 and Fc52 showed the highest level of HER2-mediated ADCC across all the tested HER2-overexpressing cell lines without increasing TfR-mediated ADCC activation.

ADCP levels of Fc1, Fc41, Fc5, Fc45, Fc42, Fc52, Fc44, and Fc50 variants are also shown in Table 11 compared to the control across HER2-over expressing cell lines, i.e., OE19, ZR-75-30, and SKBR3.

Example 4. In Vitro Growth Inhibition of Anti-HER2 Bispecific Antibodies

A growth inhibition assay was used to determine the viability of cells after treatment with different antibodies for different durations. Several cell lines with varying expression levels of HER2 and TfR were tested. The cells SKBR3 (ATCC HTB-30), ZR-75-30 (ATCC CRL-1504), BT-474 (ATCC HTB-20), OE-19 (Sigma 96071721), CHO-KI+HumanTfR (ChemPartner CRO agreement) were cultured in RPMI (Life Technologies 61870-036) supplemented with 10% FBS (Hyclone Bovine serum SH30080.03) and 1% Penicillin-Streptomycin (Life Technologies 15140-122) to exponential phase. After washing with PBS, the cells were resuspended at $1.0\times10^5$ cells/mL in RPMI supplemented with 10% FBS and 1% Penicillin/Streptomycin. Black Poly-D-Lysine plates (Corning 354640) were coated with 100 µl of cell culture media containing 10,000 cells/well. The plates were incubated for 24 hrs in a 37° C., 5% $CO_2$ incubator.

Antibody titrations were prepared in RPMI with 10% FBS serum and 1% Penicillin/Streptomycin. The antibodies were added to each plate at 65 µl per well, then covered and incubated for 72 hrs (for OE-19 cell line only) and at 37° C., 5% $CO_2$. For BT-474 and ZR-75-30 cell lines, an additional 65 µl of antibody were added after 72 hrs and then incubated for another 72 hrs at 37° C., 5% $CO_2$.

On Day 7, cell growth was determined using 5 µL of WST-1 reagent (Sigma Aldrich) in 50 µL of growth media. The plate was incubated for 4 hours in the presence of WST-1 reagent, and absorbance was determined at 440 nm. The percent of growth inhibition/proliferation was calculated based on A440 nM and was normalized to the untreated control.

Figure 2:
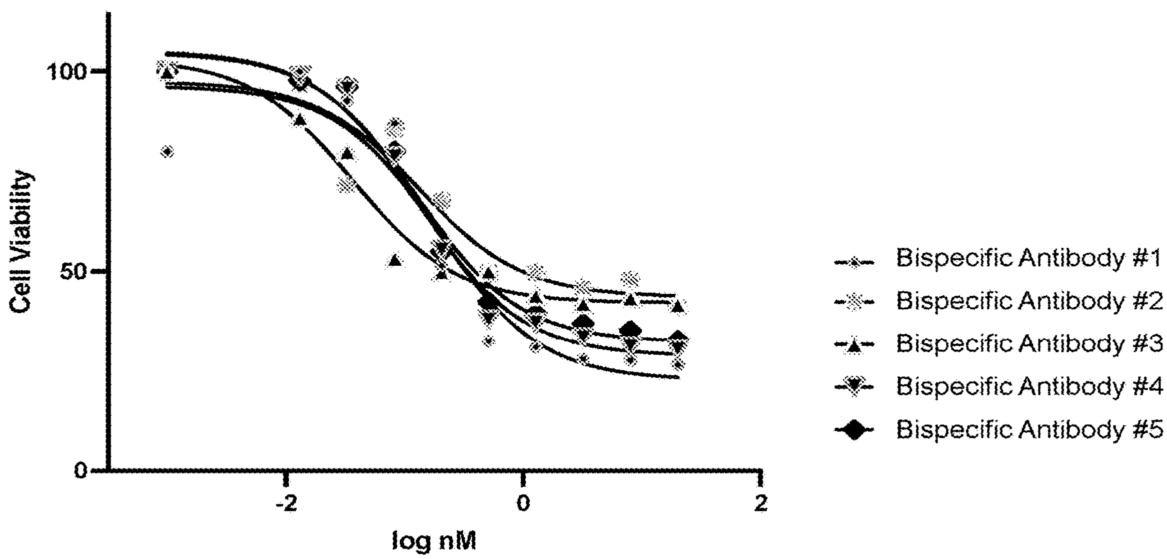
FIG. 2 shows growth inhibition assay results on ZR-75-30 cells as well as IC50 and max % growth inhibition values for the different antibodies in Table 12.

Growth inhibition assay results on ZR-75-30 cells for the different antibodies in Table 12 as well as IC50 and max 0% growth inhibition values are shown in FIG. 2. Each of Bispecific Antibody #2, #3, #4, and #5 showed improved EC50 value/efficacy compared to the control. Bispecific Antibody #4 and 5 showed comparable max 00 growth inhibition/efficacy to the control.

TABLE 12

| | HC1 | HC2 | LC |
|---|---|---|---|
| Bispecific Antibody #1 (control) | SEQ ID NO: 20 | SEQ ID NO: 24 | SEQ ID NO: 19 |
| Bispecific Antibody #2 | SEQ ID NO: 93 | SEQ ID NO: 92 | SEQ ID NO: 10 |
| Bispecific Antibody #3 | SEQ ID NO: 37 | SEQ ID NO: 26 | SEQ ID NO: 10 |
| Bispecific Antibody #4 | SEQ ID NO: 37 | SEQ ID NO: 27 | SEQ ID NO: 10 |
| Bispecific Antibody #5 | SEQ ID NO: 37 | SEQ ID NO: 25 | SEQ ID NO: 10 |

Example 5. In Vivo Xenograft Studies with ATV:CLC Bispecific Antibody

Two human HER2+ cell lines were used to evaluate response of ATV:CLC bispecific antibody #1 in subcutaneous xenograft models in immunodeficient (NOD/SCID) mice. All molecules were prepared in the same formulation buffer (10 mM NaAcetate, 600 sucrose, pH5.5) or PBS/saline except for trastuzumab (Clinical Herceptin) and pertuzumab (Clinical Perjeta) which were purchased and prepared according to instructions and/or diluted further with PBS or saline.

TABLE 13

| Anti-HER2 bispecific molecules | | | | |
|---|---|---|---|---|
| Patent nomenclature | VH_D4 (knob side) | VH_D2 (hole side) | LC | Fc Mods |
| Common light chain (CLC) bispecific antibody control (Herceptarg) | SEQ ID NO: 108 | SEQ ID NO: 109 | SEQ ID NO: 19 | No TV |
| Common light chain (CLC) bispecific antibody control #2 | SEQ ID NO: 15 | SEQ ID NO: 3 | SEQ ID NO: 10 | No TV |
| ATV: Common light chain (CLC) bispecific antibody #1 | SEQ ID NO: 108 | SEQ ID NO: 109 | SEQ ID NO: 19 | Knob side: TV35.23.4, cis-LALA |
| ATV: Common light chain (CLC) bispecific antibody #2 | SEQ ID NO: 15 | SEQ ID NO: 3 | SEQ ID NO: 10 | Knob side: TV35.23.4, cis-LALA |
| ATV: Common light chain (CLC) bispecific antibody #3 | SEQ ID NO: 15 | SEQ ID NO: 3 | SEQ ID NO: 10 | Knob side: TV35.23.4, cis-LALAPS, S239D Hole side: I332E |
| ATV: Common light chain (CLC) bispecific antibody #7 | SEQ ID NO: 15 | SEQ ID NO: 3 | SEQ ID NO: 10 | Knob side: TV35.23.4, cis-LALAPS, S239D and I332E Hole side: S239D and I332E |

For the BT-474 breast cancer cell line-derived xenograft (CDX) model, female NSG (NOD scid gamma) mice (6-7 weeks of age) were injected subcutaneously into the axilla with BT-474 cells and treatment initiated six days following inoculation when tumors were between 100-200 $mm^3$ in volume. Mice were randomized into treatment groups based on mean tumor volume, with n=11 mice per group. Trastuzumab and pertuzumab combination treatment at 40+40 mg/kg or ATV:CLC bispecific antibody #1 at 80 mg/kg was administered via intraperitoneal (IP) injection. Tumor volumes were measured three times per week using calipers.

Figure 3A:
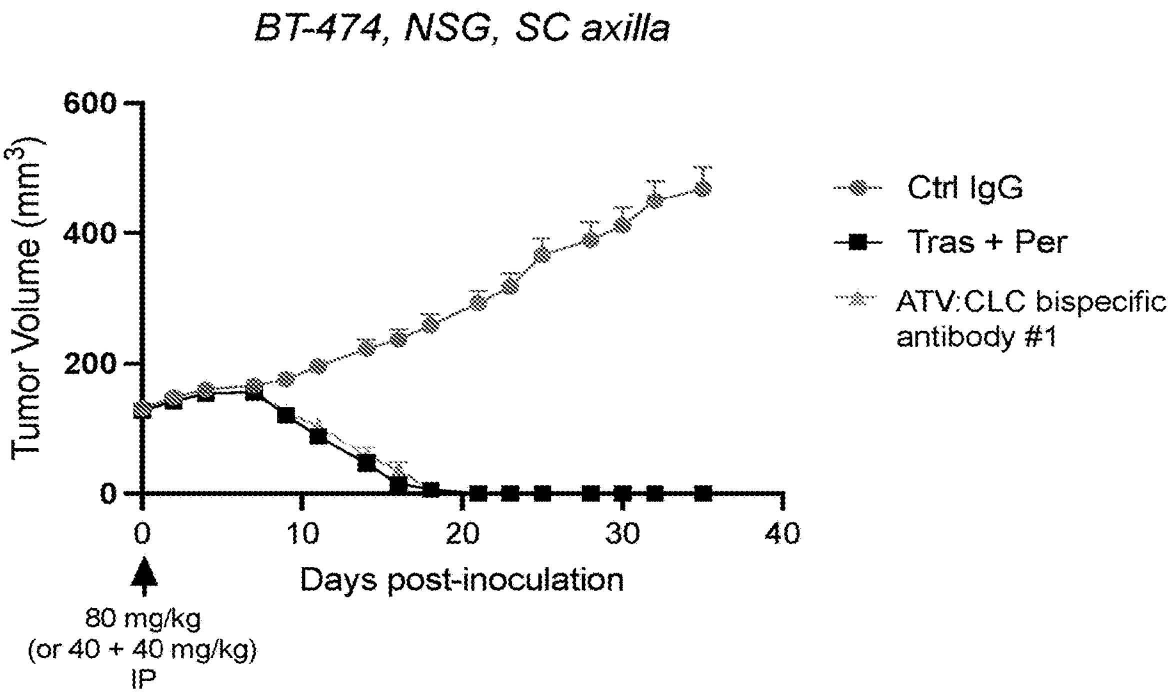
FIGS. 3A and 3B illustrate in vivo anti-tumor activity tumor in single dose study with ATV:CLC bispecific antibody in 2 human cell line derived xenograft models.

In a relatively trastuzumab-sensitive BT-474 xenograft model, ATV:CLC bispecific antibody #1 showed equivalent inhibition of tumor growth following a single dose compared with trastuzumab and pertuzumab, with complete regression of the tumors for the entire treatment group after 21 days (FIG. 3A).

For the OE19 gastro-esophageal junction CDX model, female NOD/SCID mice (6-8 weeks of age) were injected subcutaneously with OE19 cells in the right upper flank region and treatment initiated one week following inoculation when tumors were between 100-200 $mm^3$ in volume. Mice were randomized into treatment groups based on a matched distribution/stratified method, with n=11 mice per group. ATV:trastuzumab and ATV:pertuzumab combination treatment at 50+50 mg/kg or ATV:CLC bispecific antibody #1 at 100 mg/kg was administered via IP injection. Tumor volumes were measured three times per week using calipers.

Figure 3B:
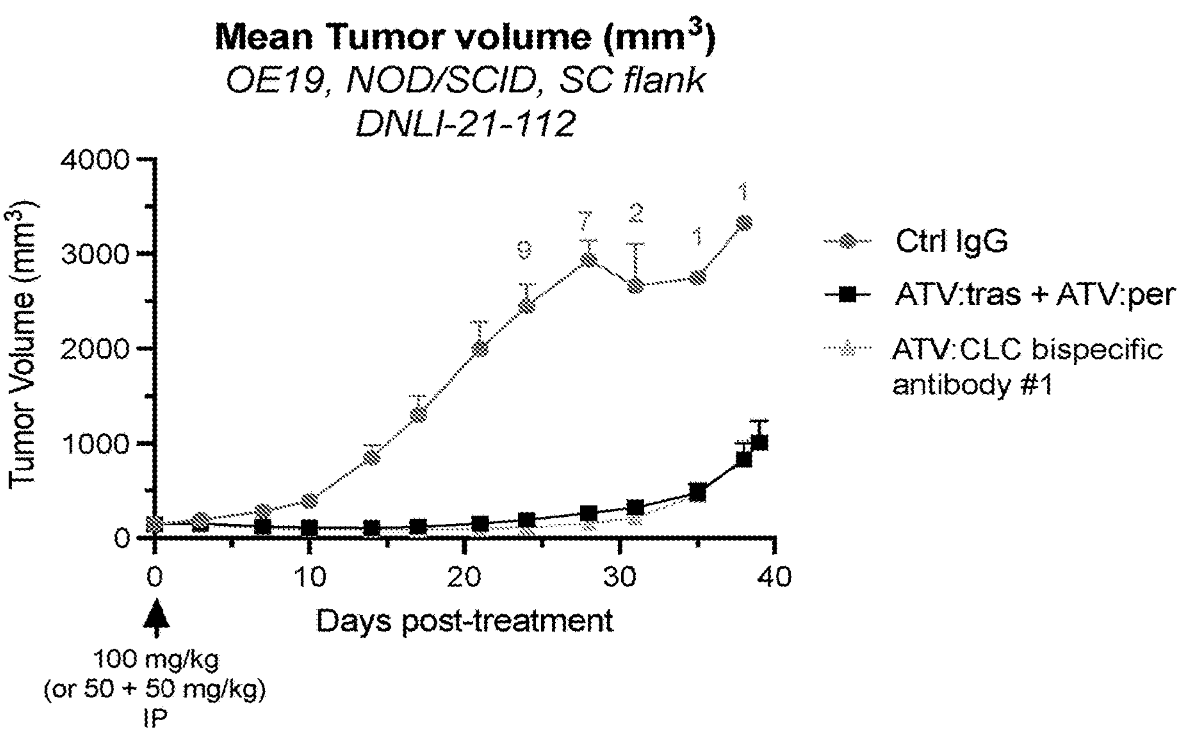

In the OE19 xenograft model, which shows relative resistance to trastuzumab and pertuzumab combination treatment, ATV:CLC bispecific antibody #1 and the combination of ATVcis-LALA:trastuzumab and ATVcis-LALA:pertuzumab both showed significant tumor growth delay compared to the control group (FIG. 3B). All groups start with n=11 mice per group. Numbers on graph represent the number of animals remaining in control group after subset of animals reached humane endpoint. One animal found dead in ATV combo group on day 17 without apparent cause. ATV:trastuzumab and ATV:pertuzumab are traztuzumab and pertuzumab antibodies comprising an Fc modification that binds to TfR ("TV") and cis-LALA mutations. These in vivo results are in line with in vitro growth inhibition data which demonstrated an increased potency and increased maximal effect of ATV:HER2 (anti-HER2 molecules with TV) in the OE19 cell line compared to anti-HER2 molecules lacking the TfR binding Fc modification.

In a follow-up lower dose study, to study the effect of TfR binding, ATV:CLC bispecific antibody #1 was compared with a CLC bispecific antibody control which had identical Fabs as ATV:CLC bispecific antibody #1 but lacked the TfR binding Fc modification. For the BT-474 breast cancer CDX model, female NOD/SCID mice (6-8 weeks of age) were implanted with estrogen pellets (0.36 mg, 17B-estradiol, 60 day pellet) one day before tumor inoculation. BT-474 cells were then injected subcutaneously into the mammary fat pad and treatment initiated eight days following inoculation when tumors were between 100-200 $mm^3$ in volume. Mice were randomized into treatment groups based on a matched distribution/stratified method, with n=11 mice per group. Tumor volumes were measured two times per week using calipers.

Figure 4A:
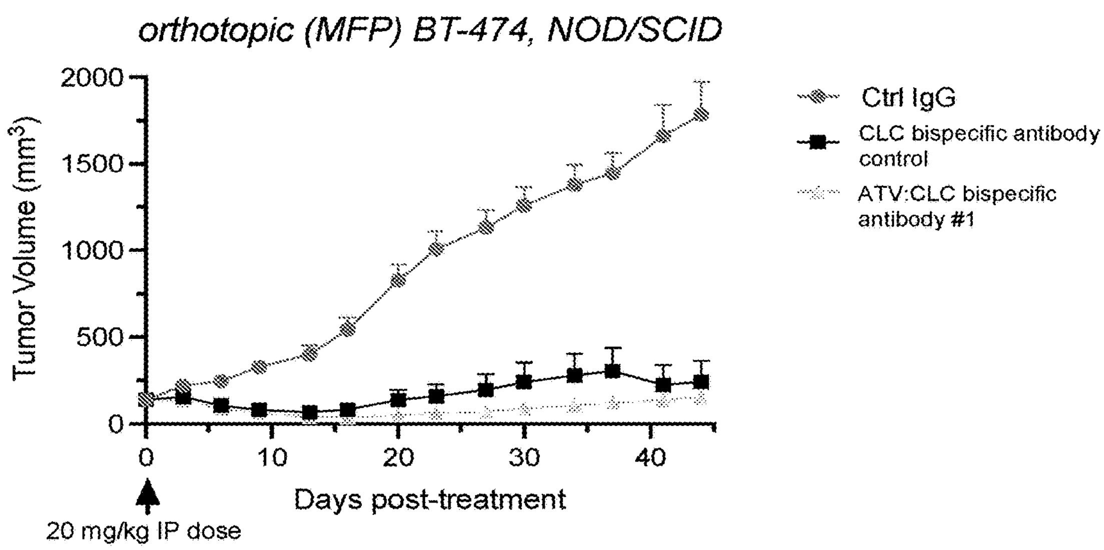
FIGS. 4A and 4B illustrate in vivo anti-tumor activity tumor in single dose lower dose study with ATV:CLC bispecific antibody in 2 human cell line derived xenograft models.
Figure 4B:
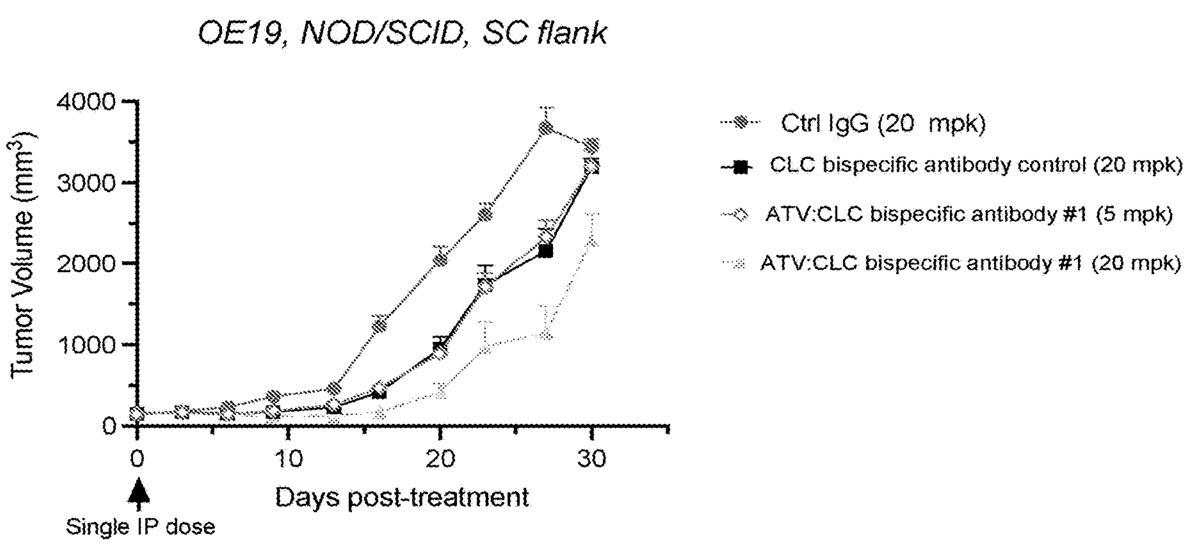

A single 20 mg/kg dose of ATV:CLC bispecific antibody #1 administered intraperitoneally showed similar tumor growth delay as the CLC bispecific antibody control (no TfR binding) in the sensitive BT-474 xenograft model (FIG. 4A). ATV:CLC bispecific antibody #1 showed an improved response in the more resistant OE19 xenograft model at equal doses of 20 mg/kg and equivalent anti-tumor response at a four-fold lower dose (5 mg/kg) than the CLC bispecific antibody control (FIG. 4B).

Figure 5A:
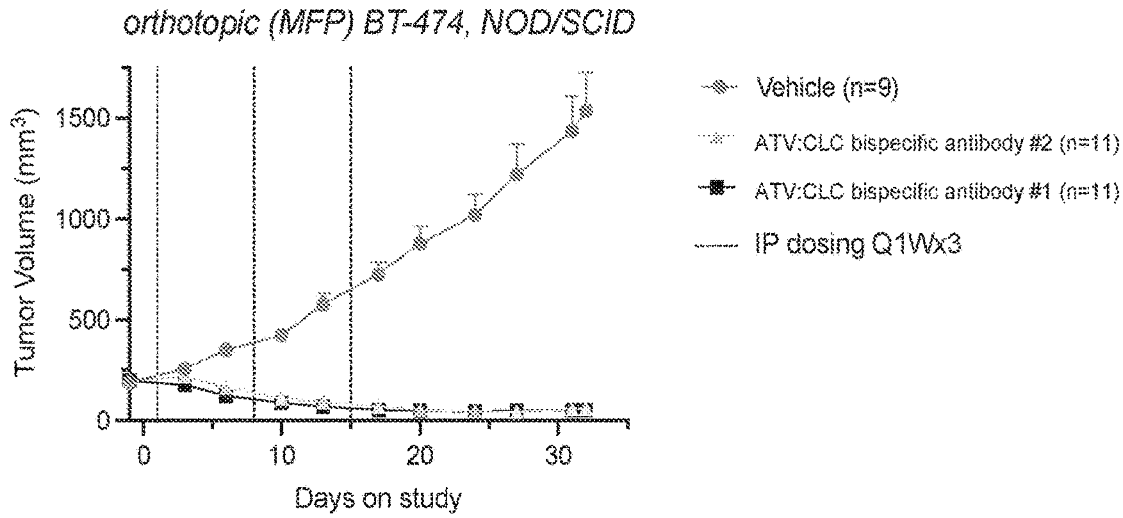
FIGS. 5A and 5B illustrate in vivo anti-tumor activity tumor in multidose study with ATV:CLC bispecific antibody in 2 human cell line derived xenograft models.

In a further bridging study, ATV:CLC bispecific antibody #1 and #2 were compared in multidose xenograft studies. In the BT-474 model, mice (n=11 for each group) were dosed Q1W via IP, i.e., mice were administered a single dose per week for 3 weeks. ATV:CLC bispecific antibody #1 and ATV:CLC bispecific antibody #2 showed equal inhibition and delay of tumor growth (FIG. 5A). Additionally, the same groups were dosed in combination with daily 50 mg/kg oral dosing of tucatinib for 21 days but no additional improvements were seen with ATV:CLC bispecific antibody #1 or #2.

Figure 5B:
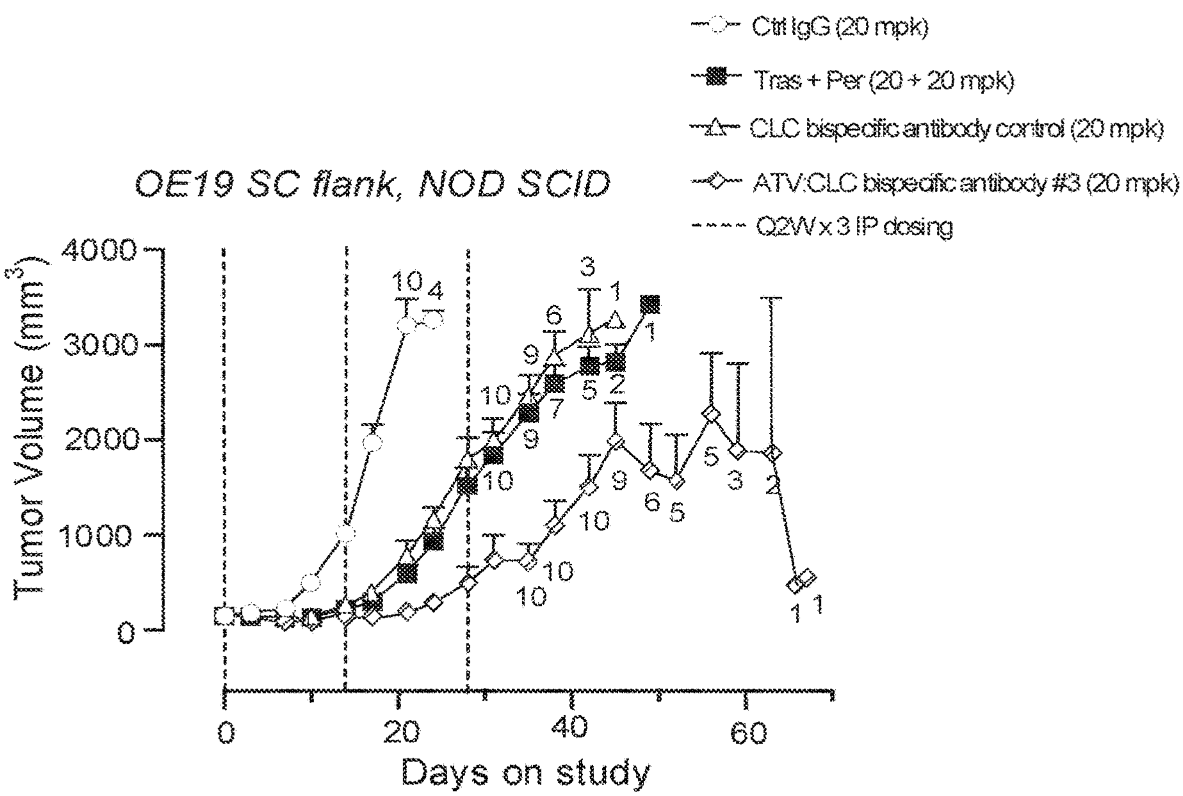

Lastly, an Fc engineered variant of ATV:CLC bispecific antibody #2, ATV:CLC bispecific antibody #3 (comprising additional Fc modifications, e.g., P329S, I332E, and S239D) was also compared to anti-HER2 molecules lacking TfR binding in a multidose OE19 xenograft study. Mice were dosed Q2W via IP, i.e., mice were administered a single dose every 2 weeks for 6 weeks. ATV:CLC bispecific antibody #3 showed increased tumor growth delay and increased survival compared to the combination of trastuzumab and pertuzumab or the CLC bispecific antibody control (FIG. 5B). All groups start with n=11 mice per group. Numbers on graph represent the number of animals remaining in group after subset of animals reached humane endpoint.

Example 6. Brain Uptake and Distribution of ATV:CLC Bispecific Antibody $TfR^{mu/hu}$ KI mice (see, e.g., International Publication No. WO 2018/152285) were administered a single 25 mg/kg IV dose of CLC bispecific antibody control or ATV:CLC bispecific antibody #3 (n=4/group). In-life blood was collected at 30 minutes and 6 hours and terminal blood and fresh frozen brain were collected at 1, 4, 7, and 10 days post-dose to evaluate huIgG concentrations in plasma and brain lysate via ELISA.

Figure 6:
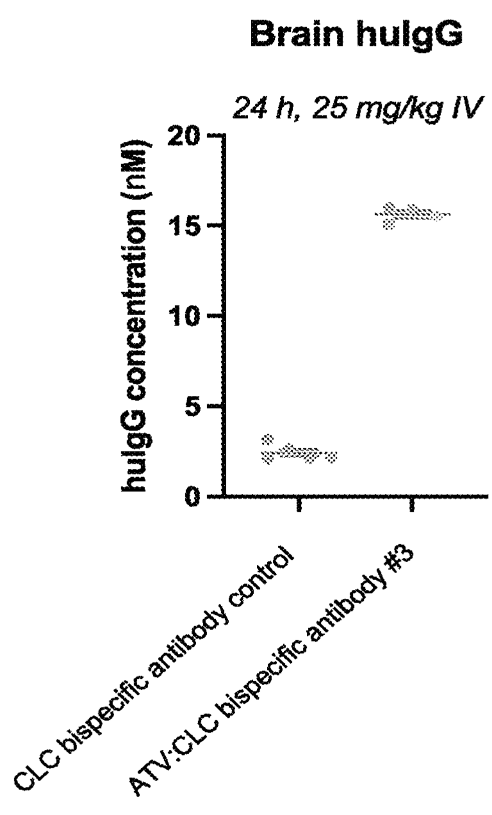
FIG. 6 illustrates brain uptake of ATV:CLC bispecific antibody.

Plasma and brain concentrations were measured following a single dose of bispecific CLC bispecific antibody control or ATV:CLC bispecific antibody #3 in $TfR^{mu/hu}$ KI mice. Brain concentrations of ATV:CLC bispecific antibody #3 were approximately 6.5-fold higher at 24 h post-dose compared to the CLC bispecific antibody control (FIG. 6). This demonstrates TfR-mediated brain delivery for the ATV molecules. Similarly, in a time course study, ATV:CLC bispecific antibody #2, #3, and #7 showed approximately 4-5-fold higher brain concentrations 24 h and up to ~2-fold higher brain concentrations 4 days after IV dosing.

Furthermore, immunohistochemistry of dosed molecules in the brain was performed. One fresh brain hemisphere per animal was immersion fixed for approximately 24 h at 4 C for immunohistochemistry before cryoprotecting in sucrose and sectioning on a freezing microtome. Coronal brain sections (40 m) were selected for each animal and stained by incubating in blocking buffer (1% BSA+1× fish gelatin+0.5% Triton X-100+0.01% sodium azide in PBS) for three hours at room temperature. Sections were then incubated overnight in dilution buffer (1% BSA+0.3% Triton X-100+0.01% sodium azide in PBS) containing primary/secondary antibodies (NeuN, Abcam, ab177487 and donkey-anti-hu-IgG, Jackson, 709-606-149) at 4 C, washed three times for 15 minutes each in PBS with 0.3% Triton X-100, and incubated for three hours in dilution buffer containing secondary antibodies (donkey-anti-rabbit, Invitrogen, A21206) and DAPI (5 g/mL, Invitrogen, D1306), and washed three times for 15 minutes each in PBS with 0.3% Triton X-100 before mounting and coverslipping with Prolong Glass (Invitrogen, P36984). Slides were imaged using a Leica SP8 confocal microscope at 20× magnification and segmentation and visualization performed using Imaris.

Figure 7B:
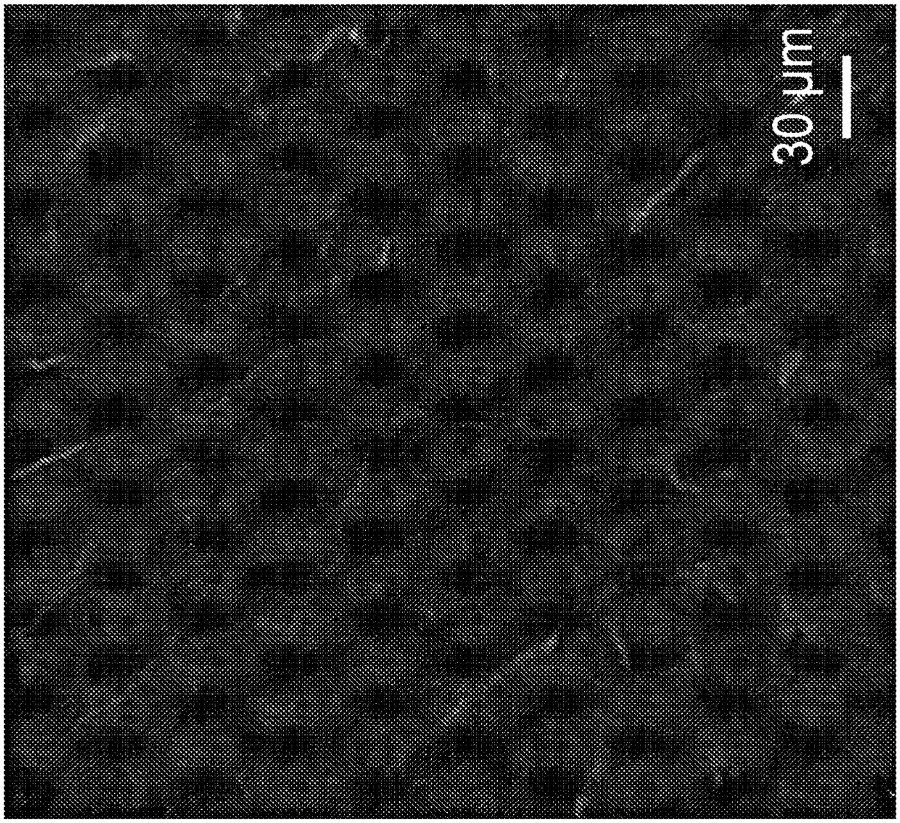
FIGS. 7A and 7B illustrate IHC brain distribution of CLC bispecific antibodies.
Figure 7A:
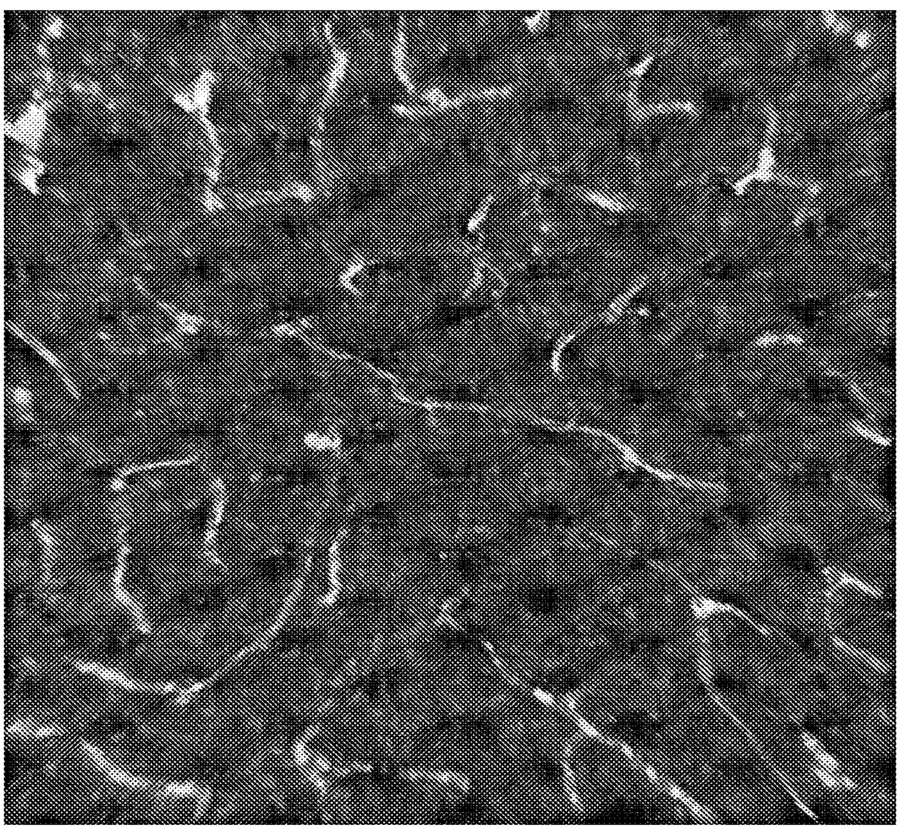

Immunohistochemistry for the huIgG backbone of the dosed molecules revealed a broad distribution of ATV:CLC bispecific antibody #3 across the normal brain, localizing within blood vessels and NeuN+ neurons along with diffuse signal within the parenchyma (FIG. 7A). In contrast, the CLC bispecific antibody control showed limited entry or distribution within the brain tissue (FIG. 7B). This is in line with the significantly lower brain concentrations observed for non-TV anti-HER2 molecules, i.e., molecules without TfR binding. Similar results, i.e., vascular and neuronal/parenchymal localization, were observed with ATV:CLC bispecific antibody #2 and ATV:CLC bispecific antibody #7.

Example 7. Plasma PK of ATV:CLC Bispecific Antibodies in Cynomolgus Monkeys

To assess the impact of the Fc modifications on systemic clearance, Fc modification variants were compared. Since TV35.23.4 (i.e., CH3C.35.23.4) does not have cyno cross-reactivity, i.e., does not bind cyno TfR, bispecific HER2 ATVs with TV35.21 (see, CH3C.35.21 in Table A above) instead of TV35.23.4 were used. As shown in Table 14 below, these molecules use the same Fabs as ATV:CLC bispecific antibody #2, #3, and #7 used in the mouse studies above.

ATV:CLC bispecific antibody #4, #5, and #6 were compared to Clinical Herceptin (trastuzumab) and serum concentrations of huIgG were measured at various time points following a single 50 mg/kg intravenous dose in female cynomolgus monkeys (n=3/group).

TABLE 14

| Anti-HER2 bispecific molecules for cyno study | | | | |
|---|---|---|---|---|
| | VH_D4 (knob side) | VH_D2 (hole side) | LC | Fc Modifications |
| ATV:CLC bispecific antibody #4 | SEQ ID NO: 15 | SEQ ID NO: 3 | SEQ ID NO: 10 | Knob side: TV35.21, cis-LALA |
| ATV:CLC bispecific antibody #5 | SEQ ID NO: 15 | SEQ ID NO: 3 | SEQ ID NO: 10 | Knob side: TV35.21, cis-LALAPS, S239D Hole side: I332E |
| ATV:CLC bispecific antibody #6 | SEQ ID NO: 15 | SEQ ID NO: 3 | SEQ ID NO: 10 | Knob side: TV35.21, cis-LALAPS, S239D and I332E Hole side: S239D and I332E |

Figure 8:
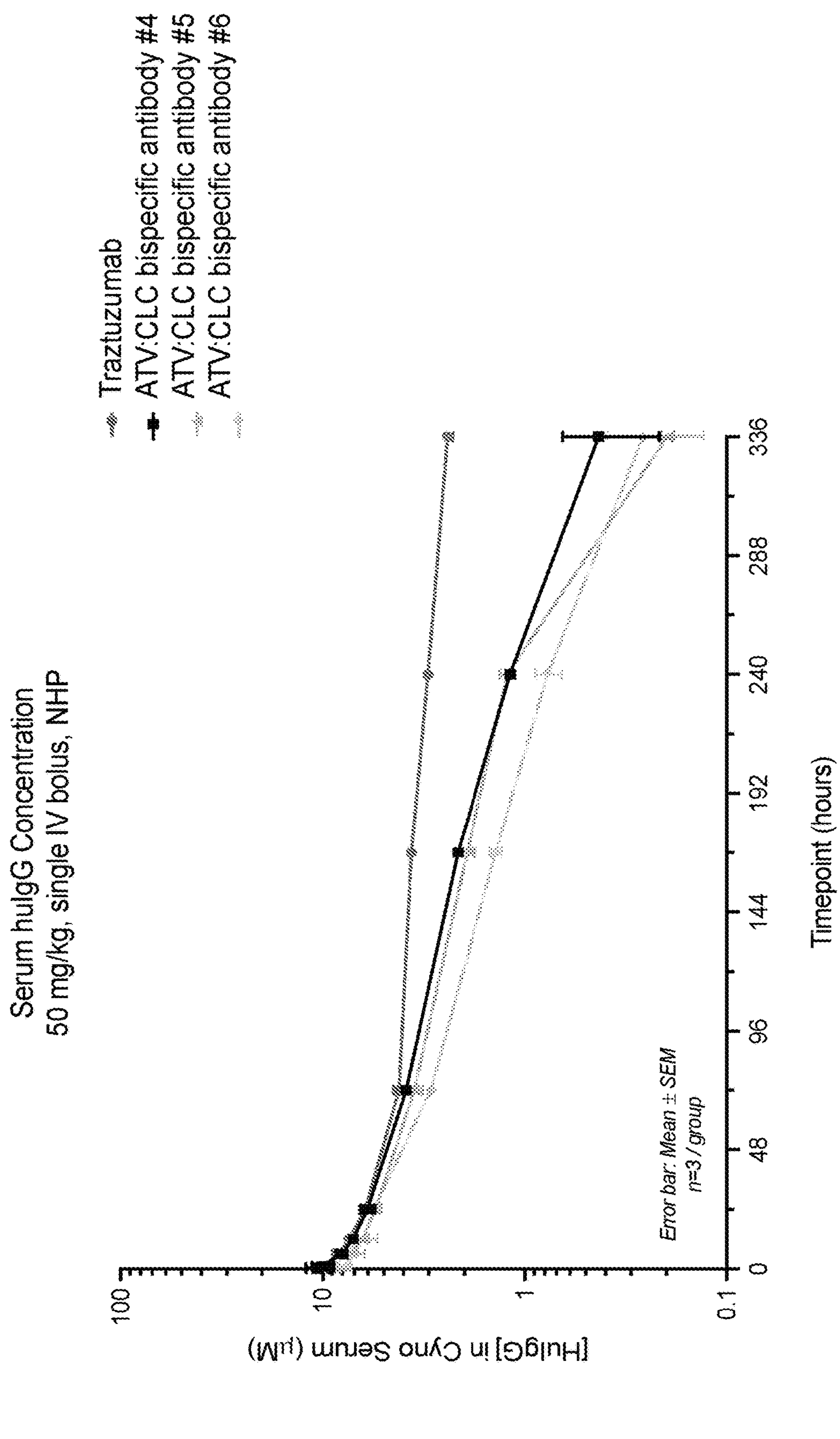
FIG. 8 illustrates plasma PK in single dose study with ATV:CLC bispecific antibodies in cynomolgus monkeys.

All ATV:HER2 molecules showed a more rapid clearance from systemic circulation compared to Herceptin (trastuzumab), as expected due to TfR-mediated clearance (FIG. 8).

Example 8. In Vitro ADCC/ADCP of Anti-HER2 Bispecific Antibodies in NK Cells

A cell-based antibody-dependent cell cytotoxicity (ADCC) assay was used to assess whether the differences in Fc gamma receptor binding affinities for the different Fc mutants impacted HER2-mediated tumor cell or TfR-mediated cell killing using isolated human NK cells.

NK cells were isolated from whole blood and were used to assess activation of human FcγRIIIa. Blood was collected on Trizma. The cells were isolated according to the RosetteSep Human NK cell enrichment Protocol (Stemcell 15065). RosetteSep Cocktail was added to Blood Samples in a SepMate tube and left at RT for 15 mins. After incubation the samples were diluted with an equal volume of PBS (Gibco 10010-0310) and 10% FBS (Hyclone Bovine serum SH30080.03). The diluted sample is then added to the Density gradient media Lymphoprep (Stemcell 07801) and centrifuged for 10 mins. The enriched cells are then collected and wash 2 times with PBS. Finally, 20 ng/ml of IL-21 is added to the cells and then left overnight for next day use.

Cell lines with varying expression levels of HER2 and TfR were tested. The cells SKBR3 (ATCC HTB-30) and CHO-KI+HumanTfR (ChemPartner CRO agreement) were cultured in RPMI (Life Technologies 61870-036) supplemented with 10% FBS (Hyclone Bovine serum SH30080.03) and 1% Penicillin-Streptomycin (Life Technologies 15140-122) to exponential phase, washed twice with PBS and resuspended at $1.0\times10^6$ cells/mL in RPMI supplemented with 10% FBS and 1% Penicillin/Streptomycin.

Clear 96-well non-treated V bottom plates (Costar 3897) were coated with 25 L of media containing 50,000 cells/well. Antibody titrations were prepared in RPMI with 10% FBS serum and 25 μl per well was added to the plates to opsonize cells, then covered and incubated for 30 minutes at 37° C., 5% $CO_2$. During antibody opsonization, the NK cells were washed one time with media containing RPMI and 10% FBS. Cells were counted and an E:T ratio of 25:1 was used for cell density. After 30-minute opsonization, NK cells were added to each plate at 25 μl per well and incubated for 4 hours. After incubation, plates were allowed to acclimate to room temperature and spun down at 300×g for 5 mins. 50 μL of the supernatant was removed to a White 96-well clear bottom plate (Thermo 165306). 50 μl of CytoTox 96® Assay Reagent was added to each well of the plate containing the supernatant. The plate was covered to protect it from light and incubate for 30 minutes at room temperature. Stop Solution is added, and the absorbance signal is measured at 490 nm in a plate reader. Released LDH in culture supernatants is measured with a 30-minute coupled enzymatic assay, which results in the conversion of a tetrazolium salt (iodonitrotetrazolium violet; INT) into a red formazan product. The amount of color formed is proportional to the number of lysed cells.

Figure 9:
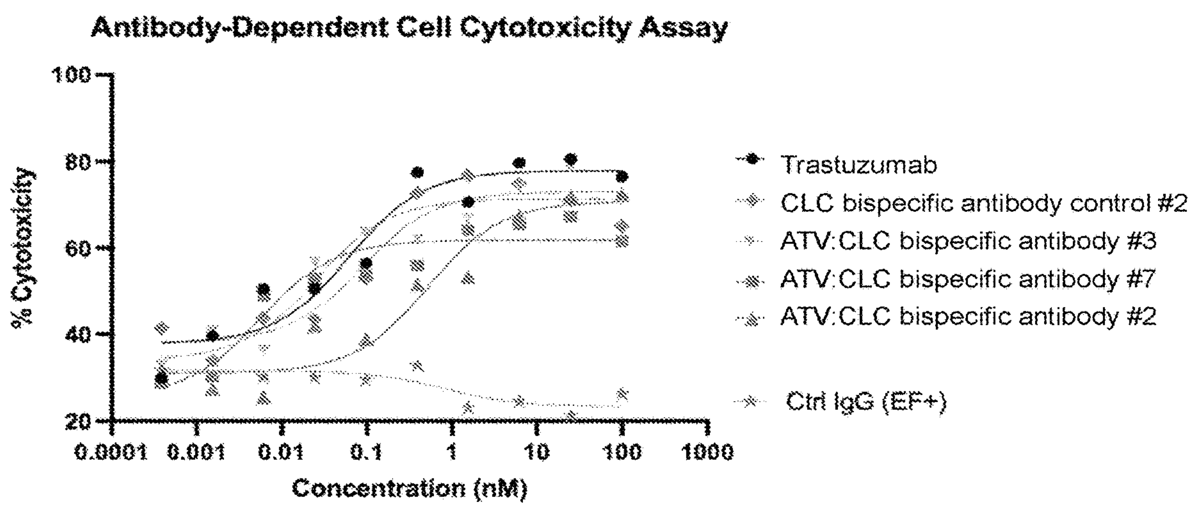
FIG. 9 illustrates ADCC of ATV:CLC bispecific antibodies.

Interestingly, in this assay on HER2 expressing tumor cells, the cis-LALA modification resulted in only a slight rightward shift in the curve indicating a slight decrease in potency, but an equal maximum effect of cell killing was observed as the non-TV anti-HER2 bispecific, i.e., CLC bispecific antibody control #2 and trastuzumab (FIG. 9).

No cell killing was observed for TfR-expressing (HER2−) cells with cis-LALA or additional Fc mutations, suggesting these molecules would not negatively impact TfR-expressing cells.

The ADCP reporter assay to measure FcgRIIA activation also demonstrated that ATV:CLC bispecific #2 and Fc variants (ATV:CLC bispecific #3 and #7) showed similar receptor activation as each other which was greater than trastuzumab and slightly less than CLC bispecific antibody control #2.

Example 9. FcgR Binding Assay of ATV:CLC Bispecific Antibodies

Fc gamma receptor binding affinities of engineered anti-HER2 antibodies were measured by SPR using a Biacore 8K instrument. Biotinylated recombinant Fc gamma receptors were captured on Biacore™ Series SA sensor chips followed by injections of serial 3-fold dilutions of Fc-engineered anti-Her2 antibodies at a flow rate of 30 L/min. Each sample was analyzed using five 60 second injections with increasing antibody concentrations followed by a 5 minute dissociation. A 1:1 Languir model of simultaneous fitting of k on and k off was used for kinetics analysis.

TABLE 15

| Fc gamma receptor binding affinities of Fc-engineered anti-Her2 antibodies | | | | |
|---|---|---|---|---|
| | Trastuzumab | ATV:CLC bispecific antibody #4 | ATV:CLC bispecific antibody #5 | ATV:CLC bispecific antibody #6 |
| FcgR2a | 48 nM | 430 nM | 39 nM | 13 nM |
| FcgR3a(V158) | 890 nM | 3.2 μM | 560 nM | 760 nM |

Increased FcgR affinities are observed in the Fc variants engineered with S239D and I332E, i.e., ATV:CLC bispecific antibody #5 and #6, compared with ATV:CLC bispecific antibody #4 and trastuzumab. However, taken together with the results in the ADCC assays described above, this increased affinity may only apply when the antibodies are bound to the Fab target, i.e., HER2.

IX. Exemplary Embodiments

Exemplary embodiments provided in accordance with the presently disclosed subject matter include, but are not limited to, the claims and the following embodiments:

1. An isolated antibody comprising one or more complementarity determining regions (CDRs) selected from the group consisting of:
   (a) a heavy chain CDR1 comprising the amino acid sequence of SEQ ID NO:89;
   (b) a heavy chain CDR2 comprising the amino acid sequence of SEQ ID NO:90; and
   (c) a heavy chain CDR3 comprising the amino acid sequence of SEQ ID NO:91,
   wherein at least one of:
   $X_1$ in SEQ ID NO: 89 is not T;
   $X_2$ in SEQ ID NO: 89 is not F;
   $X_3$ in SEQ ID NO: 89 is not T;
   $X_1$ in SEQ ID NO: 90 is not N;
   $X_2$ in SEQ ID NO: 90 is not N;
   $X_3$ in SEQ ID NO: 90 is not S;
   $X_4$ in SEQ ID NO: 90 is not G;
   $X_5$ in SEQ ID NO: 90 is not G;
   $X_6$ in SEQ ID NO: 90 is not Q;
   $X_1$ in SEQ ID NO: 91 is not L;
   $X_2$ in SEQ ID NO: 91 is not G;
   $X_3$ in SEQ ID NO: 91 is not P; and
   $X_4$ in SEQ ID NO: 91 is not S.
2. The isolated antibody of embodiment 1, wherein the heavy chain CDR1 comprises the amino acid sequence of SEQ ID NO:89, wherein $X_1$ is N, K, M, or H.
3. The isolated antibody of embodiment 1, wherein the heavy chain CDR2 comprises the amino acid sequence of SEQ ID NO:90, wherein $X_5$ is Q.
4. The isolated antibody of embodiment 1, wherein the heavy chain CDR2 comprises the amino acid sequence of SEQ ID NO:90, wherein $X_6$ is R, H, or T.
5. The isolated antibody of embodiment 1, wherein the heavy chain CDR3 comprises the amino acid sequence of SEQ ID NO:91, wherein $X_4$ is W, F, D, L, or Y.
6. The isolated antibody of embodiment 1, wherein the heavy chain CDR3 comprises the amino acid sequence of SEQ ID NO:91, wherein $X_4$ is L.
7. The isolated antibody of embodiment 1, comprising one or more CDRs selected from the group consisting of:
   (a) a heavy chain CDR1 comprising the amino acid sequence of SEQ ID NO:89;
   (b) a heavy chain CDR2 comprising the amino acid sequence of SEQ ID NO:90, wherein $X_5$ is Q; and
   (c) a heavy chain CDR3 comprising the amino acid sequence of SEQ ID NO:91, wherein $X_4$ is L.
8. The isolated antibody of embodiment 1, comprising one or more CDRs selected from the group consisting of:
   (a) a heavy chain CDR1 having at least 90% sequence identity to an amino acid sequence selected from the group consisting of SEQ ID NOS:4 and 49-52 or having up to two amino acid substitutions relative to an amino acid sequence selected from the group consisting of SEQ ID NOS:4 and 49-52;
   (b) a heavy chain CDR2 having at least 90% sequence identity to an amino acid sequence selected from the group consisting of SEQ ID NOS:5-6 and 53-55 or having up to two amino acid substitutions relative to an amino acid sequence selected from the group consisting of SEQ ID NOS:5-6 and 53-55; and
   (c) a heavy chain CDR3 having at least 90% sequence identity to an amino acid sequence selected from the group consisting of SEQ ID NOS:7-8 and 56-59 or having up to two amino acid substitutions relative to an amino acid sequence selected from the group consisting of SEQ ID NOS:7-8 and 56-59.
9. The isolated antibody of embodiment 8, comprising one or more CDRs selected from the group consisting of:
   (a) a heavy chain CDR1 having at least 90% sequence identity to the amino acid sequence of SEQ ID NO:4 or having up to two amino acid substitutions relative to the amino acid sequence of SEQ ID NO:4;
   (b) a heavy chain CDR2 having at least 90% sequence identity to the amino acid sequence of SEQ ID NO:5 or SEQ ID NO:6 or having up to two amino acid substitutions relative to the amino acid sequence of SEQ ID NO:5 or SEQ ID NO:6; and
   (c) a heavy chain CDR3 having at least 90% sequence identity to the amino acid sequence of SEQ ID NO:7 or SEQ ID NO:8 or having up to two amino acid substitutions relative to the amino acid sequence of SEQ ID NO:7 or SEQ ID NO:8.
10. The isolated antibody of embodiment 9, comprising one or more CDRs selected from the group consisting of:
   (a) a heavy chain CDR1 comprising the amino acid sequence of SEQ ID NO:4;
   (b) a heavy chain CDR2 comprising the amino acid sequence of SEQ ID NO:5 or SEQ ID NO:6; and
   (c) a heavy chain CDR3 comprising the amino acid sequence of SEQ ID NO:7 or SEQ ID NO:8.
11. The isolated antibody of embodiment 10, comprising one or more CDRs selected from the group consisting of:
   (a) a heavy chain CDR1 comprising the amino acid sequence of SEQ ID NO:4;
   (b) a heavy chain CDR2 comprising the amino acid sequence of SEQ ID NO:6; and
   (c) a heavy chain CDR3 comprising the amino acid sequence of SEQ ID NO:7.
12. The isolated antibody of embodiment 10, comprising one or more CDRs selected from the group consisting of:
   (a) a heavy chain CDR1 comprising the amino acid sequence of SEQ ID NO:4;
   (b) a heavy chain CDR2 comprising the amino acid sequence of SEQ ID NO:5; and
   (c) a heavy chain CDR3 comprising the amino acid sequence of SEQ ID NO:8.
13. The isolated antibody of embodiment 10, comprising one or more CDRs selected from the group consisting of:
   (a) a heavy chain CDR1 comprising the amino acid sequence of SEQ ID NO:4;
   (b) a heavy chain CDR2 comprising the amino acid sequence of SEQ ID NO:6; and
   (c) a heavy chain CDR3 comprising the amino acid sequence of SEQ ID NO:8.
14. The isolated antibody of embodiment 8, comprising a heavy chain variable region comprising an amino acid sequence having at least 90% sequence identity to any one of SEQ ID NOS:1-3.
15. The isolated antibody of embodiment 8, comprising a heavy chain variable region comprising the amino acid sequence of any one of SEQ ID NOS:1-3.

16. An isolated antibody comprising:

(a) alight chain CDR3 comprising the amino acid sequence of SEQ ID NO:13 or 14.

17. The isolated antibody of embodiment 16, further comprising one or more CDRs selected from the group consisting of:

(b) a light chain CDR1 having at least 90% sequence identity to the amino acid sequence of SEQ ID NO:11 or having up to two amino acid substitutions relative to the amino acid sequence of SEQ ID NO:11; and (c) a light chain CDR2 having up to two amino acid substitutions relative to the amino acid sequence of SEQ ID NO: 12.

18. The isolated antibody of embodiment 16, further comprising one or more CDRs selected from the group consisting of:

(b) a light chain CDR1 comprising the amino acid sequence of SEQ ID NO:11; and (c) a light chain CDR2 comprising the amino acid sequence of SEQ ID NO:12.

19. The isolated antibody of any one of embodiments 16 to 18, wherein the light chain CDR3 comprises the amino acid sequence of SEQ ID NO:13.

20. The isolated antibody of any one of embodiments 16 to 18, wherein the light chain CDR3 comprises the amino acid sequence of SEQ ID NO:14.

21. The isolated antibody of embodiment 17, comprising a light chain variable region comprising an amino acid sequence having at least 90% sequence identity to any one of SEQ ID NOS:9-10.

22. The isolated antibody of embodiment 17, comprising a light chain variable region comprising the amino acid sequence of any one of SEQ ID NOS:9-10.

23. An isolated antibody comprising an antigen binding site comprising:

(a) a heavy chain CDR1 having at least 90% sequence identity to an amino acid sequence selected from the group consisting of SEQ ID NOS:4 and 49-52 or having up to two amino acid substitutions relative to an amino acid sequence selected from the group consisting of SEQ ID NOS:4 and 49-52;

(b) a heavy chain CDR2 having at least 90% sequence identity to an amino acid sequence selected from the group consisting of SEQ ID NOS:5-6 and 53-55 or having up to two amino acid substitutions relative to an amino acid sequence selected from the group consisting of SEQ ID NOS:5-6 and 53-55; and (c) a heavy chain CDR3 having at least 90% sequence identity to an amino acid sequence selected from the group consisting of SEQ ID NOS:7-8 and 56-59 or having up to two amino acid substitutions relative to an amino acid sequence selected from the group consisting of SEQ ID NOS:7-8 and 56-59;

(d) a light chain CDR1 having at least 90% sequence identity to the amino acid sequence of SEQ ID NO:11 or having up to two amino acid substitutions relative to the amino acid sequence of SEQ ID NO:11;

(e) a light chain CDR2 having up to two amino acid substitutions relative to the amino acid sequence of SEQ ID NO: 12; and (f) a light chain CDR3 comprising the amino acid sequence of SEQ ID NO:13 or 14.

24. The isolated antibody of embodiment 23, wherein the antigen binding site comprises:

(a) a heavy chain CDR1 having at least 90% sequence identity to the amino acid sequence of SEQ ID NO:4 or having up to two amino acid substitutions relative to the amino acid sequence of SEQ ID NO:4;

(b) a heavy chain CDR2 having at least 90% sequence identity to the amino acid sequence of SEQ ID NO:5 or SEQ ID NO:6 or having up to two amino acid substitutions relative to the amino acid sequence of SEQ ID NO:5 or SEQ ID NO:6;

(c) a heavy chain CDR3 having at least 90% sequence identity to the amino acid sequence of SEQ ID NO:7 or SEQ ID NO:8 or having up to two amino acid substitutions relative to the amino acid sequence of SEQ ID NO:7 or SEQ ID NO:8;

(d) a light chain CDR1 having at least 90% sequence identity to the amino acid sequence of SEQ ID NO:11 or having up to two amino acid substitutions relative to the amino acid sequence of SEQ ID NO:11;

(e) a light chain CDR2 having up to two amino acid substitutions relative to the amino acid sequence of SEQ ID NO: 12; and (f) a light chain CDR3 comprising the amino acid sequence of SEQ ID NO:13 or 14.

25. The isolated antibody of embodiment 24, wherein the antigen binding site comprises a heavy chain variable region comprising an amino acid sequence having at least 90% sequence identity to any one of SEQ ID NOS:1-3 and a light chain variable region comprising an amino acid sequence having at least 90% sequence identity to any one of SEQ ID NOS:9-10.

26. The isolated antibody of embodiment 24, wherein the antigen binding site comprises a heavy chain variable region comprising the amino acid sequence of any one of SEQ ID NOS:1-3 and a light chain variable region comprising the amino acid sequence of any one of SEQ ID NOS:9-10.

27. The isolated antibody of any one of embodiments 23-26, further comprising a second antigen binding site comprising one or more CDRs selected from the group consisting of:

(a) a heavy chain CDR1 comprising the amino acid sequence of SEQ ID NO:16 or having up to two amino acid substitutions relative to the amino acid sequence of SEQ ID NO: 16;

(b) a heavy chain CDR2 having at least 90% sequence identity to the amino acid sequence of SEQ ID NO: 17 or having up to two amino acid substitutions relative to the amino acid sequence of SEQ ID NO:17; and (c) a heavy chain CDR3 having at least 90% sequence identity to the amino acid sequence of SEQ ID NO: 18 or having up to two amino acid substitutions relative to the amino acid sequence of SEQ ID NO: 18.

28. The isolated antibody of embodiment 27, wherein the second antigen binding site comprises a heavy chain variable region comprising an amino acid sequence having at least 90% sequence identity to SEQ ID NO:15.

29. The isolated antibody of embodiment 27 or 28, wherein the second antigen binding site further comprises one or more CDRs selected from the group consisting of:

(a) a light chain CDR1 having at least 90% sequence identity to the amino acid sequence of SEQ ID NO:11 or having up to two amino acid substitutions relative to the amino acid sequence of SEQ ID NO:11;

(b) a light chain CDR2 having up to two amino acid substitutions relative to the amino acid sequence of SEQ ID NO: 12; and (c) a light chain CDR3 having up to two amino acid substitutions relative to the amino acid sequence of SEQ ID NO: 13 or 14.

30. The isolated antibody of embodiment 29, wherein the second antigen binding site comprises a light chain variable region comprising an amino acid sequence having at least 90% sequence identity to any one of SEQ ID NOS:9-10.

31. The isolated antibody of embodiment 29 or 30, wherein the first and second antigen binding sites comprise the same light chain CDR1, CDR2, and CDR3 sequences.

32. The isolated antibody of embodiment 31, comprising heavy and light chain CDRs selected from the combinations listed in Table 1.

33. An isolated antibody comprising heavy and light chains selected from the combinations listed in Table 2.

34. An isolated antibody comprising:

(a) a first antigen binding site for human epidermal growth factor receptor 2 (HER2) subdomain IV;

(b) a second antigen binding site for human HER2 subdomain II; and (c) a modified Fc polypeptide dimer comprising a first Fc polypeptide that contains modifications that create a TfR-binding site, wherein a light chain polypeptide sequence in the first antigen binding site is identical to a light chain polypeptide sequence in the second antigen binding site.

35. The isolated antibody of embodiment 34, wherein the first Fc polypeptide comprises a modified CH3 domain comprising the TfR-binding site.

36. The isolated antibody of embodiment 35, wherein the modified CH3 domain is derived from a human IgG1, IgG2, IgG3, or IgG4 CH3 domain.

37. The isolated antibody of embodiment 35 or 36, wherein the modified CH3 domain comprises one, two, three, four, five, six, seven, eight, nine, ten, or eleven substitutions in a set of amino acid positions comprising 380, 384, 386, 387, 388, 389, 390, 413, 415, 416, and 421, according to EU numbering.

38. The isolated antibody of any one of embodiments 35 to 37, wherein the modified CH3 domain comprises Glu, Leu, Ser, Val, Trp, Tyr, or Gln at position 380; Leu, Tyr, Phe, Trp, Met, Pro, or Val at position 384; Leu, Thr, His, Pro, Asn, Val, or Phe at position 386; Val, Pro, Ile, or an acidic amino acid at position 387; Trp at position 388; an aliphatic amino acid, Gly, Ser, Thr, or Asn at position 389; Gly, His, Gln, Leu, Lys, Val, Phe, Ser, Ala, Asp, Glu, Asn, Arg, or Thr at position 390; an acidic amino acid, Ala, Ser, Leu, Thr, Pro, Ile, or His at position 413; Glu, Ser, Asp, Gly, Thr, Pro, Gln, or Arg at position 415; Thr, Arg, Asn, or an acidic amino acid at position 416; and/or an aromatic amino acid, His, or Lys at position 421, according to EU numbering.

39. The isolated antibody of any one of embodiments 34 to 38, wherein the first Fc polypeptide that contains modifications that create the TfR-binding site binds to the apical domain of TfR.

40. The isolated antibody of any one of embodiments 34 to 39, wherein the first Fc polypeptide and the second Fc polypeptide each comprises modifications that promote heterodimerization.

41. The isolated antibody of embodiment 40, wherein the first Fc polypeptide comprises a T366W substitution and the second Fc polypeptide comprises T366S, L368A, and Y407V substitutions, according to EU numbering.

42. The isolated antibody of embodiment 40, wherein the first Fc polypeptide comprises T366S, L368A, and Y407V substitutions and the second Fc polypeptide comprises a T366W substitution, according to EU numbering.

43. The isolated antibody of any one of embodiments 34 to 42, wherein the first Fc polypeptide and/or the second Fc polypeptide independently comprises modifications that reduce TfR-mediated effector function.

44. The isolated antibody of embodiment 43, wherein the modifications that reduce effector function are L234A and L235A substitutions, according to EU numbering.

45. The isolated antibody of embodiment 44, wherein the first Fc polypeptide specifically binds to TfR and comprises L234A and L235A substitutions.

46. The isolated antibody of embodiment 45, wherein the first Fc polypeptide further comprises a P329G or a P329S substitution, according to EU numbering.

47. The isolated antibody of embodiment 46, wherein the second Fc polypeptide comprises Leu at positions 234 and 235 and a proline at position 329, according to EU numbering.

48. The isolated antibody of embodiment 44, wherein the second Fc polypeptide specifically binds to TfR and comprises L234A and L235A substitutions.

49. The isolated antibody of embodiment 48, wherein the second Fc polypeptide further comprises a P329G or a P329S substitution, according to EU numbering.

50. The isolated antibody of embodiment 49, wherein the first Fc polypeptide comprises Leu at positions 234 and 235 and a proline at position 329, according to EU numbering.

51. The isolated antibody of any one of embodiments 34 to 50, wherein a hinge region or a portion thereof is linked to the N-terminus of the first Fc polypeptide and/or the second Fc polypeptide.

52. The isolated antibody of any one of embodiments 34 to 51, wherein the first Fc polypeptide and/or the second Fc polypeptide independently comprises a sequence having at least 90% identity to a sequence selected from the group consisting of SEQ ID NOS: 71-86 and 98-100.

53. The isolated antibody of embodiment 52, wherein the first Fc polypeptide or the second Fc polypeptide comprises a sequence having at least 90% identity to a sequence selected from the group consisting of SEQ ID NOS:71-73, 85, and 99-100.

54. The isolated antibody of embodiment 52, wherein the first Fc polypeptide or the second Fc polypeptide comprises a sequence having at least 90% identity to a sequence selected from the group consisting of SEQ ID NOS: 74-84, 86 and 98.

55. The isolated antibody of embodiment 34, wherein:

the first antigen binding site comprises the amino acid sequence of SEQ ID NO:15;

the second antigen binding site comprises an amino acid sequence selected from the group consisting of SEQ ID NOS:1-3 and 60-70;

the first Fc polypeptide that contains modifications that create the TfR-binding site comprises an amino acid sequence selected from the group consisting of SEQ ID NOS:74-84, 86, and 98; and the light chain polypeptide sequence comprises the amino acid sequence of SEQ ID NO:9 or SEQ ID NO: 10.

56. The isolated antibody of embodiment 55, further comprising a second Fc polypeptide comprising an amino acid sequence selected from the group consisting of SEQ ID NOS:71-73, 85, and 99-100.

57. The isolated antibody of any one of embodiments 34 to 56, wherein the first Fc polypeptide and/or the second Fc polypeptide independently comprises a S239D and/or a I332E substitution, according to EU numbering.

58. The isolated antibody of embodiment 57, wherein the first Fc polypeptide and/or the second Fc polypeptide independently comprising the S239D and/or the I332E substitution is capable of enhancing HER2-mediated effector function.

59. The isolated antibody of embodiment 57 or 58, wherein:

(a) the first Fc polypeptide comprises a S239D substitution and the second Fc polypeptide comprises a S239D substitution, according to EU numbering;

(b) the first Fc polypeptide comprises a I332E substitution and the second Fc polypeptide comprises a S239D substitution, according to EU numbering;

(c) the first Fc polypeptide comprises a S239D and a I332E substitution and the second Fc polypeptide comprises a S239D substitution, according to EU numbering;

(d) the second Fc polypeptide comprises a S239D substitution, according to EU numbering;

(e) the first Fc polypeptide comprises a S239D substitution and the second Fc polypeptide comprises a I332E substitution, according to EU numbering;

(f) the first Fc polypeptide comprises a I332E substitution and the second Fc polypeptide comprises a I332E substitution, according to EU numbering;

(g) the first Fc polypeptide comprises a S239D and a I332E substitution and the second Fc polypeptide comprises a I332E substitution, according to EU numbering;

(h) the second Fc polypeptide comprises a I332E substitution, according to EU numbering;

(i) the first Fc polypeptide comprises a S239D substitution and the second Fc polypeptide comprises a S239D and a I332E substitution, according to EU numbering;

(j) the first Fc polypeptide comprises a I332E substitution and the second Fc polypeptide comprises a S239D and a I332E substitution, according to EU numbering;

(k) the first Fc polypeptide comprises a S239D and a I332E substitution and the second Fc polypeptide comprises a S239D and a I332E substitution, according to EU numbering;

(l) the second Fc polypeptide comprises a S239D and a I332E substitution, according to EU numbering;

(m) the first Fc polypeptide comprises a S239D substitution, according to EU numbering;

(n) the first Fc polypeptide comprises a I332E substitution, according to EU numbering; or (o) the first Fc polypeptide comprises a S239D and a I332E substitution, according to EU numbering.

60. The isolated antibody of embodiment 59, wherein:

(a) the first Fc polypeptide comprises a I332E substitution and the second Fc polypeptide comprises a S239D substitution, according to EU numbering;

(b) the first Fc polypeptide comprises a S239D and a I332E substitution and the second Fc polypeptide comprises a S239D substitution, according to EU numbering;

(c) the first Fc polypeptide comprises a S239D substitution and the second Fc polypeptide comprises a I332E substitution, according to EU numbering;

(d) the second Fc polypeptide comprises a I332E substitution, according to EU numbering;

(e) the first Fc polypeptide comprises a S239D substitution and the second Fc polypeptide comprises a S239D and a I332E substitution, according to EU numbering; or (f) the first Fc polypeptide comprises a I332E substitution, according to EU numbering.

61. The isolated antibody of embodiment 60, wherein:

(a) the first Fc polypeptide comprises a I332E substitution and a serine at position 239, and the second Fc polypeptide comprises a S239D substitution and a isoleucine at position 332, according to EU numbering;

(b) the first Fc polypeptide comprises a S239D and a I332E substitution, and the second Fc polypeptide comprises a S239D substitution and a isoleucine at position 332, according to EU numbering;

(c) the first Fc polypeptide comprises a S239D substitution and a isoleucine at position 332, and the second Fc polypeptide comprises a I332E substitution and a serine at position 239, according to EU numbering;

(d) the first Fc polypeptide comprises a serine at position 239 and a isoleucine at 332, and the second Fc polypeptide comprises a I332E substitution and a serine at position 239, according to EU numbering;

(e) the first Fc polypeptide comprises a S239D substitution and a isoleucine at position 332, and the second Fc polypeptide comprises a S239D and a I332E substitution, according to EU numbering; or (f) the first Fc polypeptide comprises a I332E substitution and a serine at position 239, according to EU numbering, and the second Fc polypeptide comprises a serine at position 239 and a isoleucine at 332.

62. The isolated antibody of any one of embodiments 34 to 61, comprising two heavy chains and two light chains.

63. The isolated antibody of embodiment 62, comprising heavy and light chains selected from the combinations listed in Table 2.

64. The isolated antibody of embodiment 62, wherein the first heavy chain comprises a $V_H$ and a Fc sequence selected from the combinations in Table 3 and the second heavy chain comprises a $V_H$ and a Fc sequence selected from the combinations in Table 4.

65. The isolated antibody of embodiment 62, wherein the first heavy chain comprises a $V_H$ and a Fc sequence selected from the combinations in Table 5 and the second heavy chain comprises a $V_H$ and a Fc sequence selected from the combinations in Table 6.

66. A pharmaceutical composition comprising the isolated antibody of any one of embodiments 1 to 65 and a pharmaceutically acceptable carrier.

67. An isolated polynucleotide comprising a nucleotide sequence encoding the isolated antibody of any one of embodiments 1 to 65.

68. A vector comprising the polynucleotide of embodiment 67.

69. A host cell comprising the polynucleotide of embodiment 67 or the vector of embodiment 68.

70. A method for treating a cancer or treating brain metastasis of a cancer in a subject, the method comprising administering to the subject a therapeutically effective amount of the isolated antibody of any one of embodiments 1 to 65 or the pharmaceutical composition of embodiment 66.

71. The method of embodiment 70, wherein the isolated antibody is adminstered in combination with a chemotherapy or radiation therapy.

72. The method of embodiment 70 or 71, wherein the cancer is a metastatic cancer.

73. The method of any one of embodiments 70 to 72, wherein the cancer is a breast cancer.

74. The method of any one of embodiments 70 to 73, wherein the cancer is a HER2-positive cancer.

It is understood that the examples and embodiments described herein are for illustrative purposes only and that various modifications or changes in light thereof will be suggested to persons skilled in the art and are to be included within the spirit and purview of this application and scope of the appended claims. The sequences of the sequence accession numbers cited herein are hereby incorporated by reference.

TABLE 1

| CDR combinations | | | | | | | | | |
|---|---|---|---|---|---|---|---|---|---|
| Combo # | HC1_D4 CDR1 SEQ ID NO | HC1_D4 CDR2 SEQ ID NO | HC1_D4 CDR3 SEQ ID NO | HC2_D2 CDR1 SEQ ID NO | HC2_D2 CDR2 SEQ ID NO | HC2_D2 CDR3 SEQ ID NO | LC CDR1 SEQ ID NO | LC CDR2 SEQ ID NO | LC CDR3 SEQ ID NO |
| A | 16 | 17 | 18 | 4 | 6 | 7 | 11 | 12 | 13 |
| B | 16 | 17 | 18 | 4 | 5 | 8 | 11 | 12 | 13 |
| C | 16 | 17 | 18 | 4 | 6 | 8 | 11 | 12 | 13 |
| D | 16 | 17 | 18 | 4 | 6 | 7 | 11 | 12 | 14 |
| E | 16 | 17 | 18 | 4 | 5 | 8 | 11 | 12 | 14 |
| F | 16 | 17 | 18 | 4 | 6 | 8 | 11 | 12 | 14 |
| G | 16 | 17 | 18 | 49 | 5 | 7 | 11 | 12 | 13 |
| H | 16 | 17 | 18 | 50 | 5 | 7 | 11 | 12 | 13 |
| I | 16 | 17 | 18 | 51 | 5 | 7 | 11 | 12 | 13 |
| J | 16 | 17 | 18 | 52 | 5 | 7 | 11 | 12 | 13 |
| K | 16 | 17 | 18 | 4 | 53 | 7 | 11 | 12 | 13 |
| L | 16 | 17 | 18 | 4 | 54 | 7 | 11 | 12 | 13 |
| M | 16 | 17 | 18 | 4 | 55 | 7 | 11 | 12 | 13 |
| N | 16 | 17 | 18 | 4 | 5 | 56 | 11 | 12 | 13 |
| O | 16 | 17 | 18 | 4 | 5 | 57 | 11 | 12 | 13 |
| P | 16 | 17 | 18 | 4 | 5 | 58 | 11 | 12 | 13 |
| Q | 16 | 17 | 18 | 4 | 5 | 59 | 11 | 12 | 13 |
| R | 16 | 17 | 18 | 49 | 5 | 7 | 11 | 12 | 14 |
| S | 16 | 17 | 18 | 50 | 5 | 7 | 11 | 12 | 14 |
| T | 16 | 17 | 18 | 51 | 5 | 7 | 11 | 12 | 14 |
| U | 16 | 17 | 18 | 52 | 5 | 7 | 11 | 12 | 14 |
| V | 16 | 17 | 18 | 4 | 53 | 7 | 11 | 12 | 14 |
| W | 16 | 17 | 18 | 4 | 54 | 7 | 11 | 12 | 14 |
| X | 16 | 17 | 18 | 4 | 55 | 7 | 11 | 12 | 14 |
| Y | 16 | 17 | 18 | 4 | 5 | 56 | 11 | 12 | 14 |
| Z | 16 | 17 | 18 | 4 | 5 | 57 | 11 | 12 | 14 |
| AB | 16 | 17 | 18 | 4 | 5 | 58 | 11 | 12 | 14 |
| AC | 16 | 17 | 18 | 4 | 5 | 59 | 11 | 12 | 14 |

TABLE 2

| Heavy chain (HC) and light chain (LC) combinations | | | |
|---|---|---|---|
| Combo # | HC1_D4 SEQ ID NO | HC2_D2 SEQ ID NO | LC SEQ ID NO |
| A | 37 | 25 | 9 |
| B | 31 | 30 | 9 |
| C | 31 | 29 | 9 |
| D | 38 | 30 | 9 |
| E | 32 | 30 | 9 |
| F | 32 | 29 | 9 |
| G | 39 | 30 | 9 |
| H | 37 | 26 | 9 |
| I | 31 | 34 | 9 |
| J | 31 | 33 | 9 |
| K | 38 | 34 | 9 |
| L | 32 | 34 | 9 |
| M | 32 | 33 | 9 |
| N | 39 | 34 | 9 |
| O | 37 | 27 | 9 |
| P | 31 | 36 | 9 |
| Q | 31 | 35 | 9 |
| R | 38 | 36 | 9 |
| S | 32 | 36 | 9 |
| T | 32 | 35 | 9 |
| U | 39 | 46 | 9 |
| V | 37 | 25 | 10 |
| W | 31 | 30 | 10 |
| X | 31 | 29 | 10 |
| Y | 38 | 30 | 10 |
| Z | 32 | 30 | 10 |
| AA | 32 | 29 | 10 |
| AB | 39 | 30 | 10 |
| AC | 37 | 26 | 10 |
| AD | 31 | 34 | 10 |
| AE | 31 | 33 | 10 |
| AF | 38 | 34 | 10 |
| AG | 32 | 34 | 10 |
| AH | 32 | 33 | 10 |

TABLE 2-continued

| Heavy chain (HC) and light chain (LC) combinations | | | |
|---|---|---|---|
| Combo # | HC1_D4 SEQ ID NO | HC2_D2 SEQ ID NO | LC SEQ ID NO |
| AI | 39 | 34 | 10 |
| AJ | 37 | 27 | 10 |
| AK | 31 | 36 | 10 |
| AL | 31 | 35 | 10 |
| AM | 38 | 36 | 10 |
| AN | 32 | 36 | 10 |
| AO | 32 | 35 | 10 |
| AP | 39 | 46 | 10 |
| AQ | 20 | 24 | 19 |
| AR | 21 | 24 | 19 |
| AS | 22 | 24 | 19 |
| AT | 23 | 24 | 19 |

TABLE 3

| HC_D2 $V_H$ and Fc (hole) combinations | | |
|---|---|---|
| Combo # | $V_H$_D2 SEQ ID NO | Fc SEQ ID NO |
| A | 1 | 71 |
| B | 2 | 71 |
| C | 3 | 71 |
| D | 1 | 72 |
| E | 2 | 72 |
| F | 3 | 72 |
| G | 1 | 73 |
| H | 2 | 73 |
| I | 3 | 73 |
| J | 1 | 85 |
| K | 2 | 85 |
| L | 3 | 85 |

TABLE 4

| HC_D4 $V_H$ and Fc (knob) combinations | | |
|---|---|---|
| Combo # | $V_H$_D4 SEQ ID NO | Fc SEQ ID NO |
| A | 15 | 86 |
| B | 15 | 74 |
| C | 15 | 75 |
| D | 15 | 76 |
| E | 15 | 77 |
| F | 15 | 78 |
| G | 15 | 79 |
| H | 15 | 80 |
| I | 15 | 81 |
| J | 15 | 82 |
| K | 15 | 83 |
| L | 15 | 84 |

TABLE 5

| HC_D2 $V_H$ and Fc (knob) combinations | | |
|---|---|---|
| Combo # | $V_H$_D2 SEQ ID NO | Fc SEQ ID NO |
| A | 1 | 86 |
| B | 1 | 74 |
| C | 1 | 75 |
| D | 1 | 76 |
| E | 1 | 77 |
| F | 1 | 78 |
| G | 1 | 79 |
| H | 1 | 80 |
| I | 1 | 81 |
| J | 1 | 82 |
| K | 1 | 83 |
| L | 1 | 84 |
| M | 2 | 86 |
| N | 2 | 74 |
| O | 2 | 75 |

TABLE 5-continued

| HC_D2 $V_H$ and Fc (knob) combinations | | |
|---|---|---|
| Combo # | $V_H$_D2 SEQ ID NO | Fc SEQ ID NO |
| P | 2 | 76 |
| Q | 2 | 77 |
| R | 2 | 78 |
| S | 2 | 79 |
| T | 2 | 80 |
| U | 2 | 81 |
| V | 2 | 82 |
| W | 2 | 83 |
| X | 2 | 84 |
| Y | 2 | 86 |
| Z | 2 | 74 |
| AA | 2 | 75 |
| AB | 3 | 76 |
| AC | 3 | 77 |
| AD | 3 | 78 |
| AE | 3 | 79 |
| AF | 3 | 80 |
| AG | 3 | 81 |
| AH | 3 | 82 |
| AI | 3 | 83 |
| AJ | 3 | 84 |

TABLE 6

| HC_D4 $V_H$ and Fc (hole) combinations | | |
|---|---|---|
| Combo # | $V_H$_D4 SEQ ID NO | Fc SEQ ID NO |
| A | 15 | 71 |
| B | 15 | 72 |
| C | 15 | 73 |
| D | 15 | 85 |

INFORMAL SEQUENCE LISTING

| SEQ ID NO | Sequence | Description |
|---|---|---|
| 1 | EVQLVESGGGLVQPGGSLRLSCAASGFTFTDYTMDWVRQAP GKGLEWVADVNPNSGQSIYNQRFKGRFTLSVDRSKNTLYLQ MNSLRAEDTAVYYCARNLGPSFYFDYWGQGTLVTVSS | Anti-HER2_D2_VH_v1 |
| 2 | EVQLVESGGGLVQPGGSLRLSCAASGFTFTDYTMDWVRQAP GKGLEWVADVNPNSGGSIYNQRFKGRFTLSVDRSKNTLYLQ MNSLRAEDTAVYYCARNLGPLFYFDYWGQGTLVTVSS | Anti-HER2_D2_VH_v2 |
| 3 | EVQLVESGGGLVQPGGSLRLSCAASGFTFTDYTMDWVRQAP GKGLEWVADVNPNSGQSIYNQRFKGRFTLSVDRSKNTLYLQ MNSLRAEDTAVYYCARNLGPLFYFDYWGQGTLVTVSS | Anti-HER2_D2_VH_v3 |
| 4 | GFTFTDYTMD | Anti-HER2_D2_CDR-H1 |
| 5 | DVNPNSGGSIYNQRFKG | Anti-HER2_D2_CDR-H2 |
| 6 | DVNPNSGQSIYNQRFKG | Anti-HER2_D2_CDR-H2.1 |
| 7 | ARNLGPSFYFDY | Anti-HER2_D2_CDR-H3 |
| 8 | ARNLGPLFYFDY | Anti-HER2_D2_CDR-H3.1 |
| 9 | DIQMTQSPSSLSASVGDRVTITCRASQDVNTAVAWYQQKPGK APKLLIYSASFLYSGVPSRFSGSRSGTDFTLTISSLQPEDFATYY CQQFYTTPPTFGQGTKVEIKRTVAAPSVFIFPPSDEQLKSGTAS VVCLLNNFYPREAKVQWKVDNALQSGNSQESVTEQDSKDST YSLSSTLTLSKADYEKHKVYACEVTHQGLSSPVTKSFNRGEC | Anti-HER2_light chain_v1 |

-continued

INFORMAL SEQUENCE LISTING

| SEQ ID NO | Sequence | Description |
|---|---|---|
| 10 | DIQMTQSPSSLSASVGDRVTITCRASQDVNTAVAWYQQKPGK APKLLIYSASFLYSGVPSRFSGSRSGTDFTLTISSLQPEDFATYY CQQYYTTPPTFGQGTKVEIKRTVAAPSVFIFPPSDEQLKSGTAS VVCLLNNFYPREAKVQWKVDNALQSGNSQESVTEQDSKDST YSLSSTLTLSKADYEKHKVYACEVTHQGLSSPVTKSFNRGEC | Anti-HER2_light chain_v2 |
| 11 | RASQDVNTAVA | Anti-HER2_CDR-L1 |
| 12 | SASFLYS | Anti-HER2_CDR-L2 |
| 13 | QQFYTTPPT | Anti-HER2_CDR-L3.1 |
| 14 | QQYYTTPPT | Anti-HER2_CDR-L3.2 |
| 15 | EVQLVESGGGLVQPGGSLRLSCAASGFNIKDTYIHWVRQAPG KGLEWVARIYPTNGYTRYADSVKGRFTISADTSKNTAYLQM NSLRAEDTAVYYCSRWGGDGFYAMDYWGQGTLVTVSSAST KGPSVFPLAPSSKSTSGGTAALGCLVKDYFPEPVTVSWNSGA LTSGVHTFPAVLQSS | Anti-HER2_D4_VH |
| 16 | GFNIKDTYIH | Anti-HER2_D4_CDR-H1 |
| 17 | RIYPTNGYTRYADSVKG | Anti-HER2_D4_CDR-H2 |
| 18 | RWGGDGFYAMDY | Anti-HER2_D4_CDR-H3 |
| 19 | DIQMTQSPSSLSASVGDRVTITCKASQDVSTAVAWYQQKPGK APKLLIYSASFRYTGVPSRFSGSRSGTDFTLTISSLQPEDFATY YCQQHYTTPPTFGQGTKVEIKRTVAAPSVFIFPPSDEQLKSGT ASVVCLLNNFYPREAKVQWKVDNALQSGNSQESVTEQDSKD STYSLSSTLTLSKADYEKHKVYACEVTHQGLSSPVTKSFNRG EC | Anti-HER2_light chain_v3 |
| 20 | EVQLVESGGGLVQPGGSLRLSCAASGFNIKDTYIHWVRQAPG KGLEWVARIYPTNGYTRYADSVKGRFTISADTSKNTAYLQM NSLRAEDTAVYYCSRWGGEGFYAMDYWGQGTLVTVSSAST KGPSVFPLAPSSKSTSGGTAALGCLVKDYFPEPVTVSWNSGA LTSGVHTFPAVLQSSGLYSLSSVVTVPSSSLGTQTYICNVNHK PSNTKVDKKVEPKSCDKTHTCPPCPAPELLGGPSVFLFPPKPK DTLMISRTPEVTCVVVDVSHEDPEVKFNWYVDGVEVHNAKT KPREEQYNSTYRVVSVLTVLHQDWLNGKEYKCKVSNKALPA PIEKTISKAKGQPREPQVYTLPPSRDELTKNQVSLWCLVKGFY PSDIAVEWESNGQPENNYKTTPPVLDSDGSFFLYSKLTVDKSR WQQGNVFSCSVMHEALHNHYTQKSLSLSPGK | Anti-HER2_D4_heavy chain_ v1 |
| 21 | EVQLVESGGGLVQPGGSLRLSCAASGFNIKDTYIHWVRQAPG KGLEWVARIYPTNGYTRYADSVKGRFTISADTSKNTAYLQM NSLRAEDTAVYYCSRWGGEGFYAMDYWGQGTLVTVSSAST KGPSVFPLAPSSKSTSGGTAALGCLVKDYFPEPVTVSWNSGA LTSGVHTFPAVLQSSGLYSLSSVVTVPSSSLGTQTYICNVNHK PSNTKVDKKVEPKSCDKTHTCPPCPAPEAAGGPSVFLFPPKPK DTLMISRTPEVTCVVVDVSHEDPEVKFNWYVDGVEVHNAKT KPREEQYNSTYRVVSVLTVLHQDWLNGKEYKCKVSNKALPA PIEKTISKAKGQPREPQVYTLPPSRDELTKNQVSLWCLVKGFY PSDIAVEWESYGTEWSNYKTTPPVLDSDGSFFLYSKLTVSKEE WQQGFVFSCSVMHEALHNHYTQKSLSLSPGK | Anti-HER2_D4_heavy chain v2 |
| 22 | EVQLVESGGGLVQPGGSLRLSCAASGFNIKDTYIHWVRQAPG KGLEWVARIYPTNGYTRYADSVKGRFTISADTSKNTAYLQM NSLRAEDTAVYYCSRWGGEGFYAMDYWGQGTLVTVSSAST KGPSVFPLAPSSKSTSGGTAALGCLVKDYFPEPVTVSWNSGA LTSGVHTFPAVLQSSGLYSLSSVVTVPSSSLGTQTYICNVNHK PSNTKVDKKVEPKSCDKTHTCPPCPAPEAAGGPSVFLFPPKPK DTLMISRTPEVTCVVVDVSHEDPEVKFNWYVDGVEVHNAKT KPREEQYNSTYRVVSVLTVLHQDWLNGKEYKCKVSNKALG APIEKTISKAKGQPREPQVYTLPPSRDELTKNQVSLWCLVKGF YPSDIAVEWESYGTEWSNYKTTPPVLDSDGSFFLYSKLTVSKE EWQQGFVFSCSVMHEALHNHYTQKSLSLSPGK | Anti-HER2_D4_heavy chain_v3 |
| 23 | EVQLVESGGGLVQPGGSLRLSCAASGFNIKDTYIHWVRQAPG KGLEWVARIYPTNGYTRYADSVKGRFTISADTSKNTAYLQM NSLRAEDTAVYYCSRWGGEGFYAMDYWGQGTLVTVSSAST KGPSVFPLAPSSKSTSGGTAALGCLVKDYFPEPVTVSWNSGA | Anti-HER2_D4_heavy chain_v4 |

-continued

INFORMAL SEQUENCE LISTING

| SEQ ID NO | Sequence | Description |
|---|---|---|
| | LTSGVHTFPAVLQSSGLYSLSSVVTVPSSSLGTQTYICNVNHK PSNTKVDKKVEPKSCDKTHTCPPCPAPEAAGGPSVFLFPPKPK DTLMISRTPEVTCVVVDVSHEDPEVKFNWYVDGVEVHNAKT KPREEQYNSTYRVVSVLTVLHQDWLNGKEYKCKVSNKALSA PIEKTISKAKGQPREPQVYTLPPSRDELTKNQVSLWCLVKGFY PSDIAVEWESYGTEWSNYKTTPPVLDSDGSFFLYSKLTVSKEE WQQGFVFSCSVMHEALHNHYTQKSLSLSPGK | |
| 24 | EVQLVESGGGLVQPGGSLRLSCAASGFTFNDYTMDWVRQAP GKGLEWVADVNPNSGGSIVNRRFKGRFTLSVDRSKNTLYLQ MNSLRAEDTAVYYCARNLGPFFYFDYWGQGTLVTVSSASTK GPSVFPLAPSSKSTSGGTAALGCLVKDYFPEPVTVSWNSGALT SGVHTFPAVLQSSGLYSLSSVVTVPSSSLGTQTYICNVNHKPS NTKVDKKVEPKSCDKTHTCPPCPAPELLGGPSVFLFPPKPKDT LMISRTPEVTCVVVDVSHEDPEVKFNWYVDGVEVHNAKTKP REEQYNSTYRVVSVLTVLHQDWLNGKEYKCKVSNKALPAPI EKTISKAKGQPREPQVYTLPPSRDELTKNQVSLSCAVKGFYPS DIAVEWESNGQPENNYKTTPPVLDSDGSFFLVSKLTVDKSRW QQGNVFSCSVMHEALHNHYTQKSLSLSPGK | Anti-HER2_D2 heavy chain_v1 |
| 25 | EVQLVESGGGLVQPGGSLRLSCAASGFTFTDYTMDWVRQAP GKGLEWVADVNPNSGQSIYNQRFKGRFTLSVDRSKNTLYLQ MNSLRAEDTAVYYCARNLGPSFYFDYWGQGTLVTVSSASTK GPSVFPLAPSSKSTSGGTAALGCLVKDYFPEPVTVSWNSGALT SGVHTFPAVLQSSGLYSLSSVVTVPSSSLGTQTYICNVNHKPS NTKVDKKVEPKSCDKTHTCPPCPAPELLGGPSVFLFPPKPKDT LMISRTPEVTCVVVDVSHEDPEVKFNWYVDGVEVHNAKTKP REEQYNSTYRVVSVLTVLHQDWLNGKEYKCKVSNKALPAPI EKTISKAKGQPREPQVYTLPPSRDELTKNQVSLSCAVKGFYPS DIAVEWESNGQPENNYKTTPPVLDSDGSFFLVSKLTVDKSRW QQGNVFSCSVMHEALHNHYTQKSLSLSPGK | Anti-HER2_D2 heavy chain_v2 |
| 26 | EVQLVESGGGLVQPGGSLRLSCAASGFTFTDYTMDWVRQAP GKGLEWVADVNPNSGGSIYNQRFKGRFTLSVDRSKNTLYLQ MNSLRAEDTAVYYCARNLGPLFYFDYWGQGTLVTVSSASTK GPSVFPLAPSSKSTSGGTAALGCLVKDYFPEPVTVSWNSGALT SGVHTFPAVLQSSGLYSLSSVVTVPSSSLGTQTYICNVNHKPS NTKVDKKVEPKSCDKTHTCPPCPAPELLGGPSVFLFPPKPKDT LMISRTPEVTCVVVDVSHEDPEVKFNWYVDGVEVHNAKTKP REEQYNSTYRVVSVLTVLHQDWLNGKEYKCKVSNKALPAPI EKTISKAKGQPREPQVYTLPPSRDELTKNQVSLSCAVKGFYPS DIAVEWESNGQPENNYKTTPPVLDSDGSFFLVSKLTVDKSRW QQGNVFSCSVMHEALHNHYTQKSLSLSPGK | Anti-HER2_D2 heavy chain_v3 |
| 27 | EVQLVESGGGLVQPGGSLRLSCAASGFTFTDYTMDWVRQAP GKGLEWVADVNPNSGQSIYNQRFKGRFTLSVDRSKNTLYLQ MNSLRAEDTAVYYCARNLGPLFYFDYWGQGTLVTVSSASTK GPSVFPLAPSSKSTSGGTAALGCLVKDYFPEPVTVSWNSGALT SGVHTFPAVLQSSGLYSLSSVVTVPSSSLGTQTYICNVNHKPS NTKVDKKVEPKSCDKTHTCPPCPAPELLGGPSVFLFPPKPKDT LMISRTPEVTCVVVDVSHEDPEVKFNWYVDGVEVHNAKTKP REEQYNSTYRVVSVLTVLHQDWLNGKEYKCKVSNKALPAPI EKTISKAKGQPREPQVYTLPPSRDELTKNQVSLSCAVKGFYPS DIAVEWESNGQPENNYKTTPPVLDSDGSFFLVSKLTVDKSRW QQGNVFSCSVMHEALHNHYTQKSLSLSPGK | Anti-HER2_D2_heavy chain_v4 |
| 28 | EVQLVESGGGLVQPGGSLRLSCAASGFNIKDTYIHWVRQAPG KGLEWVARIYPTNGYTRYADSVKGRFTISADTSKNTAYLQM NSLRAEDTAVYYCSRWGGDGFYAMDYWGQGTLVTVSSAST KGPSVFPLAPSSKSTSGGTAALGCLVKDYFPEPVTVSWNSGA LTSGVHTFPAVLQSSGLYSLSSVVTVPSSSLGTQTYICNVNHK PSNTKVDKKVEPKSCDKTHTCPPCPAPEAAGGPDVFLFPPKPK DTLMISRTPEVTCVVVDVSHEDPEVKFNWYVDGVEVHNAKT KPREEQYNSTYRVVSVLTVLHQDWLNGKEYKCKVSNKALPA PIEKTISKAKGQPREPQVYTLPPSRDELTKNQVSLWCLVKGFY PSDIAVEWESYGTEWSNYKTTPPVLDSDGSFFLYSKLTVSKEE WQQGFVFSCSVMHEALHNHYTQKSLSLSPGK | Anti-HER2_D4_heavy chain_v5 |
| 29 | EVQLVESGGGLVQPGGSLRLSCAASGFTFTDYTMDWVRQAP GKGLEWVADVNPNSGQSIYNQRFKGRFTLSVDRSKNTLYLQ MNSLRAEDTAVYYCARNLGPSFYFDYWGQGTLVTVSSASTK GPSVFPLAPSSKSTSGGTAALGCLVKDYFPEPVTVSWNSGALT SGVHTFPAVLQSSGLYSLSSVVTVPSSSLGTQTYICNVNHKPS | Anti-HER2_D2_heavy chain_v5 |

-continued

INFORMAL SEQUENCE LISTING

| SEQ ID NO | Sequence | Description |
|---|---|---|
| | NTKVDKKVEPKSCDKTHTCPPCPAPELLGGPDVFLFPPKPKDT LMISRTPEVTCVVVDVSHEDPEVKFNWYVDGVEVHNAKTKP REEQYNSTYRVVSVLTVLHQDWLNGKEYKCKVSNKALPAPE EKTISKAKGQPREPQVYTLPPSRDELTKNQVSLSCAVKGFYPS DIAVEWESNGQPENNYKTTPPVLDSDGSFFLVSKLTVDKSRW QQGNVFSCSVMHEALHNHYTQKSLSLSPGK | |
| 30 | EVQLVESGGGLVQPGGSLRLSCAASGFTFTDYTMDWVRQAP GKGLEWVADVNPNSGQSIYNQRFKGRFTLSVDRSKNTLYLQ MNSLRAEDTAVYYCARNLGPSFYFDYWGQGTLVTVSSASTK GPSVFPLAPSSKSTSGGTAALGCLVKDYFPEPVTVSWNSGALT SGVHTFPAVLQSSGLYSLSSVVTVPSSSLGTQTYICNVNHKPS NTKVDKKVEPKSCDKTHTCPPCPAPELLGGPDVFLFPPKPKDT LMISRTPEVTCVVVDVSHEDPEVKFNWYVDGVEVHNAKTKP REEQYNSTYRVVSVLTVLHQDWLNGKEYKCKVSNKALPAPE EKTISKAKGQPREPQVYTLPPSRDELTKNQVSLSCAVKGFYPS DIAVEWESNGQPENNYKTTPPVLDSDGSFFLVSKLTVDKSRW QQGNVFSCSVMHEALHNHYTQKSLSLSPGK | Anti-HER2_D2_heavy chain_v6 |
| 31 | EVQLVESGGGLVQPGGSLRLSCAASGFNIKDTYIHWVRQAPG KGLEWVARIYPTNGYTRYADSVKGRFTISADTSKNTAYLQM NSLRAEDTAVYYCSRWGGDGFYAMDYWGQGTLVTVSSAST KGPSVFPLAPSSKSTSGGTAALGCLVKDYFPEPVTVSWNSGA LTSGVHTFPAVLQSSGLYSLSSVVTVPSSSLGTQTYICNVNHK PSNTKVDKKVEPKSCDKTHTCPPCPAPEAAGGPDVFLFPPKPK DTLMISRTPEVTCVVVDVSHEDPEVKFNWYVDGVEVHNAKT KPREEQYNSTYRVVSVLTVLHQDWLNGKEYKCKVSNKALG APIEKTISKAKGQPREPQVYTLPPSRDELTKNQVSLWCLVKGF YPSDIAVEWESYGTEWSNYKTTPPVLDSDGSFFLYSKLTVSKE EWQQGFVFSCSVMHEALHNHYTQKSLSLSPGK | Anti-HER2_D4_heavy chain_v6 |
| 32 | EVQLVESGGGLVQPGGSLRLSCAASGFNIKDTYIHWVRQAPG KGLEWVARIYPTNGYTRYADSVKGRFTISADTSKNTAYLQM NSLRAEDTAVYYCSRWGGDGFYAMDYWGQGTLVTVSSAST KGPSVFPLAPSSKSTSGGTAALGCLVKDYFPEPVTVSWNSGA LTSGVHTFPAVLQSSGLYSLSSVVTVPSSSLGTQTYICNVNHK PSNTKVDKKVEPKSCDKTHTCPPCPAPEAAGGPDVFLFPPKPK DTLMISRTPEVTCVVVDVSHEDPEVKFNWYVDGVEVHNAKT KPREEQYNSTYRVVSVLTVLHQDWLNGKEYKCKVSNKALSA PIEKTISKAKGQPREPQVYTLPPSRDELTKNQVSLWCLVKGFY PSDIAVEWESYGTEWSNYKTTPPVLDSDGSFFLYSKLTVSKEE WQQGFVFSCSVMHEALHNHYTQKSLSLSPGK | Anti-HER2_D4_heavy chain_v7 |
| 33 | EVQLVESGGGLVQPGGSLRLSCAASGFTFTDYTMDWVRQAP GKGLEWVADVNPNSGGSIYNQRFKGRFTLSVDRSKNTLYLQ MNSLRAEDTAVYYCARNLGPLFYFDYWGQGTLVTVSSASTK GPSVFPLAPSSKSTSGGTAALGCLVKDYFPEPVTVSWNSGALT SGVHTFPAVLQSSGLYSLSSVVTVPSSSLGTQTYICNVNHKPS NTKVDKKVEPKSCDKTHTCPPCPAPELLGGPDVFLFPPKPKDT LMISRTPEVTCVVVDVSHEDPEVKFNWYVDGVEVHNAKTKP REEQYNSTYRVVSVLTVLHQDWLNGKEYKCKVSNKALPAPE EKTISKAKGQPREPQVYTLPPSRDELTKNQVSLSCAVKGFYPS DIAVEWESNGQPENNYKTTPPVLDSDGSFFLVSKLTVDKSRW QQGNVFSCSVMHEALHNHYTQKSLSLSPGK | Anti-HER2_D2_heavy chain_v7 |
| 34 | EVQLVESGGGLVQPGGSLRLSCAASGFTFTDYTMDWVRQAP GKGLEWVADVNPNSGGSIYNQRFKGRFTLSVDRSKNTLYLQ MNSLRAEDTAVYYCARNLGPLFYFDYWGQGTLVTVSSASTK GPSVFPLAPSSKSTSGGTAALGCLVKDYFPEPVTVSWNSGALT SGVHTFPAVLQSSGLYSLSSVVTVPSSSLGTQTYICNVNHKPS NTKVDKKVEPKSCDKTHTCPPCPAPELLGGPSVFLFPPKPKDT LMISRTPEVTCVVVDVSHEDPEVKFNWYVDGVEVHNAKTKP REEQYNSTYRVVSVLTVLHQDWLNGKEYKCKVSNKALPAPE EKTISKAKGQPREPQVYTLPPSRDELTKNQVSLSCAVKGFYPS DIAVEWESNGQPENNYKTTPPVLDSDGSFFLVSKLTVDKSRW QQGNVFSCSVMHEALHNHYTQKSLSLSPGK | Anti-HER2_D2_heavy chain_v8 |
| 35 | EVQLVESGGGLVQPGGSLRLSCAASGFTFTDYTMDWVRQAP GKGLEWVADVNPNSGQSIYNQRFKGRFTLSVDRSKNTLYLQ MNSLRAEDTAVYYCARNLGPLFYFDYWGQGTLVTVSSASTK GPSVFPLAPSSKSTSGGTAALGCLVKDYFPEPVTVSWNSGALT SGVHTFPAVLQSSGLYSLSSVVTVPSSSLGTQTYICNVNHKPS NTKVDKKVEPKSCDKTHTCPPCPAPELLGGPDVFLFPPKPKDT | Anti-HER2_D2_heavy chain_v9 |

-continued

INFORMAL SEQUENCE LISTING

| SEQ ID NO | Sequence | Description |
|---|---|---|
| | LMISRTPEVTCVVVDVSHEDPEVKFNWYVDGVEVHNAKTKP REEQYNSTYRVVSVLTVLHQDWLNGKEYKCKVSNKALPAPE EKTISKAKGQPREPQVYTLPPSRDELTKNQVSLSCAVKGFYPS DIAVEWESNGQPENNYKTTPPVLDSDGSFFLVSKLTVDKSRW QQGNVFSCSVMHEALHNHYTQKSLSLSPGK | |
| 36 | EVQLVESGGGLVQPGGSLRLSCAASGFTFTDYTMDWVRQAP GKGLEWVADVNPNSGQSIYNQRFKGRFTLSVDRSKNTLYLQ MNSLRAEDTAVYYCARNLGPLFYFDYWGQGTLVTVSSASTK GPSVFPLAPSSKSTSGGTAALGCLVKDYFPEPVTVSWNSGALT SGVHTFPAVLQSSGLYSLSSVVTVPSSSLGTQTYICNVNHKPS NTKVDKKVEPKSCDKTHTCPPCPAPELLGGPSVFLFPPKPKDT LMISRTPEVTCVVVDVSHEDPEVKFNWYVDGVEVHNAKTKP REEQYNSTYRVVSVLTVLHQDWLNGKEYKCKVSNKALPAPE EKTISKAKGQPREPQVYTLPPSRDELTKNQVSLSCAVKGFYPS DIAVEWESNGQPENNYKTTPPVLDSDGSFFLVSKLTVDKSRW QQGNVFSCSVMHEALHNHYTQKSLSLSPGK | Anti-HER2_D2_heavy chain_v10 |
| 37 | EVQLVESGGGLVQPGGSLRLSCAASGFNIKDTYIHWVRQAPG KGLEWVARIYPTNGYTRYADSVKGRFTISADTSKNTAYLQM NSLRAEDTAVYYCSRWGGDGFYAMDYWGQGTLVTVSSAST KGPSVFPLAPSSKSTSGGTAALGCLVKDYFPEPVTVSWNSGA LTSGVHTFPAVLQSSGLYSLSSVVTVPSSSLGTQTYICNVNHK PSNTKVDKKVEPKSCDKTHTCPPCPAPEAAGGPSVFLFPPKPK DTLMISRTPEVTCVVVDVSHEDPEVKFNWYVDGVEVHNAKT KPREEQYNSTYRVVSVLTVLHQDWLNGKEYKCKVSNKALPA PIEKTISKAKGQPREPQVYTLPPSRDELTKNQVSLWCLVKGFY PSDIAVEWESYGTEWSNYKTTPPVLDSDGSFFLYSKLTVSKEE WQQGFVFSCSVMHEALHNHYTQKSLSLSPGK | Anti-HER2_D4_heavy chain_v8 |
| 38 | EVQLVESGGGLVQPGGSLRLSCAASGFNIKDTYIHWVRQAPG KGLEWVARIYPTNGYTRYADSVKGRFTISADTSKNTAYLQM NSLRAEDTAVYYCSRWGGDGFYAMDYWGQGTLVTVSSAST KGPSVFPLAPSSKSTSGGTAALGCLVKDYFPEPVTVSWNSGA LTSGVHTFPAVLQSSGLYSLSSVVTVPSSSLGTQTYICNVNHK PSNTKVDKKVEPKSCDKTHTCPPCPAPEAAGGPSVFLFPPKPK DTLMISRTPEVTCVVVDVSHEDPEVKFNWYVDGVEVHNAKT KPREEQYNSTYRVVSVLTVLHQDWLNGKEYKCKVSNKALG APIEKTISKAKGQPREPQVYTLPPSRDELTKNQVSLWCLVKGF YPSDIAVEWESYGTEWSNYKTTPPVLDSDGSFFLYSKLTVSKE EWQQGFVFSCSVMHEALHNHYTQKSLSLSPGK | Anti-HER2_D4_heavy chain_v9 |
| 39 | EVQLVESGGGLVQPGGSLRLSCAASGFNIKDTYIHWVRQAPG KGLEWVARIYPTNGYTRYADSVKGRFTISADTSKNTAYLQM NSLRAEDTAVYYCSRWGGDGFYAMDYWGQGTLVTVSSAST KGPSVFPLAPSSKSTSGGTAALGCLVKDYFPEPVTVSWNSGA LTSGVHTFPAVLQSSGLYSLSSVVTVPSSSLGTQTYICNVNHK PSNTKVDKKVEPKSCDKTHTCPPCPAPEAAGGPSVFLFPPKPK DTLMISRTPEVTCVVVDVSHEDPEVKFNWYVDGVEVHNAKT KPREEQYNSTYRVVSVLTVLHQDWLNGKEYKCKVSNKALSA PIEKTISKAKGQPREPQVYTLPPSRDELTKNQVSLWCLVKGFY PSDIAVEWESYGTEWSNYKTTPPVLDSDGSFFLYSKLTVSKEE WQQGFVFSCSVMHEALHNHYTQKSLSLSPGK | Anti-HER2_D4_heavy chain_v10 |
| 40 | EVQLVESGGGLVQPGGSLRLSCAASGFNIKDTYIHWVRQAPG KGLEWVARIYPTNGYTRYADSVKGRFTISADTSKNTAYLQM NSLRAEDTAVYYCSRWGGDGFYAMDYWGQGTLVTVSSAST KGPSVFPLAPSSKSTSGGTAALGCLVKDYFPEPVTVSWNSGA LTSGVHTFPAVLQSSGLYSLSSVVTVPSSSLGTQTYICNVNHK PSNTKVDKKVEPKSCDKTHTCPPCPAPEAAGGPSVFLFPPKPK DTLMISRTPEVTCVVVDVSHEDPEVKFNWYVDGVEVHNAKT KPREEQYNSTYRVVSVLTVLHQDWLNGKEYKCKVSNKALSA PEEKTISKAKGQPREPQVYTLPPSRDELTKNQVSLWCLVKGF YPSDIAVEWESYGTEWSNYKTTPPVLDSDGSFFLYSKLTVSKE EWQQGFVFSCSVMHEALHNHYTQKSLSLSPGK | Anti-HER2_D4_heavy chain_v11 |
| 41 | EVQLVESGGGLVQPGGSLRLSCAASGFNIKDTYIHWVRQAPG KGLEWVARIYPTNGYTRYADSVKGRFTISADTSKNTAYLQM NSLRAEDTAVYYCSRWGGDGFYAMDYWGQGTLVTVSSAST KGPSVFPLAPSSKSTSGGTAALGCLVKDYFPEPVTVSWNSGA LTSGVHTFPAVLQSSGLYSLSSVVTVPSSSLGTQTYICNVNHK PSNTKVDKKVEPKSCDKTHTCPPCPAPEAAGGPDVFLFPPKPK DTLMISRTPEVTCVVVDVSHEDPEVKFNWYVDGVEVHNAKT | Anti-HER2_D4_heavy chain_v12 |

-continued

INFORMAL SEQUENCE LISTING

| SEQ ID NO | Sequence | Description |
|---|---|---|
| | KPREEQYNSTYRVVSVLTVLHQDWLNGKEYKCKVSNKALSA PEEKTISKAKGQPREPQVYTLPPSRDELTKNQVSLWCLVKGF YPSDIAVEWESYGTEWSNYKTTPPVLDSDGSFFLYSKLTVSKE EWQQGFVFSCSVMHEALHNHYTQKSLSLSPGK | |
| 42 | EVQLVESGGGLVQPGGSLRLSCAASGFNIKDTYIHWVRQAPG KGLEWVARIYPTNGYTRYADSVKGRFTISADTSKNTAYLQM NSLRAEDTAVYYCSRWGGDGFYAMDYWGQGTLVTVSSAST KGPSVFPLAPSSKSTSGGTAALGCLVKDYFPEPVTVSWNSGA LTSGVHTFPAVLQSSGLYSLSSVVTVPSSSLGTQTYICNVNHK PSNTKVDKKVEPKSCDKTHTCPPCPAPELLGGPSVFLFPPKPK DTLMISRTPEVTCVVVDVSHEDPEVKFNWYVDGVEVHNAKT KPREEQYNSTYRVVSVLTVLHQDWLNGKEYKCKVSNKALPA PIEKTISKAKGQPREPQVYTLPPSRDELTKNQVSLSCAVKGFY PSDIAVEWESNGQPENNYKTTPPVLDSDGSFFLVSKLTVDKSR WQQGNVFSCSVMHEALHNHYTQKSLSLSPGK | Anti-HER2_D4_heavy chain_v13 |
| 43 | EVQLVESGGGLVQPGGSLRLSCAASGFTFTDYTMDWVRQAP GKGLEWVADVNPNSGQSIYNQRFKGRFTLSVDRSKNTLYLQ MNSLRAEDTAVYYCARNLGPSFYFDYWGQGTLVTVSSASTK GPSVFPLAPSSKSTSGGTAALGCLVKDYFPEPVTVSWNSGALT SGVHTFPAVLQSSGLYSLSSVVTVPSSSLGTQTYICNVNHKPS NTKVDKKVEPKSCDKTHTCPPCPAPEAAGGPSVFLFPPKPKD TLMISRTPEVTCVVVDVSHEDPEVKFNWYVDGVEVHNAKTK PREEQYNSTYRVVSVLTVLHQDWLNGKEYKCKVSNKALPAP IEKTISKAKGQPREPQVYTLPPSRDELTKNQVSLWCLVKGFYP SDIAVEWESYGTEWSNYKTTPPVLDSDGSFFLYSKLTVSKEE WQQGFVFSCSVMHEALHNHYTQKSLSLSPGK | Anti-HER2_D2_heavy chain_v11 |
| 44 | EVQLVESGGGLVQPGGSLRLSCAASGFTFTDYTMDWVRQAP GKGLEWVADVNPNSGGSIYNQRFKGRFTLSVDRSKNTLYLQ MNSLRAEDTAVYYCARNLGPLFYFDYWGQGTLVTVSSASTK GPSVFPLAPSSKSTSGGTAALGCLVKDYFPEPVTVSWNSGALT SGVHTFPAVLQSSGLYSLSSVVTVPSSSLGTQTYICNVNHKPS NTKVDKKVEPKSCDKTHTCPPCPAPEAAGGPSVFLFPPKPKD TLMISRTPEVTCVVVDVSHEDPEVKFNWYVDGVEVHNAKTK PREEQYNSTYRVVSVLTVLHQDWLNGKEYKCKVSNKALPAP IEKTISKAKGQPREPQVYTLPPSRDELTKNQVSLWCLVKGFYP SDIAVEWESYGTEWSNYKTTPPVLDSDGSFFLYSKLTVSKEE WQQGFVFSCSVMHEALHNHYTQKSLSLSPGK | Anti-HER2_D2_heavy chain_v12 |
| 45 | EVQLVESGGGLVQPGGSLRLSCAASGFTFTDYTMDWVRQAP GKGLEWVADVNPNSGQSIYNQRFKGRFTLSVDRSKNTLYLQ MNSLRAEDTAVYYCARNLGPLFYFDYWGQGTLVTVSSASTK GPSVFPLAPSSKSTSGGTAALGCLVKDYFPEPVTVSWNSGALT SGVHTFPAVLQSSGLYSLSSVVTVPSSSLGTQTYICNVNHKPS NTKVDKKVEPKSCDKTHTCPPCPAPEAAGGPSVFLFPPKPKD TLMISRTPEVTCVVVDVSHEDPEVKFNWYVDGVEVHNAKTK PREEQYNSTYRVVSVLTVLHQDWLNGKEYKCKVSNKALPAP IEKTISKAKGQPREPQVYTLPPSRDELTKNQVSLWCLVKGFYP SDIAVEWESYGTEWSNYKTTPPVLDSDGSFFLYSKLTVSKEE WQQGFVFSCSVMHEALHNHYTQKSLSLSPGK | Anti-HER2_D2_heavy chain_v13 |
| 46 | EVQLVESGGGLVQPGGSLRLSCAASGFTFTDYTMDWVRQAP GKGLEWVADVNPNSGQSIYNQRFKGRFTLSVDRSKNTLYLQ MNSLRAEDTAVYYCARNLGPSFYFDYWGQGTLVTVSSASTK GPSVFPLAPSSKSTSGGTAALGCLVKDYFPEPVTVSWNSGALT SGVHTFPAVLQSSGLYSLSSVVTVPSSSLGTQTYICNVNHKPS NTKVDKKVEPKSCDKTHTCPPCPAPELLGGPDVFLFPPKPKDT LMISRTPEVTCVVVDVSHEDPEVKFNWYVDGVEVHNAKTKP REEQYNSTYRVVSVLTVLHQDWLNGKEYKCKVSNKALPAPI EKTISKAKGQPREPQVYTLPPSRDELTKNQVSLSCAVKGFYPS DIAVEWESNGQPENNYKTTPPVLDSDGSFFLVSKLTVDKSRW QQGNVFSCSVMHEALHNHYTQKSLSLSPGK | Anti-HER2_D2_heavy chain_v14 |
| 47 | EVQLVESGGGLVQPGGSLRLSCAASGFTFTDYTMDWVRQAP GKGLEWVADVNPNSGGSIYNQRFKGRFTLSVDRSKNTLYLQ MNSLRAEDTAVYYCARNLGPLFYFDYWGQGTLVTVSSASTK GPSVFPLAPSSKSTSGGTAALGCLVKDYFPEPVTVSWNSGALT SGVHTFPAVLQSSGLYSLSSVVTVPSSSLGTQTYICNVNHKPS NTKVDKKVEPKSCDKTHTCPPCPAPELLGGPDVFLFPPKPKDT LMISRTPEVTCVVVDVSHEDPEVKFNWYVDGVEVHNAKTKP REEQYNSTYRVVSVLTVLHQDWLNGKEYKCKVSNKALPAPI | Anti-HER2_D2_heavy chain_v15 |

-continued

INFORMAL SEQUENCE LISTING

| SEQ ID NO | Sequence | Description |
|---|---|---|
| | EKTISKAKGQPREPQVYTLPPSRDELTKNQVSLSCAVKGFYPS DIAVEWESNGQPENNYKTTPPVLDSDGSFFLVSKLTVDKSRW QQGNVFSCSVMHEALHNHYTQKSLSLSPGK | |
| 48 | EVQLVESGGGLVQPGGSLRLSCAASGFTFTDYTMDWVRQAP GKGLEWVADVNPNSGQSIYNQRFKGRFTLSVDRSKNTLYLQ MNSLRAEDTAVYYCARNLGPLFYFDYWGQGTLVTVSSASTK GPSVFPLAPSSKSTSGGTAALGCLVKDYFPEPVTVSWNSGALT SGVHTFPAVLQSSGLYSLSSVVTVPSSSLGTQTYICNVNHKPS NTKVDKKVEPKSCDKTHTCPPCPAPELLGGPDVFLFPPKPKDT LMISRTPEVTCVVVDVSHEDPEVKFNWYVDGVEVHNAKTKP REEQYNSTYRVVSVLTVLHQDWLNGKEYKCKVSNKALPAPI EKTISKAKGQPREPQVYTLPPSRDELTKNQVSLSCAVKGFYPS DIAVEWESNGQPENNYKTTPPVLDSDGSFFLVSKLTVDKSRW QQGNVFSCSVMHEALHNHYTQKSLSLSPGK | Anti-HER2_D2_heavy chain_v16 |
| 49 | GFNFTDYTMD | Anti-HER2_CDR-H1.1 |
| 50 | GFKFTDYTMD | Anti-HER2_CDR-H1.2 |
| 51 | GFMFTDYTMD | Anti-HER2_CDR-H1.3 |
| 52 | GFHFTDYTMD | Anti-HER2_CDR-H1.4 |
| 53 | DVNPNSGGSIYNRRFKG | Anti-HER2_CDR-H2.2 |
| 54 | DVNPNSGGSIYNHRFKG | Anti-HER2_CDR-H2.3 |
| 55 | DVNPNSGGSIYNTRFKG | Anti-HER2_CDR-H2.4 |
| 56 | ARNLGPWFYFDY | Anti-HER2_CDR-H3.2 |
| 57 | ARNLGPFFYFDY | Anti-HER2_CDR-H3.3 |
| 58 | ARNLGPDFYFDY | Anti-HER2_CDR-H3.4 |
| 59 | ARNLGPYFYFDY | Anti-HER2_CDR-H3.5 |
| 60 | EVQLVESGGGLVQPGGSLRLSCAASGFNFTDYTMDWVRQAP GKGLEWVADVNPNSGGSIYNQRFKGRFTLSVDRSKNTLYLQ MNSLRAEDTAVYYCARNLGPSFYFDYWGQGTLVTVSS | Anti-HER2_D2_VH_v4 |
| 61 | EVQLVESGGGLVQPGGSLRLSCAASGFKFTDYTMDWVRQAP GKGLEWVADVNPNSGGSIYNQRFKGRFTLSVDRSKNTLYLQ MNSLRAEDTAVYYCARNLGPSFYFDYWGQGTLVTVSS | Anti-HER2_D2_VH_v5 |
| 62 | EVQLVESGGGLVQPGGSLRLSCAASGFMFTDYTMDWVRQAP GKGLEWVADVNPNSGGSIYNQRFKGRFTLSVDRSKNTLYLQ MNSLRAEDTAVYYCARNLGPSFYFDYWGQGTLVTVSS | Anti-HER2_D2_VH_v6 |
| 63 | EVQLVESGGGLVQPGGSLRLSCAASGFHFTDYTMDWVRQAP GKGLEWVADVNPNSGGSIYNQRFKGRFTLSVDRSKNTLYLQ MNSLRAEDTAVYYCARNLGPSFYFDYWGQGTLVTVSS | Anti-HER2_D2_VH_v7 |
| 64 | EVQLVESGGGLVQPGGSLRLSCAASGFTFTDYTMDWVRQAP GKGLEWVADVNPNSGGSIYNRRFKGRFTLSVDRSKNTLYLQ MNSLRAEDTAVYYCARNLGPSFYFDYWGQGTLVTVSS | Anti-HER2_D2_VH_v8 |
| 65 | EVQLVESGGGLVQPGGSLRLSCAASGFTFTDYTMDWVRQAP GKGLEWVADVNPNSGGSIYNHRFKGRFTLSVDRSKNTLYLQ MNSLRAEDTAVYYCARNLGPSFYFDYWGQGTLVTVSS | Anti-HER2_D2_VH_v9 |
| 66 | EVQLVESGGGLVQPGGSLRLSCAASGFTFTDYTMDWVRQAP GKGLEWVADVNPNSGGSIYNTRFKGRFTLSVDRSKNTLYLQ MNSLRAEDTAVYYCARNLGPSFYFDYWGQGTLVTVSS | Anti-HER2_D2_VH_v10 |
| 67 | EVQLVESGGGLVQPGGSLRLSCAASGFTFTDYTMDWVRQAP GKGLEWVADVNPNSGGSIYNQRFKGRFTLSVDRSKNTLYLQ MNSLRAEDTAVYYCARNLGPWFYFDYWGQGTLVTVSS | Anti-HER2_D2_VH_v11 |
| 68 | EVQLVESGGGLVQPGGSLRLSCAASGFTFTDYTMDWVRQAP GKGLEWVADVNPNSGGSIYNQRFKGRFTLSVDRSKNTLYLQ MNSLRAEDTAVYYCARNLGPFFYFDYWGQGTLVTVSS | Anti-HER2_D2_VH_v12 |

-continued

INFORMAL SEQUENCE LISTING

| SEQ ID NO | Sequence | Description |
|---|---|---|
| 69 | EVQLVESGGGLVQPGGSLRLSCAASGFTFTDYTMDWVRQAP GKGLEWVADVNPNSGGSIYNQRFKGRFTLSVDRSKNTLYLQ MNSLRAEDTAVYYCARNLGPDFYFDYWGQGTLVTVSS | Anti-HER2_D2_VH_v13 |
| 70 | EVQLVESGGGLVQPGGSLRLSCAASGFTFTDYTMDWVRQAP GKGLEWVADVNPNSGGSIYNQRFKGRFTLSVDRSKNTLYLQ MNSLRAEDTAVYYCARNLGPYFYFDYWGQGTLVTVSS | Anti-HER2_D2_VH_v4 |
| 71 | APELLGGPDVFLFPPKPKDTLMISRTPEVTCVVVDVSHEDPEV KFNWYVDGVEVHNAKTKPREEQYNSTYRVVSVLTVLHQDW LNGKEYKCKVSNKALPAPIEKTISKAKGQPREPQVYTLPPSRD ELTKNQVSLSCAVKGFYPSDIAVEWESNGQPENNYKTTPPVL DSDGSFFLVSKLTVDKSRWQQGNVFSCSVMHEALHNHYTQK SLSLSPGK | Fc sequence with hole mutations.hD |
| 72 | APELLGGPSVFLFPPKPKDTLMISRTPEVTCVVVDVSHEDPEV KFNWYVDGVEVHNAKTKPREEQYNSTYRVVSVLTVLHQDW LNGKEYKCKVSNKALPAPEEKTISKAKGQPREPQVYTLPPSR DELTKNQVSLSCAVKGFYPSDIAVEWESNGQPENNYKTTPPV LDSDGSFFLVSKLTVDKSRWQQGNVFSCSVMHEALHNHYTQ KSLSLSPGK | Fc sequence with hole mutations.hE |
| 73 | APELLGGPDVFLFPPKPKDTLMISRTPEVTCVVVDVSHEDPEV KFNWYVDGVEVHNAKTKPREEQYNSTYRVVSVLTVLHQDW LNGKEYKCKVSNKALPAPEEKTISKAKGQPREPQVYTLPPSR DELTKNQVSLSCAVKGFYPSDIAVEWESNGQPENNYKTTPPV LDSDGSFFLVSKLTVDKSRWQQGNVFSCSVMHEALHNHYTQ KSLSLSPGK | Fc sequence with hole mutations.hDE |
| 74 | APEAAGGPDVFLFPPKPKDTLMISRTPEVTCVVVDVSHEDPEV KFNWYVDGVEVHNAKTKPREEQYNSTYRVVSVLTVLHQDW LNGKEYKCKVSNKALPAPIEKTISKAKGQPREPQVYTLPPSRD ELTKNQVSLWCLVKGFYPSDIAVEWESYGTEWSNYKTTPPVL DSDGSFFLYSKLTVSKEEWQQGFVFSCSVMHEALHNHYTQK SLSLSPGK | Clone CH3C.35.23.4 with knob, LALA, and kD |
| 75 | APEAAGGPSVFLFPPKPKDTLMISRTPEVTCVVVDVSHEDPEV KFNWYVDGVEVHNAKTKPREEQYNSTYRVVSVLTVLHQDW LNGKEYKCKVSNKALPAPEEKTISKAKGQPREPQVYTLPPSR DELTKNQVSLWCLVKGFYPSDIAVEWESYGTEWSNYKTTPP VLDSDGSFFLYSKLTVSKEEWQQGFVFSCSVMHEALHNHYT QKSLSLSPGK | Clone CH3C.35.23.4 with knob, LALA, and kE |
| 76 | APEAAGGPDVFLFPPKPKDTLMISRTPEVTCVVVDVSHEDPEV KFNWYVDGVEVHNAKTKPREEQYNSTYRVVSVLTVLHQDW LNGKEYKCKVSNKALPAPEEKTISKAKGQPREPQVYTLPPSR DELTKNQVSLWCLVKGFYPSDIAVEWESYGTEWSNYKTTPP VLDSDGSFFLYSKLTVSKEEWQQGFVFSCSVMHEALHNHYT QKSLSLSPGK | Clone CH3C.35.23.4 with knob, LALA, and kDE |
| 77 | APEAAGGPSVFLFPPKPKDTLMISRTPEVTCVVVDVSHEDPEV KFNWYVDGVEVHNAKTKPREEQYNSTYRVVSVLTVLHQDW LNGKEYKCKVSNKALGAPIEKTISKAKGQPREPQVYTLPPSRD ELTKNQVSLWCLVKGFYPSDIAVEWESYGTEWSNYKTTPPVL DSDGSFFLYSKLTVSKEEWQQGFVFSCSVMHEALHNHYTQK SLSLSPGK | Clone CH3C.35.23.4 with knob, LALA, and PG |
| 78 | APEAAGGPSVFLFPPKPKDTLMISRTPEVTCVVVDVSHEDPEV KFNWYVDGVEVHNAKTKPREEQYNSTYRVVSVLTVLHQDW LNGKEYKCKVSNKALSAPIEKTISKAKGQPREPQVYTLPPSRD ELTKNQVSLWCLVKGFYPSDIAVEWESYGTEWSNYKTTPPVL DSDGSFFLYSKLTVSKEEWQQGFVFSCSVMHEALHNHYTQK SLSLSPGK | Clone CH3C.35.23.4 with knob, LALA, and PS |
| 79 | APEAAGGPDVFLFPPKPKDTLMISRTPEVTCVVVDVSHEDPEV KFNWYVDGVEVHNAKTKPREEQYNSTYRVVSVLTVLHQDW LNGKEYKCKVSNKALGAPIEKTISKAKGQPREPQVYTLPPSRD ELTKNQVSLWCLVKGFYPSDIAVEWESYGTEWSNYKTTPPVL DSDGSFFLYSKLTVSKEEWQQGFVFSCSVMHEALHNHYTQK SLSLSPGK | Clone CH3C.35.23.4 with knob, LALA, PG, and kD |

-continued

INFORMAL SEQUENCE LISTING

| SEQ ID NO | Sequence | Description |
|---|---|---|
| 80 | APEAAGGPDVFLFPPKPKDTLMISRTPEVTCVVVDVSHEDPEV KFNWYVDGVEVHNAKTKPREEQYNSTYRVVSVLTVLHQDW LNGKEYKCKVSNKALSAPIEKTISKAKGQPREPQVYTLPPSRD ELTKNQVSLWCLVKGFYPSDIAVEWESYGTEWSNYKTTPPVL DSDGSFFLYSKLTVSKEEWQQGFVFSCSVMHEALHNHYTQ KSLSLSPGK | Clone CH3C.35.23.4 with knob, LALA, PS, and kD |
| 81 | APEAAGGPSVFLFPPKPKDTLMISRTPEVTCVVVDVSHEDPEV KFNWYVDGVEVHNAKTKPREEQYNSTYRVVSVLTVLHQDW LNGKEYKCKVSNKALGAPEEKTISKAKGQPREPQVYTLPPSR DELTKNQVSLWCLVKGFYPSDIAVEWESYGTEWSNYKTTPP VLDSDGSFFLYSKLTVSKEEWQQGFVFSCSVMHEALHNHYT QKSLSLSPGK | Clone CH3C.35.23.4 with knob, LALA, PG, and kE |
| 82 | APEAAGGPSVFLFPPKPKDTLMISRTPEVTCVVVDVSHEDPEV KFNWYVDGVEVHNAKTKPREEQYNSTYRVVSVLTVLHQDW LNGKEYKCKVSNKALSAPEEKTISKAKGQPREPQVYTLPPSR DELTKNQVSLWCLVKGFYPSDIAVEWESYGTEWSNYKTTPP VLDSDGSFFLYSKLTVSKEEWQQGFVFSCSVMHEALHNHYT QKSLSLSPGK | Clone CH3C.35.23.4 with knob, LALA, PS, and kE |
| 83 | APEAAGGPDVFLFPPKPKDTLMISRTPEVTCVVVDVSHEDPEV KFNWYVDGVEVHNAKTKPREEQYNSTYRVVSVLTVLHQDW LNGKEYKCKVSNKALGAPEEKTISKAKGQPREPQVYTLPPSR DELTKNQVSLWCLVKGFYPSDIAVEWESYGTEWSNYKTTPP VLDSDGSFFLYSKLTVSKEEWQQGFVFSCSVMHEALHNHYT QKSLSLSPGK | Clone CH3C.35.23.4 with knob, LALA, PG, and kDE |
| 84 | APEAAGGPDVFLFPPKPKDTLMISRTPEVTCVVVDVSHEDPEV KFNWYVDGVEVHNAKTKPREEQYNSTYRVVSVLTVLHQDW LNGKEYKCKVSNKALSAPEEKTISKAKGQPREPQVYTLPPSR DELTKNQVSLWCLVKGFYPSDIAVEWESYGTEWSNYKTTPP VLDSDGSFFLYSKLTVSKEEWQQGFVFSCSVMHEALHNHYT QKSLSLSPGK | Clone CH3C.35.23.4 with knob, LALA, PS, and kDE |
| 85 | APELLGGPSVFLFPPKPKDTLMISRTPEVTCVVVDVSHEDPEV KFNWYVDGVEVHNAKTKPREEQYNSTYRVVSVLTVLHQDW LNGKEYKCKVSNKALPAPIEKTISKAKGQPREPQVYTLPPSRD ELTKNQVSLSCAVKGFYPSDIAVEWESNGQPENNYKTTPPVL DSDGSFFLVSKLTVDKSRWQQGNVFSCSVMHEALHNHYTQK SLSLSPGK | Fc sequence with hole mutations |
| 86 | APEAAGGPSVFLFPPKPKDTLMISRTPEVTCVVVDVSHEDPEV KFNWYVDGVEVHNAKTKPREEQYNSTYRVVSVLTVLHQDW LNGKEYKCKVSNKALPAPIEKTISKAKGQPREPQVYTLPPSRD ELTKNQVSLWCLVKGFYPSDIAVEWESYGTEWSNYKTTPPVL DSDGSFFLYSKLTVSKEEWQQGFVFSCSVMHEALHNHYTQK SLSLSPGK | Clone CH3C.35.23.4 with knob and LALA mutations |
| 87 | DIQMTQSPSSLSASVGDRVTITCRASQDVNTAVAWYQQKPGK APKLLIYSASFLYSGVPSRFSGSRSGTDFTLTISSLQPEDFATYY CQQHYTTPPTFGQGTKVEIKRTVAAPSVFIFPPSDEQLKSGTAS VVCLLNNFYPREAKVQWKVDNALQSGNSQESVTEQDSKDST YSLSSTLTLSKADYEKHKVYACEVTHQGLSSPVTKSFNRGEC | Anti-HER2_D4_light chain_control |
| 88 | DIQMTQSPSSLSASVGDRVTITCRASQDVNTAVAWYQQKPGK APKLLIYSASFLYSGVPSRFSGSRSGTDFTLTISSLQPEDFATYY CQQXYTTPPTFGQGTKVEIKRTVAAPSVFIFPPSDEQLKSGTAS VVCLLNNFYPREAKVQWKVDNALQSGNSQESVTEQDSKDST YSLSSTLTLSKADYEKHKVYACEVTHQGLSSPVTKSFNRGEC | Anti-HER2_light chain_consensus |
| 89 | GF$X_1X_2X_3$DYTMD | Anti-HER2_CDR1_consensus |
| 90 | DV$X_1$P$X_2X_3X_4X_5$SIYN$X_6$RFKG | Anti-HER2_CDR2_consensus |
| 91 | ARN$X_1X_2X_3X_4$FYFDY | Anti-HER2_CDR3_consensus |
| 92 | EVQLVESGGGLVQPGGSLRLSCAASGFTFTDYTMDWVRQAP GKGLEWVADVNPNSGGSIYNQRFKGRFTLSVDRSKNTLYLQ MNSLRAEDTAVYYCARNLGPSFYFDYWGQGTLVTVSSASTK | Anti-HER2_D2_heavy chain_control |

-continued

INFORMAL SEQUENCE LISTING

| SEQ ID NO | Sequence | Description |
|---|---|---|
| | GPSVFPLAPSSKSTSGGTAALGCLVKDYFPEPVTVSWNSGALT SGVHTFPAVLQSSGLYSLSSVVTVPSSSLGTQTYICNVNHKPS NTKVDKKVEPKSCDKTHTCPPCPAPELLGGPSVFLFPPKPKDT LMISRTPEVTCVVVDVSHEDPEVKFNWYVDGVEVHNAKTKP REEQYNSTYRVVSVLTVLHQDWLNGKEYKCKVSNKALPAPI EKTISKAKGQPREPQVYTLPPSREEMTKNQVSLTCLVKGFYPS DIAVEWESNGQPENNYKTTPPVLDSDGSFFLYSKLTVDKSRW QQGNVFSCSVMHEALHNHYTQKSLSLSPG | |
| 93 | EVQLVESGGGLVQPGGSLRLSCAASGFNIKDTYIHWVRQAPG KGLEWVARIYPTNGYTRYADSVKGRFTISADTSKNTAYLQM NSLRAEDTAVYYCSRWGGDGFYAMDYWGQGTLVTVSSAST KGPSVFPLAPSSKSTSGGTAALGCLVKDYFPEPVTVSWNSGA LTSGVHTFPAVLQSSGLYSLSSVVTVPSSSLGTQTYICNVNHK PSNTKVDKKVEPKSCDKTHTCPPCPAPELLGGPSVFLFPPKPK DTLMISRTPEVTCVVVDVSHEDPEVKFNWYVDGVEVHNAKT KPREEQYNSTYRVVSVLTVLHQDWLNGKEYKCKVSNKALPA PIEKTISKAKGQPREPQVYTLPPSREEMTKNQVSLTCLVKGFY PSDIAVEWESNGQPENNYKTTPPVLDSDGSFFLYSKLTVDKSR WQQGNVFSCSVMHEALHNHYTQKSLSLSPG | Anti-HER2_D4_heavy chain_control |
| 94 | DIQMTQSPSSLSASVGDRVTITCKASQDVSIGVAWYQQKPGK APKLLIYSASYRYTGVPSRFSGSGSGTDFTLTISSLQPEDFATY YCQQYYIYPYTFGQGTKVEIKRTVAAPSVFIFPPSDEQLKSGT ASVVCLLNNFYPREAKVQWKVDNALQSGNSQESVTEQDSKD STYSLSSTLTLSKADYEKHKVYACEVTHQGLSSPVTKSFNRG EC | Anti-HER2_D2_light chain_control |
| 95 | APELLGGPSVFLFPPKPKDTLMISRTPEVTCVVVDVSHEDPEV KFNWYVDGVEVHNAKTKPREEQYNSTYRVVSVLTVLHQDW LNGKEYKCKVSNKALPAPIEKTISKAKGQPREPQVYTLPPSRD ELTKNQVSLTCLVKGFYPSDIAVEWESNGQPENNYKTTPPVL DSDGSFFLYSKLTVDKSRWQQGNVFSCSVMHEALHNHYTQK SLSLSPGK | Wild-type human Fc sequence |
| 96 | EPKSCDKTHTCPPCP | Human IgG1 hinge region |
| 97 | APELLGGPSVFLFPPKPKDTLMISRTPEVTCVVVDVSHEDPEV KFNWYVDGVEVHNAKTKPREEQYNSTYRVVSVLTVLHQDW LNGKEYKCKVSNKALPAPIEKTISKAKGQPREPQVYTLPPSRD ELTKNQVSLTCLVKGFYPSDIAVEWESYGTEWSNYKTTPPVL DSDGSFFLYSKLTVSKEEWQQGFVFSCSVMHEALHNHYTQK SLSLSPGK | Clone CH3C.35.23.4 |
| 98 | APELLGGPSVFLFPPKPKDTLMISRTPEVTCVVVDVSHEDPEV KFNWYVDGVEVHNAKTKPREEQYNSTYRVVSVLTVLHQDW LNGKEYKCKVSNKALPAPIEKTISKAKGQPREPQVYTLPPSRD ELTKNQVSLWCLVKGFYPSDIAVEWESYGTEWSNYKTTPPVL DSDGSFFLYSKLTVSKEEWQQGFVFSCSVMHEALHNHYTQK SLSLSPGK | Clone CH3C.35.23.4 with knob mutation |
| 99 | APELLGGPSVFLFPPKPKDTLMISRTPEVTCVVVDVSHEDPEV KFNWYVDGVEVHNAKTKPREEQYNSTYRVVSVLTVLHQDW LNGKEYKCKVSNKALPAPIEKTISKAKGQPREPQVYTLPPSRD ELTKNQVSLSCAVKGFYPSDIAVEWESYGTEWSNYKTTPPVL DSDGSFFLVSKLTVSKEEWQQGFVFSCSVMHEALHNHYTQK SLSLSPGK | Clone CH3C.35.23.4 with hole mutations |
| 100 | APEAAGGPSVFLFPPKPKDTLMISRTPEVTCVVVDVSHEDPEV KFNWYVDGVEVHNAKTKPREEQYNSTYRVVSVLTVLHQDW LNGKEYKCKVSNKALPAPIEKTISKAKGQPREPQVYTLPPSRD ELTKNQVSLSCAVKGFYPSDIAVEWESYGTEWSNYKTTPPVL DSDGSFFLVSKLTVSKEEWQQGFVFSCSVMHEALHNHYTQK SLSLSPGK | Clone CH3C.35.23.4 with hole and LALA mutations |
| 101 | APELLGGPSVFLFPPKPKDTLMISRTPEVTCVVVDVSHEDPEV KFNWYVDGVEVHNAKTKPREEQYNSTYRVVSVLTVLHQDW LNGKEYKCKVSNKALPAPIEKTISKAKGQPREPQVYTLPPSRD ELTKNQVSLTCLVKGFYPSDIAVEWESYGTEWANYKTTPPVL DSDGSFFLYSKLTVTKEEWQQGFVFSCSVMHEALHNHYTQK SLSLSPGK | Clone CH3C.35.23.2 |

-continued

INFORMAL SEQUENCE LISTING

| SEQ ID NO | Sequence | Description |
|---|---|---|
| 102 | APELLGGPSVFLFPPKPKDTLMISRTPEVTCVVVDVSHEDPEV KFNWYVDGVEVHNAKTKPREEQYNSTYRVVSVLTVLHQDW LNGKEYKCKVSNKALPAPIEKTISKAKGQPREPQVYTLPPSRD ELTKNQVSLWCLVKGFYPSDIAVEWESYGTEWANYKTTPPV LDSDGSFFLYSKLTVTKEEWQQGFVFSCSVMHEALHNHYTQ KSLSLSPGK | Clone CH3C.35.23.2 with knob mutation |
| 103 | APEAAGGPSVFLFPPKPKDTLMISRTPEVTCVVVDVSHEDPEV KFNWYVDGVEVHNAKTKPREEQYNSTYRVVSVLTVLHQDW LNGKEYKCKVSNKALPAPIEKTISKAKGQPREPQVYTLPPSRD ELTKNQVSLWCLVKGFYPSDIAVEWESYGTEWANYKTTPPV LDSDGSFFLYSKLTVTKEEWQQGFVFSCSVMHEALHNHYTQ KSLSLSPGK | Clone CH3C.35.23.2 with knob and LALA mutations |
| 104 | APELLGGPSVFLFPPKPKDTLMISRTPEVTCVVVDVSHEDPEV KFNWYVDGVEVHNAKTKPREEQYNSTYRVVSVLTVLHQDW LNGKEYKCKVSNKALPAPIEKTISKAKGQPREPQVYTLPPSRD ELTKNQVSLSCAVKGFYPSDIAVEWESYGTEWANYKTTPPVL DSDGSFFLVSKLTVTKEEWQQGFVFSCSVMHEALHNHYTQK SLSLSPGK | Clone CH3C.35.23.2 with hole mutations |
| 105 | APEAAGGPSVFLFPPKPKDTLMISRTPEVTCVVVDVSHEDPEV KFNWYVDGVEVHNAKTKPREEQYNSTYRVVSVLTVLHQDW LNGKEYKCKVSNKALPAPIEKTISKAKGQPREPQVYTLPPSRD ELTKNQVSLSCAVKGFYPSDIAVEWESYGTEWANYKTTPPVL DSDGSFFLVSKLTVTKEEWQQGFVFSCSVMHEALHNHYTQK SLSLSPGK | Clone CH3C.35.23.2 with hole and LALA mutations |
| 106 | APELLGGPSVFLFPPKPKDTLMISRTPEVTCVVVDVSHEDPEV KFNWYVDGVEVHNAKTKPREEQYNSTYRVVSVLTVLHQDW LNGKEYKCKVSNKALPAPIEKTISKAKGQPREPQVYTLPPSRD ELTKNQVSLTCLVKGFYPSDIAVEWESFGTEWSSYKTTPPVL DSDGSFFLYSKLTVTKEEWQQGFVFSCSVMHEALHNHYTQK SLSLSPGK | Clone CH3C.35.20.1 |
| 107 | APELLGGPSVFLFPPKPKDTLMISRTPEVTCVVVDVSHEDPEV KFNWYVDGVEVHNAKTKPREEQYNSTYRVVSVLTVLHQDW LNGKEYKCKVSNKALPAPIEKTISKAKGQPREPQVYTLPPSRD ELTKNQVSLWCLVKGFYPSDIAVEWESNGQPENNYKTTPPVL DSDGSFFLYSKLTVDKSRWQQGNVFSCSVMHEALHNHYTQK SLSLSPGK | Fc sequence with knob mutation |
| 108 | EVQLVESGGGLVQPGGSLRLSCAASGFNIKDTYIHWVRQAPG KGLEWVARIYPTNGYTRYADSVKGRFTISADTSKNTAYLQM NSLRAEDTAVYYCSRWGGEGFYAMDYWGQGTLVTVSS | Anti-HER2_D4_VH_v1 |
| 109 | EVQLVESGGGLVQPGGSLRLSCAASGFTFNDYTMDWVRQAP GKGLEWVADVNPNSGGSIVNRRFKGRFTLSVDRSKNTLYLQ MNSLRAEDTAVYYCARNLGPFFYFDYWGQGTLVTVSS | Anti-HER2_D2_VH_v4 |

The invention claimed is:

1. An isolated antibody comprising:

(a) a first heavy chain comprising a first heavy chain CDR1 comprising the amino acid sequence of SEQ ID NO:16, a first heavy chain CDR2 comprising the amino acid sequence of SEQ ID NO:17, and a first heavy chain CDR3 comprising the amino acid sequence of SEQ ID NO: 18;

(b) a second heavy chain comprises a second heavy chain CDR1 comprising the amino acid sequence of SEQ ID NO:4; a second heavy chain CDR2 comprising the amino acid sequence of SEQ ID NO:6, and a second heavy chain CDR3 comprising the amino acid sequence of SEQ ID NO:8;

(c) first and second light chains, wherein the first and second light chains each comprise a light chain CDR1 comprising the amino acid sequence of SEQ ID NO:11, a light chain CDR2 comprising the amino acid sequence of SEQ ID NO:12, and a light chain CDR 3 comprising the amino acid sequence of SEQ ID NO:14;

(d) a first Fc polypeptide comprising:

(i) Glu at position 380; Tyr at position 384; Thr at position 386; Glu at position 387; Trp at position 388; Val at position 389; Asn at position 390; Thr at position 413; Glu or Ser at position 415; Glu at position 416; and Phe at position 421, according to EU numbering; and (ii) an Ala at position 234 and Ala at position 235, according to EU numbering; and (e) a second Fc polypeptide does not contain a TfR-binding site or any modifications that reduce effector function.

2. The isolated antibody of claim 1, wherein the first Fc polypeptide further comprises a P329G or a P329S substitution, according to EU numbering.

3. The isolated antibody of claim 2, wherein the second Fc polypeptide comprises: a Leu at position 234, a Leu at position 235, and a Pro at position 329, according to EU numbering.

4. The isolated antibody of claim 3, wherein:

(a) the first heavy chain comprises the first Fc polypeptide and the second heavy chain comprises the second Fc polypeptide; or (b) the first heavy chain comprises the second Fc polypeptide and the second heavy chain comprises the first Fc polypeptide.

5. The isolated antibody of claim 4, wherein an antibody hinge region or a portion thereof is linked to the N-terminus of the first Fc polypeptide and/or the second Fc polypeptide.

6. The isolated antibody of claim 5, wherein the first Fc polypeptide and/or the second Fc polypeptide independently comprises a S239D and/or an I332E substitution, according to EU numbering.

7. The isolated antibody of claim 6, wherein:
(a) the first Fc polypeptide comprises a S239D substitution;
(b) the second Fc polypeptide comprises a S239D substitution;
(c) the first Fc polypeptide comprises a S239D substitution and the second Fc polypeptide comprises a S239D substitution;
(d) the first Fc polypeptide comprises an I332E substitution;
(e) the second Fc polypeptide comprises an I332E substitution;
(f) the first Fc polypeptide comprises an I332E substitution and the second Fc polypeptide comprises an I332E substitution;
(g) the first Fc polypeptide comprises a S239D substitution and the second Fc polypeptide comprises an I332E substitution;
(h) the first Fc polypeptide comprises an I332E substitution and the second Fc polypeptide comprises a S239D substitution;
(i) the first Fc polypeptide comprises a S239D and an I332E substitution;
(j) the second Fc polypeptide comprises a S239D and an I332E substitution;
(k) the first Fc polypeptide comprises a S239D and an I332E substitution and the second Fc polypeptide comprises a S239D substitution;
(l) the first Fc polypeptide comprises a S239D and an I332E substitution and the second Fc polypeptide comprises an I332E substitution;
(m) the first Fc polypeptide comprises a S239D substitution and the second Fc polypeptide comprises a S239D and an I332E substitution;
(n) the first Fc polypeptide comprises an I332E substitution and the second Fc polypeptide comprises a S239D and an I332E substitution; or
(o) the first Fc polypeptide comprises a S239D and an I332E substitution and the second Fc polypeptide comprises a S239D and an I332E substitution.

8. The isolated antibody of claim 7, wherein the first Fc polypeptide and the second Fc polypeptide each comprises modifications that promote heterodimerization.

9. The isolated antibody of claim 8, wherein:
(a) the first Fc polypeptide comprises a T366W substitution and the second Fc polypeptide comprises a T366S substitution;
(b) the second Fc polypeptide comprises a T366W substitution and the first Fc polypeptide comprises a T366S substitution;
(c) the first Fc polypeptide comprises a T366W substitution and the second Fc polypeptide comprises T366S, L368A, and Y407V; or
(d) the second Fc polypeptide comprises a T366W substitution and the first Fc polypeptide comprises T366S, L368A, and Y407V substitutions,
wherein the positions are according to EU numbering.

10. The isolated antibody of claim 9, wherein the first Fc polypeptide comprises a Glu at position 415.

11. The isolated antibody of claim 9, wherein the first Fc polypeptide comprises a Ser at position 415.

12. An anti-HER2 antibody comprising:
(a) a first heavy chain comprising (i) a first heavy chain CDR1 comprising the amino acid sequence of SEQ ID NO:16, a first heavy chain CDR2 comprising the amino acid sequence of SEQ ID NO:17, and a first heavy chain CDR3 comprising the amino acid sequence of SEQ ID NO:18; (ii) a hinge region comprising SEQ ID NO:96; and (iii) a first Fc polypeptide comprising: an Ala at position 234, an Ala at position 235, an Asp at position 239, a Ser at position 329, a Trp at position 366, a Glu at position 380, a Tyr at position 384, a Thr at position 386, a Glu at position 387, a Trp at position 388, a Val at position 389, a Gln at position 390, a Thr at position 413, a Glu or Ser at position 415, a Glu at position 416, a Phe at position 421, wherein the positions are according to EU numbering;
(b) (i) a second heavy chain comprises a second heavy chain CDR1 comprising the amino acid sequence of SEQ ID NO:4; a second heavy chain CDR2 comprising the amino acid sequence of SEQ ID NO:6, and a second heavy chain CDR3 comprising the amino acid sequence of SEQ ID NO:8; (ii) a hinge region comprising SEQ ID NO:96; and (iii) a second Fc polypeptide comprising: a Glu at position 332, a Ser at position 366, an Ala at position 368, and a Val at position 407, wherein the positions are according to EU numbering; and
(c) first and second light chains, wherein the first and second light chains each comprise a light chain CDR1 comprising the amino acid sequence of SEQ ID NO:11, a light chain CDR2 comprising the amino acid sequence of SEQ ID NO:12, and a light chain CDR 3 comprising the amino acid sequence of SEQ ID NO: 14.

13. A pharmaceutical composition comprising the anti-HER2 antibody of claim 12 and a pharmaceutically acceptable carrier and/or excipient.

14. Isolated polynucleotides or one or more expression vectors comprising nucleotide sequences encoding polypeptides that comprise the anti-HER2 antibody of claim 12.

15. One or more host cells comprising the nucleotide sequences of claim 14.

16. A method of making an anti-HER2 antibody comprising culturing the one or more host cells of claim 13 under conditions appropriate for expressing the nucleic acid sequences encoding polypeptides that comprise the anti-HER2 antibody, and isolating the polypeptides that comprise the anti-HER2 antibody expressed by the one or more host cells, wherein the isolate polypeptide are used to make the anti-HER2 antibody.

17. A method of treating a HER2-positive cancer in a subject, the method comprising administering to the subject a therapeutically effective amount of the pharmaceutical composition of claim 13.

18. The method of claim 17, wherein the cancer is: a breast cancer, an ovarian cancer, a bladder cancer, a salivary gland cancer, an endometrial cancer, a pancreatic cancer, a non-small-cell lung cancer, a gastric adenocarcinoma, or a gastroesophageal junction adenocarcinoma.

19. The method of claim 18, wherein the cancer is: a metastatic cancer or a brain metastasis of the cancer.

20. The method of claim 18, wherein the isolated antibody is administered in combination with a chemotherapy or radiation therapy.

21. The method of claim 19, wherein the isolated antibody is administered in combination with a chemotherapy or radiation therapy.

* * * * *

SEQUENCE LISTING

```
Sequence total quantity: 109
SEQ ID NO: 1            moltype = AA  length = 119
FEATURE                 Location/Qualifiers
REGION                  1..119
                        note = Description of sequence: Anti-HER2 D2 VH v1
source                  1..119
                        mol_type = protein
                        organism = synthetic construct
SEQUENCE: 1
EVQLVESGGG LVQPGGSLRL SCAASGFTFT DYTMDWVRQA PGKGLEWVAD VNPNSGQSIY  60
NQRFKGRFTL SVDRSKNTLY LQMNSLRAED TAVYYCARNL GPSFYFDYWG QGTLVTVSS   119

SEQ ID NO: 2            moltype = AA  length = 119
FEATURE                 Location/Qualifiers
REGION                  1..119
                        note = Description of sequence: Anti-HER2 D2 VH v2
source                  1..119
```

-continued

```
                         mol_type = protein
                         organism = synthetic construct
SEQUENCE: 2
EVQLVESGGG LVQPGGSLRL SCAASGFTFT DYTMDWVRQA PGKGLEWVAD VNPNSGGSIY  60
NQRFKGRFTL SVDRSKNTLY LQMNSLRAED TAVYYCARNL GPLFYFDYWG QGTLVTVSS   119

SEQ ID NO: 3             moltype = AA  length = 119
FEATURE                  Location/Qualifiers
REGION                   1..119
                         note = Description of sequence: Anti-HER2 D2 VH v3
source                   1..119
                         mol_type = protein
                         organism = synthetic construct
SEQUENCE: 3
EVQLVESGGG LVQPGGSLRL SCAASGFTFT DYTMDWVRQA PGKGLEWVAD VNPNSGQSIY  60
NQRFKGRFTL SVDRSKNTLY LQMNSLRAED TAVYYCARNL GPLFYFDYWG QGTLVTVSS   119

SEQ ID NO: 4             moltype = AA  length = 10
FEATURE                  Location/Qualifiers
REGION                   1..10
                         note = Description of sequence: Anti-HER2 D2 CDR-H1
source                   1..10
                         mol_type = protein
                         organism = synthetic construct
SEQUENCE: 4
GFTFTDYTMD                                                         10

SEQ ID NO: 5             moltype = AA  length = 17
FEATURE                  Location/Qualifiers
REGION                   1..17
                         note = Description of sequence: Anti-HER2D2 CDR-H2
source                   1..17
                         mol_type = protein
                         organism = synthetic construct
SEQUENCE: 5
DVNPNSGGSI YNQRFKG                                                 17

SEQ ID NO: 6             moltype = AA  length = 17
FEATURE                  Location/Qualifiers
REGION                   1..17
                         note = Description of sequence: Anti-HER2D2 CDR-H2.1
source                   1..17
                         mol_type = protein
                         organism = synthetic construct
SEQUENCE: 6
DVNPNSGQSI YNQRFKG                                                 17

SEQ ID NO: 7             moltype = AA  length = 12
FEATURE                  Location/Qualifiers
REGION                   1..12
                         note = Description of sequence: Anti-HER2 D2 CDR-H3
source                   1..12
                         mol_type = protein
                         organism = synthetic construct
SEQUENCE: 7
ARNLGPSFYF DY                                                      12

SEQ ID NO: 8             moltype = AA  length = 12
FEATURE                  Location/Qualifiers
REGION                   1..12
                         note = Description of sequence: Anti-HER2 D2 CDR-H3.1
source                   1..12
                         mol_type = protein
                         organism = synthetic construct
SEQUENCE: 8
ARNLGPLFYF DY                                                      12

SEQ ID NO: 9             moltype = AA  length = 214
FEATURE                  Location/Qualifiers
REGION                   1..214
                         note = Description of sequence: Anti-HER2 light chain v1
source                   1..214
                         mol_type = protein
                         organism = synthetic construct
SEQUENCE: 9
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ FYTTPPTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214
```

-continued

```
SEQ ID NO: 10           moltype = AA  length = 214
FEATURE                 Location/Qualifiers
REGION                  1..214
                        note = Description of sequence: Anti-HER2 light chain v2
source                  1..214
                        mol_type = protein
                        organism = synthetic construct
SEQUENCE: 10
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ YYTTPPTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 11           moltype = AA  length = 11
FEATURE                 Location/Qualifiers
REGION                  1..11
                        note = Description of sequence: Anti-HER2 CDR-L1
source                  1..11
                        mol_type = protein
                        organism = synthetic construct
SEQUENCE: 11
RASQDVNTAV A                                                       11

SEQ ID NO: 12           moltype = AA  length = 7
FEATURE                 Location/Qualifiers
REGION                  1..7
                        note = Description of sequence: Anti-HER2 CDR-L2
source                  1..7
                        mol_type = protein
                        organism = synthetic construct
SEQUENCE: 12
SASFLYS                                                            7

SEQ ID NO: 13           moltype = AA  length = 9
FEATURE                 Location/Qualifiers
REGION                  1..9
                        note = Description of sequence: Anti-HER2 CDR-L3.1
source                  1..9
                        mol_type = protein
                        organism = synthetic construct
SEQUENCE: 13
QQFYTTPPT                                                          9

SEQ ID NO: 14           moltype = AA  length = 9
FEATURE                 Location/Qualifiers
REGION                  1..9
                        note = Description of sequence: Anti-HER2 CDR-L3.2
source                  1..9
                        mol_type = protein
                        organism = synthetic construct
SEQUENCE: 14
QQYYTTPPT                                                          9

SEQ ID NO: 15           moltype = AA  length = 180
FEATURE                 Location/Qualifiers
REGION                  1..180
                        note = Description of sequence: Anti-HER2 D4 VH
source                  1..180
                        mol_type = protein
                        organism = synthetic construct
SEQUENCE: 15
EVQLVESGGG LVQPGGSLRL SCAASGFNIK DTYIHWVRQA PGKGLEWVAR IYPTNGYTRY  60
ADSVKGRFTI SADTSKNTAY LQMNSLRAED TAVYYCSRWG GDGFYAMDYW GQGTLVTVSS  120
ASTKGPSVFP LAPSSKSTSG GTAALGCLVK DYFPEPVTVS WNSGALTSGV HTFPAVLQSS  180

SEQ ID NO: 16           moltype = AA  length = 10
FEATURE                 Location/Qualifiers
REGION                  1..10
                        note = Description of sequence: Anti-HER2 D4 CDR-H1
source                  1..10
                        mol_type = protein
                        organism = synthetic construct
SEQUENCE: 16
GFNIKDTYIH                                                         10

SEQ ID NO: 17           moltype = AA  length = 17
FEATURE                 Location/Qualifiers
REGION                  1..17
```

-continued

```
                        note = Description of sequence: Anti-HER2 D4 CDR-H2
source                  1..17
                        mol_type = protein
                        organism = synthetic construct
SEQUENCE: 17
RIYPTNGYTR YADSVKG                                              17

SEQ ID NO: 18           moltype = AA  length = 12
FEATURE                 Location/Qualifiers
REGION                  1..12
                        note = Description of sequence: Anti-HER2 D4 CDR-H3
source                  1..12
                        mol_type = protein
                        organism = synthetic construct
SEQUENCE: 18
RWGGDGFYAM DY                                                   12

SEQ ID NO: 19           moltype = AA  length = 214
FEATURE                 Location/Qualifiers
REGION                  1..214
                        note = Description of sequence: Anti-HER2 light chain v3
source                  1..214
                        mol_type = protein
                        organism = synthetic construct
SEQUENCE: 19
DIQMTQSPSS LSASVGDRVT ITCKASQDVS TAVAWYQQKP GKAPKLLIYS ASFRYTGVPS  60
RFSGSRSGTD FTLTISSLQP EDFATYYCQQ HYTTPPTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                           214

SEQ ID NO: 20           moltype = AA  length = 450
FEATURE                 Location/Qualifiers
REGION                  1..450
                        note = Description of sequence: Anti-HER2 D4 heavy chain v1
source                  1..450
                        mol_type = protein
                        organism = synthetic construct
SEQUENCE: 20
EVQLVESGGG LVQPGGSLRL SCAASGFNIK DTYIHWVRQA PGKGLEWVAR IYPTNGYTRY  60
ADSVKGRFTI SADTSKNTAY LQMNSLRAED TAVYYCSRWG GEGFYAMDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLWC LVKGFYPSDI AVEWESNGQP ENNYKTTPPV LDSDGSFFLY SKLTVDKSRW  420
QQGNVFSCSV MHEALHNHYT QKSLSLSPGK                                450

SEQ ID NO: 21           moltype = AA  length = 450
FEATURE                 Location/Qualifiers
REGION                  1..450
                        note = Description of sequence: Anti-HER2 D4 heavy chain v2
source                  1..450
                        mol_type = protein
                        organism = synthetic construct
SEQUENCE: 21
EVQLVESGGG LVQPGGSLRL SCAASGFNIK DTYIHWVRQA PGKGLEWVAR IYPTNGYTRY  60
ADSVKGRFTI SADTSKNTAY LQMNSLRAED TAVYYCSRWG GEGFYAMDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLWC LVKGFYPSDI AVEWESYGTE WSNYKTTPPV LDSDGSFFLY SKLTVSKEEW  420
QQGFVFSCSV MHEALHNHYT QKSLSLSPGK                                450

SEQ ID NO: 22           moltype = AA  length = 450
FEATURE                 Location/Qualifiers
REGION                  1..450
                        note = Description of sequence: Anti-HER2 D4 heavy chain v3
source                  1..450
                        mol_type = protein
                        organism = synthetic construct
SEQUENCE: 22
EVQLVESGGG LVQPGGSLRL SCAASGFNIK DTYIHWVRQA PGKGLEWVAR IYPTNGYTRY  60
ADSVKGRFTI SADTSKNTAY LQMNSLRAED TAVYYCSRWG GEGFYAMDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LGAPIEKTIS KAKGQPREPQ VYTLPPSRDE  360
LTKNQVSLWC LVKGFYPSDI AVEWESYGTE WSNYKTTPPV LDSDGSFFLY SKLTVSKEEW  420
```

-continued

```
QQGFVFSCSV MHEALHNHYT QKSLSLSPGK                                 450

SEQ ID NO: 23          moltype = AA  length = 450
FEATURE                Location/Qualifiers
REGION                 1..450
                       note = Description of sequence: Anti-HER2 D4 heavy chain v4
source                 1..450
                       mol_type = protein
                       organism = synthetic construct
SEQUENCE: 23
EVQLVESGGG LVQPGGSLRL SCAASGFNIK DTYIHWVRQA PGKGLEWVAR IYPTNGYTRY  60
ADSVKGRFTI SADTSKNTAY LQMNSLRAED TAVYYCSRWG GEGFYAMDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LSAPIEKTIS KAKGQPREPQ VYTLPPSRDE  360
LTKNQVSLWC LVKGFYPSDI AVEWESYGTE WSNYKTTPPV LDSDGSFFLY SKLTVSKEEW  420
QQGFVFSCSV MHEALHNHYT QKSLSLSPGK                                 450

SEQ ID NO: 24          moltype = AA  length = 449
FEATURE                Location/Qualifiers
REGION                 1..449
                       note = Description of sequence: Anti-HER2 D2 heavy chain v1
source                 1..449
                       mol_type = protein
                       organism = synthetic construct
SEQUENCE: 24
EVQLVESGGG LVQPGGSLRL SCAASGFTFN DYTMDWVRQA PGKGLEWVAD VNPNSGGSIV  60
NRRFKGRFTL SVDRSKNTLY LQMNSLRAED TAVYYCARNL GPFFYFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLSCA VKGFYPSDIA VEWESNGQPE NNYKTTPPVL DSDGSFFLVS KLTVDKSRWQ  420
QGNVFSCSVM HEALHNHYTQ KSLSLSPGK                                  449

SEQ ID NO: 25          moltype = AA  length = 449
FEATURE                Location/Qualifiers
REGION                 1..449
                       note = Description of sequence: Anti-HER2 D2 heavy chain v2
source                 1..449
                       mol_type = protein
                       organism = synthetic construct
SEQUENCE: 25
EVQLVESGGG LVQPGGSLRL SCAASGFTFT DYTMDWVRQA PGKGLEWVAD VNPNSGQSIY  60
NQRFKGRFTL SVDRSKNTLY LQMNSLRAED TAVYYCARNL GPSFYFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLSCA VKGFYPSDIA VEWESNGQPE NNYKTTPPVL DSDGSFFLVS KLTVDKSRWQ  420
QGNVFSCSVM HEALHNHYTQ KSLSLSPGK                                  449

SEQ ID NO: 26          moltype = AA  length = 449
FEATURE                Location/Qualifiers
REGION                 1..449
                       note = Description of sequence: Anti-HER2 D2 heavy chain v3
source                 1..449
                       mol_type = protein
                       organism = synthetic construct
SEQUENCE: 26
EVQLVESGGG LVQPGGSLRL SCAASGFTFT DYTMDWVRQA PGKGLEWVAD VNPNSGGSIY  60
NQRFKGRFTL SVDRSKNTLY LQMNSLRAED TAVYYCARNL GPLFYFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLSCA VKGFYPSDIA VEWESNGQPE NNYKTTPPVL DSDGSFFLVS KLTVDKSRWQ  420
QGNVFSCSVM HEALHNHYTQ KSLSLSPGK                                  449

SEQ ID NO: 27          moltype = AA  length = 449
FEATURE                Location/Qualifiers
REGION                 1..449
                       note = Description of sequence: Anti-HER2 D2 heavy chain v4
source                 1..449
                       mol_type = protein
                       organism = synthetic construct
SEQUENCE: 27
EVQLVESGGG LVQPGGSLRL SCAASGFTFT DYTMDWVRQA PGKGLEWVAD VNPNSGQSIY  60
```

```
NQRFKGRFTL SVDRSKNTLY LQMNSLRAED TAVYYCARNL GPLFYFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLSCA VKGFYPSDIA VEWESNGQPE NNYKTTPPVL DSDGSFFLVS KLTVDKSRWQ  420
QGNVFSCSVM HEALHNHYTQ KSLSLSPGK                                   449

SEQ ID NO: 28          moltype = AA  length = 450
FEATURE                Location/Qualifiers
REGION                 1..450
                       note = Description of sequence: Anti-HER2 D4 heavy chain v5
source                 1..450
                       mol_type = protein
                       organism = synthetic construct
SEQUENCE: 28
EVQLVESGGG LVQPGGSLRL SCAASGFNIK DTYIHWVRQA PGKGLEWVAR IYPTNGYTRY  60
ADSVKGRFTI SADTSKNTAY LQMNSLRAED TAVYYCSRWG GDGFYAMDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PDVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLWC LVKGFYPSDI AVEWESYGTE WSNYKTTPPV LDSDGSFFLY SKLTVSKEEW  420
QQGFVFSCSV MHEALHNHYT QKSLSLSPGK                                  450

SEQ ID NO: 29          moltype = AA  length = 449
FEATURE                Location/Qualifiers
REGION                 1..449
                       note = Description of sequence: Anti-HER2 D2 heavy chain v5
source                 1..449
                       mol_type = protein
                       organism = synthetic construct
SEQUENCE: 29
EVQLVESGGG LVQPGGSLRL SCAASGFTFT DYTMDWVRQA PGKGLEWVAD VNPNSGQSIY  60
NQRFKGRFTL SVDRSKNTLY LQMNSLRAED TAVYYCARNL GPSFYFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
DVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPEEKTISK AKGQPREPQV YTLPPSRDEL  360
TKNQVSLSCA VKGFYPSDIA VEWESNGQPE NNYKTTPPVL DSDGSFFLVS KLTVDKSRWQ  420
QGNVFSCSVM HEALHNHYTQ KSLSLSPGK                                   449

SEQ ID NO: 30          moltype = AA  length = 449
FEATURE                Location/Qualifiers
REGION                 1..449
                       note = Description of sequence: Anti-HER2 D2 heavy chain v6
source                 1..449
                       mol_type = protein
                       organism = synthetic construct
SEQUENCE: 30
EVQLVESGGG LVQPGGSLRL SCAASGFTFT DYTMDWVRQA PGKGLEWVAD VNPNSGQSIY  60
NQRFKGRFTL SVDRSKNTLY LQMNSLRAED TAVYYCARNL GPSFYFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPEEKTISK AKGQPREPQV YTLPPSRDEL  360
TKNQVSLSCA VKGFYPSDIA VEWESNGQPE NNYKTTPPVL DSDGSFFLVS KLTVDKSRWQ  420
QGNVFSCSVM HEALHNHYTQ KSLSLSPGK                                   449

SEQ ID NO: 31          moltype = AA  length = 450
FEATURE                Location/Qualifiers
REGION                 1..450
                       note = Description of sequence: Anti-HER2 D4 heavy chain v6
source                 1..450
                       mol_type = protein
                       organism = synthetic construct
SEQUENCE: 31
EVQLVESGGG LVQPGGSLRL SCAASGFNIK DTYIHWVRQA PGKGLEWVAR IYPTNGYTRY  60
ADSVKGRFTI SADTSKNTAY LQMNSLRAED TAVYYCSRWG GDGFYAMDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PDVFLFPPKP KDTLMISRTP EVTCVVVDVS HEDPEVKFNW YVDGVEVHNA KTKPREEQYN  300
STYRVVSVLT VLHQDWLNGK EYKCKVSNKA LGAPIEKTIS KAKGQPREPQ VYTLPPSRDE  360
LTKNQVSLWC LVKGFYPSDI AVEWESYGTE WSNYKTTPPV LDSDGSFFLY SKLTVSKEEW  420
QQGFVFSCSV MHEALHNHYT QKSLSLSPGK                                  450

SEQ ID NO: 32          moltype = AA  length = 450
FEATURE                Location/Qualifiers
REGION                 1..450
```

```
                          note = Description of sequence: Anti-HER2 D4 heavy chain v7
source                    1..450
                          mol_type = protein
                          organism = synthetic construct
SEQUENCE: 32
EVQLVESGGG LVQPGGSLRL SCAASGFNIK DTYIHWVRQA PGKGLEWVAR IYPTNGYTRY  60
ADSVKGRFTI SADTSKNTAY LQMNSLRAED TAVYYCSRWG GDGFYAMDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PDVFLFPPKP KDTLMISRTP EVTCVVVDVS HEDPEVKFNW YVDGVEVHNA KTKPREEQYN  300
STYRVVSVLT VLHQDWLNGK EYKCKVSNKA LSAPIEKTIS KAKGQPREPQ VYTLPPSRDE  360
LTKNQVSLWC LVKGFYPSDI AVEWESYGTE WSNYKTTPPV LDSDGSFFLY SKLTVSKEEW  420
QQGFVFSCSV MHEALHNHYT QKSLSLSPGK                                 450

SEQ ID NO: 33             moltype = AA  length = 449
FEATURE                   Location/Qualifiers
REGION                    1..449
                          note = Description of sequence: Anti-HER2 D2 heavy chain v7
source                    1..449
                          mol_type = protein
                          organism = synthetic construct
SEQUENCE: 33
EVQLVESGGG LVQPGGSLRL SCAASGFTFT DYTMDWVRQA PGKGLEWVAD VNPNSGGSIY  60
NQRFKGRFTL SVDRSKNTLY LQMNSLRAED TAVYYCARNL GPLFYFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
DVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPEEKTISK AKGQPREPQV YTLPPSRDEL  360
TKNQVSLSCA VKGFYPSDIA VEWESNGQPE NNYKTTPPVL DSDGSFFLVS KLTVDKSRWQ  420
QGNVFSCSVM HEALHNHYTQ KSLSLSPGK                                  449

SEQ ID NO: 34             moltype = AA  length = 449
FEATURE                   Location/Qualifiers
REGION                    1..449
                          note = Description of sequence: Anti-HER2 D2 heavy chain v8
source                    1..449
                          mol_type = protein
                          organism = synthetic construct
SEQUENCE: 34
EVQLVESGGG LVQPGGSLRL SCAASGFTFT DYTMDWVRQA PGKGLEWVAD VNPNSGGSIY  60
NQRFKGRFTL SVDRSKNTLY LQMNSLRAED TAVYYCARNL GPLFYFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPEEKTISK AKGQPREPQV YTLPPSRDEL  360
TKNQVSLSCA VKGFYPSDIA VEWESNGQPE NNYKTTPPVL DSDGSFFLVS KLTVDKSRWQ  420
QGNVFSCSVM HEALHNHYTQ KSLSLSPGK                                  449

SEQ ID NO: 35             moltype = AA  length = 449
FEATURE                   Location/Qualifiers
REGION                    1..449
                          note = Description of sequence: Anti-HER2 D2 heavy chain v9
source                    1..449
                          mol_type = protein
                          organism = synthetic construct
SEQUENCE: 35
EVQLVESGGG LVQPGGSLRL SCAASGFTFT DYTMDWVRQA PGKGLEWVAD VNPNSGQSIY  60
NQRFKGRFTL SVDRSKNTLY LQMNSLRAED TAVYYCARNL GPLFYFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
DVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPEEKTISK AKGQPREPQV YTLPPSRDEL  360
TKNQVSLSCA VKGFYPSDIA VEWESNGQPE NNYKTTPPVL DSDGSFFLVS KLTVDKSRWQ  420
QGNVFSCSVM HEALHNHYTQ KSLSLSPGK                                  449

SEQ ID NO: 36             moltype = AA  length = 449
FEATURE                   Location/Qualifiers
REGION                    1..449
                          note = Description of sequence: Anti-HER2 D2 heavy chain v10
source                    1..449
                          mol_type = protein
                          organism = synthetic construct
SEQUENCE: 36
EVQLVESGGG LVQPGGSLRL SCAASGFTFT DYTMDWVRQA PGKGLEWVAD VNPNSGQSIY  60
NQRFKGRFTL SVDRSKNTLY LQMNSLRAED TAVYYCARNL GPLFYFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPEEKTISK AKGQPREPQV YTLPPSRDEL  360
```

```
TKNQVSLSCA VKGFYPSDIA VEWESNGQPE NNYKTTPPVL DSDGSFFLVS KLTVDKSRWQ  420
QGNVFSCSVM HEALHNHYTQ KSLSLSPGK                                    449

SEQ ID NO: 37           moltype = AA  length = 450
FEATURE                 Location/Qualifiers
REGION                  1..450
                        note = Description of sequence: Anti-HER2 D4 heavy chain v8
source                  1..450
                        mol_type = protein
                        organism = synthetic construct
SEQUENCE: 37
EVQLVESGGG LVQPGGSLRL SCAASGFNIK DTYIHWVRQA PGKGLEWVAR IYPTNGYTRY  60
ADSVKGRFTI SADTSKNTAY LQMNSLRAED TAVYYCSRWG GDGFYAMDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLWC LVKGFYPSDI AVEWESYGTE WSNYKTTPPV LDSDGSFFLY SKLTVSKEEW  420
QQGFVFSCSV MHEALHNHYT QKSLSLSPGK                                   450

SEQ ID NO: 38           moltype = AA  length = 450
FEATURE                 Location/Qualifiers
REGION                  1..450
                        note = Description of sequence: Anti-HER2 D4 heavy chain v9
source                  1..450
                        mol_type = protein
                        organism = synthetic construct
SEQUENCE: 38
EVQLVESGGG LVQPGGSLRL SCAASGFNIK DTYIHWVRQA PGKGLEWVAR IYPTNGYTRY  60
ADSVKGRFTI SADTSKNTAY LQMNSLRAED TAVYYCSRWG GDGFYAMDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LGAPIEKTIS KAKGQPREPQ VYTLPPSRDE  360
LTKNQVSLWC LVKGFYPSDI AVEWESYGTE WSNYKTTPPV LDSDGSFFLY SKLTVSKEEW  420
QQGFVFSCSV MHEALHNHYT QKSLSLSPGK                                   450

SEQ ID NO: 39           moltype = AA  length = 450
FEATURE                 Location/Qualifiers
REGION                  1..450
                        note = Description of sequence: Anti-HER2 D4 heavy chain v10
source                  1..450
                        mol_type = protein
                        organism = synthetic construct
SEQUENCE: 39
EVQLVESGGG LVQPGGSLRL SCAASGFNIK DTYIHWVRQA PGKGLEWVAR IYPTNGYTRY  60
ADSVKGRFTI SADTSKNTAY LQMNSLRAED TAVYYCSRWG GDGFYAMDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LSAPIEKTIS KAKGQPREPQ VYTLPPSRDE  360
LTKNQVSLWC LVKGFYPSDI AVEWESYGTE WSNYKTTPPV LDSDGSFFLY SKLTVSKEEW  420
QQGFVFSCSV MHEALHNHYT QKSLSLSPGK                                   450

SEQ ID NO: 40           moltype = AA  length = 450
FEATURE                 Location/Qualifiers
REGION                  1..450
                        note = Description of sequence: Anti-HER2 D4 heavy chain v11
source                  1..450
                        mol_type = protein
                        organism = synthetic construct
SEQUENCE: 40
EVQLVESGGG LVQPGGSLRL SCAASGFNIK DTYIHWVRQA PGKGLEWVAR IYPTNGYTRY  60
ADSVKGRFTI SADTSKNTAY LQMNSLRAED TAVYYCSRWG GDGFYAMDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LSAPEEKTIS KAKGQPREPQ VYTLPPSRDE  360
LTKNQVSLWC LVKGFYPSDI AVEWESYGTE WSNYKTTPPV LDSDGSFFLY SKLTVSKEEW  420
QQGFVFSCSV MHEALHNHYT QKSLSLSPGK                                   450

SEQ ID NO: 41           moltype = AA  length = 450
FEATURE                 Location/Qualifiers
REGION                  1..450
                        note = Description of sequence: Anti-HER2 D4 heavy chain v12
source                  1..450
                        mol_type = protein
                        organism = synthetic construct
SEQUENCE: 41
```

-continued

```
EVQLVESGGG LVQPGGSLRL SCAASGFNIK DTYIHWVRQA PGKGLEWVAR IYPTNGYTRY  60
ADSVKGRFTI SADTSKNTAY LQMNSLRAED TAVYYCSRWG GDGFYAMDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PDVFLFPPKP KDTLMISRTP EVTCVVVDVS HEDPEVKFNW YVDGVEVHNA KTKPREEQYN  300
STYRVVSVLT VLHQDWLNGK EYKCKVSNKA LSAPEEKTIS KAKGQPREPQ VYTLPPSRDE  360
LTKNQVSLWC LVKGFYPSDI AVEWESYGTE WSNYKTTPPV LDSDGSFFLY SKLTVSKEEW  420
QQGFVFSCSV MHEALHNHYT QKSLSLSPGK                                  450

SEQ ID NO: 42          moltype = AA  length = 450
FEATURE                Location/Qualifiers
REGION                 1..450
                       note = Description of sequence: Anti-HER2 D4 heavy chain v13
source                 1..450
                       mol_type = protein
                       organism = synthetic construct
SEQUENCE: 42
EVQLVESGGG LVQPGGSLRL SCAASGFNIK DTYIHWVRQA PGKGLEWVAR IYPTNGYTRY  60
ADSVKGRFTI SADTSKNTAY LQMNSLRAED TAVYYCSRWG GDGFYAMDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLSC AVKGFYPSDI AVEWESNGQP ENNYKTTPPV LDSDGSFFLV SKLTVDKSRW  420
QQGNVFSCSV MHEALHNHYT QKSLSLSPGK                                  450

SEQ ID NO: 43          moltype = AA  length = 449
FEATURE                Location/Qualifiers
REGION                 1..449
                       note = Description of sequence: Anti-HER2 D2 heavy chain v11
source                 1..449
                       mol_type = protein
                       organism = synthetic construct
SEQUENCE: 43
EVQLVESGGG LVQPGGSLRL SCAASGFTFT DYTMDWVRQA PGKGLEWVAD VNPNSGQSIY  60
NQRFKGRFTL SVDRSKNTLY LQMNSLRAED TAVYYCARNL GPSFYFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLWCL VKGFYPSDIA VEWESYGTEW SNYKTTPPVL DSDGSFFLYS KLTVSKEEWQ  420
QGFVFSCSVM HEALHNHYTQ KSLSLSPGK                                   449

SEQ ID NO: 44          moltype = AA  length = 449
FEATURE                Location/Qualifiers
REGION                 1..449
                       note = Description of sequence: Anti-HER2 D2 heavy chain v12
source                 1..449
                       mol_type = protein
                       organism = synthetic construct
SEQUENCE: 44
EVQLVESGGG LVQPGGSLRL SCAASGFTFT DYTMDWVRQA PGKGLEWVAD VNPNSGGSIY  60
NQRFKGRFTL SVDRSKNTLY LQMNSLRAED TAVYYCARNL GPLFYFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLWCL VKGFYPSDIA VEWESYGTEW SNYKTTPPVL DSDGSFFLYS KLTVSKEEWQ  420
QGFVFSCSVM HEALHNHYTQ KSLSLSPGK                                   449

SEQ ID NO: 45          moltype = AA  length = 449
FEATURE                Location/Qualifiers
REGION                 1..449
                       note = Description of sequence: Anti-HER2 D2 heavy chain v13
source                 1..449
                       mol_type = protein
                       organism = synthetic construct
SEQUENCE: 45
EVQLVESGGG LVQPGGSLRL SCAASGFTFT DYTMDWVRQA PGKGLEWVAD VNPNSGQSIY  60
NQRFKGRFTL SVDRSKNTLY LQMNSLRAED TAVYYCARNL GPLFYFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLWCL VKGFYPSDIA VEWESYGTEW SNYKTTPPVL DSDGSFFLYS KLTVSKEEWQ  420
QGFVFSCSVM HEALHNHYTQ KSLSLSPGK                                   449

SEQ ID NO: 46          moltype = AA  length = 449
FEATURE                Location/Qualifiers
```

```
REGION                  1..449
                        note = Description of sequence: Anti-HER2 D2 heavy chain v14
source                  1..449
                        mol_type = protein
                        organism = synthetic construct
SEQUENCE: 46
EVQLVESGGG LVQPGGSLRL SCAASGFTFT DYTMDWVRQA PGKGLEWVAD VNPNSGQSIY  60
NQRFKGRFTL SVDRSKNTLY LQMNSLRAED TAVYYCARNL GPSFYFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
DVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLSCA VKGFYPSDIA VEWESNGQPE NNYKTTPPVL DSDGSFFLVS KLTVDKSRWQ  420
QGNVFSCSVM HEALHNHYTQ KSLSLSPGK                                   449

SEQ ID NO: 47           moltype = AA  length = 449
FEATURE                 Location/Qualifiers
REGION                  1..449
                        note = Description of sequence: Anti-HER2 D2 heavy chain v15
source                  1..449
                        mol_type = protein
                        organism = synthetic construct
SEQUENCE: 47
EVQLVESGGG LVQPGGSLRL SCAASGFTFT DYTMDWVRQA PGKGLEWVAD VNPNSGGSIY  60
NQRFKGRFTL SVDRSKNTLY LQMNSLRAED TAVYYCARNL GPLFYFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
DVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLSCA VKGFYPSDIA VEWESNGQPE NNYKTTPPVL DSDGSFFLVS KLTVDKSRWQ  420
QGNVFSCSVM HEALHNHYTQ KSLSLSPGK                                   449

SEQ ID NO: 48           moltype = AA  length = 449
FEATURE                 Location/Qualifiers
REGION                  1..449
                        note = Description of sequence: Anti-HER2 D2 heavy chain v16
source                  1..449
                        mol_type = protein
                        organism = synthetic construct
SEQUENCE: 48
EVQLVESGGG LVQPGGSLRL SCAASGFTFT DYTMDWVRQA PGKGLEWVAD VNPNSGQSIY  60
NQRFKGRFTL SVDRSKNTLY LQMNSLRAED TAVYYCARNL GPLFYFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
DVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLSCA VKGFYPSDIA VEWESNGQPE NNYKTTPPVL DSDGSFFLVS KLTVDKSRWQ  420
QGNVFSCSVM HEALHNHYTQ KSLSLSPGK                                   449

SEQ ID NO: 49           moltype = AA  length = 10
FEATURE                 Location/Qualifiers
REGION                  1..10
                        note = Description of sequence: Anti-HER2 CDR-H1.1
source                  1..10
                        mol_type = protein
                        organism = synthetic construct
SEQUENCE: 49
GFNFTDYTMD                                                        10

SEQ ID NO: 50           moltype = AA  length = 10
FEATURE                 Location/Qualifiers
REGION                  1..10
                        note = Description of sequence: Anti-HER2 CDR-H1.2
source                  1..10
                        mol_type = protein
                        organism = synthetic construct
SEQUENCE: 50
GFKFTDYTMD                                                        10

SEQ ID NO: 51           moltype = AA  length = 10
FEATURE                 Location/Qualifiers
REGION                  1..10
                        note = Description of sequence: Anti-HER2 CDR-H1.3
source                  1..10
                        mol_type = protein
                        organism = synthetic construct
SEQUENCE: 51
GFMFTDYTMD                                                        10
```

-continued

```
SEQ ID NO: 52            moltype = AA  length = 10
FEATURE                  Location/Qualifiers
REGION                   1..10
                         note = Description of sequence: Anti-HER2 CDR-H1.4
source                   1..10
                         mol_type = protein
                         organism = synthetic construct
SEQUENCE: 52
GFHFTDYTMD                                                                 10

SEQ ID NO: 53            moltype = AA  length = 17
FEATURE                  Location/Qualifiers
REGION                   1..17
                         note = Description of sequence: Anti-HER2 CDR-H2.2
source                   1..17
                         mol_type = protein
                         organism = synthetic construct
SEQUENCE: 53
DVNPNSGGSI YNRRFKG                                                         17

SEQ ID NO: 54            moltype = AA  length = 17
FEATURE                  Location/Qualifiers
REGION                   1..17
                         note = Description of sequence: Anti-HER2 CDR-H2.3
source                   1..17
                         mol_type = protein
                         organism = synthetic construct
SEQUENCE: 54
DVNPNSGGSI YNHRFKG                                                         17

SEQ ID NO: 55            moltype = AA  length = 17
FEATURE                  Location/Qualifiers
REGION                   1..17
                         note = Description of sequence: Anti-HER2 CDR-H2.4
source                   1..17
                         mol_type = protein
                         organism = synthetic construct
SEQUENCE: 55
DVNPNSGGSI YNTRFKG                                                         17

SEQ ID NO: 56            moltype = AA  length = 12
FEATURE                  Location/Qualifiers
REGION                   1..12
                         note = Description of sequence: Anti-HER2 CDR-H3.2
source                   1..12
                         mol_type = protein
                         organism = synthetic construct
SEQUENCE: 56
ARNLGPWFYF DY                                                              12

SEQ ID NO: 57            moltype = AA  length = 12
FEATURE                  Location/Qualifiers
REGION                   1..12
                         note = Description of sequence: Anti-HER2 CDR-H3.3
source                   1..12
                         mol_type = protein
                         organism = synthetic construct
SEQUENCE: 57
ARNLGPFFYF DY                                                              12

SEQ ID NO: 58            moltype = AA  length = 12
FEATURE                  Location/Qualifiers
REGION                   1..12
                         note = Description of sequence: Anti-HER2 CDR-H3.4
source                   1..12
                         mol_type = protein
                         organism = synthetic construct
SEQUENCE: 58
ARNLGPDFYF DY                                                              12

SEQ ID NO: 59            moltype = AA  length = 12
FEATURE                  Location/Qualifiers
REGION                   1..12
                         note = Description of sequence: Anti-HER2 CDR-H3.5
source                   1..12
                         mol_type = protein
                         organism = synthetic construct
SEQUENCE: 59
ARNLGPYFYF DY                                                              12
```

```
SEQ ID NO: 60          moltype = AA  length = 119
FEATURE                Location/Qualifiers
REGION                 1..119
                       note = Description of sequence: Anti-HER2 D2 VH v4
source                 1..119
                       mol_type = protein
                       organism = synthetic construct
SEQUENCE: 60
EVQLVESGGG LVQPGGSLRL SCAASGFNFT DYTMDWVRQA PGKGLEWVAD VNPNSGGSIY  60
NQRFKGRFTL SVDRSKNTLY LQMNSLRAED TAVYYCARNL GPSFYFDYWG QGTLVTVSS   119

SEQ ID NO: 61          moltype = AA  length = 119
FEATURE                Location/Qualifiers
REGION                 1..119
                       note = Description of sequence: Anti-HER2 D2 VH v5
source                 1..119
                       mol_type = protein
                       organism = synthetic construct
SEQUENCE: 61
EVQLVESGGG LVQPGGSLRL SCAASGFKFT DYTMDWVRQA PGKGLEWVAD VNPNSGGSIY  60
NQRFKGRFTL SVDRSKNTLY LQMNSLRAED TAVYYCARNL GPSFYFDYWG QGTLVTVSS   119

SEQ ID NO: 62          moltype = AA  length = 119
FEATURE                Location/Qualifiers
REGION                 1..119
                       note = Description of sequence: Anti-HER2 D2 VH v6
source                 1..119
                       mol_type = protein
                       organism = synthetic construct
SEQUENCE: 62
EVQLVESGGG LVQPGGSLRL SCAASGFMFT DYTMDWVRQA PGKGLEWVAD VNPNSGGSIY  60
NQRFKGRFTL SVDRSKNTLY LQMNSLRAED TAVYYCARNL GPSFYFDYWG QGTLVTVSS   119

SEQ ID NO: 63          moltype = AA  length = 119
FEATURE                Location/Qualifiers
REGION                 1..119
                       note = Description of sequence: Anti-HER2 D2 VH v7
source                 1..119
                       mol_type = protein
                       organism = synthetic construct
SEQUENCE: 63
EVQLVESGGG LVQPGGSLRL SCAASGFHFT DYTMDWVRQA PGKGLEWVAD VNPNSGGSIY  60
NQRFKGRFTL SVDRSKNTLY LQMNSLRAED TAVYYCARNL GPSFYFDYWG QGTLVTVSS   119

SEQ ID NO: 64          moltype = AA  length = 119
FEATURE                Location/Qualifiers
REGION                 1..119
                       note = Description of sequence: Anti-HER2 D2 VH v8
source                 1..119
                       mol_type = protein
                       organism = synthetic construct
SEQUENCE: 64
EVQLVESGGG LVQPGGSLRL SCAASGFTFT DYTMDWVRQA PGKGLEWVAD VNPNSGGSIY  60
NRRFKGRFTL SVDRSKNTLY LQMNSLRAED TAVYYCARNL GPSFYFDYWG QGTLVTVSS   119

SEQ ID NO: 65          moltype = AA  length = 119
FEATURE                Location/Qualifiers
REGION                 1..119
                       note = Description of sequence: Anti-HER2 D2 VH v9
source                 1..119
                       mol_type = protein
                       organism = synthetic construct
SEQUENCE: 65
EVQLVESGGG LVQPGGSLRL SCAASGFTFT DYTMDWVRQA PGKGLEWVAD VNPNSGGSIY  60
NHRFKGRFTL SVDRSKNTLY LQMNSLRAED TAVYYCARNL GPSFYFDYWG QGTLVTVSS   119

SEQ ID NO: 66          moltype = AA  length = 119
FEATURE                Location/Qualifiers
REGION                 1..119
                       note = Description of sequence: Anti-HER2 D2 VH v10
source                 1..119
                       mol_type = protein
                       organism = synthetic construct
SEQUENCE: 66
EVQLVESGGG LVQPGGSLRL SCAASGFTFT DYTMDWVRQA PGKGLEWVAD VNPNSGGSIY  60
NTRFKGRFTL SVDRSKNTLY LQMNSLRAED TAVYYCARNL GPSFYFDYWG QGTLVTVSS   119

SEQ ID NO: 67          moltype = AA  length = 119
```

-continued

```
FEATURE                Location/Qualifiers
REGION                 1..119
                       note = Description of sequence: Anti-HER2 D2 VH v11
source                 1..119
                       mol_type = protein
                       organism = synthetic construct
SEQUENCE: 67
EVQLVESGGG LVQPGGSLRL SCAASGFTFT DYTMDWVRQA PGKGLEWVAD VNPNSGGSIY  60
NQRFKGRFTL SVDRSKNTLY LQMNSLRAED TAVYYCARNL GPWFYFDYWG QGTLVTVSS   119

SEQ ID NO: 68          moltype = AA  length = 119
FEATURE                Location/Qualifiers
REGION                 1..119
                       note = Description of sequence: Anti-HER2 D2 VH v12
source                 1..119
                       mol_type = protein
                       organism = synthetic construct
SEQUENCE: 68
EVQLVESGGG LVQPGGSLRL SCAASGFTFT DYTMDWVRQA PGKGLEWVAD VNPNSGGSIY  60
NQRFKGRFTL SVDRSKNTLY LQMNSLRAED TAVYYCARNL GPFFYFDYWG QGTLVTVSS   119

SEQ ID NO: 69          moltype = AA  length = 119
FEATURE                Location/Qualifiers
REGION                 1..119
                       note = Description of sequence: Anti-HER2 D2 VH v13
source                 1..119
                       mol_type = protein
                       organism = synthetic construct
SEQUENCE: 69
EVQLVESGGG LVQPGGSLRL SCAASGFTFT DYTMDWVRQA PGKGLEWVAD VNPNSGGSIY  60
NQRFKGRFTL SVDRSKNTLY LQMNSLRAED TAVYYCARNL GPDFYFDYWG QGTLVTVSS   119

SEQ ID NO: 70          moltype = AA  length = 119
FEATURE                Location/Qualifiers
REGION                 1..119
                       note = Description of sequence: Anti-HER2 D2 VH v4
source                 1..119
                       mol_type = protein
                       organism = synthetic construct
SEQUENCE: 70
EVQLVESGGG LVQPGGSLRL SCAASGFTFT DYTMDWVRQA PGKGLEWVAD VNPNSGGSIY  60
NQRFKGRFTL SVDRSKNTLY LQMNSLRAED TAVYYCARNL GPYFYFDYWG QGTLVTVSS   119

SEQ ID NO: 71          moltype = AA  length = 217
FEATURE                Location/Qualifiers
REGION                 1..217
                       note = Description of sequence: Fc sequence with hole
                        mutations.hD
source                 1..217
                       mol_type = protein
                       organism = synthetic construct
SEQUENCE: 71
APELLGGPDV FLFPPKPKDT LMISRTPEVT CVVVDVSHED PEVKFNWYVD GVEVHNAKTK  60
PREEQYNSTY RVVSVLTVLH QDWLNGKEYK CKVSNKALPA PIEKTISKAK GQPREPQVYT  120
LPPSRDELTK NQVSLSCAVK GFYPSDIAVE WESNGQPENN YKTTPPVLDS DGSFFLVSKL  180
TVDKSRWQQG NVFSCSVMHE ALHNHYTQKS LSLSPGK                          217

SEQ ID NO: 72          moltype = AA  length = 217
FEATURE                Location/Qualifiers
REGION                 1..217
                       note = Description of sequence: Fc sequence with hole
                        mutations.hE
source                 1..217
                       mol_type = protein
                       organism = synthetic construct
SEQUENCE: 72
APELLGGPSV FLFPPKPKDT LMISRTPEVT CVVVDVSHED PEVKFNWYVD GVEVHNAKTK  60
PREEQYNSTY RVVSVLTVLH QDWLNGKEYK CKVSNKALPA PEEKTISKAK GQPREPQVYT  120
LPPSRDELTK NQVSLSCAVK GFYPSDIAVE WESNGQPENN YKTTPPVLDS DGSFFLVSKL  180
TVDKSRWQQG NVFSCSVMHE ALHNHYTQKS LSLSPGK                          217

SEQ ID NO: 73          moltype = AA  length = 217
FEATURE                Location/Qualifiers
REGION                 1..217
                       note = Description of sequence: Fc sequence with hole
                        mutations.hDE
source                 1..217
                       mol_type = protein
                       organism = synthetic construct
```

-continued

```
SEQUENCE: 73
APELLGGPDV FLFPPKPKDT LMISRTPEVT CVVVDVSHED PEVKFNWYVD GVEVHNAKTK  60
PREEQYNSTY RVVSVLTVLH QDWLNGKEYK CKVSNKALPA PEEKTISKAK GQPREPQVYT  120
LPPSRDELTK NQVSLSCAVK GFYPSDIAVE WESNGQPENN YKTTPPVLDS DGSFFLVSKL  180
TVDKSRWQQG NVFSCSVMHE ALHNHYTQKS LSLSPGK                          217

SEQ ID NO: 74           moltype = AA  length = 217
FEATURE                 Location/Qualifiers
REGION                  1..217
                        note = Description of sequence: "Clone CH3C.35.23.4 with
                         knob LALA and kD"
source                  1..217
                        mol_type = protein
                        organism = synthetic construct
SEQUENCE: 74
APEAAGGPDV FLFPPKPKDT LMISRTPEVT CVVVDVSHED PEVKFNWYVD GVEVHNAKTK  60
PREEQYNSTY RVVSVLTVLH QDWLNGKEYK CKVSNKALPA PIEKTISKAK GQPREPQVYT  120
LPPSRDELTK NQVSLWCLVK GFYPSDIAVE WESYGTEWSN YKTTPPVLDS DGSFFLYSKL  180
TVSKEEWQQG FVFSCSVMHE ALHNHYTQKS LSLSPGK                          217

SEQ ID NO: 75           moltype = AA  length = 217
FEATURE                 Location/Qualifiers
REGION                  1..217
                        note = Description of sequence: "Clone CH3C.35.23.4 with
                         knob LALA and kE"
source                  1..217
                        mol_type = protein
                        organism = synthetic construct
SEQUENCE: 75
APEAAGGPSV FLFPPKPKDT LMISRTPEVT CVVVDVSHED PEVKFNWYVD GVEVHNAKTK  60
PREEQYNSTY RVVSVLTVLH QDWLNGKEYK CKVSNKALPA PEEKTISKAK GQPREPQVYT  120
LPPSRDELTK NQVSLWCLVK GFYPSDIAVE WESYGTEWSN YKTTPPVLDS DGSFFLYSKL  180
TVSKEEWQQG FVFSCSVMHE ALHNHYTQKS LSLSPGK                          217

SEQ ID NO: 76           moltype = AA  length = 217
FEATURE                 Location/Qualifiers
REGION                  1..217
                        note = Description of sequence: "Clone CH3C.35.23.4 with
                         knob LALA and kDE"
source                  1..217
                        mol_type = protein
                        organism = synthetic construct
SEQUENCE: 76
APEAAGGPDV FLFPPKPKDT LMISRTPEVT CVVVDVSHED PEVKFNWYVD GVEVHNAKTK  60
PREEQYNSTY RVVSVLTVLH QDWLNGKEYK CKVSNKALPA PEEKTISKAK GQPREPQVYT  120
LPPSRDELTK NQVSLWCLVK GFYPSDIAVE WESYGTEWSN YKTTPPVLDS DGSFFLYSKL  180
TVSKEEWQQG FVFSCSVMHE ALHNHYTQKS LSLSPGK                          217

SEQ ID NO: 77           moltype = AA  length = 217
FEATURE                 Location/Qualifiers
REGION                  1..217
                        note = Description of sequence: "Clone CH3C.35.23.4 with
                         knob LALA and PG"
source                  1..217
                        mol_type = protein
                        organism = synthetic construct
SEQUENCE: 77
APEAAGGPSV FLFPPKPKDT LMISRTPEVT CVVVDVSHED PEVKFNWYVD GVEVHNAKTK  60
PREEQYNSTY RVVSVLTVLH QDWLNGKEYK CKVSNKALGA PIEKTISKAK GQPREPQVYT  120
LPPSRDELTK NQVSLWCLVK GFYPSDIAVE WESYGTEWSN YKTTPPVLDS DGSFFLYSKL  180
TVSKEEWQQG FVFSCSVMHE ALHNHYTQKS LSLSPGK                          217

SEQ ID NO: 78           moltype = AA  length = 217
FEATURE                 Location/Qualifiers
REGION                  1..217
                        note = Description of sequence: "Clone CH3C.35.23.4 with
                         knob LALA and PS"
source                  1..217
                        mol_type = protein
                        organism = synthetic construct
SEQUENCE: 78
APEAAGGPSV FLFPPKPKDT LMISRTPEVT CVVVDVSHED PEVKFNWYVD GVEVHNAKTK  60
PREEQYNSTY RVVSVLTVLH QDWLNGKEYK CKVSNKALSA PIEKTISKAK GQPREPQVYT  120
LPPSRDELTK NQVSLWCLVK GFYPSDIAVE WESYGTEWSN YKTTPPVLDS DGSFFLYSKL  180
TVSKEEWQQG FVFSCSVMHE ALHNHYTQKS LSLSPGK                          217

SEQ ID NO: 79           moltype = AA  length = 217
FEATURE                 Location/Qualifiers
REGION                  1..217
```

-continued

```
                       note = Description of sequence: "Clone CH3C.35.23.4 with
                        knob LALA PG and kD"
source                 1..217
                       mol_type = protein
                       organism = synthetic construct
SEQUENCE: 79
APEAAGGPDV FLFPPKPKDT LMISRTPEVT CVVVDVSHED PEVKFNWYVD GVEVHNAKTK  60
PREEQYNSTY RVVSVLTVLH QDWLNGKEYK CKVSNKALGA PIEKTISKAK GQPREPQVYT  120
LPPSRDELTK NQVSLWCLVK GFYPSDIAVE WESYGTEWSN YKTTPPVLDS DGSFFLYSKL  180
TVSKEEWQQG FVFSCSVMHE ALHNHYTQKS LSLSPGK                           217

SEQ ID NO: 80          moltype = AA  length = 217
FEATURE                Location/Qualifiers
REGION                 1..217
                       note = Description of sequence: "Clone CH3C.35.23.4 with
                        knob LALA PS and kD"
source                 1..217
                       mol_type = protein
                       organism = synthetic construct
SEQUENCE: 80
APEAAGGPDV FLFPPKPKDT LMISRTPEVT CVVVDVSHED PEVKFNWYVD GVEVHNAKTK  60
PREEQYNSTY RVVSVLTVLH QDWLNGKEYK CKVSNKALSA PIEKTISKAK GQPREPQVYT  120
LPPSRDELTK NQVSLWCLVK GFYPSDIAVE WESYGTEWSN YKTTPPVLDS DGSFFLYSKL  180
TVSKEEWQQG FVFSCSVMHE ALHNHYTQKS LSLSPGK                           217

SEQ ID NO: 81          moltype = AA  length = 217
FEATURE                Location/Qualifiers
REGION                 1..217
                       note = Description of sequence: "Clone CH3C.35.23.4 with
                        knob LALA PG and kE"
source                 1..217
                       mol_type = protein
                       organism = synthetic construct
SEQUENCE: 81
APEAAGGPSV FLFPPKPKDT LMISRTPEVT CVVVDVSHED PEVKFNWYVD GVEVHNAKTK  60
PREEQYNSTY RVVSVLTVLH QDWLNGKEYK CKVSNKALGA PEEKTISKAK GQPREPQVYT  120
LPPSRDELTK NQVSLWCLVK GFYPSDIAVE WESYGTEWSN YKTTPPVLDS DGSFFLYSKL  180
TVSKEEWQQG FVFSCSVMHE ALHNHYTQKS LSLSPGK                           217

SEQ ID NO: 82          moltype = AA  length = 217
FEATURE                Location/Qualifiers
REGION                 1..217
                       note = Description of sequence: "Clone CH3C.35.23.4 with
                        knob LALA PS and kE"
source                 1..217
                       mol_type = protein
                       organism = synthetic construct
SEQUENCE: 82
APEAAGGPSV FLFPPKPKDT LMISRTPEVT CVVVDVSHED PEVKFNWYVD GVEVHNAKTK  60
PREEQYNSTY RVVSVLTVLH QDWLNGKEYK CKVSNKALSA PEEKTISKAK GQPREPQVYT  120
LPPSRDELTK NQVSLWCLVK GFYPSDIAVE WESYGTEWSN YKTTPPVLDS DGSFFLYSKL  180
TVSKEEWQQG FVFSCSVMHE ALHNHYTQKS LSLSPGK                           217

SEQ ID NO: 83          moltype = AA  length = 217
FEATURE                Location/Qualifiers
REGION                 1..217
                       note = Description of sequence: "Clone CH3C.35.23.4 with
                        knob LALA PG and kDE"
source                 1..217
                       mol_type = protein
                       organism = synthetic construct
SEQUENCE: 83
APEAAGGPDV FLFPPKPKDT LMISRTPEVT CVVVDVSHED PEVKFNWYVD GVEVHNAKTK  60
PREEQYNSTY RVVSVLTVLH QDWLNGKEYK CKVSNKALGA PEEKTISKAK GQPREPQVYT  120
LPPSRDELTK NQVSLWCLVK GFYPSDIAVE WESYGTEWSN YKTTPPVLDS DGSFFLYSKL  180
TVSKEEWQQG FVFSCSVMHE ALHNHYTQKS LSLSPGK                           217

SEQ ID NO: 84          moltype = AA  length = 217
FEATURE                Location/Qualifiers
REGION                 1..217
                       note = Description of sequence: "Clone CH3C.35.23.4 with
                        knob LALA PS and kDE"
source                 1..217
                       mol_type = protein
                       organism = synthetic construct
SEQUENCE: 84
APEAAGGPDV FLFPPKPKDT LMISRTPEVT CVVVDVSHED PEVKFNWYVD GVEVHNAKTK  60
PREEQYNSTY RVVSVLTVLH QDWLNGKEYK CKVSNKALSA PEEKTISKAK GQPREPQVYT  120
LPPSRDELTK NQVSLWCLVK GFYPSDIAVE WESYGTEWSN YKTTPPVLDS DGSFFLYSKL  180
```

```
TVSKEEWQQG FVFSCSVMHE ALHNHYTQKS LSLSPGK                     217

SEQ ID NO: 85          moltype = AA  length = 217
FEATURE                Location/Qualifiers
REGION                 1..217
                       note = Description of sequence: Fc sequence with hole
                        mutations
source                 1..217
                       mol_type = protein
                       organism = synthetic construct
SEQUENCE: 85
APELLGGPSV FLFPPKPKDT LMISRTPEVT CVVVDVSHED PEVKFNWYVD GVEVHNAKTK  60
PREEQYNSTY RVVSVLTVLH QDWLNGKEYK CKVSNKALPA PIEKTISKAK GQPREPQVYT  120
LPPSRDELTK NQVSLSCAVK GFYPSDIAVE WESNGQPENN YKTTPPVLDS DGSFFLVSKL  180
TVDKSRWQQG NVFSCSVMHE ALHNHYTQKS LSLSPGK                     217

SEQ ID NO: 86          moltype = AA  length = 217
FEATURE                Location/Qualifiers
REGION                 1..217
                       note = Description of sequence: Clone CH3C.35.23.4 with
                        knob and LALA mutations
source                 1..217
                       mol_type = protein
                       organism = synthetic construct
SEQUENCE: 86
APEAAGGPSV FLFPPKPKDT LMISRTPEVT CVVVDVSHED PEVKFNWYVD GVEVHNAKTK  60
PREEQYNSTY RVVSVLTVLH QDWLNGKEYK CKVSNKALPA PIEKTISKAK GQPREPQVYT  120
LPPSRDELTK NQVSLWCLVK GFYPSDIAVE WESYGTEWSN YKTTPPVLDS DGSFFLYSKL  180
TVSKEEWQQG FVFSCSVMHE ALHNHYTQKS LSLSPGK                     217

SEQ ID NO: 87          moltype = AA  length = 214
FEATURE                Location/Qualifiers
REGION                 1..214
                       note = Description of sequence: Anti-HER2 D4 light chain
                        control
source                 1..214
                       mol_type = protein
                       organism = synthetic construct
SEQUENCE: 87
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ HYTTPPTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                        214

SEQ ID NO: 88          moltype = AA  length = 214
FEATURE                Location/Qualifiers
REGION                 1..214
                       note = Description of sequence: Anti-HER2 light chain
                        consensus
VAR_SEQ                91
                       note = X = any naturally occurring amino acid
source                 1..214
                       mol_type = protein
                       organism = synthetic construct
SEQUENCE: 88
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ XYTTPPTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                        214

SEQ ID NO: 89          moltype = AA  length = 10
FEATURE                Location/Qualifiers
REGION                 1..10
                       note = Description of sequence: Anti-HER2 CDR1 consensus
VAR_SEQ                3
                       note = X = any standard amino acid, except Thr.
VAR_SEQ                4
                       note = X = any standard amino acid, except Phe
VAR_SEQ                5
                       note = X = any standard amino acid, except Thr
source                 1..10
                       mol_type = protein
                       organism = synthetic construct
SEQUENCE: 89
GFXXXDYTMD                                                   10

SEQ ID NO: 90          moltype = AA  length = 17
FEATURE                Location/Qualifiers
REGION                 1..17
```

```
                        note = Description of sequence: Anti-HER2 CDR2 consensus
VAR_SEQ                 3
                        note = X = any standard amino acid, except Asn
VAR_SEQ                 5
                        note = X = any standard amino acid, except Asn
VAR_SEQ                 6
                        note = X = any standard amino acid, except Ser
VAR_SEQ                 7
                        note = X = any standard amino acid, except Gly
VAR_SEQ                 7
                        note = X = any standard amino acid, except Gly
VAR_SEQ                 13
                        note = X = any standard amino acid, except Gln
source                  1..17
                        mol_type = protein
                        organism = synthetic construct
SEQUENCE: 90
DVXPXXXXSI YNXRFKG                                                    17

SEQ ID NO: 91           moltype = AA  length = 12
FEATURE                 Location/Qualifiers
REGION                  1..12
                        note = Description of sequence: Anti-HER2 CDR3 consensus
VAR_SEQ                 4
                        note = X = any standard amino acid, except Lys
VAR_SEQ                 5
                        note = X = any standard amino acid, except Gly
VAR_SEQ                 6
                        note = X = any standard amino acid, except Pro
VAR_SEQ                 7
                        note = X = ny standard amino acid, except Ser
source                  1..12
                        mol_type = protein
                        organism = synthetic construct
SEQUENCE: 91
ARNXXXXFYF DY                                                         12

SEQ ID NO: 92           moltype = AA  length = 448
FEATURE                 Location/Qualifiers
REGION                  1..448
                        note = Description of sequence: Anti-HER2 D2 heavy chain
                         control
source                  1..448
                        mol_type = protein
                        organism = synthetic construct
SEQUENCE: 92
EVQLVESGGG LVQPGGSLRL SCAASGFTFT DYTMDWVRQA PGKGLEWVAD VNPNSGGSIY  60
NQRFKGRFTL SVDRSKNTLY LQMNSLRAED TAVYYCARNL GPSFYFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPG                                     448

SEQ ID NO: 93           moltype = AA  length = 449
FEATURE                 Location/Qualifiers
REGION                  1..449
                        note = Description of sequence: Anti-HER2 D4 heavy chain
                         control
source                  1..449
                        mol_type = protein
                        organism = synthetic construct
SEQUENCE: 93
EVQLVESGGG LVQPGGSLRL SCAASGFNIK DTYIHWVRQA PGKGLEWVAR IYPTNGYTRY  60
ADSVKGRFTI SADTSKNTAY LQMNSLRAED TAVYYCSRWG GDGFYAMDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                                    449

SEQ ID NO: 94           moltype = AA  length = 214
FEATURE                 Location/Qualifiers
REGION                  1..214
                        note = Description of sequence: Anti-HER2 D2 light chain
                         control
source                  1..214
```

-continued

```
                        mol_type = protein
                        organism = synthetic construct
SEQUENCE: 94
DIQMTQSPSS LSASVGDRVT ITCKASQDVS IGVAWYQQKP GKAPKLLIYS ASYRYTGVPS  60
RFSGSGSGTD FTLTISSLQP EDFATYYCQQ YYIYPYTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 95           moltype = AA  length = 217
FEATURE                 Location/Qualifiers
REGION                  1..217
                        note = Description of sequence: Wild-type human Fc sequence
source                  1..217
                        mol_type = protein
                        organism = synthetic construct
SEQUENCE: 95
APELLGGPSV FLFPPKPKDT LMISRTPEVT CVVVDVSHED PEVKFNWYVD GVEVHNAKTK  60
PREEQYNSTY RVVSVLTVLH QDWLNGKEYK CKVSNKALPA PIEKTISKAK GQPREPQVYT  120
LPPSRDELTK NQVSLTCLVK GFYPSDIAVE WESNGQPENN YKTTPPVLDS DGSFFLYSKL  180
TVDKSRWQQG NVFSCSVMHE ALHNHYTQKS LSLSPGK                          217

SEQ ID NO: 96           moltype = AA  length = 15
FEATURE                 Location/Qualifiers
REGION                  1..15
                        note = Description of sequence: Human IgG1 hinge region
source                  1..15
                        mol_type = protein
                        organism = synthetic construct
SEQUENCE: 96
EPKSCDKTHT CPPCP                                                  15

SEQ ID NO: 97           moltype = AA  length = 217
FEATURE                 Location/Qualifiers
REGION                  1..217
                        note = Description of sequence: Clone CH3C.35.23.4
source                  1..217
                        mol_type = protein
                        organism = synthetic construct
SEQUENCE: 97
APELLGGPSV FLFPPKPKDT LMISRTPEVT CVVVDVSHED PEVKFNWYVD GVEVHNAKTK  60
PREEQYNSTY RVVSVLTVLH QDWLNGKEYK CKVSNKALPA PIEKTISKAK GQPREPQVYT  120
LPPSRDELTK NQVSLTCLVK GFYPSDIAVE WESYGTEWSN YKTTPPVLDS DGSFFLYSKL  180
TVSKEEWQQG FVFSCSVMHE ALHNHYTQKS LSLSPGK                          217

SEQ ID NO: 98           moltype = AA  length = 217
FEATURE                 Location/Qualifiers
REGION                  1..217
                        note = Description of sequence: Clone CH3C.35.23.4 with
                         knob mutation
source                  1..217
                        mol_type = protein
                        organism = synthetic construct
SEQUENCE: 98
APELLGGPSV FLFPPKPKDT LMISRTPEVT CVVVDVSHED PEVKFNWYVD GVEVHNAKTK  60
PREEQYNSTY RVVSVLTVLH QDWLNGKEYK CKVSNKALPA PIEKTISKAK GQPREPQVYT  120
LPPSRDELTK NQVSLWCLVK GFYPSDIAVE WESYGTEWSN YKTTPPVLDS DGSFFLYSKL  180
TVSKEEWQQG FVFSCSVMHE ALHNHYTQKS LSLSPGK                          217

SEQ ID NO: 99           moltype = AA  length = 217
FEATURE                 Location/Qualifiers
REGION                  1..217
                        note = Description of sequence: Clone CH3C.35.23.4 with
                         hole mutations
source                  1..217
                        mol_type = protein
                        organism = synthetic construct
SEQUENCE: 99
APELLGGPSV FLFPPKPKDT LMISRTPEVT CVVVDVSHED PEVKFNWYVD GVEVHNAKTK  60
PREEQYNSTY RVVSVLTVLH QDWLNGKEYK CKVSNKALPA PIEKTISKAK GQPREPQVYT  120
LPPSRDELTK NQVSLSCAVK GFYPSDIAVE WESYGTEWSN YKTTPPVLDS DGSFFLVSKL  180
TVSKEEWQQG FVFSCSVMHE ALHNHYTQKS LSLSPGK                          217

SEQ ID NO: 100          moltype = AA  length = 217
FEATURE                 Location/Qualifiers
REGION                  1..217
                        note = Description of sequence: Clone CH3C.35.23.4 with
                         hole and LALA mutations
source                  1..217
                        mol_type = protein
```

```
                        organism = synthetic construct
SEQUENCE: 100
APEAAGGPSV FLFPPKPKDT LMISRTPEVT CVVVDVSHED PEVKFNWYVD GVEVHNAKTK  60
PREEQYNSTY RVVSVLTVLH QDWLNGKEYK CKVSNKALPA PIEKTISKAK GQPREPQVYT  120
LPPSRDELTK NQVSLSCAVK GFYPSDIAVE WESYGTEWSN YKTTPPVLDS DGSFFLVSKL  180
TVSKEEWQQG FVFSCSVMHE ALHNHYTQKS LSLSPGK                           217

SEQ ID NO: 101          moltype = AA  length = 217
FEATURE                 Location/Qualifiers
REGION                  1..217
                        note = Description of sequence: Clone CH3C.35.23.2
source                  1..217
                        mol_type = protein
                        organism = synthetic construct
SEQUENCE: 101
APELLGGPSV FLFPPKPKDT LMISRTPEVT CVVVDVSHED PEVKFNWYVD GVEVHNAKTK  60
PREEQYNSTY RVVSVLTVLH QDWLNGKEYK CKVSNKALPA PIEKTISKAK GQPREPQVYT  120
LPPSRDELTK NQVSLTCLVK GFYPSDIAVE WESYGTEWAN YKTTPPVLDS DGSFFLYSKL  180
TVTKEEWQQG FVFSCSVMHE ALHNHYTQKS LSLSPGK                           217

SEQ ID NO: 102          moltype = AA  length = 217
FEATURE                 Location/Qualifiers
REGION                  1..217
                        note = Description of sequence: Clone CH3C.35.23.2 with
                         knob mutation
source                  1..217
                        mol_type = protein
                        organism = synthetic construct
SEQUENCE: 102
APELLGGPSV FLFPPKPKDT LMISRTPEVT CVVVDVSHED PEVKFNWYVD GVEVHNAKTK  60
PREEQYNSTY RVVSVLTVLH QDWLNGKEYK CKVSNKALPA PIEKTISKAK GQPREPQVYT  120
LPPSRDELTK NQVSLWCLVK GFYPSDIAVE WESYGTEWAN YKTTPPVLDS DGSFFLYSKL  180
TVTKEEWQQG FVFSCSVMHE ALHNHYTQKS LSLSPGK                           217

SEQ ID NO: 103          moltype = AA  length = 217
FEATURE                 Location/Qualifiers
REGION                  1..217
                        note = Description of sequence: Clone CH3C.35.23.2 with
                         knob and LALA mutations
source                  1..217
                        mol_type = protein
                        organism = synthetic construct
SEQUENCE: 103
APEAAGGPSV FLFPPKPKDT LMISRTPEVT CVVVDVSHED PEVKFNWYVD GVEVHNAKTK  60
PREEQYNSTY RVVSVLTVLH QDWLNGKEYK CKVSNKALPA PIEKTISKAK GQPREPQVYT  120
LPPSRDELTK NQVSLWCLVK GFYPSDIAVE WESYGTEWAN YKTTPPVLDS DGSFFLYSKL  180
TVTKEEWQQG FVFSCSVMHE ALHNHYTQKS LSLSPGK                           217

SEQ ID NO: 104          moltype = AA  length = 217
FEATURE                 Location/Qualifiers
REGION                  1..217
                        note = Description of sequence: Clone CH3C.35.23.2 with
                         hole mutations
source                  1..217
                        mol_type = protein
                        organism = synthetic construct
SEQUENCE: 104
APELLGGPSV FLFPPKPKDT LMISRTPEVT CVVVDVSHED PEVKFNWYVD GVEVHNAKTK  60
PREEQYNSTY RVVSVLTVLH QDWLNGKEYK CKVSNKALPA PIEKTISKAK GQPREPQVYT  120
LPPSRDELTK NQVSLSCAVK GFYPSDIAVE WESYGTEWAN YKTTPPVLDS DGSFFLVSKL  180
TVTKEEWQQG FVFSCSVMHE ALHNHYTQKS LSLSPGK                           217

SEQ ID NO: 105          moltype = AA  length = 217
FEATURE                 Location/Qualifiers
REGION                  1..217
                        note = Description of sequence: Clone CH3C.35.23.2 with
                         hole and LALA mutations
source                  1..217
                        mol_type = protein
                        organism = synthetic construct
SEQUENCE: 105
APEAAGGPSV FLFPPKPKDT LMISRTPEVT CVVVDVSHED PEVKFNWYVD GVEVHNAKTK  60
PREEQYNSTY RVVSVLTVLH QDWLNGKEYK CKVSNKALPA PIEKTISKAK GQPREPQVYT  120
LPPSRDELTK NQVSLSCAVK GFYPSDIAVE WESYGTEWAN YKTTPPVLDS DGSFFLVSKL  180
TVTKEEWQQG FVFSCSVMHE ALHNHYTQKS LSLSPGK                           217

SEQ ID NO: 106          moltype = AA  length = 217
FEATURE                 Location/Qualifiers
REGION                  1..217
```

-continued

```
                         note = Description of sequence: Clone CH3C.35.20.1
source                   1..217
                         mol_type = protein
                         organism = synthetic construct
SEQUENCE: 106
APELLGGPSV FLFPPKPKDT LMISRTPEVT CVVVDVSHED PEVKFNWYVD GVEVHNAKTK  60
PREEQYNSTY RVVSVLTVLH QDWLNGKEYK CKVSNKALPA PIEKTISKAK GQPREPQVYT  120
LPPSRDELTK NQVSLTCLVK GFYPSDIAVE WESFGTEWSS YKTTPPVLDS DGSFFLYSKL  180
TVTKEEWQQG FVFSCSVMHE ALHNHYTQKS LSLSPGK                          217

SEQ ID NO: 107           moltype = AA  length = 217
FEATURE                  Location/Qualifiers
REGION                   1..217
                         note = Description of sequence: Fc sequence with knob
                          mutation
source                   1..217
                         mol_type = protein
                         organism = synthetic construct
SEQUENCE: 107
APELLGGPSV FLFPPKPKDT LMISRTPEVT CVVVDVSHED PEVKFNWYVD GVEVHNAKTK  60
PREEQYNSTY RVVSVLTVLH QDWLNGKEYK CKVSNKALPA PIEKTISKAK GQPREPQVYT  120
LPPSRDELTK NQVSLWCLVK GFYPSDIAVE WESNGQPENN YKTTPPVLDS DGSFFLYSKL  180
TVDKSRWQQG NVFSCSVMHE ALHNHYTQKS LSLSPGK                          217

SEQ ID NO: 108           moltype = AA  length = 120
FEATURE                  Location/Qualifiers
REGION                   1..120
                         note = Description of sequence: Anti-HER2 D4 VH v1
source                   1..120
                         mol_type = protein
                         organism = synthetic construct
SEQUENCE: 108
EVQLVESGGG LVQPGGSLRL SCAASGFNIK DTYIHWVRQA PGKGLEWVAR IYPTNGYTRY  60
ADSVKGRFTI SADTSKNTAY LQMNSLRAED TAVYYCSRWG GEGFYAMDYW GQGTLVTVSS  120

SEQ ID NO: 109           moltype = AA  length = 119
FEATURE                  Location/Qualifiers
REGION                   1..119
                         note = Description of sequence: Anti-HER2 D2 VH v4
source                   1..119
                         mol_type = protein
                         organism = synthetic construct
SEQUENCE: 109
EVQLVESGGG LVQPGGSLRL SCAASGFTFN DYTMDWVRQA PGKGLEWVAD VNPNSGGSIV  60
NRRFKGRFTL SVDRSKNTLY LQMNSLRAED TAVYYCARNL GPFFYFDYWG QGTLVTVSS   119
```